United States Patent
Sahagun-Krause et al.

(10) Patent No.: US 7,262,215 B2
(45) Date of Patent: Aug. 28, 2007

(54) N-CARBACYCLE MONOSUBSTITUTED INDOLOCARBAZOLES AS PROTEIN KINASE INHIBITORS

(75) Inventors: Heidi Sahagun-Krause, München (DE); Olivier Thillaye Du Boullay, Schwabhausen (DE); Valerie Thillaye Du Boullay, Schwabhausen (DE); Laura Casiraghi, München (DE); Hans-Wolfgang Klafki, München (DE); Pierfausto Seneci, München (DE); Tobias Braxmeier, München (DE); Silvia Müller, München (DE); Wolfgang Fröhner, München (DE); Barbara Monse, Weichs (DE); Sandra Gordon, München (DE); Hanno M. Roder, Westport, CT (US)

(73) Assignee: NAD AG, Munich (DE)

( * ) Notice: Subject to any disclaimer, the term of this patent is extended or adjusted under 35 U.S.C. 154(b) by 0 days.

(21) Appl. No.: 10/496,505

(22) PCT Filed: Dec. 4, 2002

(86) PCT No.: PCT/EP02/13753

§ 371 (c)(1),
(2), (4) Date: Oct. 28, 2004

(87) PCT Pub. No.: WO03/051887

PCT Pub. Date: Jun. 26, 2003

(65) Prior Publication Data

US 2005/0075386 A1   Apr. 7, 2005

(30) Foreign Application Priority Data

Dec. 17, 2001 (DE) ................................ 101 61 940

(51) Int. Cl.
| | | |
|---|---|---|
| *A61K 31/4035* | (2006.01) | |
| *A61K 31/5377* | (2006.01) | |
| *A61K 31/4192* | (2006.01) | |
| *A61K 31/407* | (2006.01) | |
| *C07D 249/04* | (2006.01) | |
| *C07D 413/14* | (2006.01) | |
| *C07D 487/14* | (2006.01) | |
| *C09B 5/26* | (2006.01) | |

(52) U.S. Cl. ................ 514/410; 514/231.2; 514/232.8; 514/359; 544/142; 548/416; 548/255

(58) Field of Classification Search ................ 514/410, 514/231.2, 232.8, 359; 544/142; 548/416, 548/255
See application file for complete search history.

(56) References Cited

U.S. PATENT DOCUMENTS

| 5,438,050 A * | 8/1995 | Kleinschroth et al. ...... 514/183 |
| 5,883,114 A * | 3/1999 | Kleinschroth et al. ...... 514/410 |
| 6,013,646 A * | 1/2000 | Roder et al. ................. 514/219 |
| 6,541,468 B1* | 4/2003 | Roder et al. ................. 514/219 |
| 2004/0077554 A1* | 4/2004 | Xu et al. ....................... 514/23 |
| 2004/0248892 A1* | 12/2004 | Wang ....................... 514/232.2 |

FOREIGN PATENT DOCUMENTS

| WO | 9318766 | 9/1993 |
| WO | 9604906 | 2/1996 |
| WO | 9933836 | 7/1999 |
| WO | 001699 | 1/2000 |

OTHER PUBLICATIONS

McCombie, et al. "Indolocarbazoles. I. Total Synthesis and Protein Kinase Inhibiting Characteristics of Compounds Related to K-252c" Bioorganic and Medicinal Chemistry Letters, vol. 3(8), pp. 1537-1542 (1993).*

* cited by examiner

*Primary Examiner*—Kamal A. Saeed
*Assistant Examiner*—Nyeemah Grazier
(74) *Attorney, Agent, or Firm*—McAndrews, Held & Malloy, Ltd.

(57) ABSTRACT

This invention relates to N-carbacycle monosubstituted indolocarbazole compounds. Furthermore, this invention relates to medicaments comprising N-carbacycle monosubstituted indolocarbazoles compounds and the use of such compounds for treating non-insulin dependent diabetes mellitus, acute stroke and other neurotraumatic injuries, for treating diabetes mellitus, as a chemotherapeutic for the treatment of various malignant diseases, for treating diseases caused by malfunctioning of specific signaling pathways, and for treating neurodegenerative diseases such as for example Alzheimer's disease.

16 Claims, 20 Drawing Sheets

Fig. 16

| Cpd N° | R1 | R2R3 | R4R5 | R6R7 | R8R9 | n | R10 | R11 | R12 | R13 | R14 | R15 | R16 | R17 | R18 | Z | Y |
|---|---|---|---|---|---|---|---|---|---|---|---|---|---|---|---|---|---|
| NAD003 | H | H | H | O | O | 1 | H | Absent | H | Absent | H | OSi | H | H | H | Double | Single |
| NAD006 | H | H | H | O | O | 1 | H | Absent | H | Absent | H | OH | H | H | H | Double | Single |
| NAD018 | H | H | H | O | O | 1 | PMB | Absent | H | Absent | H | H | OAc | H | H | Double | Single |
| NAD040 | H | H | H | O | O | 1 | H | Absent | H | Absent | H | H | NH$_2$ | H | H | Double | Single |
| NAD048 | H | H | H | O | O | 1 | H | Absent | H | Absent | H | H | NHiPr | H | H | Double | Single |
| NAD080 | H | H | H | O | O | 1 | H | Absent | H | Absent | H | H | Cl | H | H | Double | Single |
| NAD085 | H | H | H | O | O | 2 | H | Absent | H | Absent | H | H | Cl | H | H | Double | Single |
| NAD101 | H | H | H | O | O | 1 | H | Absent | H | Absent | H | NHMe | H | H | H | Double | Single |
| NAD102 | H | H | H | O | O | 1 | H | Absent | H | Absent | H | NHBz | H | H | H | Double | Single |
| NAD106 | H | H | H | O | O | 2 | H | Absent | H | Absent | H | H | OAc | H | H | Double | Single |
| NAD116 | H | H | H | O | O | 1 | H | Absent | H | Absent | H | NH$_2$ | H | H | H | Double | Single |
| NAD117 | H | H | H | O | O | 1 | COOEt | Absent | H | Absent | H | H | NHAc | H | H | Double | Single |
| NAD119 | H | H | H | O | O | 1 | COOEt | Absent | H | Absent | H | =O | Absent | H | H | Double | Single |
| NAD130 | H | H | H | O | O | 1 | Me | Absent | H | Absent | H | OH | H | H | H | Double | Single |
| NAD131 | H | H | H | O | O | 2 | PMB | Absent | H | H | H | H | OAc | H | H | Double | Single |
| NAD132 | H | H | H | O | O | 2 | PMB | Absent | H | H | H | OAc | H | H | H | Double | Single |
| NAD133 | H | H | H | O | O | 2 | PMB | Absent | H | H | H | OH | OH | H | H | Double | Single |
| NAD135 | H | H | H | O | O | 2 | H | Absent | H | H | H | OAc | H | H | H | Double | Single |
| NAD136 | H | H | H | O | O | 2 | PMB | H | OH | H | OH | OAc | H | H | H | Single | Single |
| NAD137 | H | H | H | O | O | 2 | PMB | Absent | H | H | H | OH | H | H | H | Double | Single |
| NAD148 | H | H | H | O | O | 2 | H | Absent | H | H | H | H | NHPh | H | H | Double | Single |
| NAD149 | H | H | H | O | O | 2 | H | Absent | OH | H | OH | H | H | H | H | Double | Single |
| NAD154 | H | H | H | O | O | 1 | Me | H | OH | H | OH | OH | H | H | H | Single | Single |
| NAD157 | H | H | H | O | O | 1 | Me | H | OH | H | OH | OSi | H | H | H | Single | Single |
| NAD160 | H | H | H | O | O | 1 | H | H | OH | H | OH | OH | H | H | H | Single | Single |
| NAD161 | H | H | H | O | O | 1 | Me | Absent | H | Absent | H | H | N$_3$ | H | H | Double | Single |
| NAD162 | H | H | H | O | O | 1 | H | Absent | H | Absent | H | H | OH | H | H | Double | Single |
| NAD164 | H | H | H | O | O | 1 | Me | Absent | H | Absent | H | H | N$_3$ | H | H | Double | Single |
| NAD168 | H | H | H | O | O | 1 | Me | Absent | H | Absent | H | NH$_2$ | H | H | H | Double | Single |
| NAD169 | H | H | H | O | O | 1 | Me | Absent | H | Absent | H | H | NH$_2$ | H | H | Double | Single |

Figure 16 continued

| | | | | | | | | | | | | | | | | |
|---|---|---|---|---|---|---|---|---|---|---|---|---|---|---|---|---|
| NAD170 | H | H | H | O | O | 1 | Me | Absent | H | Absent | H | H | NHAc | H | H | Double | Single |
| NAD171 | H | 5-OCH₃ | 5-OCH₃ | O | O | 1 | PMB | Absent | H | Absent | H | H | OH | H | H | Double | Single |
| NAD173 | H | H | H | O | O | 1 | PMB | Absent | OH | H | H | OAc | H | H | H | Single | Single |
| NAD174 | H | 5-Br | 5-Br | O | O | 2 | PMB | Absent | H | Absent | OH | OAc | OAc | H | H | Double | Single |
| NAD175 | H | H | H | O | O | 2 | PMB | Absent | H | H | H | H | OH | H | H | Single | Single |
| NAD176 | H | 5-Br | 5-Br | O | O | 2 | PMB | Absent | H | Absent | H | H | OH | H | H | Double | Single |
| NAD179 | H | 5-Br | H | O | O | 1 | Me | Absent | H | Absent | OH | H | H | H | H | Double | Single |
| NAD180 | H | H | H | O | O | 1 | H | H | OH | H | OH | OH | H | H | H | Single | Single |
| NAD181 | H | H | H | O | O | 2 | H | H | OH | H | OH | OH | H | H | H | Double | Single |
| NAD182 | H | H | 5-Br | O | O | 1 | H | Absent | H | Absent | OH | OH | H | H | H | Single | Single |
| NAD183 | H | H | H | O | O | 2 | PMB | Absent | H | Absent | OH | OH | H | H | H | Double | Single |
| NAD185 | H | 5-Br | H | O | O | 1 | H | H | OH | H | H | OH | H | H | H | Single | Single |
| NAD188 | H | H | H | O | O | 2 | H | H | OH | H | OH | OH | N₃ | H | H | Single | Single |
| NAD190 | H | H | H | O | O | 1 | H | H | OAc | OAc | OAc | H | OAc | H | H | Single | Single |
| NAD195 | H | H | H | O | O | 2 | H | H | OH | H | OH | H | N₃ | H | H | Single | Single |
| NAD196 | H | H | H | O | O | 1 | H | H | OH | H | OH | H | OH | H | H | Single | Single |
| NAD198 | H | H | H | O | O | 2 | H | H | OH | H | OH | H | NH₂ | H | H | Single | Single |
| NAD200 | H | H | H | O | O | 2 | H | H | Acet | Acet | H | H | N₃ | H | H | Single | Single |
| NAD203 | H | H | 5-OMe | O | O | 1 | Me | Absent | H | Absent | H | OH | H | H | H | Double | Single |
| NAD204 | H | H | 5-OMe | O | O | 1 | Me | Absent | H | Absent | H | =O | Absent | H | H | Double | Single |
| NAD206 | H | 5-NO₂ | H | O | O | 2 | H | Absent | H | Absent | OH | H | OAc | Acet | H | Double | Single |
| NAD210 | H | H | H | O | O | 1 | H | H | H | H | OH | H | NH₂ | Acet | H | Single | Single |
| NAD211 | H | 5-Br | 5-Br | O | O | 2 | H | H | Acet | H | H | H | OAc | H | H | Double | Single |
| NAD212 | H | H | H | O | O | 2 | PMB | Absent | OH | H | H | H | Cl | H | H | Double | Single |
| NAD214 | H | H | 5-OMe | O | O | 1 | H | Absent | H | Absent | H | H | H | H | H | Double | Single |
| NAD223 | H | H | H | O | O | 2 | H | Absent | H | Absent | OH | Acet | H | Acet | H | Double | Single |
| NAD226 | H | H | H | O | O | 2 | H | Absent | H | Absent | OH | Acet | H | Acet | H | Single | Single |
| NAD234 | H | H | H | O | O | 2 | H | Absent | H | Absent | OH | H | Acet | H | Acet | Double | Single |
| NAD238 | H | 6-Cl | H | O | O | 2 | H | Absent | H | Absent | H | H | OH | H | OH | Double | Single |
| NAD240 | H | H | H | O | O | 1 | H | H | OH | H | OH | H | OH | H | H | Single | Single |
| NAD244 | H | H | 6-Cl | O | O | 1 | H | Absent | H | Absent | OH | OH | H | H | H | Single | Single |
| NAD245 | H | H | 6-Cl | O | O | 1 | H | Absent | H | Absent | H | OH | H | H | H | Double | Single |

Figure 16 continued

| ID | | | | | | | | | | | | | | | | |
|---|---|---|---|---|---|---|---|---|---|---|---|---|---|---|---|---|
| NAD246 | H | H | 6-Cl | O | O | 1 | H | H | OH | H | OH | OTBDMS | H | H | H | Single |
| NAD247 | Me | H | H | O | O | 1 | H | Absent | H | Absent | H | OH | H | H | H | Double | Single |
| NAD248 | Me | H | H | O | O | 1 | Me | Absent | H | Absent | H | OH | H | H | H | Double | Single |
| NAD253 | H | 5-OMe | 5-OMe | O | O | 1 | Me | Absent | H | Absent | H | OH | H | H | H | Double | Single |
| NAD254 | H | H | H | O | O | 1 | H | H | H | OH | H | OH | H | H | H | Single | Single |
| NAD265 | H | H | 6-Cl | O | O | 1 | H | Absent | H | Absent | H | H | OH | OH | H | Double | Single |
| NAD277 | H | H | H | O | O | 2 | H | Absent | H | Absent | H | H | CH$_2$OTBDM S | H | H | Double | Single |
| NAD278 | H | H | H | O | O | 2 | H | Absent | H | Absent | H | H | CH$_2$OH | H | H | Double | Single |
| NAD279 | H | H | H | O | O | 2 | H | Absent | H | Absent | H | OH | H | H | H | Double | Single |
| NAD284 | H | H | H | O | O | 2 | H | H | OH | H | OH | OH | H | OH | H | Single | Single |
| NAD286 | H | 6-Cl | H | O | O | 2 | H | Absent | H | Absent | H | H | OTBDMS | H | H | Double | Single |
| NAD287 | H | H | H | O | O | 2 | H | Absent | H | Absent | H | H | H | H | H | Double | Single |
| NAD291 | H | 5-F | 5-F | O | O | 1 | Me | H | H | H | H | CH$_2$OH | H | H | H | Double | Single |
| NAD292 | H | H | H | O | O | 2 | H | Absent | H | Absent | H | OH | H | H | H | Double | Single |
| NAD293 | H | 5-F | 5-F | O | O | 1 | H | Absent | H | Absent | H | OH | H | OH | H | Double | Single |
| NAD294 | H | 5-NO$_2$ | 5-NO$_2$ | O | O | 1 | H | Absent | H | Absent | H | OH | H | H | H | Double | Single |
| NAD296 | H | H | H | O | O | 2 | H | H | OH | H | OH | CH$_2$OTBDM S | H | H | H | Single | Single |
| NAD298 | H | 5-F | 5-F | O | O | 1 | Me | Absent | H | Absent | H | =O | Absent | H | H | Double | Single |
| NAD300 | H | 5-F | 5-F | O | O | 1 | Me | Absent | H | Absent | H | OAc | H | H | H | Double | Single |
| NAD302 | H | H | H | O | O | 2 | H | H | OH | H | OH | CH$_2$OH | H | H | H | Single | Single |
| NAD303 | H | H | H | O | O | 1 | H | H | Acet. | H | Acet. | OAc | H | H | H | Single | Single |
| NAD306 | H | H | H | O | O | 1 | Me | H | Acet. | H | Acet. | OAc | H | H | H | Single | Single |
| NAD311 | H | 5-F | 5-F | O | O | 1 | H | H | OH | H | OH | OH | H | H | H | Single | Single |
| NAD319 | H | H | H | O | O | 2 | H | H | H | H | H | OH | H | H | H | Single | Single |
| NAD323 | H | 5-F | 5-F | O | O | 2 | H | Absent | H | Absent | H | H | H | H | H | Double | Single |
| NAD335 | H | H | H | O | O | 1 | H | Absent | H | Absent | H | H | H | H | H | Double | Single |
| NAD336 | H | H | H | O | O | 1 | H | H | H | H | H | OTBDMS | NHBoc | H | H | Double | Single |
| NAD337 | H | 6-Cl | H | O | O | 1 | H | H | OH | H | OH | OH | NH$_2$ | H | H | Single | Single |
| NAD338 | H | 6-Cl | H | O | O | 1 | H | H | OH | H | OH | OTBDMS | H | H | H | Double | Single |
| NAD339 | H | 6-Cl | H | O | O | 1 | H | H | OH | H | OH | OTBDMS | H | H | H | Double | Single |
| NAD340 | H | H | H | O | O | 1 | H | Absent | H | Absent | H | OH | H | H | H | Single | Single |
| NAD343 | H | H | H | O | O | 1 | H | Acet. | Acet. | Acet. | Acet. | =O | Absent | H | H | Double | Single |
| NAD344 | H | H | H | O | O | 1 | H | H | H | H | H | OH | H | H | H | Single | Single |

Figure 16 continued

| | | | | | | | | | | | | | | |
|---|---|---|---|---|---|---|---|---|---|---|---|---|---|---|
| NAD349 | H | H | H | O | 0 | 1 | H | H | H | OH | H | =O | Absent | H | H | Single | Single |
| NAD352 | H | H | H | O | 0 | 1 | H | H | H | OH | OH | =O | Absent | H | H | Single | Single |
| NAD364 enantio | H | H | H | O | 0 | 1 | H | Absent | OH | H | H | OTBDMS | H | H | H | Double | Single |
| NAD365 enantio | H | H | H | O | 0 | 1 | H | H | H | OH | OH | OTBDMS | H | H | H | Single | Single |
| NAD366 enantio | H | H | H | O | 0 | 1 | H | Absent | OH | H | H | OTBDMS | H | H | H | Double | Single |
| NAD368 enantio | H | H | H | O | 0 | 1 | H | Absent | OH | H | H | OH | H | H | H | Double | Single |
| NAD369 enantio | H | H | H | O | 0 | 1 | H | Absent | OH | H | H | OH | H | H | H | Double | Single |
| NAD370 enantio | H | H | H | O | 0 | 1 | H | H | H | OH | OH | OH | H | H | H | Single | Single |
| NAD371 enantio | H | 5-CHO | H | O | 0 | 1 | H | H | H | OAc | OAc | OAc | H | H | H | Single | Single |
| NAD373 enantio | H | 5-CHO | H | O | 0 | 1 | H | H | H | OH | OH | OH | H | H | H | Single | Single |
| NAD374 enantio | H | H | H | O | 0 | 1 | H | H | H | OH | OH | OTBDMS | H | H | H | Single | Single |
| NAD396 | H | H | H | O | 0 | 2 | H | H | H | OH | OH | COOMe | H | H | H | Single | Single |
| NAD398 | H | H | H | O | 0 | 1 | H | H | H | H | H | H | H | H | H | Single | Single |
| NAD399 | H | H | H | O | 0 | 1 | H | H | H | H | H | OH | H | H | H | Single | Single |
| NAD400 | H | H | H | O | 0 | 1 | H | H | H | OH | H | H | H | H | H | Single | Single |
| NAD401 | H | 5-OH | 5-OH | O | 0 | 1 | H | Absent | OH | H | OH | H | H | H | H | Single | Double |
| NAD402 | H | 5-NH2 | 5-NH2 | O | 0 | 1 | H | H | Acet. | Acet. | H | H | H | H | H | Single | Single |
| NAD405 | H | H | H | O | 0 | 1 | H | H | H | H | H | CN | H | H | H | Single | Single |
| NAD414 | H | 5-OMe | H | O | 0 | 1 | H | Absent | H | H | H | OTBDMS | H | H | H | Double | Single |
| NAD415 | H | 5-OMe | H | O | 0 | 1 | H | H | H | OH | OH | OH | H | H | H | Single | Single |
| NAD416 | H | 5-OMe | H | O | 0 | 1 | H | Absent | H | H | H | OH | OTBDMS | H | H | Double | Single |
| NAD419 | H | 5-OMe | H | O | 0 | 1 | H | H | H | OH | OH | OH | H | H | H | Single | Single |
| NAD420 | H | 5-OMe | H | O | 0 | 1 | H | H | H | OH | OH | OTBDMS | H | H | H | Single | Single |

Figure 16 continued

| ID | | | | | | | | | | | | | | | | |
|---|---|---|---|---|---|---|---|---|---|---|---|---|---|---|---|---|
| NAD421 | H | 5-OMe | H | O | O | 1 | H | H | Absent | H | Absent | OH | H | H | H | | Single |
| NAD422 | H | 5-OH | H | O | O | 1 | H | OH | H | OH | H | OH | OH | H | H | Double | Single |
| NAD423 | H | 5-OMe | H | O | O | 1 | H | H | H | OH | H | H | H | H | Single | Single |
| NAD426 | H | 5-OMe | H | O | O | 1 | H | H | Absent | H | Absent | OAc | H | H | H | Double | Single |
| NAD427 | H | H | H | O | O | 1 | H | H | H | H | H | NH₂ | CN | H | H | Single | Single |
| NAD431 | H | 5-NO₂ | H | O | O | 1 | H | H | H | OH | H | OH | H | H | H | Single | Single |
| NAD436 | H | 5-Br | H | O | O | 1 | H | H | Absent | H | Absent | OTBDMS | H | H | H | Double | Single |
| NAD437 | H | 5-Br | H | O | O | 1 | H | H | H | OH | H | OTBDMS | H | H | H | Single | Single |
| NAD438 | H | H | 5-OMe | O | O | 1 | H | H | H | OH | H | OH | H | H | H | Single | Single |
| NAD439 | H | 5-Br | H | O | O | 1 | H | H | H | OH | H | OH | H | H | H | Single | Single |
| NAD440 | H | H | 5-OH | O | O | 1 | H | H | H | OH | H | OH | H | H | H | Single | Single |
| NAD441 | H | H | 5-Br | O | O | 1 | H | H | Absent | H | Absent | OTBDMS | H | H | H | Double | Single |
| NAD442 | H | H | 5-Br | O | O | 1 | H | H | H | OH | H | OTBDMS | H | H | H | Single | Single |
| NAD443 | H | 5-OMe | H | O | O | 1 | H | H | H | Acet. | Acet. | OH | H | H | H | Single | |
| NAD449 | H | 4-NO₂ | H | O | O | 1 | H | H | Absent | H | Absent | OH | H | H | H | Single | Single |
| NAD450 | H | H | 5-OMe | O | O | 1 | H | H | H | OH | H | OH | H | H | H | Single | Single |
| NAD451 | H | H | 5-Br | O | O | 1 | H | H | H | Acet. | Acet. | OTBDMS | H | H | H | Double | Single |
| NAD460 | H | H | 5-Br | O | O | 1 | H | H | H | Acet. | Acet. | OH | H | H | H | Single | Single |
| NAD462 | H | H | H | O | O | 1 | H | H | Absent | H | Absent | 4-COOMe-1-triazolyl | H | H | H | Double | Single |
| NAD463 | H | H | H | O | O | 1 | H | H | Absent | H | Absent | H | 4-COOMe-1-triazolyl | H | H | Double | Single |
| NAD464 | H | H | 5-OMe | O | O | 1 | H | H | Absent | H | Absent | Cl | H | H | H | Single | Single |
| NAD470 | H | 5-Br | 5-OMe | O | O | 1 | H | H | Absent | H | Absent | OTBDMS | H | H | H | Double | Single |
| NAD471 | H | 5-Br | H | O | O | 1 | H | H | Absent | H | Absent | OH | H | H | H | Double | Single |
| NAD472 | H | H | H | O | O | 1 | H | H | Absent | H | Absent | H | 4-CONHMe-1-triazolyl | H | H | Double | Single |

Figure 16 continued

| | | | | | | | | | | | | | | | | |
|---|---|---|---|---|---|---|---|---|---|---|---|---|---|---|---|---|
| NAD473 | H | H | H | O | O | 1 | H | H | OH | H | OH | H | 4-COOMe-1-triazolyl | H | H | Single | Single |
| NAD474 | H | H | H | O | O | 1 | H | H | OH | H | OH | H | 4-CONHMe-1-triazolyl | H | H | Single | Single |
| NAD475 | H | 5-Br | 5-OMe | O | O | 1 | H | H | OH | H | OTBDMS | H | H | H | H | Single | Single |
| NAD476 | H | 5-Br | 5-OMe | O | O | 1 | H | H | OH | H | OH | H | H | H | H | Single | Single |
| NAD477 | H | H | H | O | O | 1 | H | Absent | H | Absent | H | H | 4-COOH-1-triazolyl | H | H | Double | Single |
| NAD480 | H | 5-Br | 5-OH | O | O | 1 | H | H | OH | H | OH | H | H | H | H | Single | Single |
| NAD484 | H | H | H | O | O | 1 | H | H | OH | H | 4-CONHMe-1-triazolyl | H | H | H | H | Single | Single |
| NAD485 | H | H | H | O | O | 1 | H | H | OH | H | 4-COOMe-1-triazolyl | H | H | H | H | Single | Single |
| NAD486 | H | H | H | O | O | 1 | H | Absent | H | Absent | H | H | OCH$_2$O | H | OCH$_2$O | Double | Single |
| NAD489 | H | H | H | O | O | 1 | H | H | OH | H | H | H | 4-CONH$_2$-1-triazolyl | H | H | Single | Single |
| NAD494 | H | 5-OMe | 5-Br | O | O | 1 | H | Absent | H | Absent | H | H | H | H | H | Double | Single |
| NAD495 | H | 5-OMe | 5-Br | O | O | 1 | H | Absent | H | Absent | OTBDMS | H | H | H | H | Single | Single |
| NAD500 | H | 5-OMe | 5-Br | O | O | 1 | H | Absent | H | Absent | H | H | OTBDMS | H | H | Double | Single |
| NAD501 | H | 5-OMe | 5-Br | O | O | 1 | H | H | OH | H | H | H | OTBDMS | H | H | Single | Single |
| NAD502 | H | 5-OMe | 5-Br | O | O | 1 | H | H | OH | H | OTBDMS | H | H | H | H | Single | Single |
| NAD503 | H | H | H | O | O | 1 | H | H | OCONHCH$_2$CH$_2$OH | H | OH | H | H | H | H | Single | Single |
| NAD504 | H | H | H | O | O | 1 | H | H | Acet. | H | Acet. | H | H | H | H | Single | Single |
| NAD507 | H | 5-OMe | 5-Br | O | O | 1 | H | Absent | H | Absent | H | H | OH | H | H | Double | Single |

Figure 16 continued

| | 5- | 5- | | | | | | | | | | | |
|---|---|---|---|---|---|---|---|---|---|---|---|---|---|
| NAD508 | H | OMe | 5-Br | O | O | 1 | H | H | OH | H | H | OH | H | H | Single |
| NAD509 | H | 5-OH | 5-Br | O | O | 1 | H | H | OH | H | OH | H | H | Single |
| NAD512 | H | H | H | O | O | 1 | H | H | OCONHCH₃ | H | OH | H | H | Single |

PBM : p-Methoxybenzyl
Acet.: Acetonide

N-CARBACYCLE MONOSUBSTITUTED INDOLOCARBAZOLES AS PROTEIN KINASE INHIBITORS

FIELD OF INVENTION

The present invention relates to novel protein kinase inhibitors, methods for their preparation, intermediates thereof and pharmaceutical compositions comprising the same, reagents containing the same, and methods of using the same as therapeutics.

BACKGROUND OF THE INVENTION

Protein kinase enzymes constitute a large class of enzymes that catalyze the transfer of a phosphate group to a hydroxyl group located on a protein substrate. Aberrant expression of protein kinases has been shown to lead to uncontrolled cell proliferation, to disorders including bone diseases, metabolic diseases, inflammatory disorders, infectious diseases and disorders of the central nervous system.

A non complete list of kinases includes abl, ATK, bcr-abl, Blk, Brk, Btk, c-kit, c-met, c-src, CDK1, CDK2, CDK4, CDK5, CDK6, cRaf1, CSFIR, CSK, EGFR, ErbB2, ErbB3, ErbB4, ERK1, ERK2, Fak, fes, $FGFR_1$, $FGFR_2$, $FGFR_3$, $FGFR_4$, $FGFR_5$, GSK-3, Fgr, FLK-4, flt-1, Fps, Frk, Fyn, Hck, IGF-R, INS-R, Jak, KDR, Lck, Lyn, MEK, p38, PDGFR, PIK, PKC, PKA, PYK2, ros, $tie_1$, $tie_2$, TRK, Yes, Zap70.

Activation of cyclin-dependent kinases, hereinafter referred to as CDK, is involved in the control of progression of eukaryotic cells through their cell cycle. Namely, some members of this class, such as CDK1 (also known as CDC2, CDK2 and CDK4), are responsible for the initial commitment to the cell cycle entry from the resting state and to the ordered progression through the cycle phases. The loss or alteration of control in CDK regulation is an attractive target in cancer therapy and the inhibition of one or more CDKs could therefore offer a treatment for a variety of cancers.

Activation of glycogen synthase kinase 3, hereinafter referred to as GSK-3 in two isoforms, is involved in the control of several biological pathways, including the synthesis of glycogen. Its inhibition in disease states associated with elevated GSK-3 activity could produce useful compounds for the treatment, inter alia, of non-insulin dependent diabetes mellitus, acute stroke and other neurotraumatic injuries.

Activation of $Ca^{2+}$/phospholipid-dependent protein kinases, hereinafter referred to as PKC in ten isoforms, is involved in the mediation of cellular responses to extracellular stimuli intertwined with proliferation, differentiation and apoptosis, and also in the regulation of neurotransmitter release. Its inhibition in disease states associated with elevated PKC activity could produce useful compounds for the treatment, inter alia, of diabetes mellitus and as chemotherapeutics for the treatment of various malignant diseases.

Activation of the mitogen-activated protein kinases, hereinafter referred to as MAPK family is involved in important cellular regulation events related with tumor therapy, central nervous system disorders and inflammatory disorders. Inhibition of one or more MAPKs involved in a specific signaling pathways could therefore offer a treatment for these disease states.

A member of another subclass of protein kinases, the extracellular-signal-regulated kinase 2, hereinafter referred to as ERK2, is involved in the pathological hyperphosphorylation of the tau protein leading to the formation of neurofibrillary tangles (NFT) with potential implications in neurodegenerative diseases and specifically in Alzheimer's disease (AD), as shown by Drewes, G. et al., *EMBO J.*, 1992, 11, 2131–2138, and by Roder, H. M. et al., *BBRC*, 1993, 193, 639–647.

Inhibitors of kinases represent novel therapies for disorders caused by the methabolic processes in which protein kinases are involved. Some potent and selective kinase inhibitors have already been discovered both from natural sources and as results of synthetic efforts. The protein kinase inhibitors known in the prior art have very different structures for example pyrimidines, indolinones, pyridinylimidazoles, aminopurines, flavonoids and glycosylated indolocarbazoles. These protein kinase inhibitors are described for example in Adams, J. L. and Lee, D., *Curr. Opin. Drug Disc. Dev.*, 1999, 2, 96–109, Stover, D. R. et al., *Curr. Opin. Drug Disc. Dev.*, 1999, 2, 274–285, Dumas, J., *Exp. Opin. Ther. Pat.*, 2000, 11, 405–429, and Davies, S. P. et al., *Biochem. J.*, 2000, 351, 95–105.

Furthermore, WO 00/01699 describes protein kinase inhibitors based on an indolocarbazole scaffold which is bisubstituted with a carbacyclic moiety on the nitrogen atoms. It has been reported that these compounds are useful for the treatment of neurodegenerative disorders and cancers. This document also describes N-monosubstituted carbacyclic indolocarbazoles which are used as precursors for the preparation of substituted compounds. Measurements of the biological activity of monosubstituted indolocarbazoles have not been described.

One object of the present invention is to provide novel N-carbacycle monosubstituted indolocarbazoles which are kinase inhibitors. In certain objects, the compounds of the present invention are inhibitors of one or more MAP kinases, CD kinases, GSK-3 kinase or PKC kinase isoforms.

It is another object of the present invention to provide pharmaceutical compositions comprising a pharmaceutically acceptable carrier and a therapeutically effective amount of at least one of the compounds of the present invention, or a pharmaceutically acceptable salt form thereof.

SUMMARY OF THE INVENTION

This invention relates to N-carbacycle monosubstituted indolocarbazole compounds. This invention also relates to N-carbacycle monosubstituted indolocarbazole compounds for inhibiting the activity of protein kinases. In further embodiments this invention relates to N-carbacycle monosubstituted indolocarbazoles compounds for treating non-insulin dependent diabetes mellitus, acute stroke and other neurotraumatic injuries, for treating diabetes mellitus, as a chemotherapeutic for the treatment of various malignant diseases, for treating diseases caused by malfunctioning of specific signaling pathways, and for treating neurodegenerative diseases such as for example Alzheimer's disease.

BRIEF DESCRIPTION OF THE FIGURES

FIG. 16 is a list of prepared and characterized compounds according to the present invention.

DETAILED DESCRIPTION OF THE INVENTION

Figure 1:
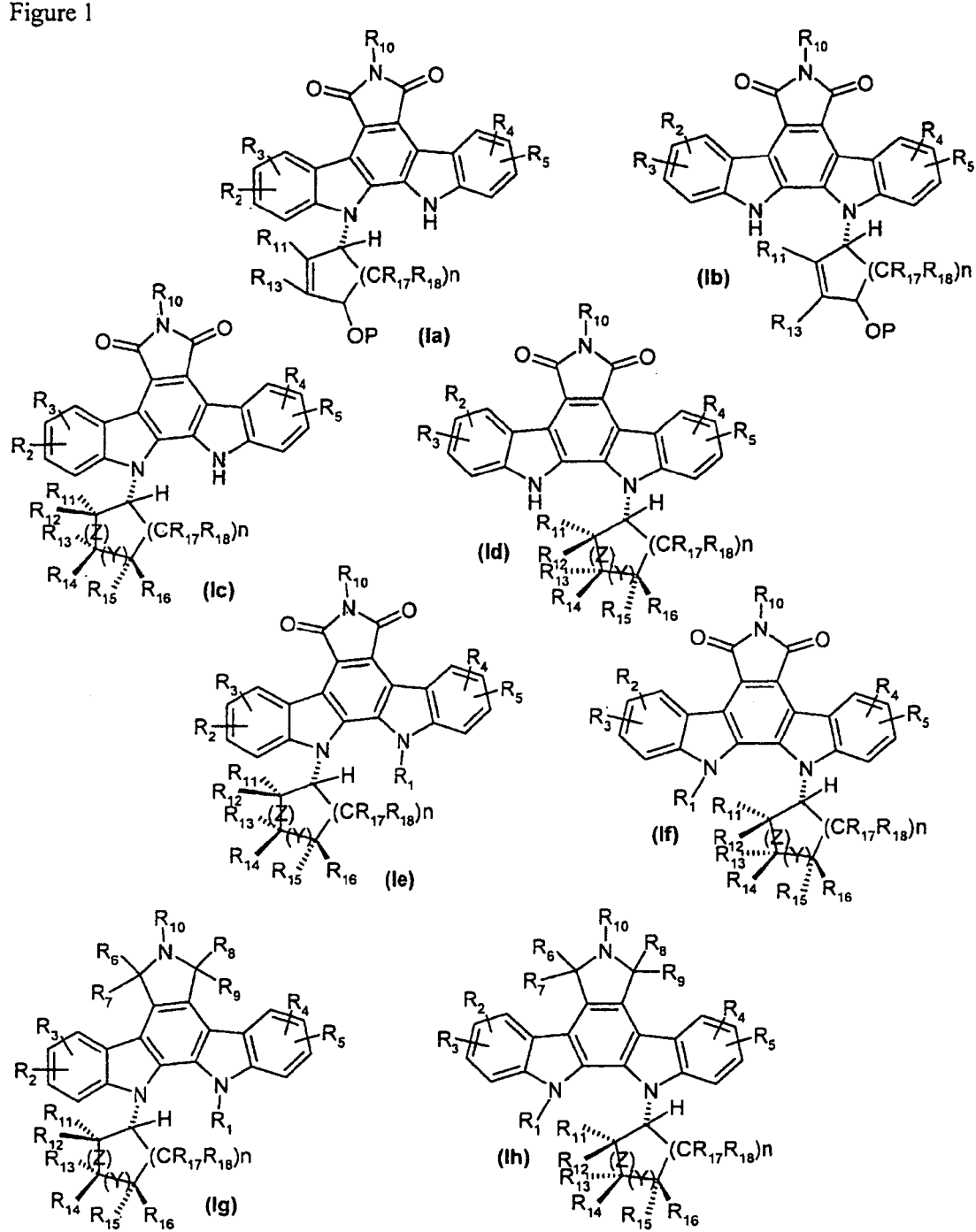
FIG. 1 shows the structures of compounds Ia–h whose synthesis has been described in detail as examples for the preparation of the members of the general class of compounds depicted in the general formula (I).

The following definitions will be useful in describing the invention and will eliminate the need for repetitive explanations.

Definitions

"Alkoxy" denotes unsubstitued and substituted straight-chain and branched chain aromatic or non aromatic alkoxy radicals derived from the removal of the hydrogen atom from the hydroxyl group of a parent alcohol or phenol.

"Alkyl" denotes unsubstitued and substituted straight-chain and branched chain hydrocarbon radicals derived from the removal of a single hydrogen atom from a parent alkane.

"Alkylene" denotes unsubstitued and substituted straight-chain and branched chain hydrocarbon radicals derived from the removal of a hydrogen atom from two terminal carbon atoms of a parent alkane.

"Alkenyl" denotes unsubstitued and substituted straight-chain and branched chain hydrocarbon radicals derived from the removal of a single hydrogen atom from a parent alkene.

"Alkynyl" denotes unsubstitued and substituted straight-chain and branched chain hydrocarbon radicals derived from the removal of a single hydrogen atom from a parent alkyne.

"Aryl" denotes unsubstituted and substituted aromatic radicals derived from the removal of a single hydrogen atom from a parent aromatic ring system.

"Carbacycle" means 5 or 6, unsubstituted or substituted cyclic, non-aromatic hydrocarbon radicals derived from the removal of a single hydrogen atom from a parent cyclic compound, wherein the cyclic compound optionally comprises one or two carbon-carbon double bonds.

"Decoration" denotes the pattern of substitution which is especially useful for specific purposes such as to provide an increase of the inhibitory activity or to increase specificity towards a specific protein kinase.

"Decorating" denotes changing the substitution pattern in order to obtain compounds with the desired properties.

"Heteroaryl" denotes unsubstitued and substituted radicals derived from the removal of a single hydrogen atom from a parent aromatic ring system in which one or more ring atoms are not carbon.

"Inhibitor" refers to a substance which, when added in a sufficient amount, is capable of reducing the catalytic activity of a given enzyme in at least one reaction which can be catalyzed by the said enzyme.

"Lower alkyl" denotes unsubstitued and substituted straight-chain and branched chain hydrocarbon radicals derived from the removal of a single hydrogen atom from a parent alkane containing 1–6 carbon atoms.

"Lower alkenyl" denotes unsubstitued and substituted straight-chain and branched chain hydrocarbon radicals derived from the removal of a single hydrogen atom from a parent alkene containing 2–6 carbon atoms.

"Lower alkynyl" denotes unsubstitued and substituted straight-chain and branched chain hydrocarbon radicals derived from the removal of a single hydrogen atom from a parent alkyne containing 2–6 carbon atoms.

"Substituted" as used herein refers to a molecule or a molecular residue, wherein one or more hydrogen atoms are replaced with one or more non-hydrogen atoms, functional groups or moieties including but not limited to alkyl, substituted alkyl, hydroxyl, thiol, alkylthiol, halogen, alkoxy, amino, substituted amino, amido, carboxyl, alkylcarboxylate, cycloalkyl, substituted cycloalkyl, heterocycle, cycloheteroalkyl, substituted cycloheteroalkyl, acyl, aryl, substituted aryl, aryloxy, heteroaryl, substituted heteroaryl, aralkyl, alkyl alkenyl, alkyl alkynyl, alkyl cycloalkyl, alkyl cycloheteroalkyl, and cyano.

The invention will now be explained in greater detail with reference to the preferred non limiting embodiments of the invention, examples of which are illustrated in the accompanying drawings.

It has been found that molecules of the general formula I are very potent inhibitors of protein kinases. Surprisingly, although conformationally less constrained, their potency is as high as the prior art compounds with a more rigid structure, e.g. those described in WO 00/01699, on an even wider panel of protein kinases.

This invention relates to a class of compounds having a structure according to the general formula (I)

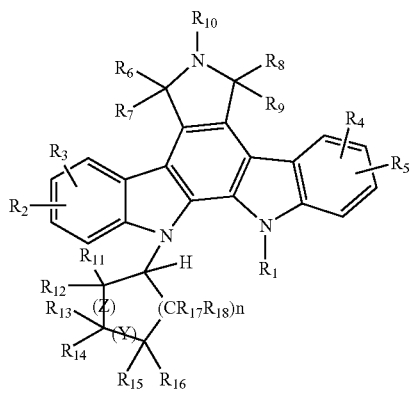

wherein $R_1$ is selected from the group consisting of H, lower alkyl, aryl, heteroaryl, $COR_{19}$, $COOR_{19}$, and $CONR_{20}R_{21}$ wherein $R_{19}$, $R_{20}$ and $R_{21}$ can be the same or different and are independently selected from the group consisting of H, a lower alkyl, aryl and heteroaryl rest;

$R_2,R_3,R_4,R_5$ taken alone can be the same or different and are each independently selected from the group consisting of H, halogen, lower alkyl, lower alkenyl, lower alkynyl, aryl, heteroaryl, CN, $COR_{22}$, $COOR_{22}$, $CONHR_{22}$, $CONR_{22}R_{23}$, $CSR_{22}$, $CSSR_{22}$, $NR_{22}R_{23}$, $NHCOR_{22}$, $NHCOOR_{22}$, $NHSO_2R_{22}$, $N_3$, $NO_2$, $OR_{22}$, $OCOR_{22}$, $SR_{22}$, $SO_2R_{22}$, and $SiR_{24}R_{25}R_{26}$; or when $R_2$ and $R_3$ or $R_4$ and $R_5$ are taken together they are an optionally substituted alkylene group, containing 2 to 4 carbon atoms or heteroatoms without substituents;

$R_6,R_7$ when taken alone they are both H, or one of them is H and the other is OH, or when taken together they are the oxygen atom of a carbonyl group or the sulfur atom of a thiocarbonyl group; and with the prioviso that when $R_8,R_9$ are different from carbonyl $R_6,R_7$ taken together are the oxygen atom of a carbonyl group or the sulfur atom of a thiocarbonyl group;

$R_8,R_9$ when taken alone they are both H, or one of them is H and the other is OH, or when taken together they are the oxygen atom of a carbonyl group or the sulfur atom of a thiocarbonyl group; and with the proviso that when $R_6,R_7$ are different from carbonyl $R_8,R_9$ taken together are the oxygen atom of a carbonyl group or the sulfur atom of a thiocarbonyl group;

$R_{10}$ is selected from the group consisting of H, lower alkyl, aryl, optionally substituted benzyl (e.g. p-methoxybenzyl), heteroaryl, $COR_{22}$, $COOR_{22}$, $NR_{22}R_{23}$, and $OR_{22}$;

$R_{11},R_{12}$ when taken alone they can be the same or different and are selected from the group consisting of H, halogen, lower alkyl, lower alkenyl, lower alkynyl, aryl, heteroaryl, CN, $COR_{22}$, $COOR_{22}$, $CONHR_{22}$, $CONR_{22}R_{23}$, $CSR_{22}$, $CSSR_{22}$, $NR_{22}R_{23}$, $NHCOR_{22}$, $NHCOOR_{22}$, $NHSO_2R_{22}$, $N_3$, $OR_{22}$, $OCOR_{22}$, $OCONHR_{22}$, $SR_{22}$, $SO_2R_{22}$, and $SiR_{24}R_{25}R_{26}$; when taken together they are the oxygen atom of a carbonyl group, the nitrogen atom of a substituted imine or the carbon atom of a substituted alkenyl rest;

$R_{13},R_{14}$ when taken alone they can be the same or different and are selected from the group consisting of H, halogen, lower alkyl, lower alkenyl, lower alkynyl, aryl, heteroaryl, CN, $COR_{22}$, $COOR_{22}$, $CONHR_{22}$, $CONR_{22}R_{23}$, $CSR_{22}$, $CSSR_{22}$, $NR_{22}R_{23}$, $NHCOR_{22}$, $NHCOOR_{22}$, $NHSO_2R_{22}$, $N_3$, $OR_{22}$, $OCOR_{22}$, $SR_{22}$, $SO_2R_{22}$, and $SiR_{24}R_{25}R_{26}$; when taken together they are the oxygen atom of a carbonyl group, the nitrogen atom of a substituted imine or the carbon atom of a substituted alkenyl rest;

$R_{15},R_{16}$ when taken alone they can be the same or different and are selected from the group consisting of H, halogen, lower alkyl, lower alkenyl, lower alkynyl, aryl heteroaryl (e.g. 4-substituted 1-triazolyl), CN, $COR_{22}$, $COOR_{22}$, $CONHR_{22}$, $CONR_{22}R_{23}$, $CSR_{22}$, $CSSR_{22}$, $NR_{22}R_{23}$, wherein $R_{22}$ and $R_{23}$ may be taken together to form a —$CH_2$—$CH_2$—O—$CH_2$—$CH_2$— group, $NHCOR_{22}$, $NHCOOR_{22}$, $NHSO_2R_{22}$, $N_3$, $OR_{22}$, $OCOR_{22}$, $SR_{22}$, $SO_2R_{22}$, $SiR_{24}R_{25}R_{26}$ and $OSiR_{24}R_{25}R_{26}$; when taken together they are the oxygen atom of a carbonyl group, the nitrogen atom of a substituted imine or the carbon atom of a substituted alkenyl rest;

$R_{17},R_{18}$ when taken alone they can be the same or different and are selected from the group consisting of H, halogen, lower alkyl, lower alkenyl, lower alkynyl, aryl, heteroaryl, CN, $COR_{22}$, $COOR_{22}$, $CONHR_{22}$, $CONR_{22}R_{23}$, $CSR_{22}$, $CSSR_{22}$, $NR_{22}R_{23}$, $NHCOR_{22}$, $NHCOOR_{22}$, $NHSO_2R_{22}$, $N_3$, $OR_{22}$, $OCOR_{22}$, $SR_{22}$, $SO_2R_{22}$, and $SiR_{24}R_{25}R_{26}$; when taken together they are the oxygen atom of a carbonyl group, the nitrogen atom of a substituted imine or the carbon atom of a substituted alkenyl rest;

Z,Y are both single bonds or one single and one double bond;

n is 1 or 2;

wherein $R_{22}$, $R_{23}$, $R_{24}$, $R_{25}$ and $R_{26}$
can be the same or different and are independently selected from the group consisting of H, lower alkyl, aryl, benzyl and heteroaryl;

$R_{11}$ and $R_{13}$, $R_{12}$ and $R_{14}$, $R_{15}$ is and $R_{17}$ or $R_{16}$ and $R_{18}$ may be taken together to form a —O—$C(R_{22})_2$—O— group wherein $R_{22}$ is H or methyl;

and wherein when n is 2 it is to be understood that the two substituents $R_{17}$ may be the same or different and that the two substituents $R_{18}$ may be the same or different.

Perferably the compounds of the present invention have the structure according to the general formula (II):

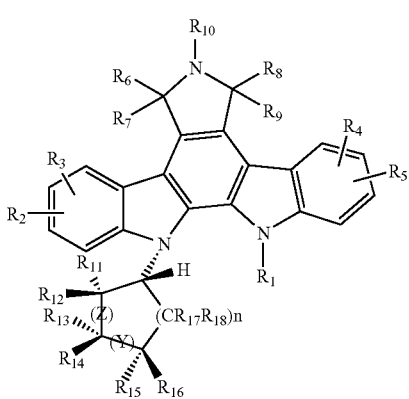

(II)

wherein $R_1$ to $R_{18}$, Z, Y and n are defined as above for formula (I).

Thus, the present invention in one embodiment relates to compounds having the structure according to the general formula (IIa):

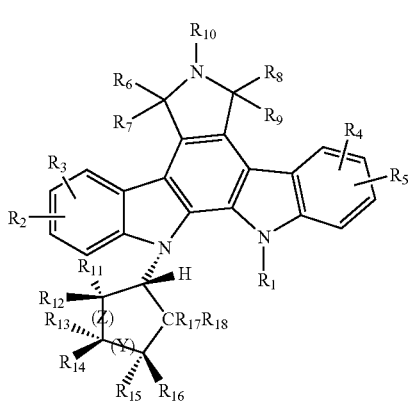

(IIa)

wherein $R_1$ to $R_{18}$, Z and Y are defined as above for formula (I).

In a further embodiment the present invention relates to compounds having the structure according to the general formula (IIb):

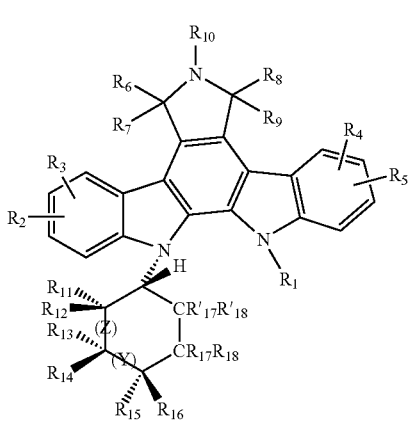

(IIb)

wherein $R_1$ to $R_{18}$, Z and Y are defined as above for formula (I), $R'_{17}$ corresponds to the above definition of $R_{17}$ in formula (I) and $R'_{17}$ corresponds to the above definition of $R_{18}$ in formula (I).

It will be appreciated by the person skilled in the art that the compounds of the present invention may contain one or more chiral centers, and may be isolated in optically active or racemic forms. Thus, all chiral, diastereomeric, racemic forms and all geometric isomeric forms of a structure are covered by the scope of the invention. Compounds falling within the scope of this invention also include the pharmaceutically acceptable salts of the above-identified compounds.

This novel class of flexible kinase inhibitors is very useful, since its properties can be modulated by structural modifications to reach selectivity and potency against a variety of therapeutically relevant kinase targets as demonstrated by the results of Table 1. It has also been found that a chemical family depicted by the general formula (I), herein named as N-carbacycle monosubstituted indolocarbazoles, is a useful source of potential therapeutic agents for the specific and selective modulation of protein kinase activities in several disorders. More specifically, N-carbacycle monosubstituted indolocarbazoles are potent inhibitors of abnormal ERK2 activity which makes them useful for the treatment of neurodegenerative diseases, including Alzheimer's disease.

The preferred protein kinase inhibitors are those of the formulae (I) and (II) in which $R_1$ is selected from the group consisting of H, lower alkyl, aryl and heteroaryl;

$R_2, R_3, R_4, R_5$ taken alone can be the same or different and are each independently selected from the group consisting of H, halogen, lower alkyl, lower alkenyl, lower alkynyl, aryl, heteroaryl, CN, $COR_{22}$, $COOR_{22}$, $CONHR_{22}$, $CONR_{22}R_{23}$, $CSR_{22}$, $CSSR_{22}$, $NR_{22}R_{23}$, $NHCOR_{22}$, $NHCOOR_{22}$, $NHSO_2R_{22}$, $N_3$, $OR_{22}$, $OCOR_{22}$, $SR_{22}$, $SO_2R_{22}$, and $SiR_{24}R_2SR_{26}$ wherein $R_{22}$, $R_{23}$, $R_{24}$, $R_{25}$ and $R_{26}$ can be the same or different and are independently selected from the group consisting of H, lower alkyl, aryl and heteroaryl; or when $R_2$ and $R_3$ or $R_4$ and $R_5$ are taken together they are an optionally substituted alkylene group, containing 2 to 4 carbon atoms or heteroatoms without substituents;

$R_6, R_7$ when taken alone they are both H, or one of them is H and the other is OH, or when taken together they are the oxygen atom of a carbonyl group; and with the proviso that when $R_8, R_9$ are different from carbonyl $R_6, R_7$ taken together are the oxygen atom of a carbonyl group;

$R_8, R_9$ when taken alone they are both H, or one of them is H and the other is OH, or when taken together they are the oxygen atom of a carbonyl group; and with the proviso that when $R_6, R_7$ are different from carbonyl $R_8, R_9$ taken together are the oxygen atom of a carbonyl group;

$R_{10}$ is selected from the group consisting of H, lower alkyl, aryl, heteroaryl, $NR_{22}R_{23}$, and $OR_{22}$, wherein $R_{22}$ and $R_{23}$ are a lower alkyl, substituted aryl or heteroaryl rest.

$R_{11}, R_{12}$ when taken alone they can be the same or different and are selected from the group consisting of H, halogen, lower alkyl, aryl, heteroaryl, $COR_{22}$, $COOR_{22}$, $CONHR_{22}$, $CONR_{22}R_{23}$, $NR_{22}R_{23}$, $NHCOR_{22}$, $NHSO_2R_{22}$, and $OR_{22}$, wherein $R_{22}$ and $R_{23}$ can be the same or different and are independently selected from the group consisting of H, a lower alkyl, aryl and heteroaryl; when taken together they are the oxygen atom of a carbonyl group, the nitrogen atom of a substituted imine or the carbon atom of a substituted alkenyl rest;

$R_{13},R_{14}$ when taken alone they can be the same or different and are selected from the group consisting of H, halogen, lower alkyl, aryl, heteroaryl, $COR_{22}$, $COOR_{22}$, $CONHR_{22}$, $CONR_{22}R_{23}$, $NR_{22}R_{23}$, $NHCOR_{22}$, $NHSO_2R_{22}$, and $OR_{22}$, wherein $R_{22}$ and $R_{23}$ can be the same or different and are independently selected from the group consisting of H, a lower alkyl, aryl and heteroaryl; when taken together they are the oxygen atom of a carbonyl group, the nitrogen atom of a substituted imine or the carbon atom of a substituted alkenyl rest;

$R_{15},R_{16}$ when taken alone they can be the same or different and are selected from the group consisting of H, halogen, lower alkyl, aryl, heteroaryl, $COR_{22}$, $COOR_{22}$, $CONHR_{22}$, $CONR_{22}R_{23}$, $NR_{22}R_{23}$, $NHCOR_{22}$, $NHSO_2R_{22}$, and $OR_{22}$, wherein $R_{22}$ and $R_{23}$ can be the same or different and are independently selected from the group consisting of H, a lower alkyl, aryl and heteroaryl; when taken together they are the oxygen atom of a carbonyl group, the nitrogen atom of a substituted imine or the carbon atom of a substituted alkenyl rest;

$R_{17},R_{18}$ when taken alone they can be the same or different and are selected from the group consisting of H, halogen, lower alkyl, aryl, heteroaryl, $COR_{22}$, $COOR_{22}$, $CONHR_{22}$, $CONR_{22}R_{23}$, $NR_{22}R_{23}$, $NHCOR_{22}$, $NHSO_2R_{22}$, and $OR_{22}$, wherein $R_{22}$ and $R_{23}$ can be the same or different and are independently selected from the group consisting of H, a lower alkyl, aryl and heteroaryl; when taken together they are the oxygen atom of a carbonyl group, the nitrogen atom of a substituted imine or the carbon atom of a substituted alkenyl rest;

Z,Y are both single bonds or one single and one double bond;

n is 1 or 2.

The preferred compounds which show an activity towards a broad variety of the protein kinases are in accordance with the general formulae (I) and (II), wherein $R_1$ is H or lower alkyl;

$R_2,R_3,R_4,R_5$ can be the same or different and are each independently selected from the group consisting of H, halogen, lower alkyl, aryl, heteroaryl, $COR_{22}$, $COOR_{22}$, $CONHR_{22}$, $NR_{22}R_{23}$, $NHCOR_{22}$, $NHSO_2R_{22}$, $OR_{22}$, and $OCOR_{22}$;

$R_6,R_7$ when taken alone they are both H, or one of them is H and the other is OH, or when taken together they are the oxygen atom of a carbonyl group; with the proviso that when $R_8,R_9$ are different from carbonyl $R_6,R_7$ taken together are the oxygen atom of a carbonyl group;

$R_8,R_9$ when taken alone they are both H, or one of them is H and the other is OH, or when taken together they are the oxygen atom of a carbonyl group; with the proviso that when $R_6,R_7$ are different from carbonyl $R_8,R_9$ taken together are the oxygen atom of a carbonyl group;

$R_{10}$ is H or lower alkyl;

$R_{11},R_{12}$ when taken alone they can be the same or different and are selected from the group consisting of H, halogen, lower alkyl, $COOR_{22}$, $CONHR_{22}$, $CONR_{22}R_{23}$, $NR_{22}R_{23}$, $NHCOR_{22}$, $NHSO_2R_{22}$, and $OR_{22}$; when taken together they are the oxygen atom of a carbonyl group;

$R_{13},R_{14}$ when taken alone they can be the same or different and are selected from the group consisting of H, halogen, lower alkyl, $COOR_{22}$, $CONHR_{22}$, $CONR_{22}R_{23}$, $NR_{22}R_{23}$, $NHCOR_{22}$, $NHSO_2R_{22}$, and $OR_{22}$; when taken together they are the oxygen atom of a carbonyl group;

$R_{15},R_{16}$ when taken alone they can be the same or different and are selected from the group consisting of H, halogen, lower alkyl, $COOR_{22}$, $CONHR_{22}$, $CONR_{22}R_{23}$, $NR_{22}R_{23}$, $NHCOR_{22}$, $NHSO_2R_{22}$, and $OR_{22}$; when taken together they are the oxygen atom of a carbonyl group;

$R_{17},R_{18}$ when taken alone they can be the same or different and are selected from the group consisting of H, halogen, lower alkyl, $COOR_{22}$, $CONHR_{22}$, $CONR_{22}R_{23}$, $NR_{22}R_{23}$, $NHCOR_{22}$, $NHSO_2R_{22}$, and $OR_{22}$; when taken together they are the oxygen atom of a carbonyl group;

Z,Y are both single bonds or one single and one double bond;

n is 1 or 2;

wherein $R_{22}$ and $R_{23}$ can be the same or different and are independently selected from the group consisting of H, lower alkyl, aryl and heteroaryl.

Even more preferred are the compounds of the general formulae (IIc) and (III),

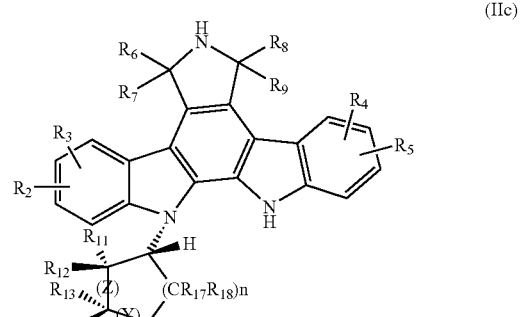

(IIc)

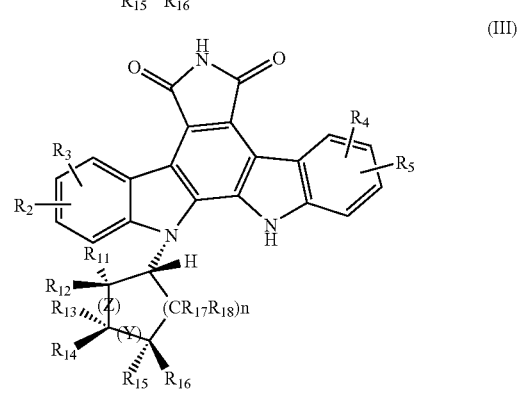

(III)

wherein in formula (IIc)

$R_6,R_7$ when taken alone they are both H, or when taken together they are the oxygen atom of a carbonyl group; with the proviso that when $R_8,R_9$ are different from carbonyl $R_6,R_7$ taken together are the oxygen atom of a carbonyl group;

$R_8,R_9$ when taken alone they are both H, or when taken together they are the oxygen atom of a carbonyl group; with the proviso that when $R_6,R_7$ are different from carbonyl $R_8,R_9$ taken together are the oxygen atom of a carbonyl group;

and wherein in formulae (IIc) and (III)

$R_2,R_3,R_4,R_5$ can be the same or different and are each independently selected from the group consisting of H, halogen, lower alkyl, $COOR_{22}$, $CONHR_{22}$, $NR_{22}R_{23}$, $NHCOR_{22}$, and $OR_{22}$;

$R_{11}, R_{12}$ when taken alone they can be the same or different and are selected from the group consisting of H, halogen, $COOR_{22}$, $CONHR_{22}$, $NR_{22}R_{23}$, $NHCOR_{22}$, and $OR_{22}$; when taken together they are the oxygen atom of a carbonyl group;

$R_{13}, R_{14}$ when taken alone they can be the same or different and are selected from the group consisting of H, halogen, $COOR_{22}$, $CONHR_{22}$, $NR_{22}R_{23}$, $NHCOR_{22}$, and $OR_{22}$; when taken together they are the oxygen atom of a carbonyl group;

$R_{15}, R_{16}$ when taken alone they can be the same or different and are selected from the group consisting of H, halogen, $COOR_{22}$, $CONHR_{22}$, $NR_{22}R_{23}$, $NHCOR_{22}$, and $OR_{22}$; when taken together they are the oxygen atom of a carbonyl group;

$R_{17}, R_{18}$ when taken alone they can be the same or different and are selected from the group consisting of H, halogen, $COOR_{22}$, $CONHR_{22}$, $NR_{22}R_{23}$, $NHCOR_{22}$, and $OR_{22}$; when taken together they are the oxygen atom of a carbonyl group;

Z,Y are both single bonds or one single and one double bond;

n is 1 or 2;

wherein $R_{22}$ and $R_{23}$ can be the same or different and are independently selected from the group consisting of H and lower alkyl.

Furthermore, the invention also relates to the use of the compounds according to the present invention for inhibiting the activity of one or more protein kinases. Preferably the protein kinase is selected from the group consisting of extracellular signal regulated kinase 2, protein kinase A, protein kinase C, and glycogen synthase kinase 3β. In a further aspect the present invention relates to the use of the compounds of the present invention for treating non-insulin dependent diabetes mellitus, acute stroke and other neurotraumatic injuries, for treating diabetes mellitus, as a chemotherapeutic for the treatment of various malignant diseases, for treating diseases caused by malfunctioning of specific signaling pathways, and for treating neurodegenerative diseases such as for example Alzheimer's disease.

The treatment is accomplished using a therapeutically effective amount of at least one compound of this invention and/or a pharmaceutically acceptable salt form thereof in admixture with a pharmaceutically acceptable excipient.

Methods of Preparation

The compounds of the present invention can be prepared by methods well known to those skilled in the art and by the methods described below, or variations thereon well known to those skilled in the art. All processes disclosed in association with the present invention are practiced on any scale from milligram to multi-kilogram commercial industrial scale.

Functional groups present in the compounds of the present invention may contain protecting groups (P) during the course of the synthesis. For example, hydroxy substituents on the carbacycles in Formula I can be substituted with protecting groups such as t-butyldimethylsilyl or trimethylsilyl groups; amino substituents on the carbacycles in Formula I can be substituted with protecting groups such as benzyloxycarbonyl or t-butoxycarbonyl groups; indole nitrogens in Formula I can be substituted with protecting groups such as acetyl or t-butoxycarbonyl groups. Protecting groups including, but not limited to, the ones mentioned above are present in a chemical compound to render the substituted functionality inert to chemical reaction conditions to which the compound is exposed during the synthesis, but can also removed selectively from the substituted functionalities at any given synthetic step by methods known to the skilled artisan. Preferred protecting groups according to the invention include, but are not limited to, the above mentioned ones. Other preferred protecting groups can be found in Greene, T. W. and Wuts, P. G. M., *Protective Groups in Organic Synthesis*, 3$^{rd}$ Ed., Wiley and Sons, 1999.

FIG. 1 shows the structures of compounds Ia–h whose synthesis has been described in detail as examples for the preparation of the members of the general class of compounds depicted in the general formula (I).

By the way of example the preparation of compounds Ia–Ih depicted in FIG. 1 will be described. The compounds shown in FIG. 1 may be prepared, for example, using key intermediates and synthetic strategies as described in FIG. 2 through FIG. 15.

Figure 2:
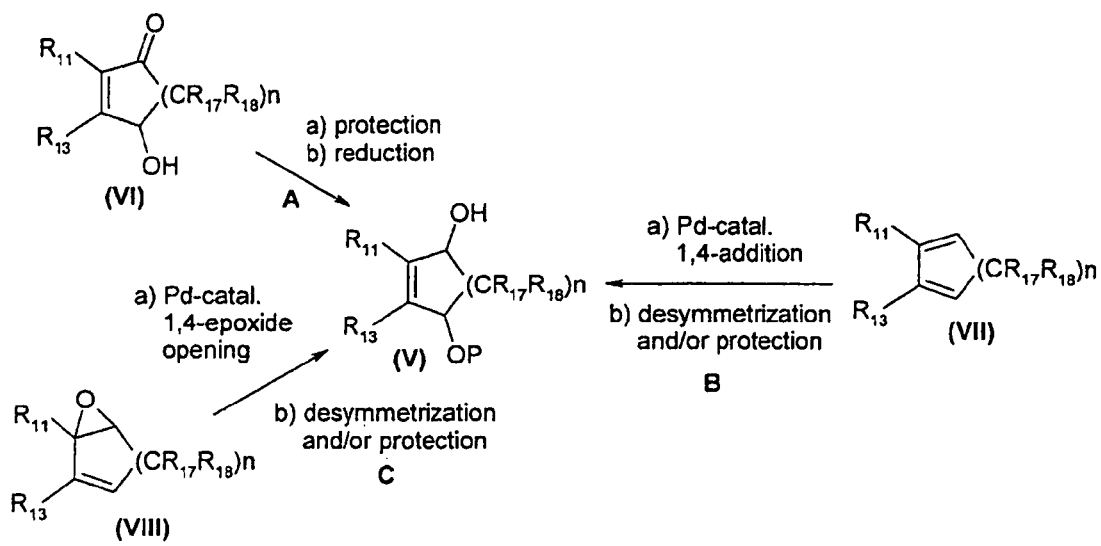
FIG. 2 shows the synthesis of the key carbacyclic intermediates V which have been used for the synthesis of the compounds of the general formula (I), especially when Z is a double bond, $R_{12}$ and $R_{14}$ are absent and when one among $R_{15}$ is and $R_{16}$ is a hydrogen atom.

FIG. 2 shows the synthesis of the key carbacyclic intermediates V which have been used for the synthesis of the compounds of the general formula (I), especially when Z is a double bond, $R_{12}$ and $R_{14}$ are absent and when one among $R_{15}$ and $R_{16}$ is a hydrogen atom.

Compounds VI–VIII can be prepared as in the cited references. An unsaturated 4-hydroxycyclopent-(or hex-)-2-en-1-one VI with a suitable OH-protecting group P, obtained for example as in Curran, T. et al., *Tetrahedron*, 1997, 53, 1983–2004, can undergo carbonyl reduction to alcohol affording compounds (V) (FIG. 2, path A). Similar reactions are, for example, also thoroughly described in Curran, T. et al., *Tetrahedron*, 1997, 53, 1983–2004.

Alternatively, compounds of formula (V) may be prepared by Pd-catalyzed 1,4-addition of the cyclic dienes VII, mostly commercially available or prepared using precursors and pathways known to those skilled in the art, introducing in positions 1,4 a variety of groups including, but not limited to, acetates, bromides and chlorides followed by desymmetrization and/or protection steps, which are well known to those skilled in the art, to afford compounds V (FIG. 2, path B). Similar reactions are, for example, thoroughly described in Bäckvall, J. E. et al., *Org Synth.*, 1997, 53, 1983–2004.

Alternatively, compounds of formula (V) may be prepared by Pd-catalyzed 1,4-epoxide opening of the cyclic unsaturated epoxides VIII, easily obtained by peracid-mediated oxidation of dienes VII, introducing in positions 1,4 a variety of groups including, but not limited to, acetates, substituted acetates and hydroxyls followed by desymmetrization and/or protection steps, which are well known to those skilled in the art, to afford compounds V (FIG. 2, path C). Similar reactions are, for example, thoroughly described in Deardoff, D. et al., *Org. Synth.*, 1997, 53, 114–115 and in *Tetrahedron Letters*, 1985, 24, 5615.

Compounds V are then activated for coupling to indolic nitrogens using a variety of chemical functionalities and experimental protocols. Coupling strategies include, but are not limited to, N-alkylations via mesylates, tosylates, triflates, chlorides, bromides and iodides, or metal-catalyzed functionalizations via acetates, carbonates, chlorides and epoxides, or Mitsunobu functionalizations via alcohols. Other preferred carbacyle activating functions can be found in Pearson, A. J. and Roush, W. J., *Activating Agents and Protecting Groups*, Wiley and Sons, 1999.

Figure 3:
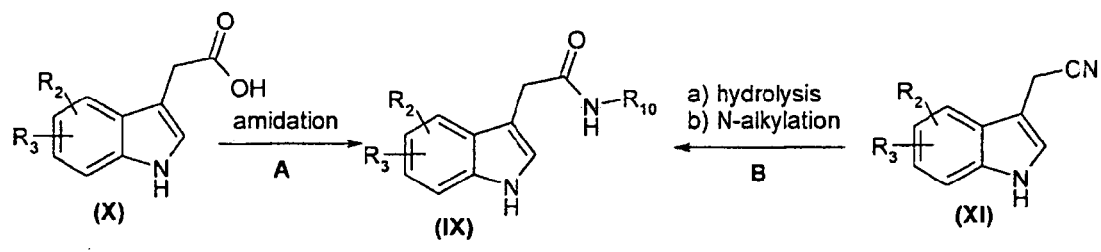
FIG. 3 shows the synthesis of the key indole-3-acetamide intermediates IX which have been used for the synthesis of the compounds of the general formula (I), especially when $R_6$—$R_7$ and $R_8$—$R_9$ are both carbonyl groups and when one or both among $R_2$ and $R_3$, or among $R_4$ and $R_5$, is a hydrogen atom.

FIG. 3 shows the synthesis of the key indole-3-acetamide intermediates IX which have been used for the synthesis of the compounds of the general formula (I), especially when $R_6$—$R_7$ and $R_8$—$R_9$ are both carbonyl groups and when one or both among $R_2$ and $R_3$, or among $R_4$ and $R_5$, is a hydrogen atom. Amidation of an indole-3-acetate X with suitable primary amines affords compounds of formula (IX) (FIG. 3, path A).

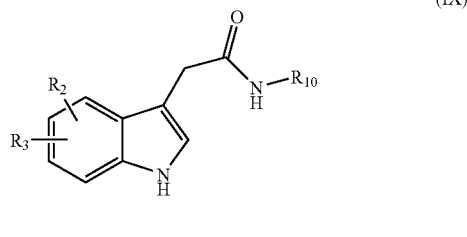
(IX)

Alternatively, indole-3-acetonitriles XI can be hydrolyzed in basic medium to provide the primary amide then N-alkylated to provide compounds of formula (IX). (FIG. 3, path B). The necessity to protect the indolic nitrogen with a suitable protecting group, such as, but not limited to, TBDMS, t-butoxycarbonyl or toluenesulfonyl, in a few specific examples can be appreciated by those skilled in the art.

Figure 4:
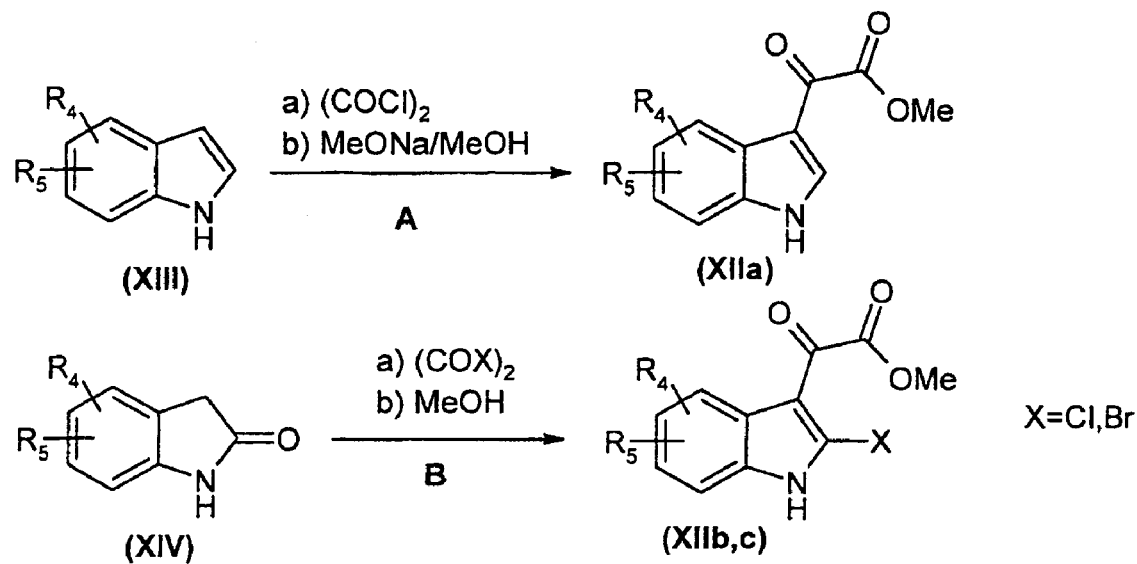
FIG. 4 shows the synthesis of the key indole-3-glyoxylate intermediates XIIa–c which have been used for the synthesis of the compounds of the general formula (I), especially when $R_6$—$R_7$ and $R_8$—$R_9$ are both carbonyl groups and when one or both among $R_2$ and $R_3$, or among $R_4$ and $R_5$, is a hydrogen atom.

FIG. 4 shows the synthesis of the key indole-3-glyoxylate intermediates XIIa–c which have been used for the synthesis of the compounds of the general formula (I), especially when $R_6$—$R_7$ and $R_8$—$R_9$ are both carbonyl groups and when one or both among $R_2$ and $R_3$, or among $R_4$ and $R_5$, is a hydrogen atom. Treatment of indoles XIII with oxalyl chloride followed by methanolysis affords 2-unsubstituted compounds of formula (XIIa) (FIG. 4, path A). Treatment of oxindoles XIV with oxalyl chloride or bromide followed by methanolysis affords respectively compounds of formula (XIIb,c) (FIG. 4, path B). Similar reactions are, for example, thoroughly described in Bergman, J. et al., *J. Heterocycl. Chem.*, 1977, 14, 1123.

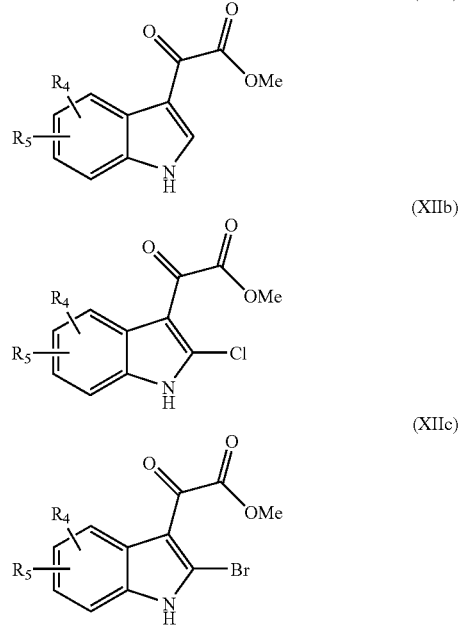

Figure 5:
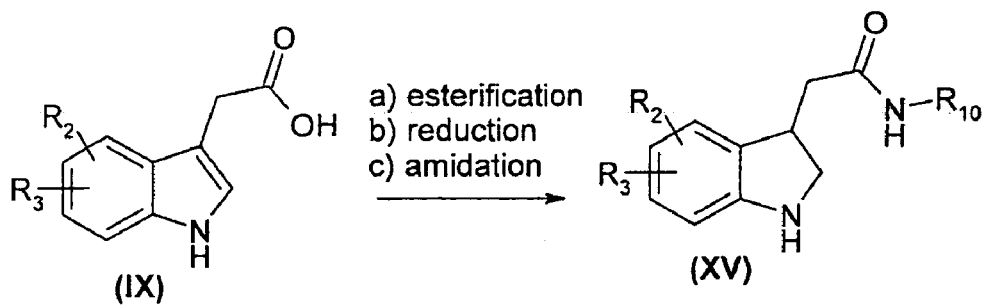
FIG. 5 shows the synthesis of the key indoline-3-acetamide intermediates XV which have been used for the synthesis of the compounds of the general formula (I), especially when $R_6$—$R_7$ and $R_8$—$R_9$ are both carbonyl groups and when one or both among $R_2$ and $R_3$, or among $R_4$ and $R_5$, is a hydrogen atom.

FIG. 5 shows the synthesis of the key indoline-3-acetamide intermediates XV which have been used for the synthesis of the compounds of the general formula (I), especially when $R_6$—$R_7$ and $R_8$—$R_9$ are both carbonyl groups and when one or both among $R_2$ and $R_3$, or among $R_4$ and $R_5$, is a hydrogen atom. Esterification of indole-3-acetates IX, followed by reduction to indoline with, for example, Mg metal and by amidation affords compounds of formula (XV).

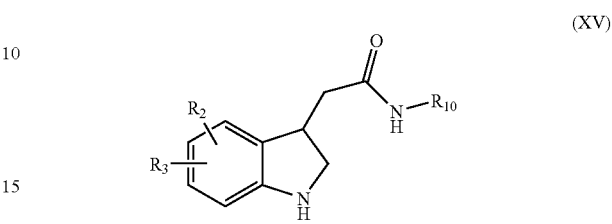
(XV)

The possibility to hydrolize the intermediate indoline ester to perform amidation with another experimental protocol may be appreciated by the skilled artisans.

Figure 6:
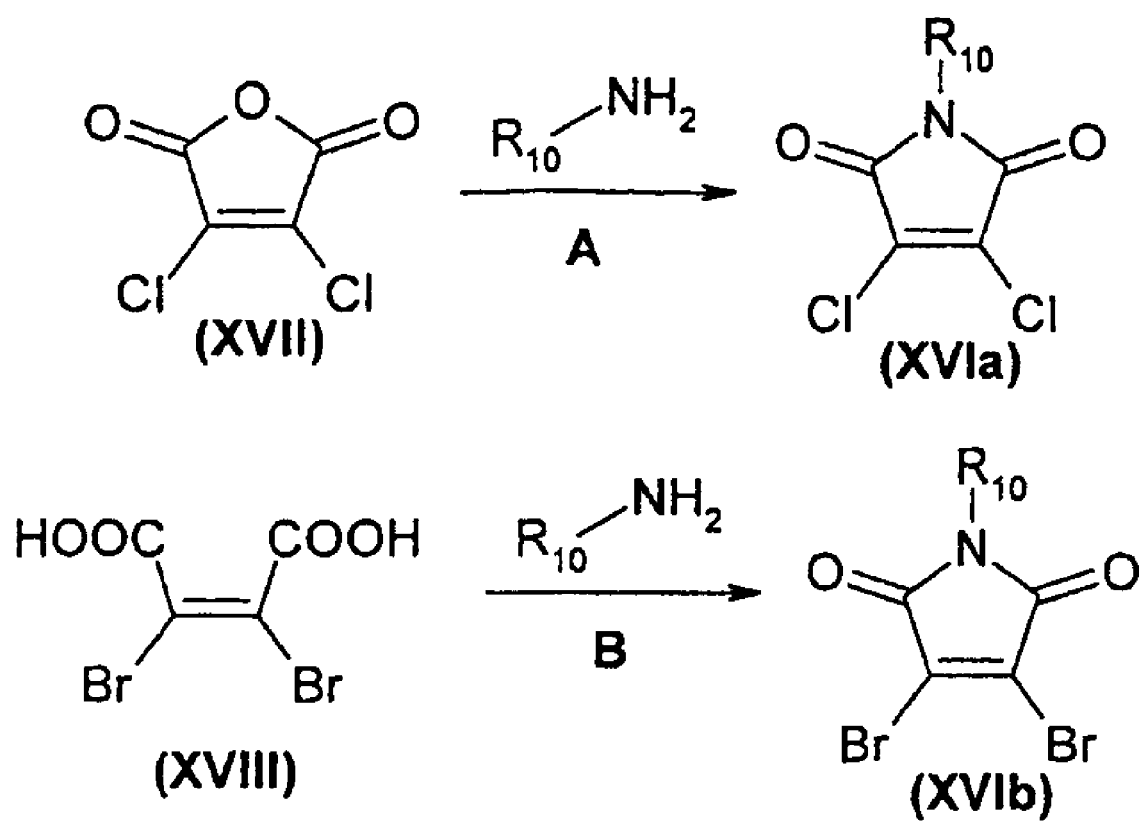
FIG. 6 shows the synthesis of the key bis-halo maleimide intermediates XVIa,b which have been used for the synthesis of the compounds of the general formula (I), especially when $R_6$—$R_7$ and $R_8$—$R_9$ are both carbonyl groups and when $R_{10}$ is not a hydrogen atom.

FIG. 6 shows the synthesis of the key bis-halo maleimide intermediates XVIa,b which have been used for the synthesis of the compounds of the general formula (I), especially when $R_6$—$R_7$ and $R_8$—$R_9$ are both carbonyl groups and when $R_{10}$ is not a hydrogen atom. Treatment of bis-chloromaleic anhydride XVII with a suitable primary amine yields the corresponding bis-chloro compounds of formula (XVIa) (FIG. 6, path A). Using 2,3-dibromomaleic acid XVIII and the same primary amines in the presence of coupling agents known to those skilled in the art the corresponding bis-bromo compounds of formula (XVIb) are obtained (FIG. 6, path B).

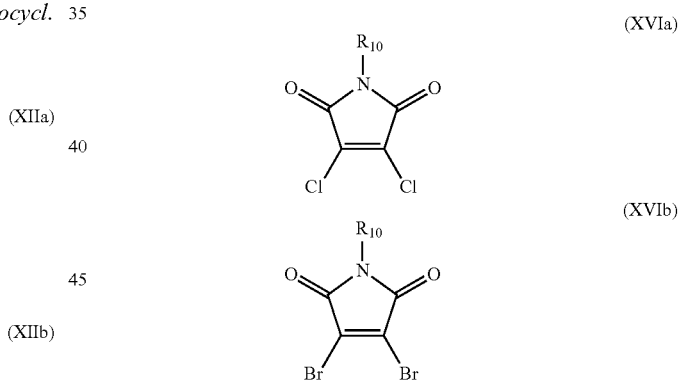

Figure 7:
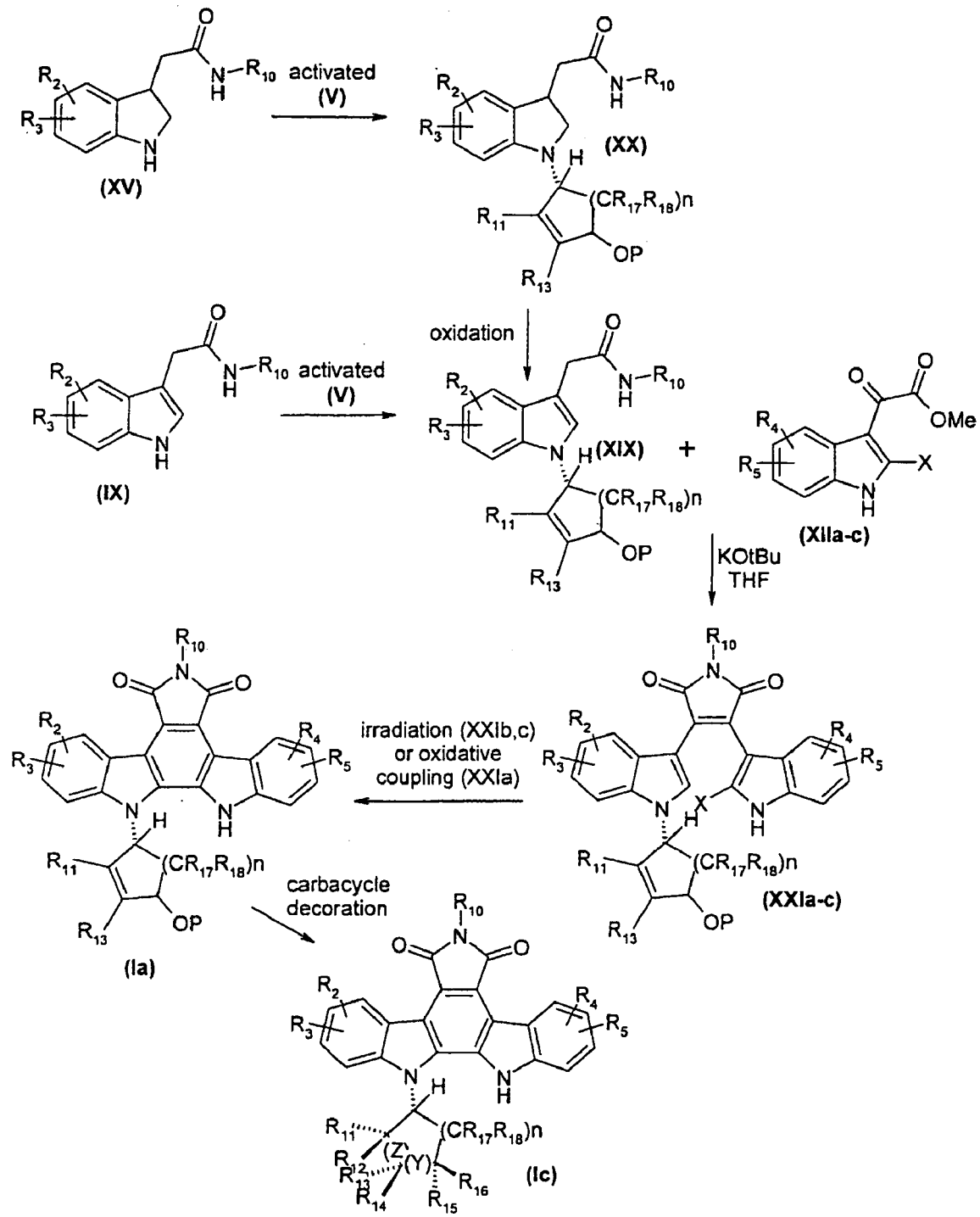
FIG. 7 shows an alternative detailed pathway for the synthesis of compounds Ia and Ic as examples for the preparation of the members of the general class of compounds depicted in the general formula (I).

FIG. 7 shows an alternative detailed pathway for the synthesis of compounds Ia and Ic as examples for the preparation of the members of the general class of compounds depicted in the general formula (I). Indole-3-acetamides IX, indoline-3-acetamides XV and indole-3-glyoxylates XIIa–c are the key intermediates for the specific synthetic strategy leading to compounds of formulae (Ia) and (Ic).

Compounds IX may be N-alkylated with activated derivatives of carbacycles V including, but not limited to, tosylates, mesylates and bromides, using coupling conditions including, but not limited to, NaH in DMF and KOH in DMSO, affording N-carbacyclic indole-3-acetamides XIX. Alternatively, compounds XIX may be prepared from indoline-3-acetamides XV via N-alkylation with activated derivatives of carbacycles V including, but not limited to, tosylates, mesylates and bromides, using coupling conditions including, but not limited to, TEA in THF and NaH in DMF, affording N-carbacyclic indoline-3-acetamides XX and subsequent aromatization using reagents such as, but not limited to, DDQ or activated $MnO_2$. Condensation between compounds XIX and glyoxylates XIIa–c in basic conditions, such as tBuOK in THF, affords bisindolylmaleimides XXIa–c which are then cyclized to provide the desired indolocarbazole structure. When 2-unsubstituted compounds XXIa are used, oxidative coupling protocols, such as $Pd(OAc)_2$ in AcOH, or $Pd(OAc)_2$ in DMF, or DDQ in toluene, afford the compounds of formula (Ia). When 2-halo compounds XXIb,c are used, irradiation in presence of a base, such as visible light and DIPEA in EtOAc, afford the compounds of formula (Ia). Related reaction pathways are, for example, described in Faul et al., *J. Org. Chem.*, 1998, 63, 6053–6058, in Kobayashi, Y. et al., *J. Am. Chem. Soc.*, 1999, 121, 6501–6502, and in Faul et al., *J. Org. Chem.*, 1999, 64, 2465–2470, the disclosure of which is incorporated herein by reference in its entirety.

The carbacyclic moiety present in (Ia) can then be thoroughly modified and decorated, affording compounds of formula (Ic) using protocols and reagents which are familiar to those skilled in the art. Examples of transformations of the double bond include, but are not limited to, mono- and bis-hydroxylations, halogenations, halohydrations, hydroborations, epoxide formation and opening with nucleophiles or with Pd-catalyzed methodologies and reductions. Examples of transformations after deprotection of the protected hydroxyls include, but are not limited to, oxidations to ketones and further elaborations to cyanohydrins, exocyclic alkenes, amines and α-amino acid derivatives, displacements via activation of the hydroxyl as mesylate, triflate or dichlorophenylphosphate to give azides, halides, cyanides and amines, alkylations to give ethers, acylations to give esters.

A modification of the synthetic strategy reported in FIG. 7 leads to compounds of formula (Ib) and (Id).

Figure 8:
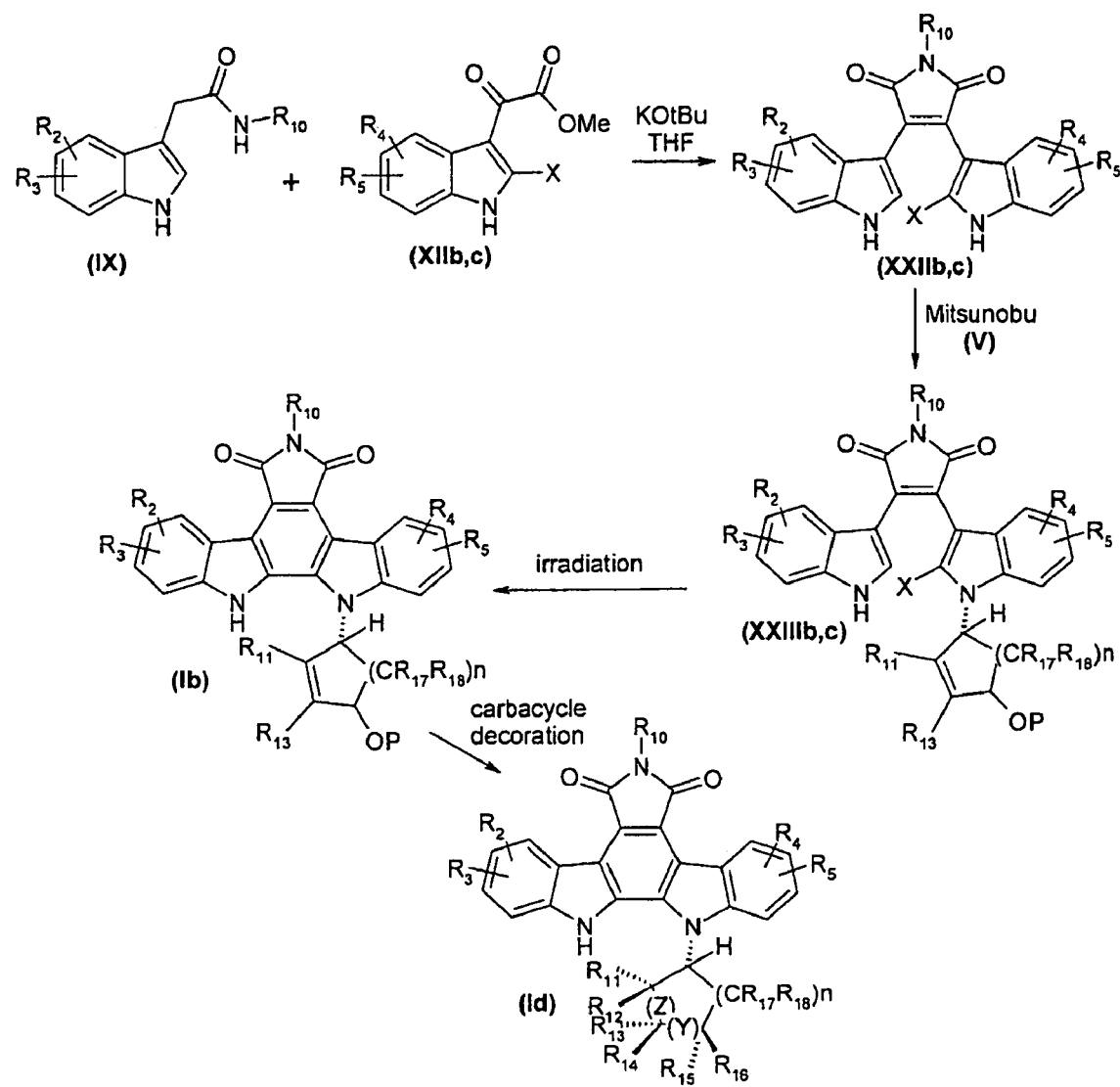
FIG. 8 shows an alternative detailed pathway for the synthesis of compounds Ib and Id as examples for the preparation of the members of the general class of compounds depicted in the general formula (I).

FIG. 8 shows an alternative detailed pathway for the synthesis of compounds Ib and Id as examples for the preparation of the members of the general class of compounds depicted in the general formula (I). Condensation between unsubstituted compounds IX and XIIb,c produced the N-unsubstituted bisindolylmaleimides XXIIb,c which can be selectively functionalized with carbacycles V on the Cl-containing indole by using one of a variety of experimental protocols based on the Mitsunobu reaction, such as $PPh_3$ and DEAD in THF, leading to carbacycle-substituted bisindolylmaleimides XXIIIb,c. Irradiation and carbacycle decoration, as seen in FIG. 7, lead respectively to compounds Ib and Id. Those skilled in the art will notice easily the difference between compounds of formula (XXIb,c) and (XXIIIb,c), and between (Ia), (Ib), (Ic) and (Id), and will appreciate the modularity and the flexibility of the two routes depicted in FIG. 7 and FIG. 8.

Figure 9:
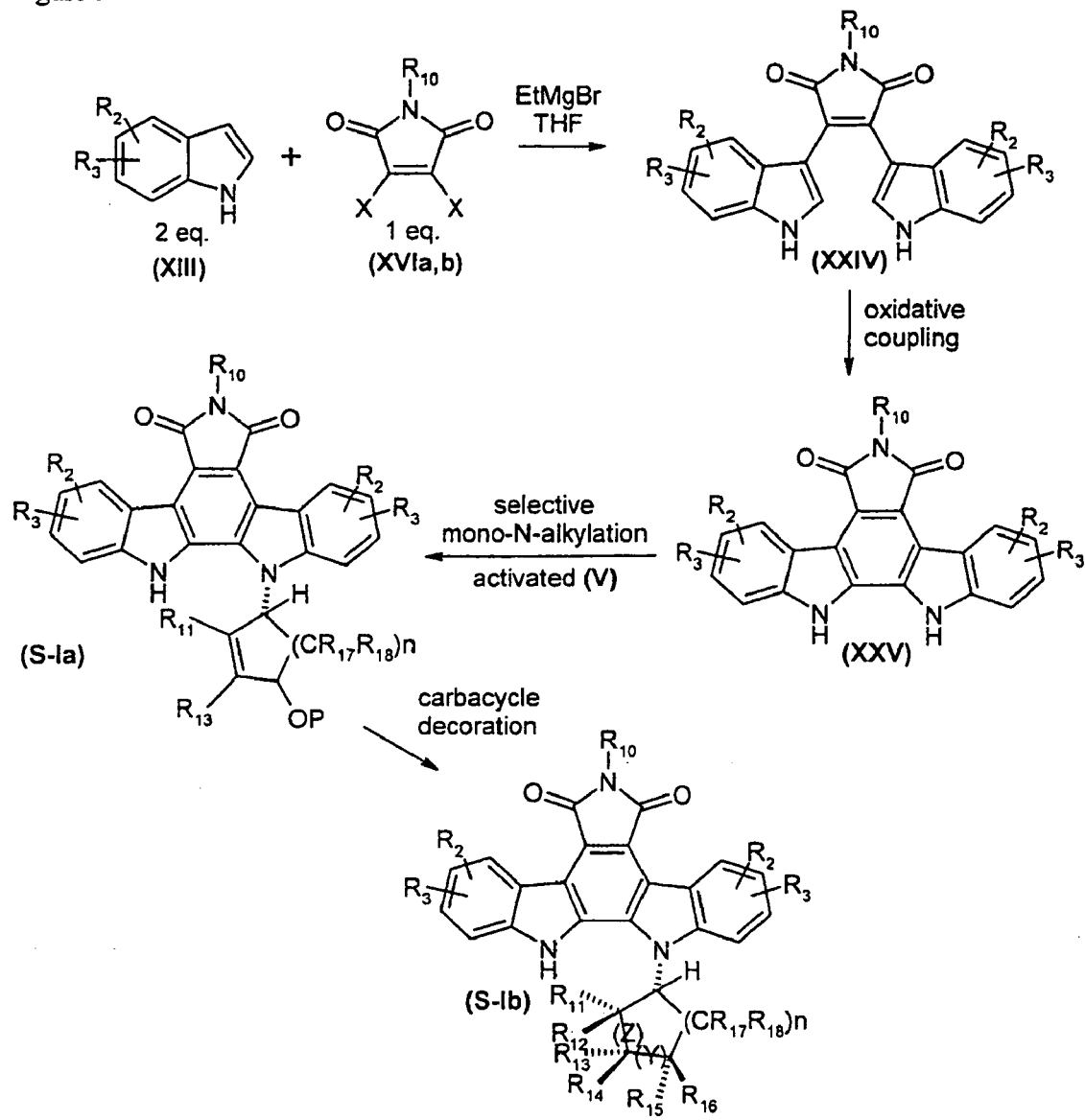
FIG. 9 shows an alternative detailed pathway for the synthesis of compounds S-Ia and S-Ib as examples for the preparation of the members of the general class of compounds depicted in the general formula (I).

Compounds of formula (XVIa,b) are the key intermediates for another synthetic strategy leading to compounds S-Ia and S-Ib. FIG. 9 shows an alternative detailed pathway for the synthesis of compounds S-Ia and S-Ib as examples for the preparation of the members of the general class of compounds depicted in the general formula (I).

Reaction of compounds XVIa,b with more than two equivalents of substituted indoles XIII in typical organometallic protocols, such as Grignard conditions using EtMgBr in THF or LiHMDS in THF, leads to symmetrical bisindolylmaleimides XXIV. Oxidative coupling protocols, such as $Pd(OAc)_2$ in AcOH, or $Pd(Otf)_2$ in DMF, or DDQ in toluene, afford the N-unsubstituted indolocarbazoles of formula (XXV) which can be selectively mono-N-functionalized using activated derivatives of compounds V in a variety of experimental protocols, reagents and conditions known to those skilled in the art to provide compounds S-Ia. For example, these conditions include, but are not limited to, the use of an excess of compounds XXV that can be subsequently recycled, or the slow addition of compounds XXV to a solution of the activated derivatives of carbacycles V. Related reaction pathways are, for example, described in Brenner, M. et al., *Tetrahedron*, 1988, 44, 2887–2895 and in Link et al., *J. Am. Chem. Soc.*, 1995, 117, 552.

The carbacyclic moiety present in (S-Ia) can then be thoroughly modified and decorated, affording compounds of formula (S-Ib) using protocols and reagents which are familiar to those skilled in the art. Examples of transformations of the double bond include, but are not limited to, mono- and bis-hydroxylations, halogenations, halohydrations, hydroborations, epoxide formation and opening with nucleophiles or with Pd-catalyzed methodologies and reductions. Examples of transformations after deprotection of the protected hydroxyls include, but are not limited to, oxidations to ketones and further elaborations to cyanohydrins, exocyclic alkenes, amines and α-amino acid derivatives, displacements via activation of the hydroxyl as mesylate, triflate or dichlorophenylphosphate to give azides, halides, cyanides and amines, alkylations to give ethers, acylations to give esters.

A modification of the synthetic strategy reported in FIG. 9 leads to compounds of formula (S-Ia) and (S-Ib).

Figure 10:
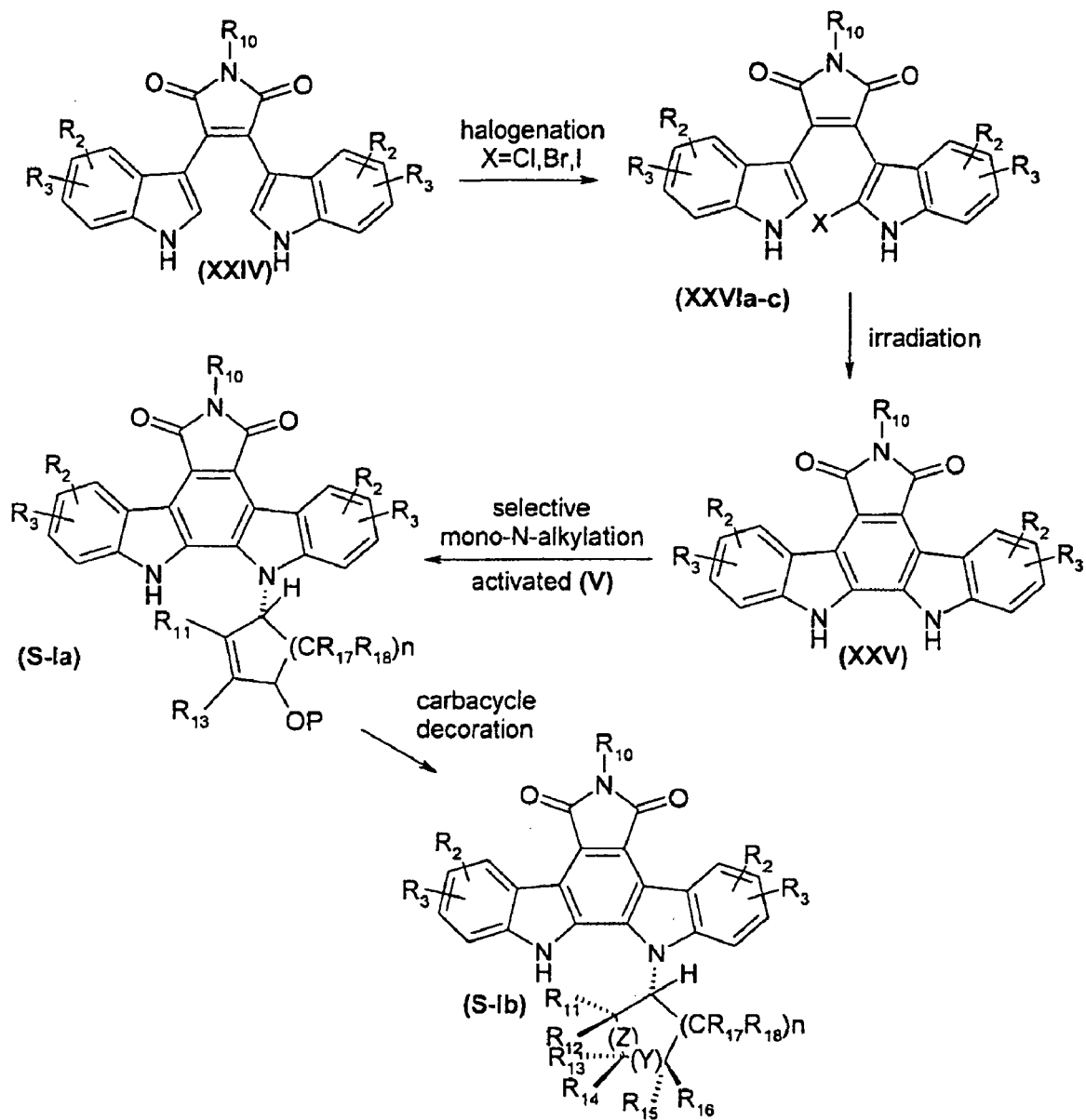
FIG. 10 shows an alternative detailed pathway for the synthesis of compounds S-Ia and S-Ib as examples for the preparation of the members of the general class of compounds depicted in the general formula (I).

FIG. 10 shows a detailed pathway for the synthesis of compounds S-Ia and S-Ib as examples for the preparation of the members of the general class of compounds depicted in the general formula (I).

Treatment of compounds XXIV with monohalogenating conditions and reagents, including, but not limited to, NBS, $Br_2$, $I_2$, NCS or $IPy_2BF_4$ yields monohalobisindolylmaleimides XXVIa–c. Irradiation of compounds XXVIa–c produces N-unsubstituted indolocarbazoles of formula (XXV) which can be selectively mono-N-functionalized and decorated to provide respectively compounds S-Ia and S-Ib as shown in FIG. 10. Related reaction pathways are, for example, described in Brennan, M. R. et al., *Heterocycles*, 1986, 10, 2879–2885.

Figure 11:
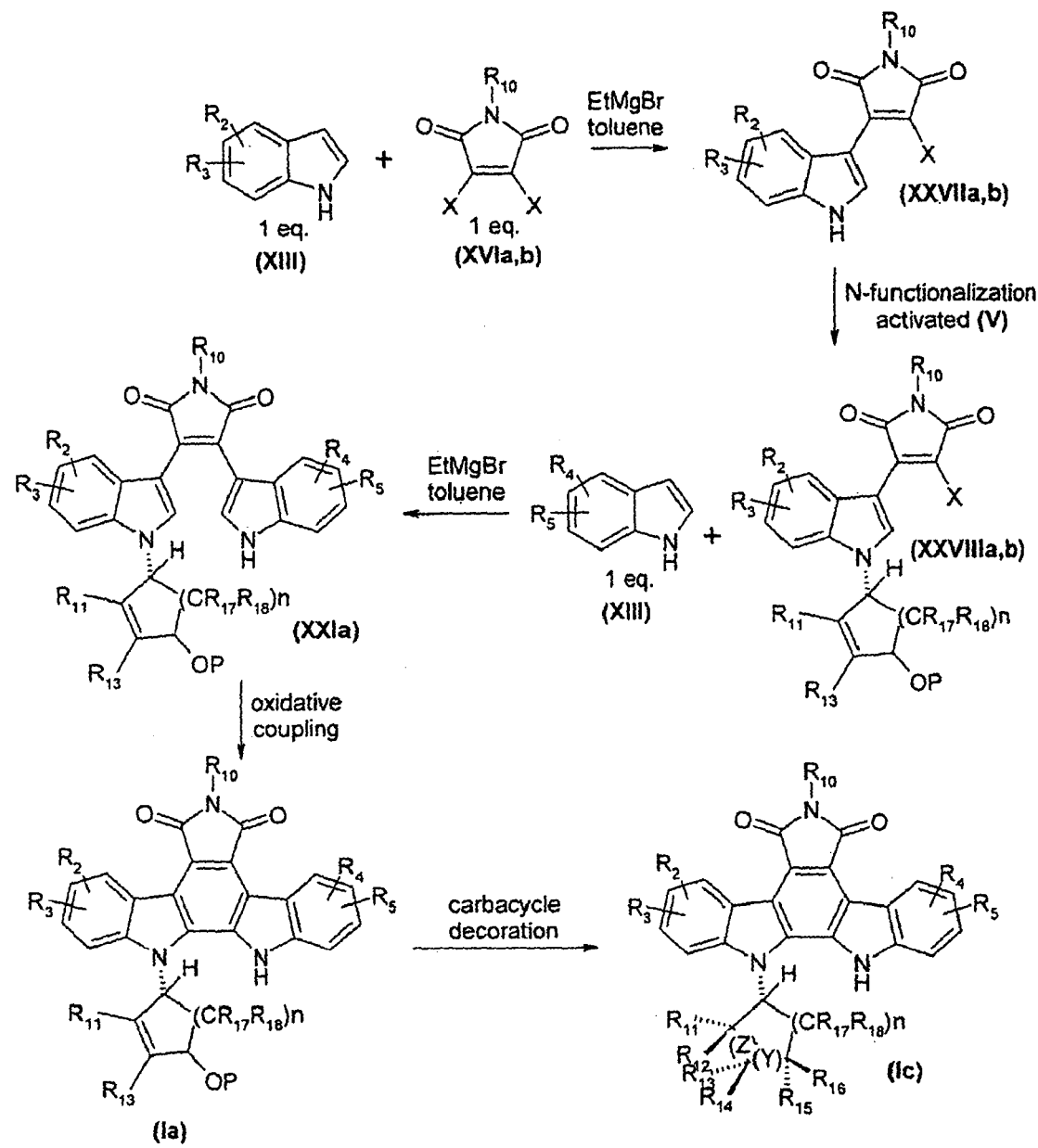
FIG. 11 shows an alternative detailed pathway for the synthesis of compounds Ia and Ic as examples for the preparation of the members of the general class of compounds depicted in the general formula (I).

FIG. 11 shows an alternative detailed pathway for the synthesis of compounds Ia and Ic as examples for the preparation of the members of the general class of compounds depicted in the general formula (I). Compounds of formula (XVIa,b) are the key intermediates for the synthetic strategy which leads to compounds Ia and Ic.

Reaction of compounds XVIa,b with slightly more than one equivalent of substituted indoles XIII in typical organometallic protocols, such as Grignard conditions using EtMgBr in toluene or LiHMDS, leads to hatoindolylmaleimides XXVIIa,b. These can be reacted with activated carbacycles V in a variety of experimental protocols including, but not limited to, alkylations with mesylates and tosylates, or Mitsunobu reactions with $PPh_3$ and DEAD, to afford N-carbacyclic haloindblylmaleimides XXVIIIa,b. Reaction of compounds XXVIIIa,b with substituted indoles XIII in typical organometallic protocols, such as Grignard conditions using EtMgBr in toluene, leads to.

N-carbacyclic bisindolylmaleimides XIa. Oxidative coupling protocols, such as $Pd(OAc)_2$ in AcOH, or $Pd(Otf)_2$ in DMF, or DDQ in toluene, afford the unsymmetrical compounds of formula (Ia). Related reaction pathways are, for example, described in Faul, M. et al., *Synthesis*, 1995, 1511–1513 and in Okhubo, M. et al., *Tetrahedron*, 1997, 53, 5937–5950.

The carbacyclic moiety present in (Ia) can then be thoroughly modified and decorated, affording compounds of formula (Ic) using protocols and reagents which are familiar to those skilled in the art. Examples of transformations of the double bond include, but are not limited to, mono- and bis-hydroxylations, halogenations, halohydrations, hydroborations, epoxide formation and opening with nucleophiles or with Pd-catalyzed methodologies and reductions. Examples of transformations after deprotection of the protected hydroxyls include, but are not limited to, oxidations to ketones and further elaborations to cyanohydrins, exocyclic alkenes, amines and α-amino acid derivatives, displacements via activation of the hydroxyl as mesylate, triflate, carbonate or dichlorophenylphosphate to give azides, halides, cyanides and amines, alkylations to give ethers, acylations to give esters.

Figure 12:
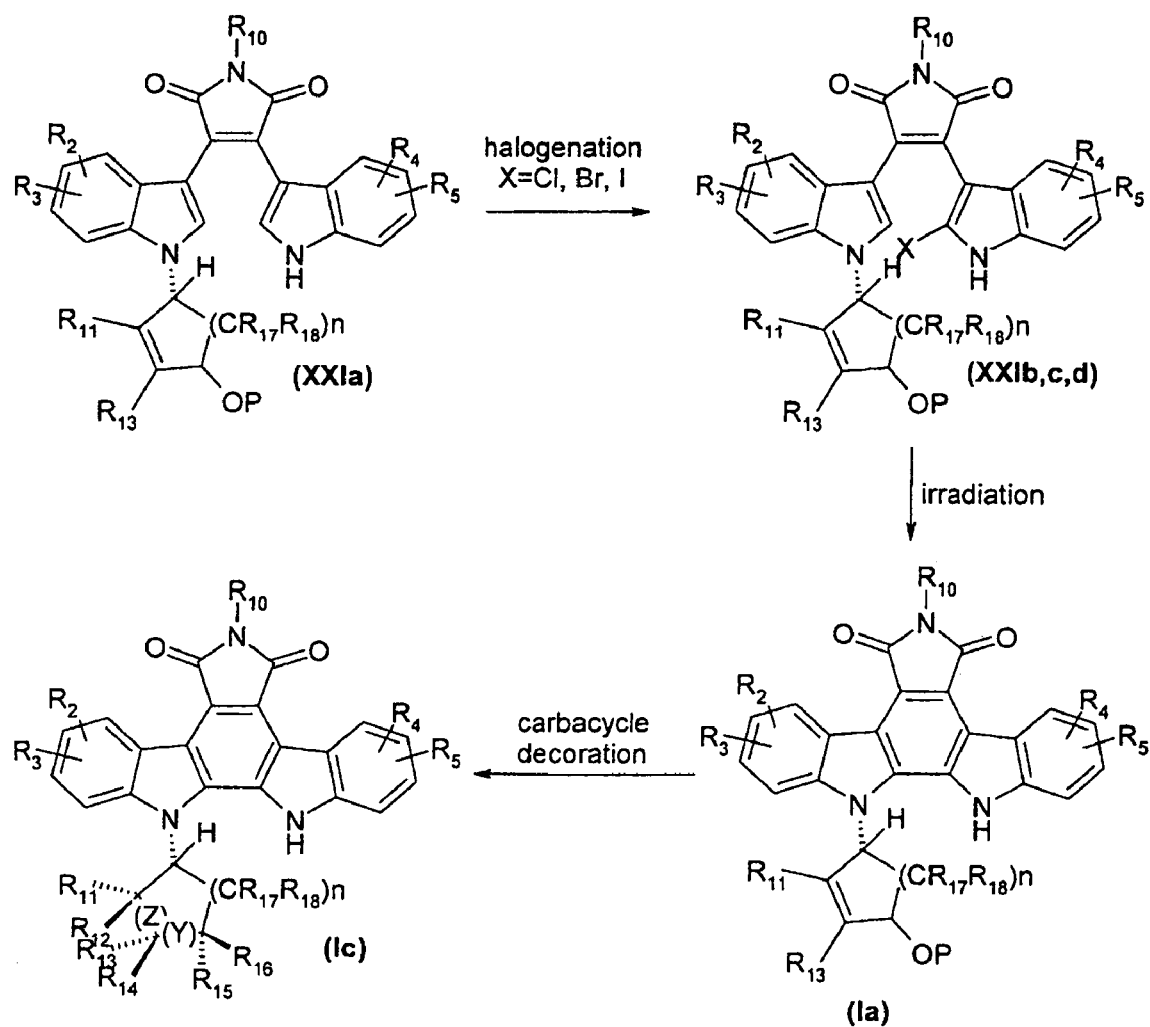
FIG. 12 shows an alternative detailed pathway for the synthesis of compounds Ia and Ic as examples for the preparation of the members of the general class of compounds depicted in the general formula (I).

FIG. 12 shows an alternative detailed pathway for the synthesis of compounds Ia and Ic as examples for the preparation of the members of the general class of compounds depicted in the general formula (I). Treatment of compounds XXIa with monohalogenating conditions and reagents, including, but not limited to, NBS, $Br_2$, $I_2$, NCS and $IPy_2BF_4$ yields N-carbacyclic monohalobisindolylmaleimides XXIb,c,d. Irradiation of compounds XIXb,c,d and carbacycle decoration provides respectively compounds Ia and Ic as shown in FIG. 12.

Figure 13:
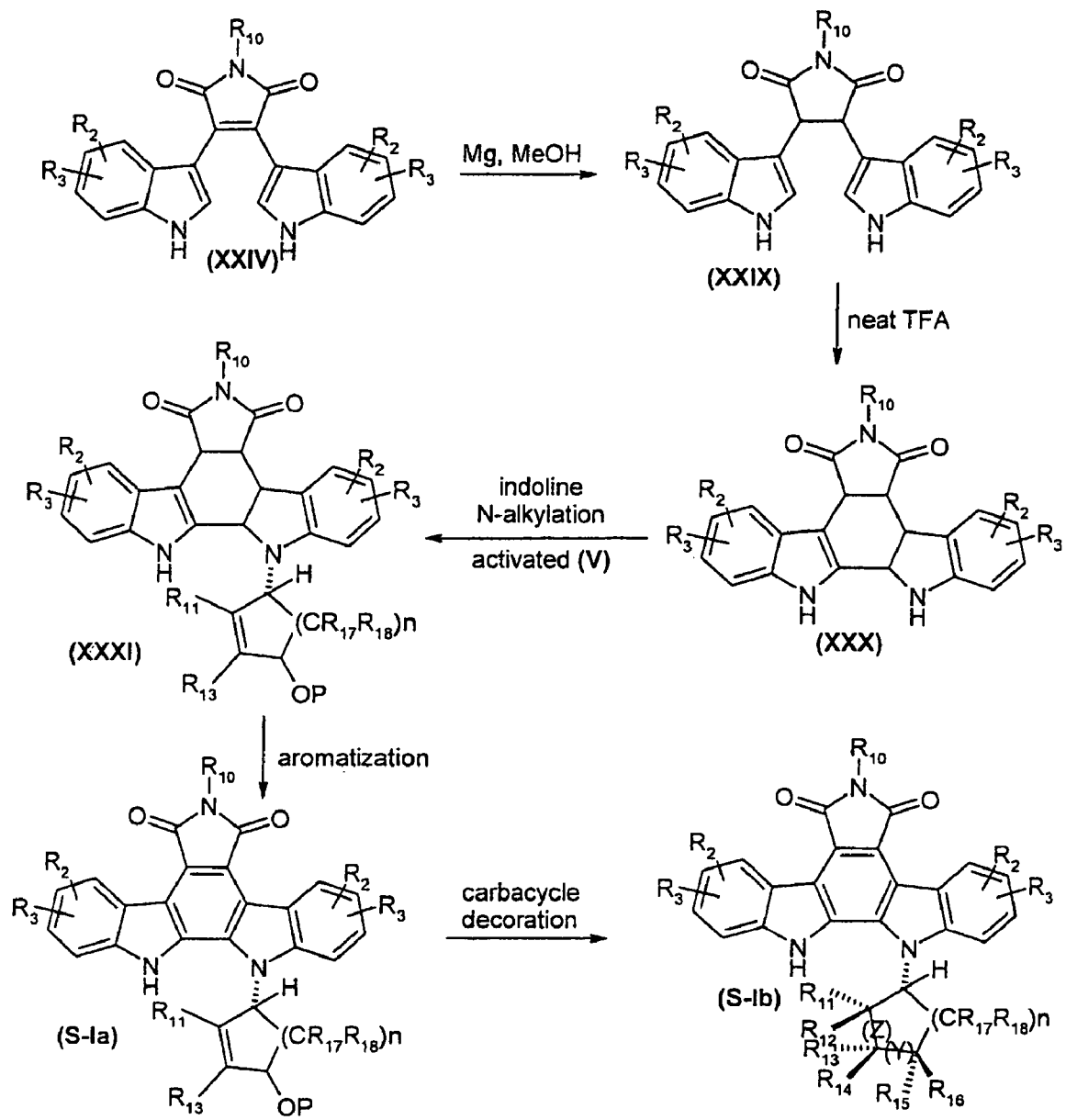
FIG. 13 shows an alternative detailed pathway for the synthesis of compounds S-Ia and S-Ib as examples for the preparation of the members of the general class of compounds depicted in the general formula (I).

FIG. 13 shows an alternative detailed pathway for the synthesis of compounds S-Ia and S-Ib as examples for the preparation of the members of the general class of compounds depicted in the general formula I. Compounds of formula (XXIV) are the key intermediates for another synthetic strategy leading to compounds S-Ia and S-Ib shown in FIG. 13.

Compounds XXIV are reduced to provide bisindolylsuccinimides XXIX using a variety of reducing agents including, but not limited to, Mg in MeOH and Pd-catalysed hydrogenation with $H_2$. Mannich cyclisation of compounds XXIX in various experimental conditions, such as TFA under $N_2$ at rt, generates the reduced indolocarbazoles XXX. Functionalization of the indoline nitrogen with activated derivatives of carbacycles V may be obtained using a variety of activated carbacycles, reagents and reaction conditions including, but not limited to, tosylates, mesylates, bromides, acetates, carbonates and epoxides, using coupling conditions including, but not limited to, TEA in THF, NaH in DMF and Pd-catalyzed functionalizations to provide N-carbacyclic reduced indolocarbazoles XXXI. Aromatization of compounds XXXI to compounds of formula (S-Ia) may happen in a variety of oxidative protocols including, but not limited to, DDQ or activated $MnO_2$. Related reaction pathways are, for example, described in Van Vranken, D. et al., *J. Org. Chem.*, 1995, 60, 6672–6673 and in Van Vranken, D. et al., *J. Org. Chem.*, 2000, 65, 7541–7553.

The carbacyclic moiety present in (S-Ia) can then be thoroughly modified and decorated, affording compounds of formula (S-Ib) using protocols and reagents which are familiar to those skilled in the art. Examples of transformations of the double bond include, but are not limited to, mono- and bis-hydroxylations, halogenations, halohydrations, hydroborations, epoxide formation and opening with nucleophiles or with Pd-catalyzed methodologies and reductions. Examples of transformations after deprotection of the protected hydroxyls include, but are not limited to, oxidations to ketones and further elaborations to cyanohydrins, exocyclic alkenes, amines and α-amino acid derivatives, displacements via activation of the hydroxyl as mesylate, triflate, carbonate or dichlorophenylphosphate to give azides, halides, cyanides and amines, alkylations to give ethers, acylations to give esters.

Figure 14:
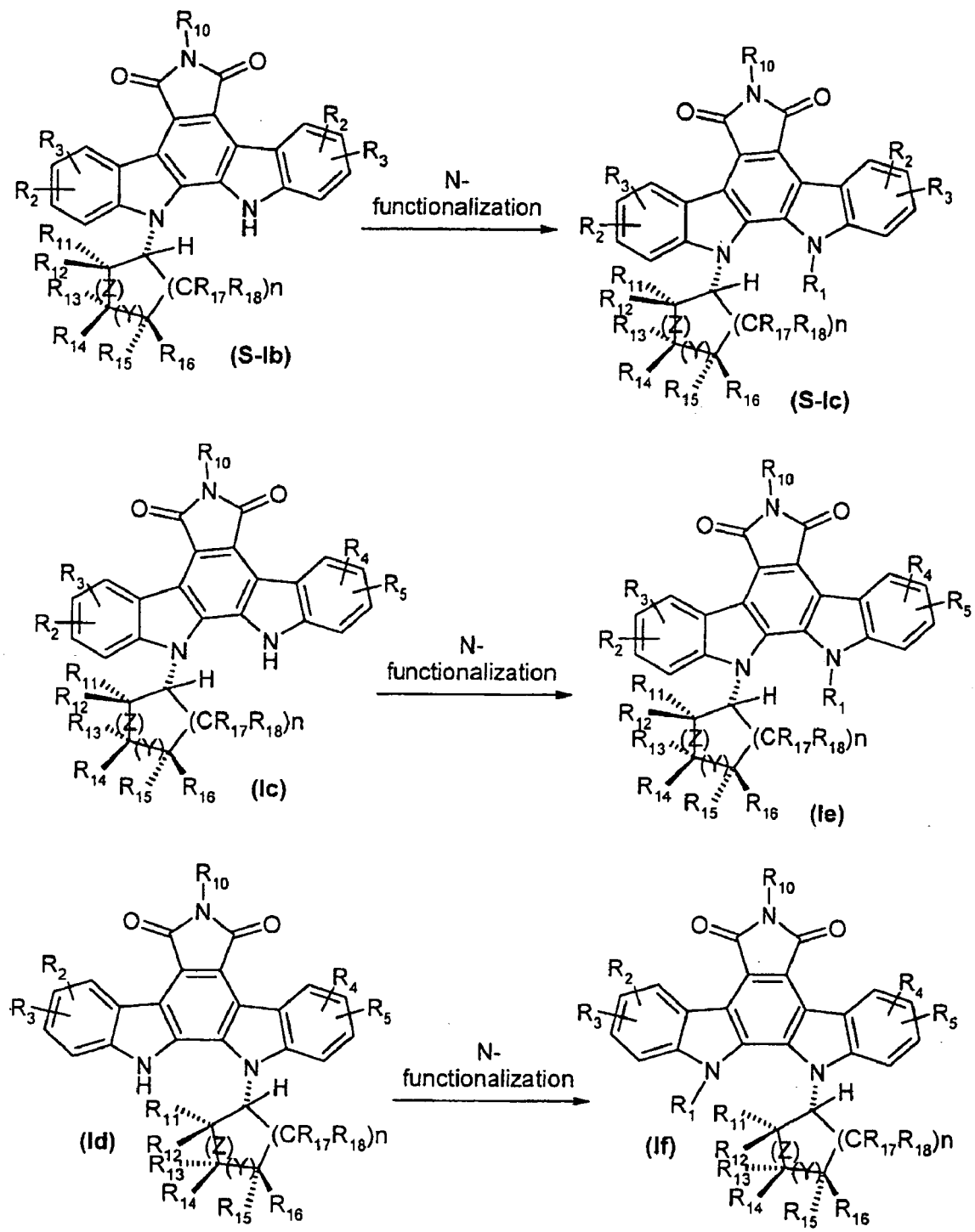
FIG. 14 shows an alternative detailed pathway for the synthesis of compounds S-Ic, Ie and If as examples for the preparation of the members of the general class of compounds depicted in the general formula (I).

Compounds of structures (S-Ib, Ic, Id) can be further modified to provide respectively the corresponding N-carbacyclic, N'-functionalized indolocarbazoles S-Ic, Ie, If as shown in FIG. 14.

FIG. 14 shows an alternative detailed pathway for the synthesis of compounds S-Ic, Ie and If as examples for the preparation of the members of the general class of compounds depicted in the general formula (I).

Compounds S-Ib, Ic, Id may be N-alkylated with alkylating agents including, but not limited to, tosylates, mesylates, bromides, iodides, chlorides, triflates and epoxides, using coupling conditions including, but not limited to, NaH in DMF, KOH in DMSO, TEA or DBU in THF, or can be functionalised by metal-catalysed functionalisations such as Pd tetrakis and carbonates, or by Mitsunobu protocols such as $PPh_3$, DEAD and alcohols, affording compounds of formula (S-Ic, Ie, If). Other activating functions and coupling protocols can be found in Pearson, A. J. and Roush, W. J., *Activating Agents and Protecting Groups*, Wiley and Sons, 1999.

Figure 15:
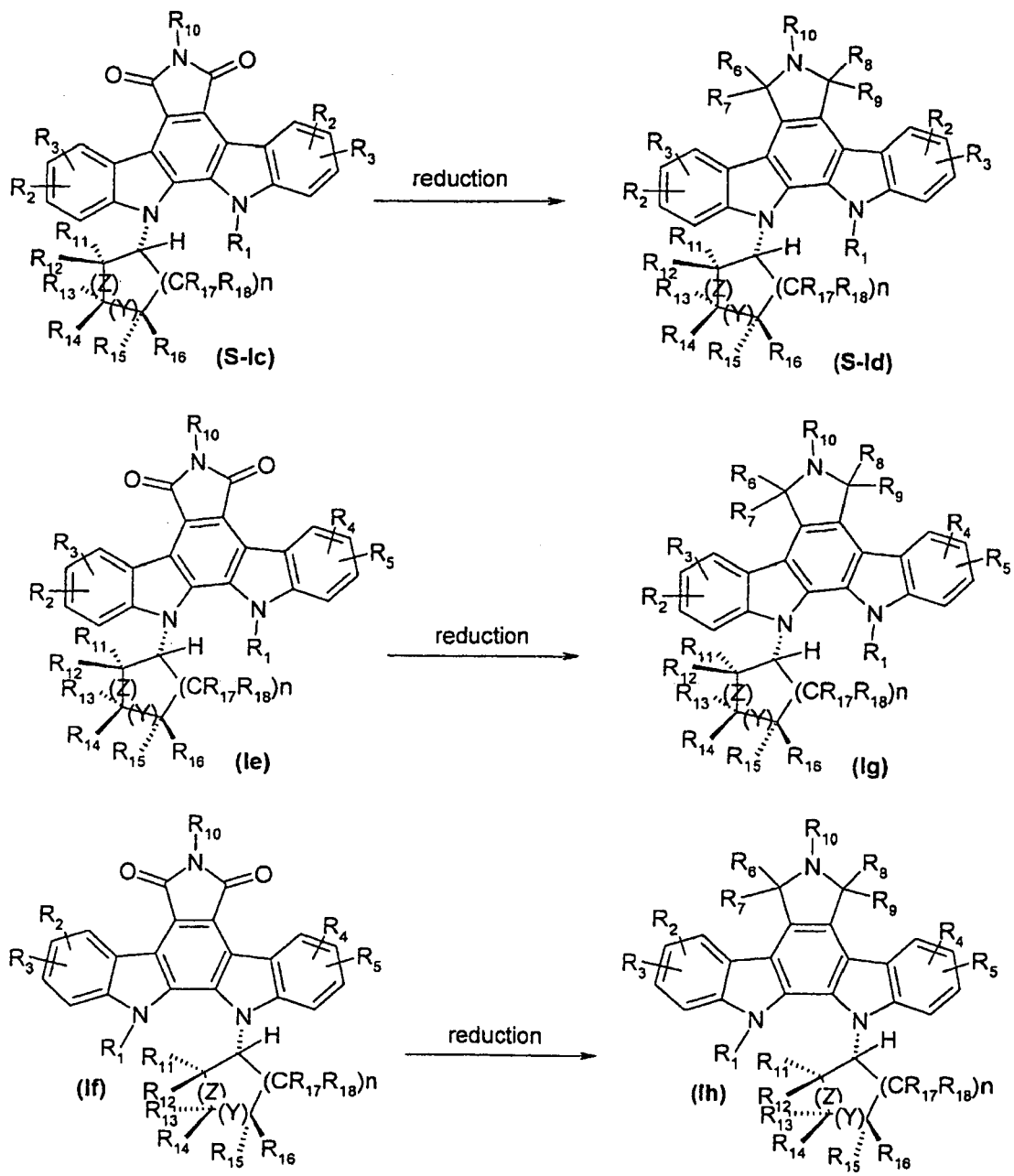
FIG. 15 shows an alternative detailed pathway for the synthesis of compounds S-Id, Ig and Ih as examples for the preparation of the members of the general class of compounds depicted in the general formula (I).

Compounds of structures (S-Ic, Ie, If) can be further modified to provide respectively the corresponding N-carbacyclic, N'-functionalized indolocarbazoles S-Id, Ig, Ih as shown in FIG. 15.

FIG. 15 shows an alternative detailed pathway for the synthesis of compounds S-Id, Ig and Ih as examples for the preparation of the members of the general class of compounds depicted in the general formula (I).

Compounds S-Ic, Ie, If may be reduced using a variety of reducing agents and conditions including, but not limited to, $LiAlH_4$, Ni Raney and catalytic hydrogenation to provide compounds S-Id, Ig, Ih. Those skilled in the art may appreciate that only one of the carbonyls present in compounds of structure (S-Ic, Ie, If) will be affected by the reaction, and that its reduction maybe partial, leading to an hydroxy substituent, or total, leading to a methylene group, depending on the nature of the reducing agents and conditions employed. Other reducing agents suitable for these transformations can be found in Pearson, A. J. and Roush, W. J., *Activating Agents and Protecting Groups*, Wiley and Sons, 1999. Related reaction pathways are, for example, described in Harris, W. et al., *Tetra. Lett.*, 1993, 34, 8361–8364, and Xue, G. and Lowe, J. W., Tetra. Lett., 1994, 31, 5555–5558.

Those skilled in the art may appreciate that the reduction process originates invariably mixtures of diastereoisomers which may be separated by standard methods including, but not limited to, normal, reverse phase and chiral chromatography, preferential salt formation, recrystallization to provide single diastereomers or single enantiomers of compounds with formula (S-Id, Ig, Ih).

The following non-limiting examples describe the synthesis of single diastereoisomers, so that final compounds 1–10 and all the chiral intermediates to their synthesis are isolated as racemates. The chosen representation arbitrarily depicts only one of the two enantiomers composing the racemic mixture. The isolation of a specific enantiomer could be performed by methods known in the art.

EXAMPLES

Example 1

NAD 006

1a)

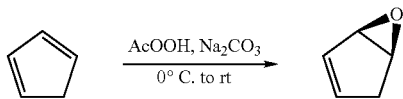

Na$_2$CO$_3$ (294 g, 2.77 mol) was added to a freshly distilled solution of cyclopentadiene (155.6 g, 2.35 mol) in DCM (1.4 L). The vigorously stirred suspension was cooled to 0° C. and 40% peracetic acid (183.2 mL, 1.1 mol) was added in 30 minutes. The reaction mixture was stirred for 24 hours at rt and then filtered. The solid residue was washed with DCM (500 mL) and the combined organic phases were concentrated at atmospheric pressure to give an oil (293 g) containing the pure target compound. (analytical estimation: 58.7 g, yield 65.1%).

1b)

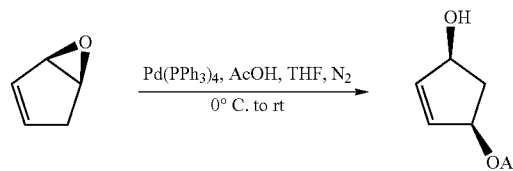

AcOH (30 mL, large excess) was added to a solution of Pd(PPh$_3$)$_4$ (1 g, catalytic) in THF (250 mL) at 0° C. under nitrogen atmosphere, followed by a solution of Ia (50 g, estimated 48.6 mmol) in THF (50 mL). The reaction mixture was then stirred for 2 hours at rt, then the solvent was removed in vacuo. Purification of the residue by flash chromatography (silica gel, PE/EtOAc 7/3 as eluant mixture) gave the pure target compound (30 g, yield 43.0%).

$^1$H-NMR (300 MHz, CDCl$_3$): δ 1.58–1.63 (1H, dt, C$\underline{H}_2$), 1.85–1.95 (1H, bs, O$\underline{H}$), 2.06 (3H, s, OCOC$\underline{H}_3$), 2.76–2.86 (1H, dt, C$\underline{H}_2$), 4.65 (1H, bs, C$\underline{H}$—OH), 5.40 (1H, m, C$\underline{H}$—OAc), 5.95 (H, dd, C$\underline{H}$=CH—CHOAc), 6.10 (1H, dd, CH=C$\underline{H}$—CHOAc). MS (ESI) m/z 143 [M+H]$^+$.

1c)

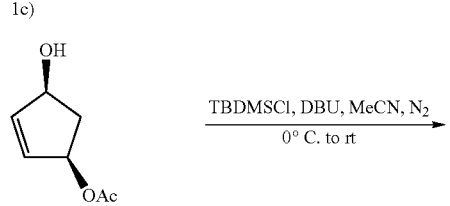

DBU (31 mL, 207 mmol) was added dropwise to a solution of compound Ib (16.3 g, 115 mmol) in MeCN (100 mL) at 0° C. and under nitrogen atmosphere. Neat TBDM-SCl (17.3 g, 115 mmol) was added portionwise within 10 minutes, the solution was stirred for 30 minutes at 0° C. and overnight at rt. The reaction mixture was poured into water (300 mL) and extracted with Et$_2$O (3×150 mL).

The organic phase was dried over sodium sulfate and concentrated in vacuo. The crude product (26.3 g) was purified by flash chromatography (silica gel, PE/EtOAc 20/1 as eluant mixture) to yield the pure target compound (24.6 g, 83.2%).

$^1$H-NMR (300 MHz, CDCl$_3$): δ 0.09 (6H, s, Si(C$\underline{H}_3$)$_2$), 0.85 (9H, s, tBu), 1.58–1.60 (1H, dt, C$\underline{H}_2$), 2.01 (3H, s, OCOC$\underline{H}_3$), 2.76–2.80 (1H, dt, C$\underline{H}_2$), 4.65 (1H, m, CH—OSi), 5.40 (1H, m, C$\underline{H}$—OAc), 5.85 (1H, dd, C$\underline{H}$=CH—CHOAc), 5.95 (1H, dd, CH=CH—CHOAc). MS (ESI) m/z 257 [M+H]$^+$.

1d)

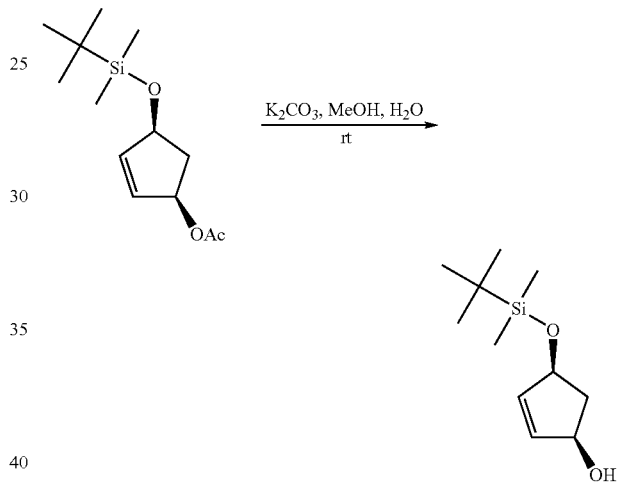

A solution of K$_2$CO$_3$ (13.9 g, 101 mmol) in water (40 mL) was added to a solution of compound Ic (24.6 g, 95.9 mmol) in MeOH (150 mL). After overnight stirring at rt, water (200 mL) was added and the mixture was extracted with Et$_2$O (2×500 mL), dried over sodium sulfate and concentrated in vacuo to yield the pure target compound (19.16 g, 88.9%).

$^1$H-NMR (300 MHz, CDCl$_3$): δ 0.03 (6H, s, Si(C$\underline{H}_3$)$_2$), 0.82 (9H, s, tBu), 1.45–1.55 (1H, dt, C$\underline{H}_2$, 1.90 (1H, bs, O$\underline{H}$), 2.76–2.80 (1H, dt, C$\underline{H}_2$), 4.55 (1H, m, C$\underline{H}$—OH), 4.60 (1H, m, CH—OSi), 5.80 (1H, dd, C$\underline{H}$=CH—CHOH), 5.90 (1H, dd, CH=C$\underline{H}$—CHOH). MS (ESI) m/z 215 [M+H]$^+$.

1e)

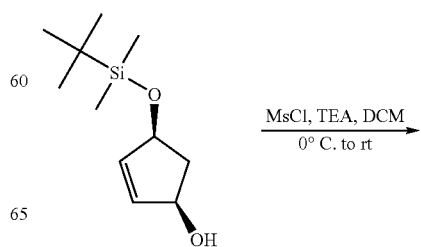

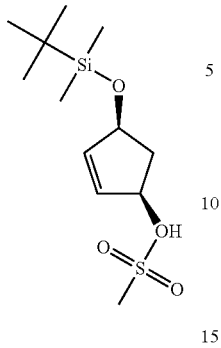

A solution of Id (9 g, 60 mmol) and triethylamine (8.75 mL, 65 mmol) in DCM (50 mL) was cooled to 0° C. and treated dropwise with methanesulfonyl chloride (4.65 ml, 60 mmol) in DCM (25 mL) at such a rate that the temperature was maintained between 01–5° C. Stirring at rt was continued for 2 hours, then the reaction mixture was poured onto a 1/1 mixture brine/DCM (800 mL). The organic phase was separated, dried over sodium sulfate, filtered and concentrated in vacuo to give a crude product which was directly used in the following step 1 g.

1f)

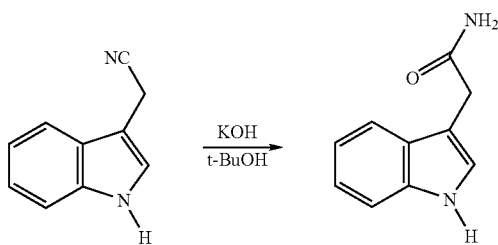

KOH (107.3 g, 1.92 mol) was added to a solution of 3-indolyl acetonitrile (37.4 g, 239 mmol) in tBuOH (360 mL) and the reaction mixture was refluxed for 4 hours. After cooling to rt and pouring into ice (4 L) N HCl was added to reach an almost neutral pH (≈335 mL). The precipitate was filtered off and the filtrate was extracted with EtOAc (2×500 mL), dried over sodium sulfate and concentrated in vacuo. The residue was triturated in Et$_2$O, filtered and dried in vacuo to yield the pure target compound (34.5 g, yield 83.4%).

$^1$H-NMR (300 MHz, DMSO-d$_6$): δ 3.35 (2H, s, C$\underline{H}_2$—CONH$_2$), 6.84 (2H, bs, N$\underline{H}_2$), 6.95–7.15 (2H, m, indole $\underline{H}$s), 7.19 (1H, d, indole $\underline{H}$-2), 7.55 (2H, t, indole $\underline{H}$s), 10.80 (1H, bs, indole N$\underline{H}$). MS (ESI) m/z 175 [M+H]$^+$.

1g)

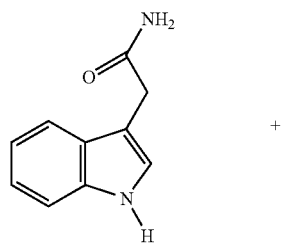

+

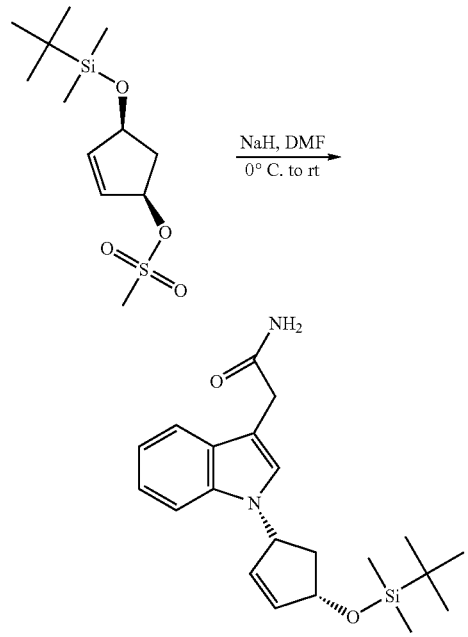

A suspension of sodium hydride (3.2 g, 60% paraffin, 80 mmol) in dry DMF (50 mL) was treated dropwise with If (8.71 g, 50 mmol) in dry DMF (50 mL) at rt under nitrogen atmosphere. The resulting mixture was stirred for 30 minutes at rt and then cooled to 0° C. A solution of the crude Ie in 100 ml of dry DMF was then added dropwise. The solution was then stirred for 18 hours, diluted with EtOAc (2 L), washed with water (2×1 L) and brine (1 L). The organic phase was dried over sodium sulfate, filtered and concentrated in vacuo to give a dark red oily residue (25.7 g). The crude was purified by flash chromatography (silica gel, DCM/MeOH 96/4 as eluant mixture) to give the pure target compound (7.7 g, yield 42%).

$^1$H-NMR (300 MHz, DMSO-d$_6$): δ 0.07 (3H, s, C$\underline{H}_3$—Si), 0.11 (3H, s, C$\underline{H}_3$—Si), 0.88 (9H, t$\underline{Bu}$), 1.55–1.63 (1H, dt, O—CH—C$\underline{H}_2$), 2.88–2.98 (1H, m, O—CH—C$\underline{H}_2$), 3.43 (2H, s, CO—C$\underline{H}_2$), 4.88 (1H, bt, C$\underline{H}$—N), 5.45 (1H, bt, C$\underline{H}$—O), 5.97–6.01 (1H, dm, C$\underline{H}$=CH—O), 6.07–6.11 (1H, dm, C$\underline{H}$—CH=CH—O), 6.84 (1H, bs, NH$_2$), 6.97–7.12 (2H, m, indole $\underline{H}$s), 7.19 (1H, s, indole $\underline{H}$-2), 7.33 (1H, bs, N$\underline{H}_2$), 7.55 (2H, t, indole $\underline{H}$s). MS (ESI) m/z 371 [M+H]$^+$.

1h)

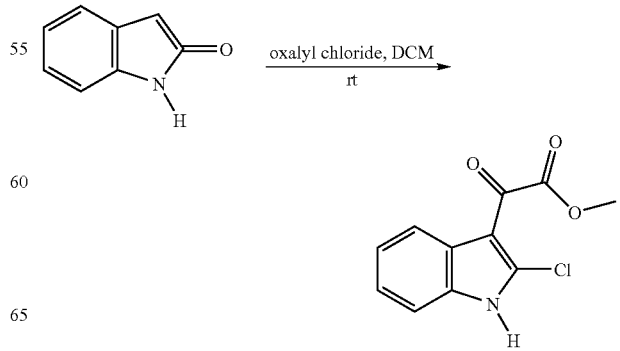

2,3-Dihydro-indol-2-one (93.4 g, 0.702 mol) was added portionwise as a solid within 40 minutes to a vigorously stirred solution of oxalyl chloride (122 ml, 1.404 mol) in methylene chloride (500 mL) at rt. After overnight stirring the suspension was filtered and the solid washed with DCM (150 mL). After drying in vacuo for 3 hours the residue (90.2 g) was suspended in Et$_2$O (900 mL) and dry methanol (46 ml, 1.02 mol) was added as a single portion to the vigorously stirred mixture at rt. The suspension was stirred for 1 hour, then filtered and the solid washed with Et$_2$O (200 mL). After drying the pure target compound (74.6 g, yield 45.3%) was obtained.

$^1$H-NMR (300 MHz, DMSO-d 8): δ 3.95 (3H, s, C$\underline{H}_3$—O), 7.27–7.37 (2H, m, indole Hs); 7.47–7.52 (1H, s, indole $\underline{H}$s), 8.05–8.10 (1H, s, indole $\underline{H}$s), 13.56 (1H, bs, N$\underline{H}$). MS (ESI) m/z 238 [M+H]$^+$.

was diluted with EtOAc (2 L), washed with water (1 L) and brine (500 mL), dried over sodium sulfate, filtered and concentrated in vacuo. The crude residue (22.7 g) was purified by flash chromatography (silica gel, PE/EtOAc 3/1 as eluant mixture) to afford the pure target compound (6.8 g, yield 61.0%).

$^1$H-NMR (300 MHz, DMSO-d$_6$): δ 0.11 (6H, s, C$\underline{H}_3$Si), 0.89 (9H, tBu), 1.58–1.62 (1H, m, C$\underline{H}_2$), 2.98–3.04 (1H, m, C$\underline{H}_2$), 5.12 (1H, bt, C$\underline{H}$—N), 5.91 (1H, bt, C$\underline{H}$—O), 6.56–6.68 (2H, dm, C$\underline{H}$=C$\underline{H}$), 6.93–7.71 (8H, m, indole $\underline{H}$s), 8.01 (1H, s, indole $\underline{H}$-2), 11.06 (1H, s, imide N$\underline{H}$), 12.23 (1H, bs, indole N$\underline{H}$). MS (ESI) m/z 558 [M+H]$^+$.

1j)

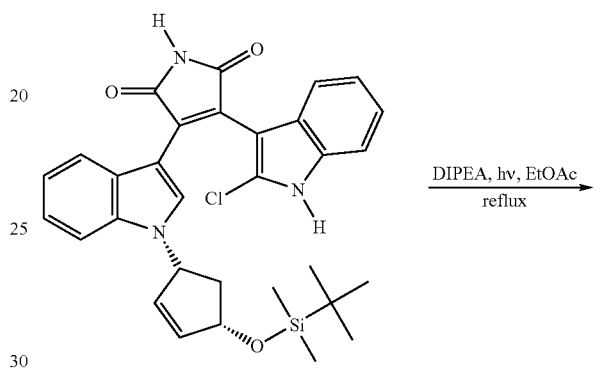

1i)

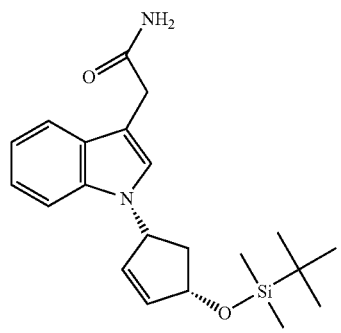

+

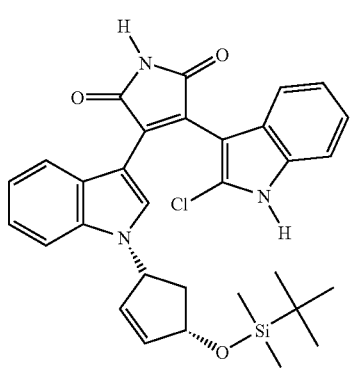

t-BuOK, THF
rt

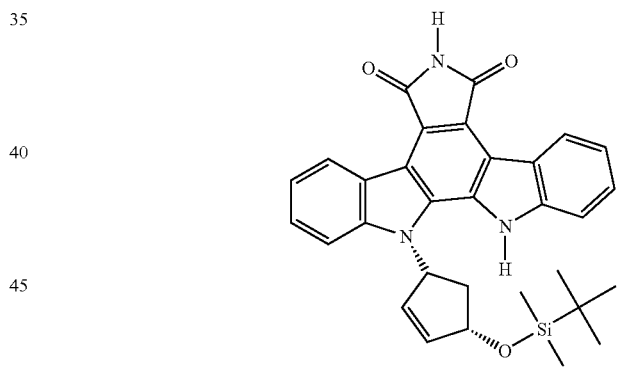

A solution of 1M KOtBu in THF (120 mL, 120 mmol) was added dropwise to a stirred solution of Ih (9.52 g, 40 mmol) and Ig (7.44 g, 20 mmol) in dry THF (400 mL) at rt under nitrogen atmosphere. After 45 minutes the reaction A solution of Ii (6.7 g, 12 mmol) and DIPEA (2.22 mL, 12 mmol) in EtOAc (300 mL) was irradiated with an halogen lamp. After 1 h irradiation the solution was cooled to rt, washed with water (120 mL), dried with sodium sulfate and concentrated in vacuo to give a solid residue (6.96 g). Purification by flash chromatography (silica gel, PE/EtOAc 3/1 as eluant mixture) afforded the pure target compound (3.6 g, yield 58%).

H-NMR (300 MHz, DMSO-d$_6$): δ 0.14 (3H, s, C$\underline{H}_3$—Si), 0.21 (3H, s, C$\underline{H}_3$—Si), 0.95 (9H, tBu), 2.13–2.24 (1H, dt, C$\underline{H}_2$), 3.24–3.36 (1H, m, C$\underline{H}_2$), 5.13 (1H, bt, C$\underline{H}$—O), 6.26–6.34 (2H, m, C$\underline{H}$=C$\underline{H}$), 6.44 (1H, bt, C$\underline{H}$—N), 7.38 (2H, t, indole $\underline{H}$s), 7.46 (1H, dt, indole $\underline{H}$s), 7.59 (1H, dt, indole $\underline{H}$s), 7.78 (1H, d, indole $\underline{H}$-7), 8.05 (1H, d, indole $\underline{H}$-7), 9.13 (1H, d, indole $\underline{H}$-4), 9.23 (1H, d, indole $\underline{H}$-4), 11.09 (1H, bs, imide N$\underline{H}$), 12.08 (1H, bs, indole N$\underline{H}$). MS (ESI) m/z 522[M+H]$^+$.

1) NAD 006

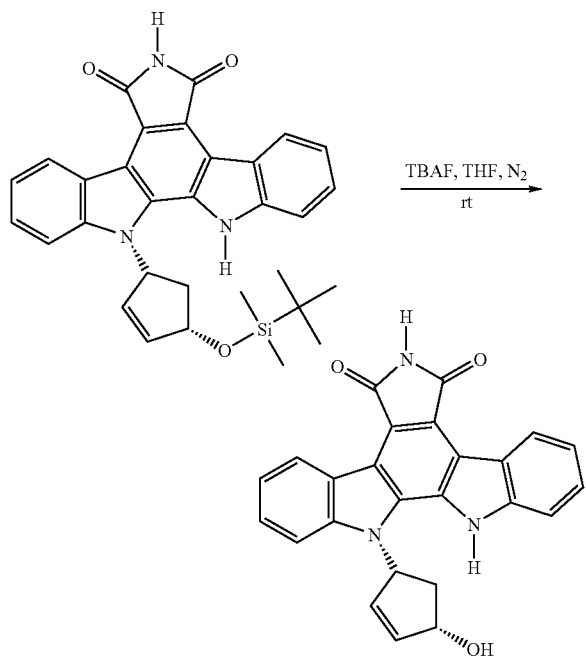

TBAF (1M in THF, 12 mL, 12 mmol) was added dropwise to a stirred solution of Ij (3.12 g, 6 mmol) in dry THF (120 mL) under nitrogen atmosphere at rt. After 2 hours the solution was diluted with EtOAc (1 L) and washed with 1N HCl (500 mL) and water (2×500 mL). The organic layer was dried over sodium sulfate, filtered and concentrated in vacuo to yield the pure target compound as an orange solid (2.27 g, yield 93%).

$^1$H-NMR (300 MHz, DMSO-$d_6$): δ 2.10–2.22 (1H, dt, C$\underline{H}_2$), 3.14–3.25 (1H, m, C$\underline{H}_2$), 4.99 (1H, bq, CH—OH), 5.58 (1H, s, O$\underline{H}$), 6.30 (2H, s, C$\underline{H}$=C$\underline{H}$), 6.41 (1H, bt, C$\underline{H}$—N), 7.39 (2H, dt, indole $\underline{H}$s), 7.53 (1H, dt, indole $\underline{H}$s), 7.60 (1H, dt, indole $\underline{H}$s), 7.79 (1H, d, indole $\underline{H}$-7), 8.04 (1H, d, indole $\underline{H}$-7), 9.14 (1H, d, indole $\underline{H}$-4), 9.23 (1H, d, indole $\underline{H}$-4), 11.10 (1H, bs, imide N$\underline{H}$), 12.07 (1H, bs, indole N$\underline{H}$). MS (ESI) m/z 408 [M+H]$^+$.

Example 2

NAD 009

2)

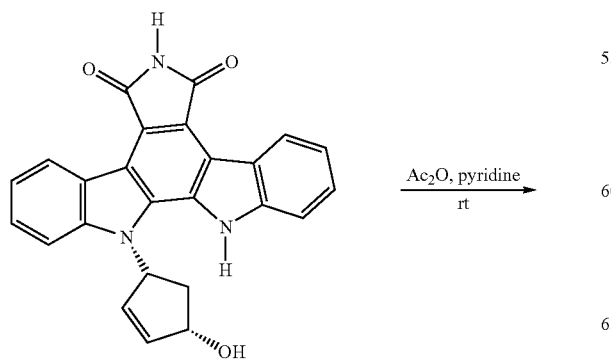

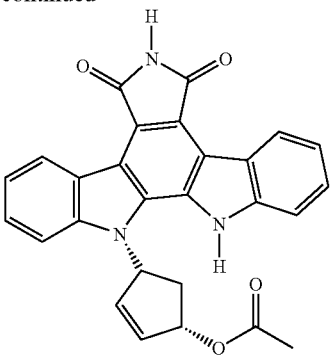

A solution of 1 (190 mg, 0.47 mmol) in pyridine (3 mL) and acetic anhydride (3 mL) was stirred for 1 hour at rt. The formed precipitate was filtered off and the solution was concentrated in vacuo at 60° C. to afford a solid residue. The crude was triturated with MeOH (10 mL) to afford the pure target compound (80 mg, yield 38%).

$^1$H-NMR (300 MHz, DMSO-$d_6$): δ 2.14 (3H, s, C$\underline{H}_3$—CO), 2.19–2.30 (1H, m, C$\underline{H}_2$), 3.36–3.44 (1H, m, C$\underline{H}_2$, 5.89 (1H, bt, C$\underline{H}$—OAc), 6.38 (1H, dt, C$\underline{H}$=CH—CH—OAc), 6.52 (1H, bt, C$\underline{H}$—N), 6.62 (1H, dt, CH=C$\underline{H}$—CH—OAc), 7.37–7.44 (2H, m, indole Hs 7.54–7.65 (2H, m, indole $\underline{H}$s), 7.80 (1H, d, indole $\underline{H}$-7), 7.85 (1H, d, indole $\underline{H}$-7), 9.15 (1H, d, indole $\underline{H}$-4), 9.24 (1H, d, indole $\underline{H}$-4), 0.13 (1H, bs, imide N$\underline{H}$), 12.11 (1H, bs, indole N$\underline{H}$). MS (ESI) m/z 450 [M+H]$^+$.

Example 3

NAD 156

3)

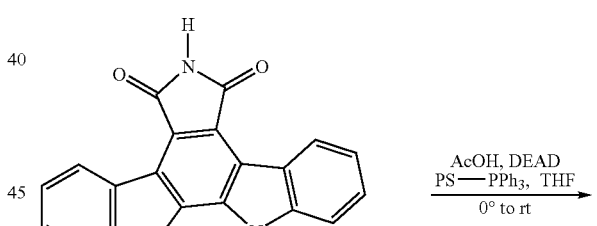

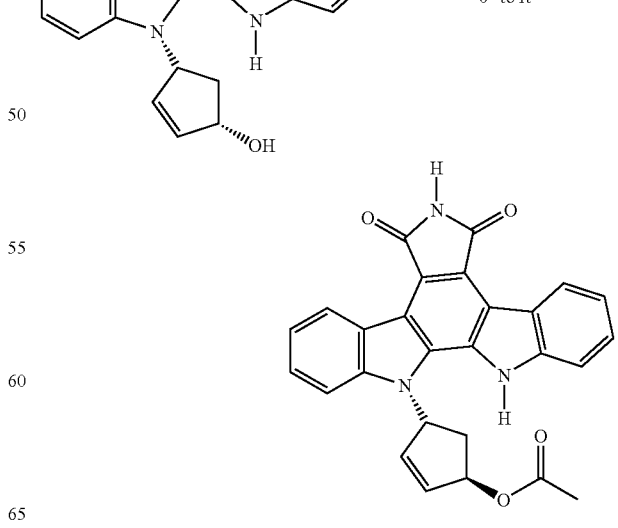

A solution of 1 (2.2 g, 5.18 mmol) and AcOH (1.26 mL, 21 mmol) in dry THF (40 ml) was treated with polystyrenebound PPh₃ (5 g, 15 mmoles) and the resulting suspension was cooled at 0° C. under N₂ atmosphere. A solution of DEAD (1.7 mL, 10.4 mmoles) in dry THF (10 mL) was added dropwise in 20 minutes, and stirring was continued for 30 minutes at 0° C. After warming to rt stirring was continued for 16 hours. The suspension was filtered and the solution was concentrated to give a solid residue (4 g). Purification by flash chromatography (silica gel, DCM/EtOAc 96/4 to 9/1 as eluant mixture) afforded the pure target compound (340 mg, yield 14.4%) together with the undesired cis-isomer (1.75 g, yield 75.1%).

¹H-NMR (300 MHz, DMSO-d₆): δ 1.83 (3H, s, CH₃—CO), 3.13–3.40 (2H, m, CH₂), 6.08–6.16 (2H, dt, CH=CH—CH—OAc), 6.25 (1H, bt, CH—N), 6.50 (1H, dt, CH=CH—OAc), 7.38–7.50 (3H, m, indole Hs), 7.60 (2H, t, indole Hs), 7.80 (1H, d, indole H-7), 9.14 (1H, d, indole 4), 9.25 (1H, d, indole H-4), 11.11 (1H, bs, imide NH), 12.11 (1H, bs, indole N. MS (ESI) m/z 450 [M+H]⁺.

Example 4

NAD 162

4)

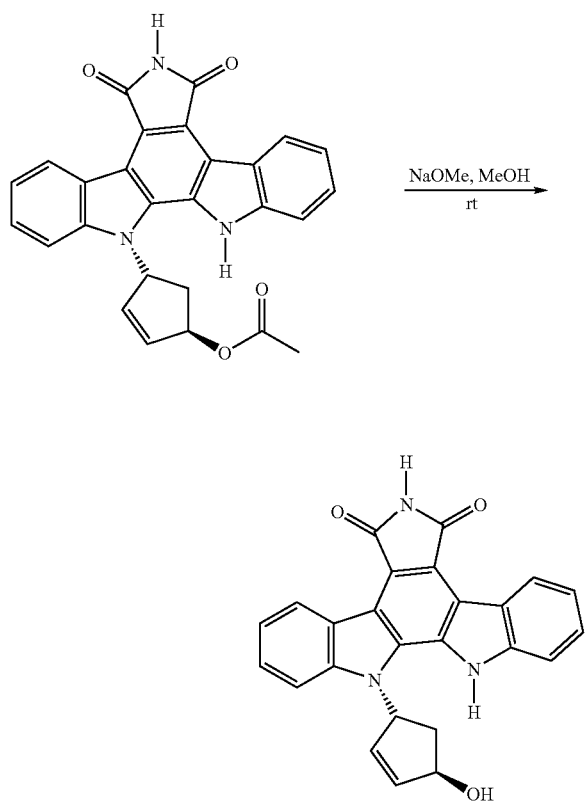

A solution of 3 (100 mg, 0.22 mmol) and NaOMe (5 mg, catalytic) in MeOH (5 mL) was stirred for 4 hours at rt. The resulting suspension was filtered, the solid was washed with cold MeOH and dried under vacuum to afford the pure target compound (43 mg, yield 47.8%).

¹H-NMR (300 MHz, DMSO-d₆): δ 3.05–3.16 (1H, dd, CH₂), 3.22–3.34 (1H, dd, CH₂), 5.40 (1H, bs, CH—OH), 5.59 (1H, bs, OH), 5.82, (1H, m, CH—N), 6.04 (1H, bt., N—CH—CH=), 6.24 (1H, dt, =CH—CH—OAc), 7.30–7.45 (3H, m, indole Hs), 7.54–762 (2H, dt, indole Hs+H-7), 7.78 (1H, d, indole H-7), 9.12 (1H, d, indole H-4), 9.22 (1H, d, indole H-4), 11.08 (1H, bs, imide NH), 12.10 (1H, bs, indole NH). MS (ESI) m/z 408 [M+H]⁺.

Example 5

NAD 040

5a)

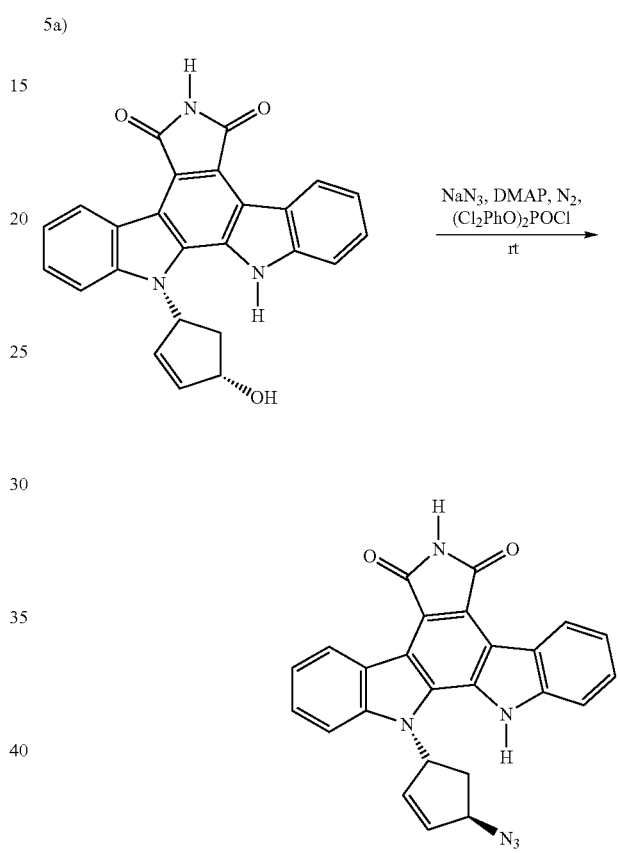

A stirred solution of 1 (1.18 g, 2.9 mmol) in dry DMF (15 mL) at rt under nitrogen atmosphere was treated sequentially with sodium azide (755 mg, 11.6 mmol), DMAP (435 mg, 3.48 mmol) and (Cl₂PhO)₂POCl (1.5 g, 3.5 mmol). After stirring for 16 hours the solution was diluted by addition of EtOAc (200 mL), washed with brine (100 mL), 32% aqueous NaOH (100 mL) and brine (2×100 mL). The organic layer was then dried over sodium sulfate, filtered and concentrated in vacuo to give a solid residue (2 g). Purification by flash chromatography (silica gel, PE/EtOAc 3/1 as eluant mixture) afforded the pure target compound (525 mg, yield 42%).

¹H-NMR (300 MHz, DMSO-d₆): δ 2.62–2.77 (2H, m, H 5.35 (1H, bd, CH—N₃), 6.41–6.46 (1H, dt, CH=CH—CH—N₃), 6.54 (1H, bd, CH=CH—CH—N₃), 6.83 (1H, bt, CH—N), 7.38 (2H, dt, indole Hs), 7.51 (1H, dt, indole Hs), 7.56–64 (2H, m, indole Hs+H-7), 7.82 (1H, d, indole H-7), 9.14 (1H, d, indole H-4), 9.24 (1H, d, indole H-4), 11.11 (1H, bs, imide NE, 12.21 (1M, bs, indole NH). MS (ESI) m/z 433 [M+H]⁺.

5) NAD 040

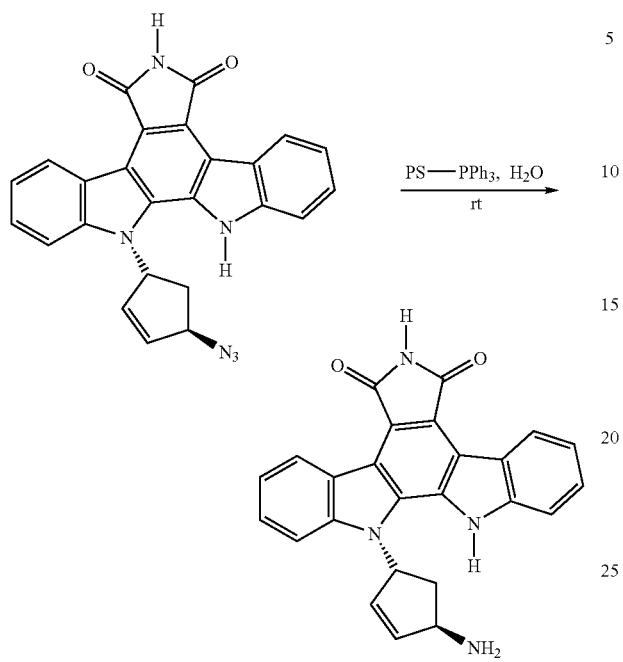

A solution of 5a (100 mg, 0.23 mmol) in THF/water 10/1 (5.5 mL) was stirred overnight at rt in presence of polymer-supported triphenylphosphine (480 mg, 1.4 mmol). The suspension was then filtered off and the insoluble material washed with THF (2×10 mL). The organic layers were then diluted with EtOAc (250 mL), dried over sodium sulfate, filtered and concentrated in vacuo to yield the pure target compound (90 mg, yield 96%).

$^1$H-NMR (300 MHz, DMSO-$d_6$): 5.2.49–2.67 (2H, m, C$\underline{H}_2$), 5.12–5.19 (1H, m, C$\underline{H}$—NH$_2$), 6.14–6.24 (2H, m, C$\underline{H}$=C$\underline{H}$), 6.87 (1H, bt, C$\underline{H}$—N), 7.34–7.42 (2H, m, indole H$\underline{s}$), 7.50–7.62 (2H, m, indole Hs), 7.73 (1H, d, indole H-7), 7.79 (1H, d, indole 7), 9.13 (1H, d, indole H-4), 9.23 (1H, d, indole H-4), 11.08 (1H, bs, imide N$\underline{H}$), 12.25 (1H, bs, indole N$\underline{H}$). MS (ESI) m/z 407 [M+H]$^+$.

Example 6

NAD 116

6a)

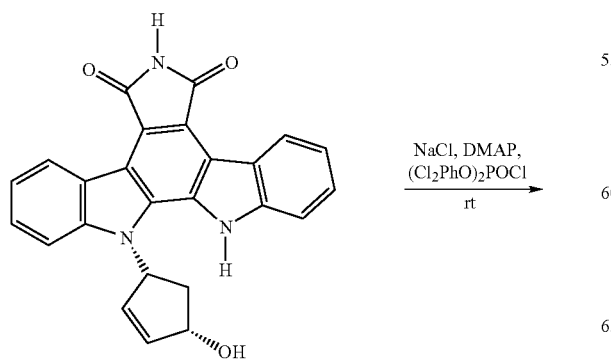

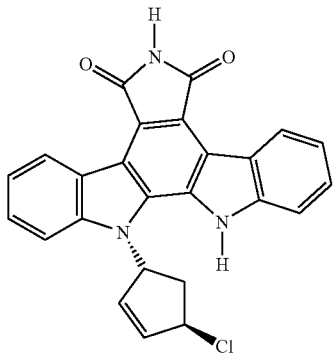

A stirred solution of 1 (2.05 g, 5 mmol) in dry DMF (30 mL) was treated under nitrogen atmosphere sequentially with NaCl (2.16 g, 36 mmol), DMAP (900 mg, 7.2 mmol) and (Cl$_2$PhO)$_2$POCl (3 g, 7.2 mmol) at rt. After stirring for 2 hours the solution was diluted by addition of EtOAc (500 mL), washed with brine (200 mL), 32% aqueous NaOH (200 mL) and brine (2×200 mL). The organic layer was then dried over sodium sulfate, filtered and concentrated in vacuo to give a solid residue (2.04 g). Purification by flash chromatography (silica gel, PE/EtOAc 7/3 to 6/4 as eluant mixture) afforded the pure target compound (960 mg, yield 45.4%).

$^1$H-NMR (300 MHz, DMSO-$d_6$): δ 2.43–2.52 (1H, m, C$\underline{H}_2$), 3.56–3.68 (1H, m, C$\underline{H}_2$), 5.48 (1H, bt, C$\underline{H}$—Cl), 6.42 (1H, dt, C$\underline{H}$=CH—CH—Cl), 6.57 (1H, dt, CH=C$\underline{H}$—CH—Cl), 6.63 (1H, bt, C$\underline{H}$—N), 7.39 (2H, q, indole H$\underline{s}$), 7.53–7.63 (2H, dt, indole H$\underline{s}$), 7.77 (1H, d, indole H-7), 7.88 (1H, d, indole H-7), 9.13 (1H, d, indole H-4), 9.24 (1H, d, indole H-4), 11.10 (1H, bs, imide N$\underline{H}$), 12.12 (1H, bs, indole N$\underline{H}$). MS (ESI) m/z 426 [M+H]$^+$.

6) NAD 116

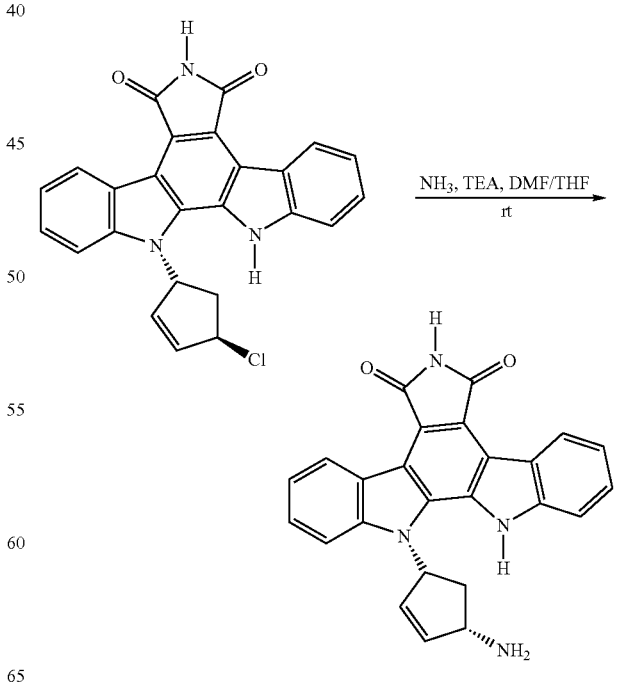

A solution of 6a (190 mg, 0.45 mmol) and TEA (0.37 ml, 2.65 mmol) in 1/1 dry DMF/THF (4 mL) was treated with gaseous ammonia for 30 minutes under stirring at rt. After 24 hours the solution was diluted with EtOAc (50 mL) and washed with water (3×20 mL). The organic layer was dried with sodium sulfate, filtered and concentrated in vacuo to afford a crude (170 mg). Purification by preparative TLC (silica gel, EtOAc/MeOH 9/1 as eluant mixture) produced the pure title compound (30 mg, yield 16.2%).

¹H-NMR (300 MHz, DMSO-$d_6$): δ 2.18–2.25 (1H, m, C<u>H</u>$_2$), 3.09–3.16 (1H, m, C<u>H</u>$_2$), 4.36–4.41 (1H, m, C<u>H</u>—NH$_2$), 6.22–6.31 (2H, m, C<u>H</u>=C<u>H</u>), 6.92 (1H, bt, C<u>H</u>—N), 7.38 (2H, t, indole <u>H</u>s), 7.51 (1H, t, indole <u>H</u>s), 7.59 (1H, t, indole <u>H</u>s), 7.69 (1H, d, indole <u>H-7</u>), 7.83 (1H, d, indole <u>H</u>s), 9.14 (1H, d, indole <u>H-7</u>), 9.22 (1H, d, indole <u>H-4</u>), 11.10 (1H, bs, imide N<u>H</u>), 12.20 (1H, bs, indole N<u>H</u>). MS (ESI) m/z 407 [M+H]⁺.

Example 7

NAD 105

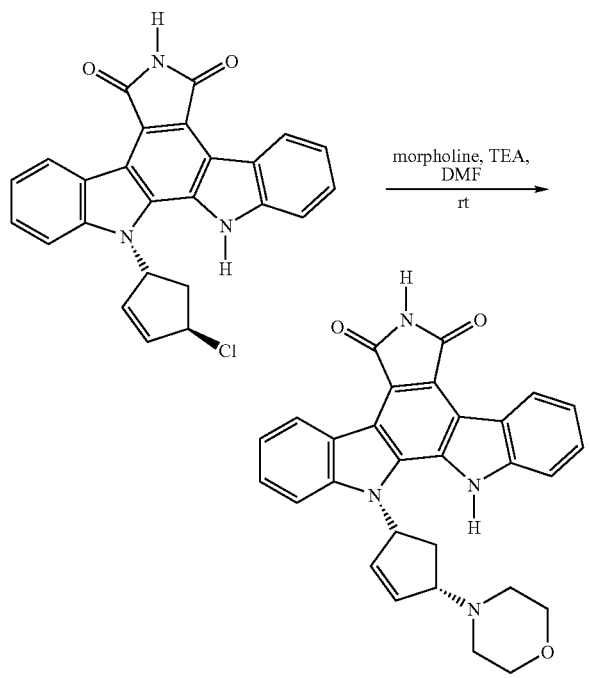

A solution of 6a (150 mg, 0.35 mmol), TEA (280 μL, 2 mmol) and morpholine (75 μL, 0.84 mmol) in dry DMF (2 mL) was stirred at rt for 6 hours under nitrogen atmosphere. The solution was then diluted with EtOAc (25 mL) and washed with water (3×10 mL). The organic layer was dried with sodium sulfate, filtered and concentrated in vacuo to afford a crude (180 mg). Purification by trituration with EtOAc/MeOH produced the pure title compound (85 mg, yield 49.0%).

¹H-NMR (300 MHz, DMSO-$d_6$): δ 2.26–2.37 (1H, m, cyclopentane C<u>H</u>$_2$), 2.56–2.86 (5H, m, morpholine C<u>H</u>$_2$—N and cyclopentane C<u>H</u>$_2$), 3.71 (4H, bt, morpholine C<u>H</u>$_2$—O), 4.24–4.32 (1H, m, C<u>H</u>—NH$_2$), 6.31 (1H, d, C<u>H</u>=CH—CH—N-morpholine), 6.43 (1H, d, CH=C<u>H</u>—CH—N-morpholine), 6.73 (1H, bt, C<u>H</u>—N), 7.41 (2H, t, indole <u>H</u>s), 7.55 (1H, t, indole Hs) 7.59–7.66 (2H, m, indole <u>H</u>s+<u>H-7</u>), 7.83 (1H, d, indole <u>H-7</u>), 9.16 (1H, d, indole <u>H-4</u>), 9.26 (1H, d, indole <u>H-4</u>), 11.11 (1H, bs, imide N<u>H</u>, 12.15 (1H, bs, indole N<u>H</u>). MS (ESI) m/z 477 [M+H]⁺.

Example 8

NAD 118

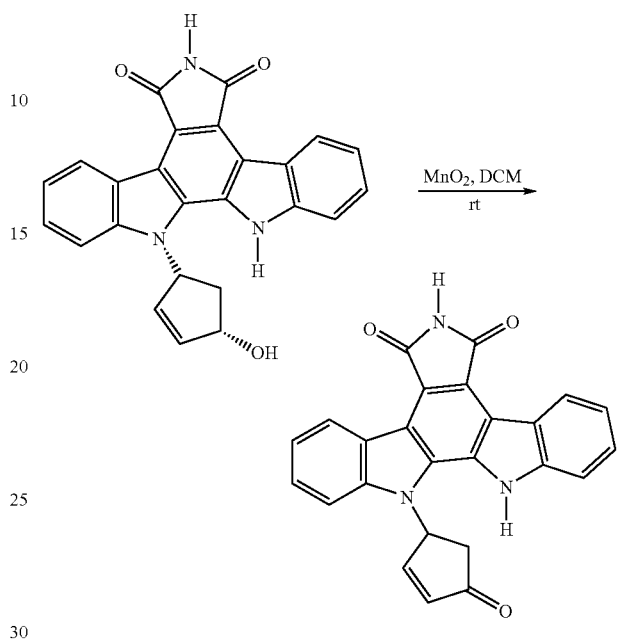

A suspension of 1 (1.95 g, 4.78 mmol) and activated MnO$_2$ (7 g, 6 mmol) in DCM (50 mL) was vigorously stirred for 24 hours at rt. The suspension was filtered through a short pad of celite and the resulting solution was concentrated in vacuo to give a crude product (1.35 g). Purification by flash chromatography (silica gel, EtOAc/THF 9/1 as eluant mixture) provided the pure target compound (390 mg, yield 20%).

¹H-NMR (300 MHz, DMSO-$d_6$): δ 2.99 (1H, dt, C<u>H</u>$_2$), 3.24–3.36 (1H, m, C<u>H</u>$_2$), 6.78 (1H, dt, CH=C<u>H</u>—CO), 6.84 (1H, bt, C<u>H</u>—N), 7.35–7.67 (5H, m, indole <u>H</u>s+<u>H-7</u>), 7.76 (1H, d, indole <u>H-7</u>), 8.31 (1H, dd, C<u>H</u>=CH—CO), 9.13 (1H, d, indole <u>H-4</u>), 9.22 (1H, d, indole <u>H-4</u>), 11.12 (1H, bs, imide N<u>H</u>), 12.12 (1H, bs, indole N<u>H</u>). MS (ESI) m/z 406 [M+H]⁺.

Example 9

NAD 160

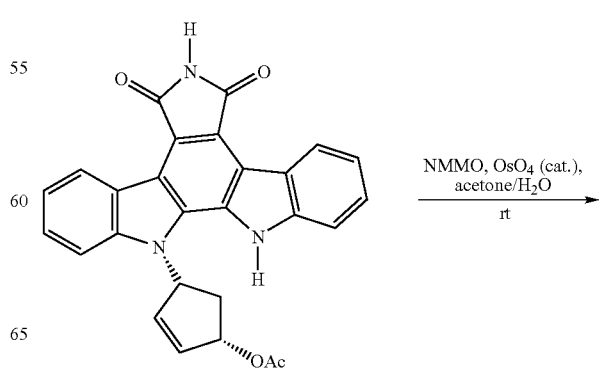

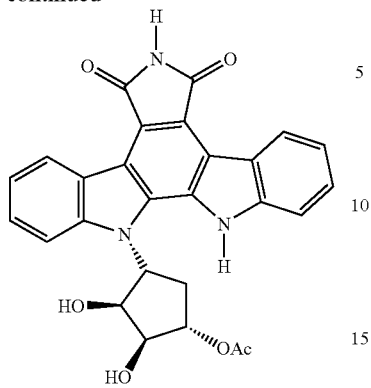

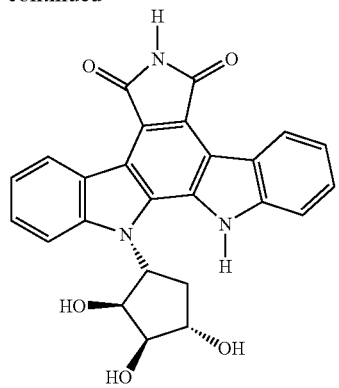

A suspension of 2 (1.1 g, 2.44 mmol) in acetone (75 mL) was treated sequentially with NMMO (445 mg, 3.66 mmol), OsO$_4$ (2.5% in tBuOH, 2 mL, catalytic) and water (1 mL). The suspension was vigorously stirred for 48 hours at rt. The suspension was filtered and the solid washed to give a first crop of pure target compound (480 mg). The solution was concentrated, dissolved in EtOAc (100 mL), washed with sodium bisulfite (25 mL) and water (2×25 mL), dried over sodium sulfate and concentrated to give a crude solid residue (800 mg). Purification by flash chromatography (silica gel, PE/EtOAc 1/1 to pure EtOAc as eluant mixture) provided a second crop of the pure target compound (290 mg, total yield 65.2%).

$^1$H-NMR (300 MHz, DMSO-d$_6$): δ 2.28 (3H, s, C$\underline{H_3}$—CO), 2.50–2.62 (1H, m, C$\underline{H_2}$), 3.08–3.22 (1H, m, C$\underline{H_2}$), 4.12 (1H, bs, O$\underline{H}$), 4.91 (1H, bs, O$\underline{H}$), 5.21 (1H, m, C$\underline{H}$—OAc), 5.38–5.50 (2H, m, C$\underline{H}$—OH), 5.68 (1H, q, C$\underline{H}$—N), 7.42 (2H, q, indole $\underline{H}$s), 7.62 (2H, t, indole $\underline{H}$s), 7.76 (1H, d, indole $\underline{H}$-7), 8.20 (1H, bd, indole $\underline{H}$-7), 9.17 (1H, d, indole $\underline{H}$-4), 9.30 (1H, d, indole $\underline{H}$-4), 11.12 (1H, bs, imide N$\underline{H}$, 12.06 (1H, bs, indole N$\underline{H}$). MS (ESI) m/z 442 [M+H]$^+$.

Example 10

NAD 180

10)

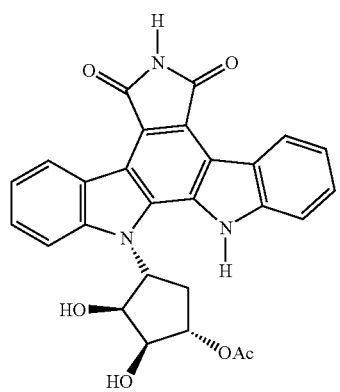

A suspension of 9 (150 g, 0.31 mmol) and NaOMe (5 mg, catalytic) in MeOH (5 mL) was stirred for 4 hours at rt. The resulting suspension was filtered, the solid was washed with cold MeOH and dried under vacuum to afford the pure target compound (65 mg, yield 47.4%).

$^1$H-NMR (300 MHz, DMSO-d$_6$): δ 2.35–2.45 (1H, m, C$\underline{H_2}$), 2.97–3.11 (1H, m, H), 3.99 (1H, bs, O$\underline{H}$), 4.27 (1H, bd, O$\underline{H}$), 5.02 (1H, m, C$\underline{H}$—OH), 5.15–5.32 (2H, m, C$\underline{H}$—OH), 5.66 (1H, q, C$\underline{H}$—N), 7.38–7.52 (2H, m, indole $\underline{H}$s), 7.66 (2H, q, indole $\underline{H}$s), 7.83 (1H, d, indole $\underline{H}$-7), 8.01 (1H, d, indole $\underline{H}$-7), 9.15 (1H, d, indole $\underline{H}$-4), 9.30 (1H, d, indole $\underline{H}$-4), 11.14 (1H, bs, imide N$\underline{H}$), 11.82 (1H, bs, indole N$\underline{H}$). MS (ESI) m/z 484 [M+H]$^+$.

Example 11

NAD 188

11)

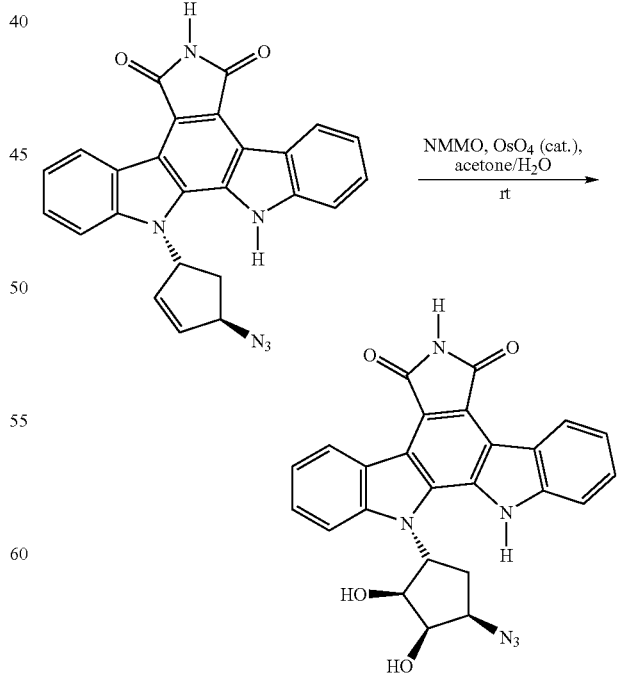

A suspension of 5a (1.5 g, 3.47 mmol) in acetone (75 mL) was treated sequentially with NMMO (630 mg, 5.2 mmol), OSO₄ (2.5% in tBuOH, 2.5 mL, catalytic) and water (1 mL). The suspension was vigorously stirred for 48 hours at rt and became a clear solution. The solution was diluted with EtOAc (500 mL), washed with sodium bisulfite (100 mL) and water (2×100 mL), dried over sodium sulfate and concentrated to give the pure target compound (1.3 g, yield 85.8%).

¹H-NMR (300 MHz, DMSO-d₆): δ 2.82 (2H, t, C$\underline{H}_2$), 4.20 (1H, m, C$\underline{H}$—N₃), 4.49 (1H, bt, C$\underline{H}$—OH), 4.67 (1H, m, C$\underline{H}$—OH), 5.47 (1H, d, O$\underline{H}$), 5.61 (1H, d, O$\underline{H}$), 5.80 (1H, q, C$\underline{H}$—N), 7.30–7.43 (2H, m, indole $\underline{H}$s), 7.54–7.60 (2H, m, indole $\underline{H}$s), 7.76 (1H, d, indole $\underline{H}$-7), 7.84 (1H, d, indole $\underline{H}$-7), 9.12 (1H, d, indole $\underline{H}$-4), 9.24 (1H, d, indole $\underline{H}$-4), 11.08 (1H, s, imide N$\underline{H}$), 11.72 (1H, s, indole N$\underline{H}$). MS (ESI) m/z 467 [M+H]⁺.

Example 12

NAD 150

12a)

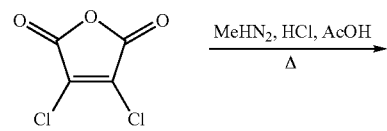

A solution of methylamine hydrochloride (40.0 g, 592 mmol) and 3,4-dichloromaleic anhydride (98.8 g, 592 mmol) in AcOH (1 L) was refluxed for 6 hours. The reaction mixture was cooled to 35° C. and the solvent was evaporated in vacuo. Water (500 mL) was added and the precipitate was filtered, washed with water (2×250 mL) and EtOH (2×250 mL) to give after drying in vacuo the pure target compound (74.5 g, yield 70.1%).

¹H-NMR (300 MHz, CDCl₃): δ 3.14 (3H, s, N—C$\underline{H}_3$). MS (ESI) m/z 271 [M+AcOH+MeOH]⁺.

12b)

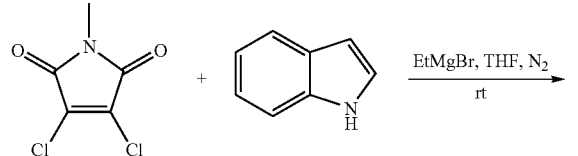

Ethylmagnesium bromide (1M solution in THF, 140 mL, 140 mmol) was added to a solution of indole (16.4 g, 140 mmol) in dry THF (46 mL) under nitrogen atmosphere at rt. The solution was heated to 40° C. for 45 minutes, then cooled to rt. A solution of 12a (20 g, 70 mmol) in THF (120 ml) was added dropwise and the reaction mixture was then stirred for 4 hours at rt. 20% citric acid solution (100 mL) was added and the mixture was extracted with AcOEt (300 mL). The organic layer was washed with water (2×150 mL), dried over sodium sulfate and concentrated in vacuo. Purification by flash chromatography (silica gel, PE/EtOAc 3/1 as eluant mixture) afforded the pure target compound (24.1 g, yield 95.2%).

¹H-NMR (300 MHz, DMSO-d₆): 3.02 (3H, s, N-C$\underline{H}_3$), 7.10–7.20 (2H, m, indole $\underline{H}$s), 7.53 (1H, dd, indole $\underline{H}$-7), 7.95 (1H, dd, indole $\underline{H}$-4), 8.10 (1H, d, indole $\underline{H}$-2), 12.17 (1H, bs, indole N$\underline{H}$). MS (ES) m/z 367 [M+H]⁺.

12c)

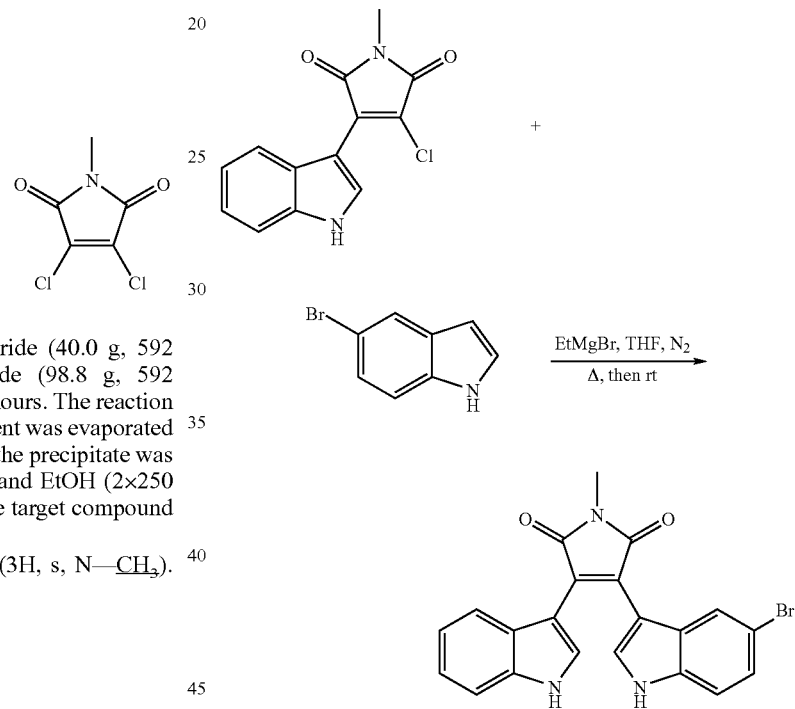

Ethylmagnesiumbromide (3M solution in Et₂O, 15 mL, 48 mmol) was added to a solution of 5-bromoindole (7.8 g, 40 mmol) in dry THF (60 mL) under nitrogen atmosphere at rt. The solution was heated at 45° C. for 1 hour, then cooled to rt. A solution of compound 12b in toluene (1.5 mL) was then added dropwise and the resulting solution was refluxed for 2.5 hours, then cooled and stirred at rt overnight. The reaction mixture was quenched by a saturated solution of ammonium chloride (80 mL) and extracted with EtOAc (200 mL). The organic phase was washed with water (100 mL), dried over sodium sulfate and concentrated in vacuo to yield a solid residue. Purification by flash chromatography (silica gel, PE/EtOAc 1/1 as eluant mixture) gave the pure target compound (5.4 g, yield 80.1%).

¹H-NMR (300 MHz, DMSO-d₆): δ 3.07 (3H, s, N—C$\underline{H}_3$), 6.65 (2H, m, indole $\underline{H}$s), 6.99 (2H, dt, indole $\underline{H}$-6), 7.10 (1H, dd, indole $\underline{H}$-7), 7.36 (1H, d, indole $\underline{H}$-4), 7.41 (H, d, indole $\underline{H}$-7'), 7.76 (1H, d, indole $\underline{H}$-2), 7.84 (1H, d, indole $\underline{H}$-2'), 11.80 (1H, s, indole N$\underline{H}$), 11.85 (1H, s, indole N$\underline{H}$). MS (ESI) m/z 420 [M+H]⁺.

12d)

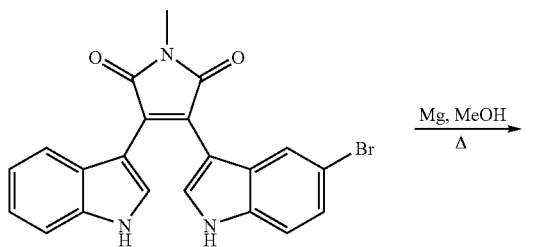

Magnesium turnings (3.7 g, 153.5 mmol) were added at rt to a solution of 12c (3.5 g, 8.3 mmol) in dry methanol (150 mL). The vigorously stirred suspension was refluxed for 1.5 hours, then cooled to rt, quenched with 5 M HCl (50 mL) and extracted with EtOAc (2×100 mL). The organic phase was washed with water (100 mL), dried over sodium sulfate and concentrated in vacuo. Purification of the solid residue by flash chromatography (silica gel, PE/EtOAc 1/1 as eluant mixture) afforded the pure target compound (2.4 g, yield 66.9%).

$^1$H-NMR (300 MHz, DMSO-d$_6$): δ 3.05 (3H, s, N—C$_3$), 4.65 (2H, s, CH—CH), 6.89 (1H, dt, indole Hs), 7.10 (1H, dt, indole Hs), 7.20 (1H, dd, indole Hs), 7.41 (4H, m, indole Hs), 7.54 (1H, d, indole H-2), 7.81 (1H, d, indole H-2'), 11.25 (1H, s, indole NH), 11.40 (1H, s, indole NH). MS (ESI) m/z 422 [M+H]$^+$.

12e)

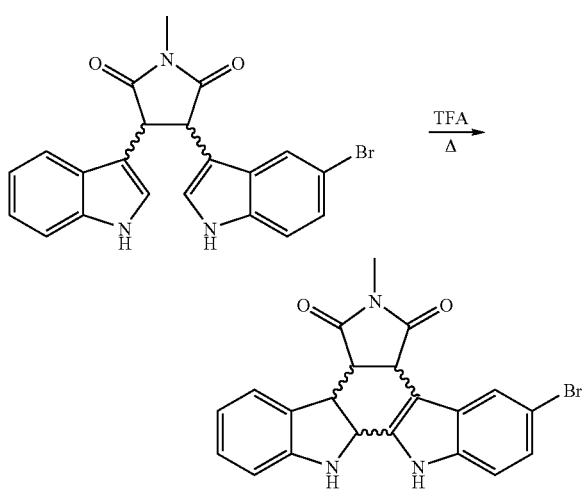

A solution of 12d (2 g, 4.7 mmol) in neat TFA (30 mL, 391 mmol) was refluxed under nitrogen atmosphere for 12 hours. The solution was then cooled to rt, treated with 1N NaOH (100 mL) and extracted with EtOAc (2×150 mL). The organic phase was washed with water (150 mL), dried over sodium sulfate and concentrated in vacuo. Purification of the solid residue by flash chromatography (silica gel, PE/EtOAc 3/2 as eluant mixture) afforded the pure target compound (0.49 g, yield 25.4%).

$^1$H-NMR (300 MHz, DMSO-d$_6$): δ 2.84 (3H, s, N—CH$_3$), 4.17 (1H, d, indoline H-2), 4.21 (1H, dd, indoline H-3), 4.31 (1H, dd, indoline NH—CH—CH—CH), 4.75 (1H, d, indole NH—CH=CH—CH), 5.90 (1H, s, indoline NH), 6.55 (1H, d, indole/ine Hs), 6.62 (1H, t, indole/ine Hs), 6.92 (1H, t, indole/ine Hs), 7.20 (2H, m, indole/ine Hs), 7.32 (1H, d, indole/ine Hs), 7.93 (1H, d, indole/ine Hs), 11.20 (1H, s, indole NH). MS (ESI) m/z 422 [M+H]$^+$.

12) NAD 150

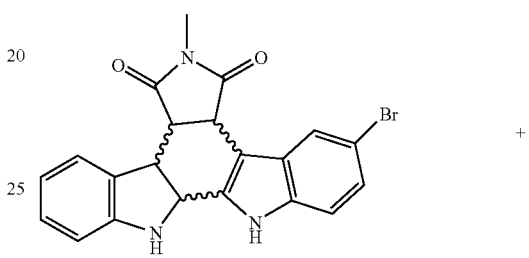

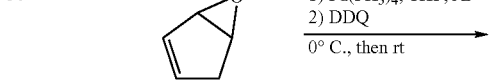

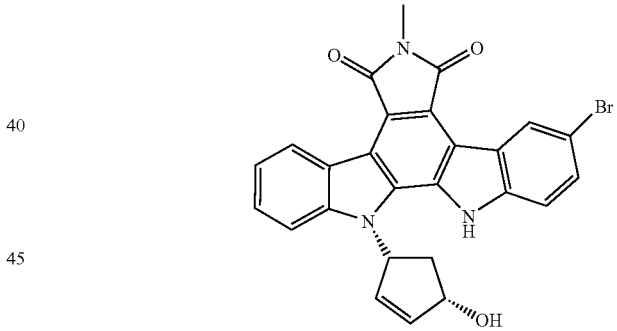

A solution of compound 12e (0.3 g, 0,71 mmol) and palladium tetrakis (5 mg, catalytic) in anhydrous THF (2 mL) was cooled at 0° C. under argon atmosphere. Ia (0.12 g, 1.5 mmol) in dry THF (2 mL) was added dropwise and the reaction was stirred at rt for 5 hours. DDQ (0.34 g, 1.5 mmol) was then added and after 1 hour stirring the solvent was concentrated in vacuo. Double purification by flash chromatography (silica gel, PE/EtOAc 3/1 and PE/EtOAc 1/1 as eluant mixtures) gave the pure target compound (90 mg, 25.0%).

$^1$H-NMR (300 MHz, DMSO-d$_6$): δ 2.16 (1H, m, CH$_2$), 3.20 (3H, s, N—CH$_3$), 3.22 (1H, m, CH$_2$), 4.97 (1H, bq, CH—OH), 5.57 (1H, bd, CH—N), 6.30 (3H, m, CH=CH+CH—OH), 7.36 (1H, bt, indole Hs), 7.50 (1H, bt, indole Hs), 7.70 (2H, bs, indole Hs), 8.00 (1H, d, indole H-7'), 9.14 (1H, d, indole H-6'), 9.21 (1H, s, indole H-4'), 12.14 (1H, s, indole NH). MS (ESI) m/z 500 [M+H]$^+$.

Example 13

NAD 182

13a)

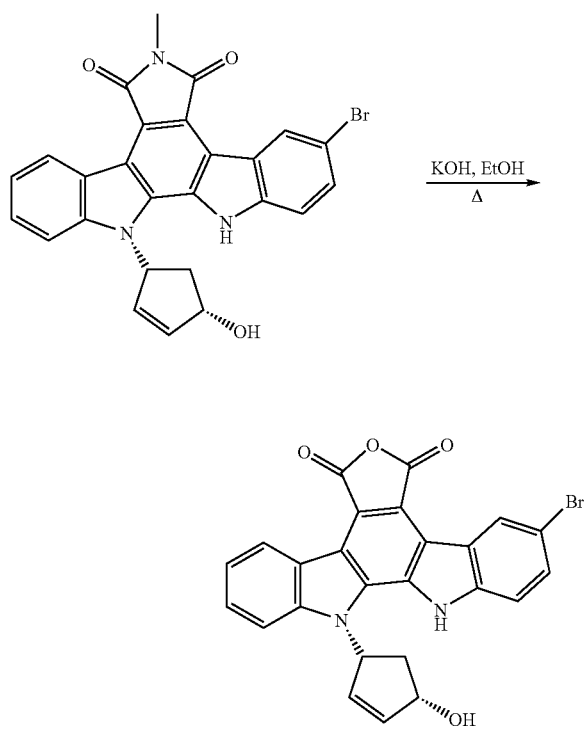

A suspension of compound 12 (0.25 g, 0.5 mmol) and KOH (0.28 g, 5 mmol) in ethanol (20 mL) was heated at reflux overnight. The reaction mixture was cooled to rt, acidified by addition of 1N HCl (10 mL) and extracted with EtOAc (2×40 mL). The organic phase was washed with water, dried over sodium sulfate and concentrated to dryness to give the pure target compound (0.25 g, quantitative yield).

$^1$H-NMR (300 MHz, DMSO-d$_6$): δ 2.17 (1H, m, CH$_2$), 3.23 (1H, m, CH$_2$), 4.96 (H, bq, CH—OH), 5.6 (1H, bs, OH), 6.30 (2H, s, CH=CH), 6.35 (1H bt CH—N), 7.33–7.76 (4H, m, indole Hs), 8.08 (1H, d, indole Hs), 8.91 (2H, m, indole Hs), 12.48 (1H, s, indole NH).

13) NAD 182

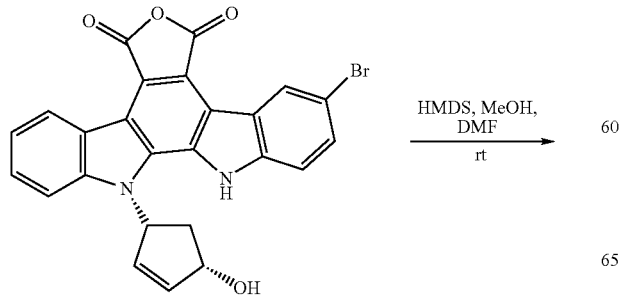

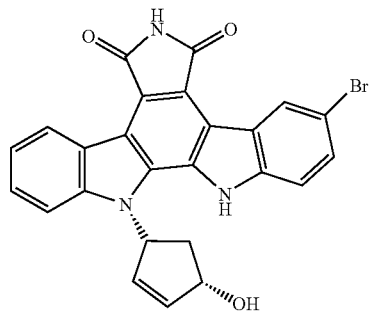

HMDS (1.06 mL, 5.1 mmol) in MeOH (130 μL, 2.55 mmol) was added to a solution of 13a (250 mg, 0.51 mmol) in dry DMF (4 mL). The mixture was stirred overnight at rt, then treated with 0.5 N HCl (10 mL) and extracted with EtOAc (80 mL). The organic phase was washed with water, dried over sodium sulfate and concentrated in vacuo. The residue was dissolved in anhydrous THF (10 mL) and TBAF (1M in THF, 1.02 mL, 1.02 mmol) was added. After 1 hour the solvent was removed in vacuo to provide a solid residue. Purification by flash chromatography (silica gel, DCM/EtOAc 9/1 as eluant mixture) afforded the pure target compound (40 mg, yield 20.5%).

$^1$H-NMR (300 MHz, DMSO-d$_6$): δ 2.13 (1H, m, CH$_2$), 3.25 (1H, m, CH$_2$), 4.9 (1H, bq, CH—OH), 5.54 (1H, bd, OH), 6.26 (2H, s, CH=CH), 6.34 (1H, bt, CH—N), 7.36 (1H, t, indole Hs), 7.53 (1H, dt, indole Hs), 7.69 (2H, m, indole Hs), 8.00 (1H, d, indole Hs), 9.17 (2H, d, indole H-4), 11.13 (1H, s, imide NH), 12.20 (1H, s, indole NH). MS (ESI) m/z 500 [M+H]$^+$.

Example 14

NAD 179

14a)

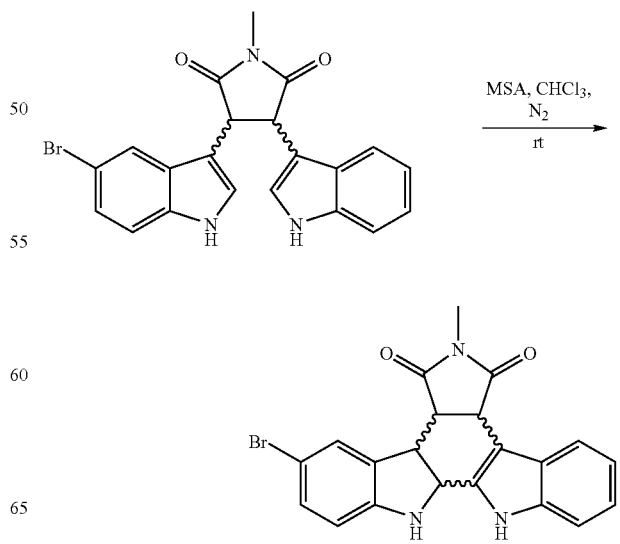

Methanesulfonic acid (0.46 mL, 7.1 mmol) was added to a solution of 12d (0.6 g, 1.42 mmol) in chloroform (26 mL) and the solution was stirred for 5 hours under nitrogen atmosphere at rt. The reaction mixture was treated with 1N NaOH (10 mL) and extracted with EtOAc (40 mL). The organic phase was washed with water (25 mL), dried over sodium sulfate and concentrated in vacuo. Purification by flash chromatography of the residue (silica gel, PE/EtOAc 1/1 as eluant mixture) afforded the pure target compound (0.24 g, yield 38.3%).

$^1$H-NMR (300 MHz, DMSO-$d_6$): δ 2.97 (3H, s, N—CH$_3$), 3.74 (1H, dd, indoline NH—CH—CH—CH), 3.97 (1H, d, indoline NH—CH), 4.48 (1H, dd, indoline NH—CH—CH), 5.22 (1H, d, indole NH—CH=CH—CH), 6.08 (1H, bs, indoline NH), 6.47 (1H, d, indole/ine Hs), 7.05 (4H, m, indole/ine Hs), 7.35 (1H, d, indole/ine Hs), 8.17 (1H, d, indole/ine Hs), 11.15 (1H, s, indole NH). MS (ESI) m/z 422 [M+H]$^+$.

14) NAD 179

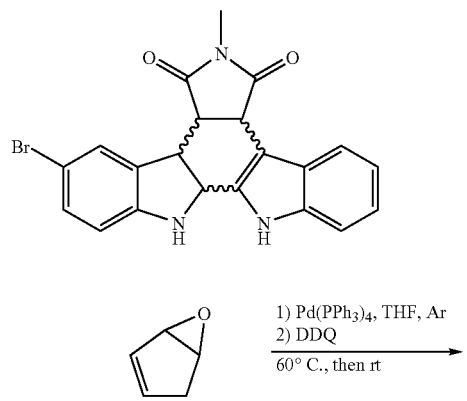

A solution of compound 14a (0.24 g, 0.6 mmol) and palladium tetrakis (12 mg, catalytic) in dry THF (3 mL) was cooled at 0° C. under argon atmosphere. 1a (0.4 g, 6 mmol) in dry THF (3 mL) was added dropwise and the reaction was stirred overnight at rt, then for 2 hours at 60° C. DDQ (0.27 g, mmol) was added and after 2 hours stirring at rt the solvent was concentrated in vacuo. Double purification by flash chromatography (silica gel, PE/EtOAc 2.5/1 and DCM/EtOAc 96/4 as eluant mixtures) gave the pure target compound (50 mg, yield 16.2%).

$^1$H-NMR (300 MHz, DMSO-$d_6$): δ 2.12 (1H, m, CH$_2$), 3.16 (3H, s, N—CH$_3$, 3.19 (1H, m, CH$_2$), 4.97 (1H, bq, CH—OH), 5.58 (1H, bd, OH), 6.30 (2H, s, CH=CH), 6.37 (1H, bt, CH—N), 7.39 (1H, t, indole Hs), 7.67–7.54 (2H, m, indole Hs), 7.8 (1H, d, indole Hs), 7.99 (1H, d, indole Hs), 9.13 (1H, d, indole H-4), 9.37 (1H, d, indole H-4), 12.13 (1H, s, indole NH). MS (ESI) m/z 500 [M+H]$^+$.

Example 15

NAD 185

15a)

A suspension of compound 14 (380 mg, 0.76 mmol) and KOH (425 mg, 7.6 mmol) in ethanol (25 mL) was heated at reflux overnight. The reaction mixture was cooled to rt, acidified by addition of 1N HCl (10 mL) and extracted with EtOAc (2×40 mL). The organic phase was washed with water, dried over sodium sulfate and concentrated to dryness to give the pure target compound (450 mg, quantitative yield).

$^1$H-NMR (300 MHz, DMSO-$d_6$): δ 2.17 (1H, m, CH$_2$), 3.23 (1H, m, CH$_2$), 4.96 (1H, bq, CH—OH), 5.6 (1H, bs, OH), 6.30 (2H, s, CH=CH), 6.35 (1H, bt, CH—N), 7.33–7.76 (4H, m, indole Hs), 8.08 (1H, d, indole Hs), 9.17 (1H, d, indole H-4), 9.38 (1H, d, indole H-4), 12.50 (1H, s, indole NH).

15) NAD 185

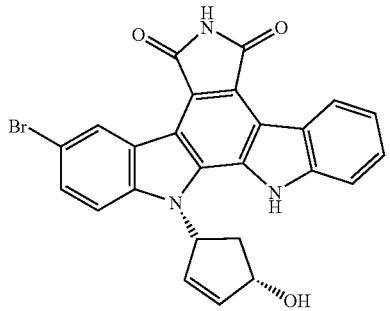

HMDS (1.58 ml, 7.6 mmol) in MeOH (0.15 ml, 3.8 mmol) was added to a solution of 15a (450 mg, 0.76 mmol) in dry DMF (5 mL). The mixture was stirred overnight at rt, then treated with 0.5 N HCl (10 mL) and extracted with EtOAc (50 mL). The organic phase was washed with water, dried over sodium sulfate and concentrated in vacuo. The residue was dissolved in dry THF (10 mL) and TBAF (1M in THF, 1.52 mL, 1.52 mmol) was added. After 1 hour stirring at rt the solvent was concentrated in vacuo. Purification by flash chromatography (silica gel, DCM/EtOAc 9/1 as eluant mixture) and crystallization from EtOAc afforded the pure target compound (40 mg, yield 11.2%).

$^1$H-NMR (300 MHz, DMSO-$d_6$): δ 2.10 (1H, m, C$\underline{H}_2$), 3.18 (1H, m, C$\underline{H}_2$), 4.95 (1H, bq, C$\underline{H}$—OH), 5.56 (1H, bd, O$\underline{H}$), 6.27 (2H, s, C$\underline{H}$=C$\underline{H}$), 6.41 (1H, bt, C$\underline{H}$—N), 7.35 (1H, t, indole $\underline{H}$s), 7.58 (1H, dt, indole $\underline{H}$s), 7.76 (1H, dd, indole $\underline{H}$s), 7.76 (1H, d, indole $\underline{H}$s), 7.96 (1H, d, indole $\underline{H}$s), 9.10 (1H, d, indole $\underline{H}$-4), 9.36 (1H, d, indole $\underline{H}$-4), 11.14 (1H, s, imide N$\underline{H}$), 12.11 (1H, s, indole N$\underline{H}$). MS (ESI) m/z 500 [M+H]$^+$.

Example 16

NAD 169

16a)

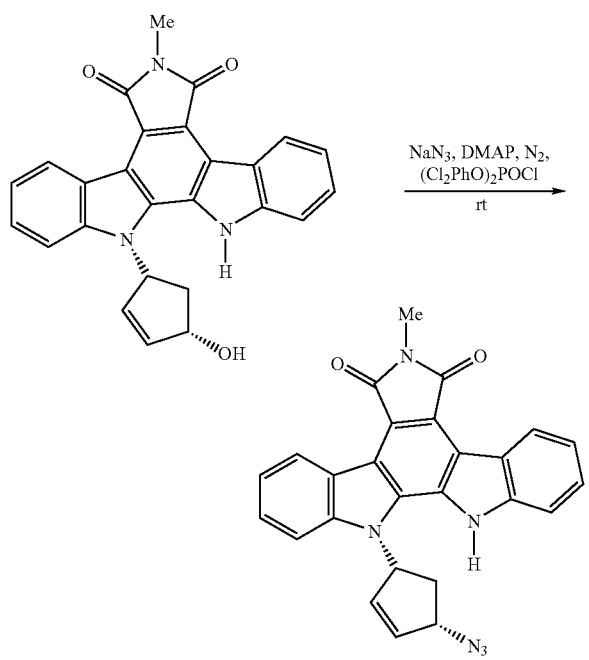

A stirred solution of 1 methylated at position $R_{10}$ (880 mg, 2.1 mmol) in dry DMF (10 mL) at rt under nitrogen atmosphere was treated sequentially with sodium azide (546 mg, 8.4 mmol), DMAP (400 mg, 3.2 mmol) and (Cl$_2$PhO)$_2$POCl (1.33 g, 3.2 mmol). After stirring for 16 hours the solution was diluted by addition of EtOAc (200 mL), washed with brine (100 mL), 32% aqueous NaOH (100 mL) and brine (2×100 mL). The organic layer was then dried over sodium sulfate, filtered and concentrated in vacuo to give a solid residue (2.3 g). Purification by flash chromatography (silica gel, PE/EtOAc 3/1 as eluant mixture) afforded the pure target compound (450 mg, yield 48.1%) together with its cis isomer (145 mg).

$^1$H-NMR (300 MHz, DMSO-$d_6$): δ 2.14–2.24 (1H, m, C$\underline{H}_2$), 3.11 (3H, s, C$\underline{H}_3$—N), 3.26–3.38 (1H, m, C$\underline{H}_2$), 5.00 (1H, bt, C$\underline{H}$—N$_3$), 6.42 (1H, dt, C$\underline{H}$=CH—CH—N$_3$), 6.51 (1H, bt, CH=C$\underline{H}$—CH—N$_3$), 6.59 (1H, dt, C$\underline{H}$—N), 7.36–7.42 (2H, m, indole $\underline{H}$s), 7.52 (1H, dt, indole $\underline{H}$s), 7.59 (1H, dt, indole $\underline{H}$s), 7.73–7.81 (2H, m, indole $\underline{H}$-7), 9.11 (1H, d, indole $\underline{H}$-4), 9.19 (1H, d, indole $\underline{H}$-4), 12.04 (1H, bs, indole N$\underline{H}$). MS (ESI) m/z 447 [M+H]$^+$.

16) NAD 169

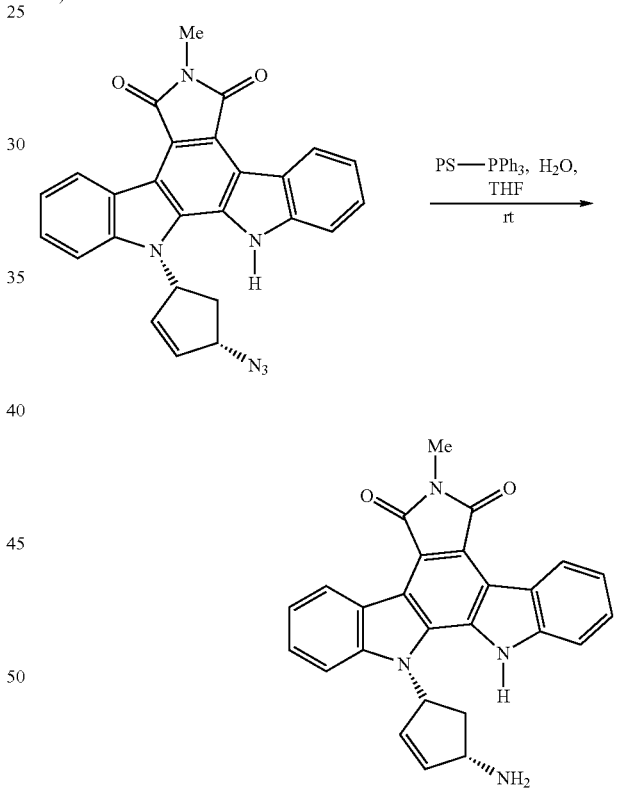

A solution of 16a (100 mg, 0.22 mmol) in THF/water 10/1 (5.5 mL) was stirred overnight at rt in presence of polymer-supported triphenylphosphine (480 mg, 1.4 mmol). The suspension was filtered off and the resulting solution was then diluted with EtOAc (250 mL), dried over sodium sulfate, filtered and concentrated in vacuo to yield the pure target compound (32 mg, yield 34.5%).

$^1$H-NMR (300 MHz, DMSO-$d_6$): δ 2.20–2.30 (1H, m, C$\underline{H}_2$), 3.18 (3H, s, C$\underline{H}_3$—N), 3.36–3.50 (1H, m, C$\underline{H}_2$), 5.05 (1H, bs, C$\underline{H}$—NH$_2$), 6.32 (1H, bt, C$\underline{H}$=CH—CH—NH$_2$), 6.40–6.54 (2H, m, CH=C$\underline{H}$—CH—NH$_2$ and C$\underline{H}$—N), 7.38–7.46 (2H, m, indole $\underline{H}$s), 7.56–7.68 (2H, dt, indole $\underline{H}$s), 7.79–7.90 (2H, m, indole H-7), 9.10 (1H, d, indole H-4), 9.21 (1H, d, indole H-4), 12.06 (1H, bs, indole NH). MS (ESI) m/z 421 [M+H]⁺.

Example 17

NAD 170

17)

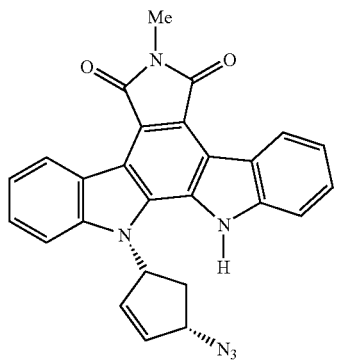

A solution of 16a (320 mg, 0.71 mmol) and Ac₂O (215 μL, 2.17 mmol) in dry THF (15 mL) was stirred overnight at rt in presence of polymer-supported triphenylphosphine (750 mg, 2.17 mmol). The suspension was filtered off and the resulting solution was then diluted with EtOAc (250 mL), dried over sodium sulfate, filtered and concentrated in vacuo to yield a solid residue (295 mg). Purification by flash chromatography (silica gel, PE/EtOAc 7/3 to 3/7 as eluant mixture) afforded the pure target compound (95 mg, yield 29.6%).

¹H-NMR (300 MHz, DMSO-d₆): δ 1.88 (3H, s, CH₃—C=O), 2.08–2.20 (1H, m, CH₂), 3.0.6–3.20 (4H, m, CH₃N and CH₂), 5.11 (1H, bm, CH—NHAc), 6.19 (1H, m, CH=CH—CH—NHAc), 6.34–6.44 (2H, m, CH=CH—CH—NHAc and CH—N), 7.37 (2H, q, indole Hs), 7.47–7.62 (2H, m, indole Hs), 7.78 (1H, m, indole H-7), 7.96 (1H, m, indole H-7), 9.12 (1H, d, indole H-4), 9.22 (1H, d, indole H-4), 12.01 (1H, bs, indole NH). MS (ESI) m/z 463 [M+H]⁺.

Example 18

NAD 157

18a)

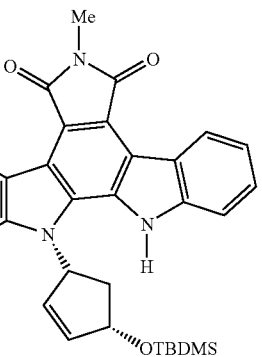

A solution of Si-protected alcohol (1.2 g, 2.24 mmol) in acetone (75 mL) was treated sequentially with N-methylmorpholine oxide hydrate (400 mg, 3.36 mmol), OsO₄ (2.5% in tBuOH, 1.5 mL, catalytic) and water (1 mL). The solution was vigorously stirred for 5 days at rt. The solution was concentrated, dissolved in EtOAc (200 mL), washed with sodium bisulfite (50 mL) and water (2×50 mL), dried over sodium sulfate and concentrated to give a crude solid residue (1.3 g). Purification by flash chromatography (silica gel, DCM/EtOAc 92/8 to 1/1 as eluant mixture) provided the pure target compound (520 mg, yield 40.8%).

¹H-NMR (300 MHz, DMSO-d₆): 8–0.82 (3H, s, CH₃—Si), –0.52 (3H, s, CH₃—Si), 0.39 (9H, s, tBu-Si), 1.88–2.00 (1H, m, CH₂), 2.64–2.78 (1H, m, CH₂), 3.22 (3H, s, CH₃—N), 4.16–4.20 (1H, bs, CH—OSi), 4.27 (1H, bs, OH), 4.85 (1H, m, OH), 4.96–5.12 (2H, m, CH—OH), 5.45 (1H, bt, CH—N), 7.38–7.48 (2H, m, indole Hs), 7.59–7.66 (2H, m, indole Hs), 7.85 (2H, d, indole H-7), 9.16 (1H, d, indole H-4), 9.28 (1H, d, indole H-4), 11.22 (1H, bs, indole NH). MS (ESI) m/z 570 [M+H]⁺.

18) NAD 157

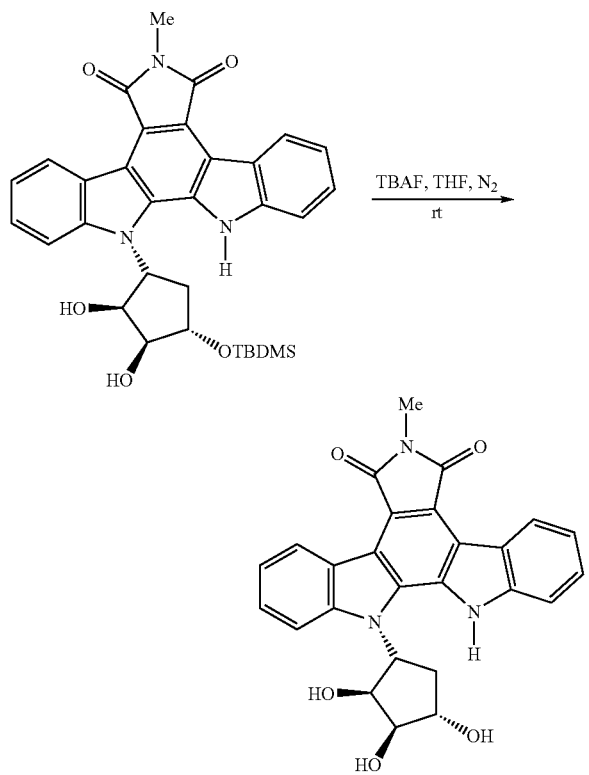

A solution of 18a (90 mg, 0.16 mmol) in dry THF (1.5 mL) was treated with TBAF (1M solution in THF, 350 µL, 0.35 mmol) and stirred under nitrogen atmosphere. After 2 hours the solution was diluted with EtOAc (50 mL) and washed with 1N HCl (25 mL) and water (2×25 mL). The organic layer was dried over sodium sulfate, filtered and concentrated in vacuo to yield the pure target compound (35 mg, yield 36.3%).

$^1$H-NMR (300 MHz, DMSO-d$_6$): δ 2.63–2.77 (1H, m, CH$_2$), 3.21 (3H, s, CH$_3$—N), 3.32–3.46 (1H, m, CH$_2$), 4.02–4.06 (1H, m, CH—OH), 4.74 (2H, bm, CH—OH), 4.91 (1H, d, OH), 5.02 (1H, d, OH), δ 5.39 (1H, d, OH), 5.79 (1H, bt, CH—N), 7.37–7.50 (2H, m, indole Hs), 7.58–7.66 (2H, t, indole Hs), 7.78 (1H, d, indole H-7), 7.86 (1H, d, indole H-7), 9.15 (1H, d, indole H-4), 9.27 (1H, d, indole H-4), 11.78 (1H, bs, indole NH). MS (ESI) m/z 456 [M+H]$^+$.

Example 19

NAD 171

19a)

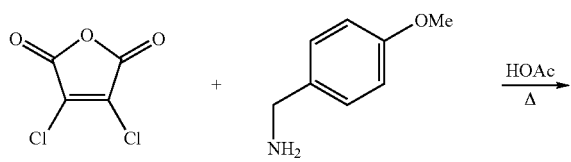

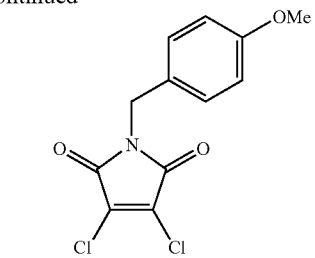

p-Methoxybenzyl amine (75.3 g, 549 mmol) was added dropwise to a stirred solution of 3,4-dichloromaleic anhydride (91.6 g, 549 mmol) in AcOH (850 mL) at rt. The solution was refluxed for 3 hours and then stirred overnight at rt. The precipitate was filtered, washed with AcOH (2×100 mL) and ice-cold EtOH (2×100 mL) to give after drying in vacuo a first crop of the pure target compound (76.4 g). The filtrate was concentrated to 300 mL and cooled to –5° C. for 4 hours to give a second crop of the pure target compound (49.5 g, total yield 80.3%).

$^1$H-NMR (300 MHz, DMSO-d$_6$): δ 3.6 (3H, s, OCH$_3$), 4.6 (2H, s, N—CH$_2$), 6.85 (2H, d, aromatic Hs), 7.20 (2H, d, aromatic Hs). MS (ESI) m/z 286 [M+H]$^+$.

19b)

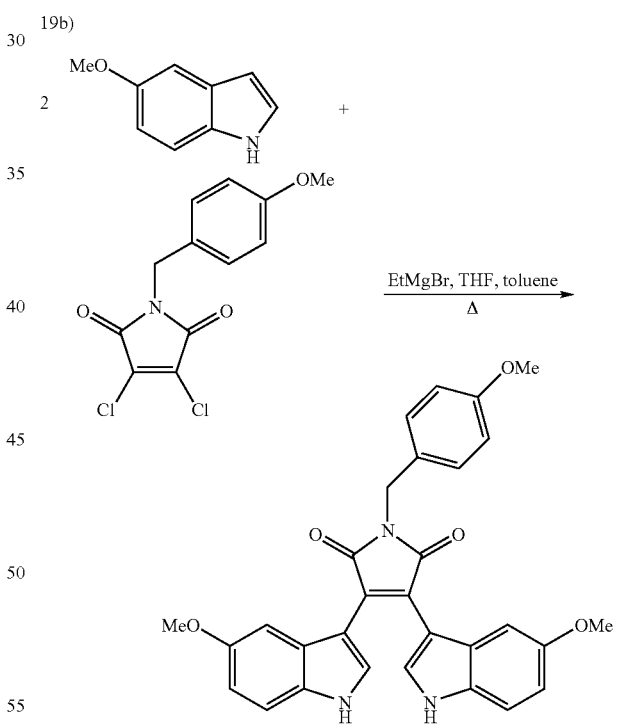

5-methoxyindole (5 g, 34 mmol) was solubilised in 1/10 THF/toluene (99 mL) and ethylmagnesium bromide (3M in Et$_2$O, 11.4 mL, 34 mmol) was added dropwise at rt, then 19a (4.6 g, 16.2 mmol) was added. The reaction mixture was refluxed for 8 hours, cooled to rt, washed with saturated ammonium chloride (50 mL) and water (50 mL), dried over sodium sulfate and concentrated in vacuo. Purification by flash chromatography of the residue (silica gel, PE/EtOAc 7/3 as eluant mixture) afforded the pure target compound (5.1 g, yield 59.8%).

¹H-NMR (300 MHz, DMSO-d₆): δ 2.95 (6H, s, indole OMe), 3.62 (3H, s, phenyl OMe), 4.10 (2H, s, N—CH₂, 6.05 (2H, d, aromatic Hs), 6.5 (2H, dd, aromatic Hs), 6.80 (2H, d, aromatic Hs), 7.25 (2H, d, aromatic Hs), 7.50 (2H, d, aromatic Hs), 7.75 (2H, s, indole H-2), 11.60 (1H, s, indole NH). MS (ESI) m/z 508 [M+H]⁺.

19c)

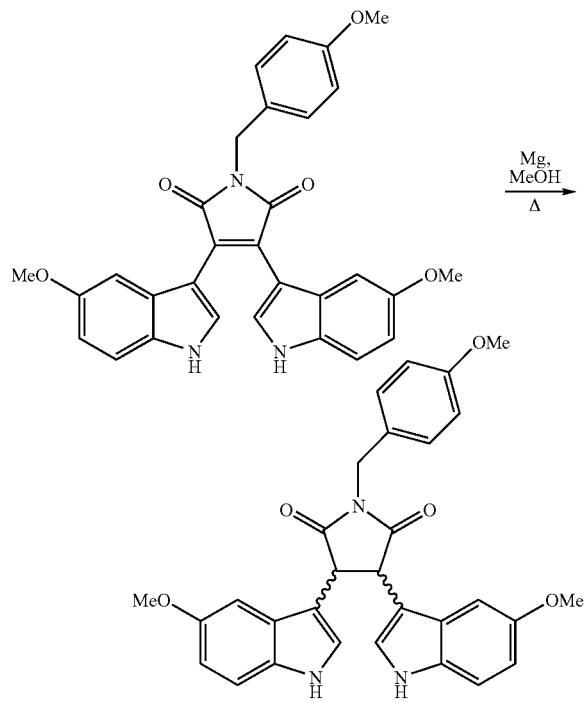

Magnesium turnings (3.63 g, 151.2 mmol) were added to a solution of 19b (1.92 g, 3.78 mmol) in dry MeOH (40 mL). The vigorously stirred suspension was refluxed for 90 minutes. After cooling to rt the reaction mixture was poured into 1N HCl (500 mL) and extracted with EtOAc (2×500 mL). The organic layer was washed with water (300 mL), dried over magnesium sulfate and concentrated in vacuo to give the pure target compound (1.78 g, yield 93.0%).

¹H-NMR (300 MHz, DMSO-d₆): δ 3.53 (6H, s, indole OMe), 3.74 (3H, s, phenyl OMe), 4.57 (2H, s, CH—CON), 4.69 (2H, s, N—CH₂), 6.70 (4H, m, aromatic Hs), 6.91 (2H, d, aromatic Hs), 7.22–7.25 (2H, d, aromatic Hs), 7.34–7,35 (4H, m, aromatic Hs), 10.91 (2H, s, indole NH). MS (ESI) m/z 510 [M+H]⁺.

19d)

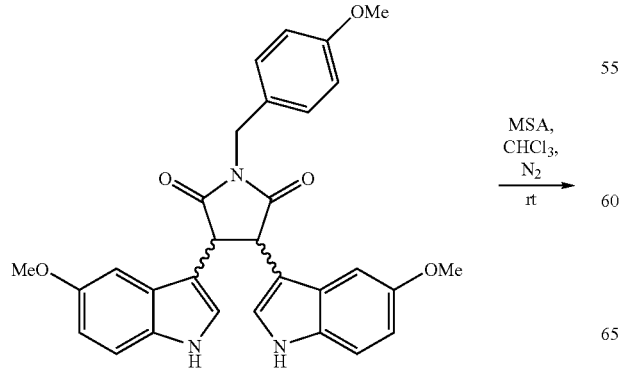

-continued

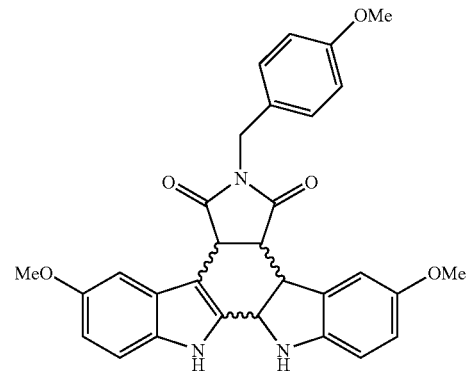

Methanesulfonic acid (111 mL, 16.7 mmol) was added to a solution of 19c (1.7 g, 3.33 mmol) in chloroform (10 mL) under nitrogen atmosphere. The reaction mixture was stirred at rt for 18 hours, then EtOAc (400 mL) and 1N NaOH (500 mL) were added. The organic layer was washed with water (200 mL), dried over sodium sulfate and concentrated in vacuo to give the pure target compound (1.25 g, yield 74.2%).

¹H-NMR (300 MHz, DMSO-d₆): δ 3.70 (3H, s, phenyl OCH₃), 3.75 (6H, s, indole OCH₃), 3.80 (1H, m, indoline NH—CH—CH), 4.37–4.63 (4H, m, indoline NH—CH+indoline NH—CH—CH—CH+N—CH₂, 5.09 (1H, d, indole N—CH=CH—CH), 5.38 (1H, bs, indoline NH), 6.45–7,06 (5H, m, aromatic Hs), 7.18–7,36 (4H, m, aromatic Hs), 7.68 (1H, m, aromatic Hs) 11.00 (1H, bs, indole NH). MS (ESI) m/z 510 [M+H]⁺.

19) NAD 171

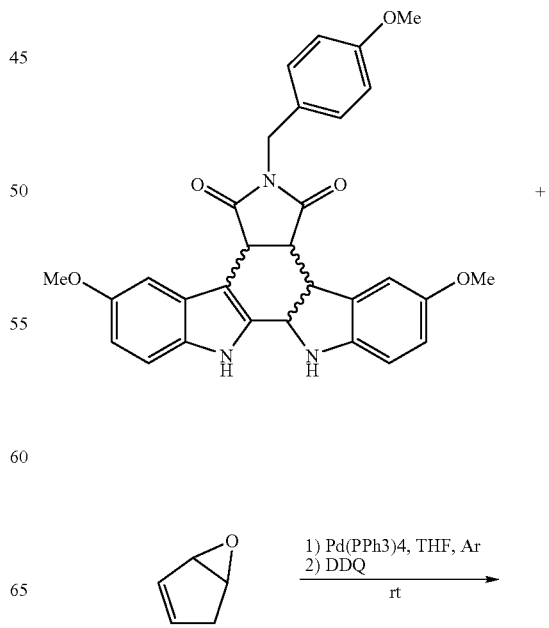

-continued

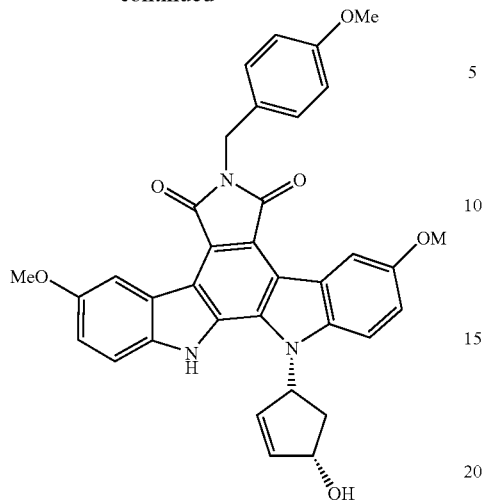

A solution of 19d (830 mg, 1.63 mmol) and palladium tetrakis (188 mg, 0.16 mmol) in dry THF (8 ml) was cooled to 0° C. under argon atmosphere. 1a (667 mg, 8.14 mmol) in dry THF (3 mL) was added dropwise and the reaction mixture was stirred overnight at rt. A solution of DDQ (268 mg, 1.18 mmol) in dry THF (6 mL) was then added and stirring at rt was continued for 18 hours. The solvent was removed in vacuo and the residue was purified by flash chromatography (silica gel, PE/EtOAc 1/1 as eluant mixture) to yield the pure target compound (213 mg, yield 25.1%).

$^1$H-NMR (300 MHz, DMSO-$d_6$): δ 2.09 (1H, m, C$\underline{H}_2$), 3.15 (1H, m, C$\underline{H}_2$), 3.71 (3H, s, phenyl O$\underline{Me}$), 3.90 (6H, s, indole O$\underline{Me}$), 4.83 (2H, s, C$\underline{H}_2$—NCO), 4.94 (1H, m, C$\underline{H}$—OH), 5.52 (1H, m, O$\underline{H}$), 6.25 (2H, s, C$\underline{H}$=C$\underline{H}$, 6.28 (1H, m, C$\underline{H}$—N), 6.91 (2H, d, aromatic $\underline{H}$s), 7.14 (1H, dd, aromatic $\underline{H}$s), 7.21 (1H, dd, aromatic $\underline{H}$s), 7.34 (2H, d, aromatic $\underline{H}$s), 7.65 (1H, d, aromatic $\underline{H}$s), 7.91 (1H, d, aromatic $\underline{H}$s), 8.66 (1H, d, indole $\underline{H}$-4), 8.77 (1H, d, indole $\underline{H}$-4), 11.90 (1H, s, indole N$\underline{H}$). MS (ESI) m/z 588 [M+H]$^+$.

Example 20

NAD 057

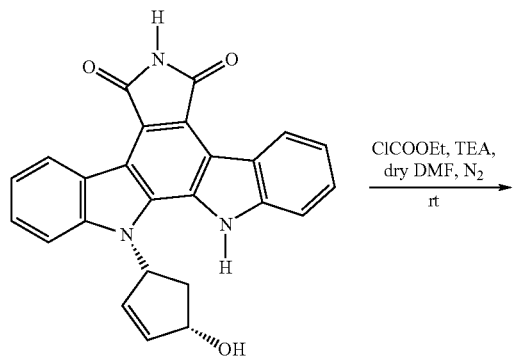

-continued

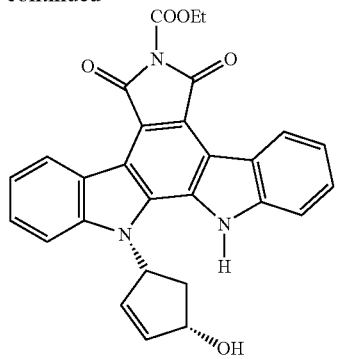

A solution of 1 (530 mg, 1.3 mmol) and TEA (840 μL, 6 mmol) in dry DMF (20 mL) was treated dropwise under nitrogen atmosphere at 0° C. with ClCOOEt (388 μL, 4 mmol) in dry DMF (5 mL). After 30 minutes the solution was warmed to rt and stirring was continued for 16 hours. The solution was diluted with EtOAc (200 mL) and washed with water (2×100 mL) and brine (100 mL). The organic layer was dried over sodium sulfate, filtered and concentrated in vacuo to yield a solid residue (550 mg). Purification by flash chromatography (silica gel, PE/EtOAc 2/8 as eluant mixture) provided the pure target compound (250 mg, yield 40.0%).

$^1$H-NMR (300 MHz, DMSO-$d_6$): δ 1.41 (3H, s, C$\underline{H}_3$—CH$_2$), 2.10–2.20 (1H, m, C$\underline{H}_2$), 3.13–3.22 (1H, m, C$\underline{H}_2$), 4.41 (2H, q, CH$_3$—C$\underline{H}_2$), 4.98 (1H, bq, C$\underline{H}$—OH), 5.30 (1H, bd, O$\underline{H}$), 6.28 (2H, bs, C$\underline{H}$=CH), 6.79 (1H, bt, C$\underline{H}$—N), 7.30–7.40 (2H, m, indole $\underline{H}$s), 7.44–7.60 (2H, m, indole $\underline{H}$s), 7.79 (1H, d, indole $\underline{H}$-7), 8.02 (1H, d, indole $\underline{H}$-7), 9.02 (1H, d, indole $\underline{H}$-4), 9.14 (1H, d, indole 1–4), 12.22 (1H, bs, indole N$\underline{H}$). MS (ESI) m/z 480 [M+H]$^+$.

Example 21

NAD 117

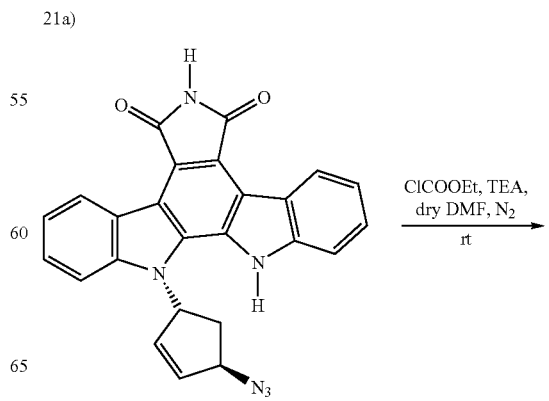

-continued

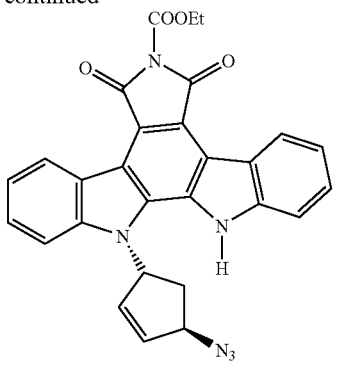

A solution of 5a (310 mg, 0.72 mmol) and TEA (315 µL, 2.2 mmol) in dry DMF (10 mL) was treated dropwise under nitrogen atmosphere at 0° C. with ClCOOEt (140 µL, 1.45 mmol) in dry DMF (2 mL). After 30 minutes the solution was warmed to rt and stirring was continued for 16 hours. The solution was diluted with EtOAc (100 mL) and washed with water (2×50 mL) and brine (50 mL). The organic layer was dried over sodium sulfate, filtered and concentrated in vacuo to yield a solid residue (370 mg). Purification by flash chromatography (silica gel, PE/EtOAc 2/1 to pure EtOAc as eluant mixture) provided the pure target compound (210 mg, yield 41.7%).

$^1$H-NMR (300 MHz, DMSO-d$_6$): δ 1.41 (3H, s, C$\underline{H}_3$—CH$_2$), 2.62–2.76 (2H, m, C$\underline{H}_2$), 4.44 (2H, q, CH$_3$—C$\underline{H}_2$), 5.37 (1H, bd, C$\underline{H}$—N$_3$), 6.42–6.49 (1H, m, C$\underline{H}$=CH—CH—N$_3$), 6.54 (1H, bd, CH=C$\underline{H}$—CH—N$_3$), 7.35–7.44 (2H, m, indole H$\underline{s}$), 7.47–7.65 (3H, m, indole H$\underline{s}$+H-7), 7.82 (1H, d, indole H-7), 9.10 (1H, d, indole H-4), 9.20 (1H, d, indole H-4), 12.36 (1H, bs, indole N$\underline{H}$). MS (ESI)$_m$ m/z 505 [M+H]$^+$.

21) - NAD 117

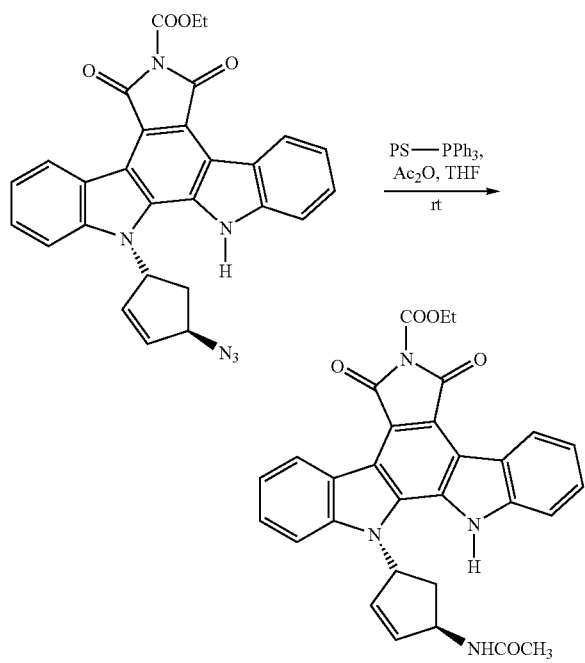

A solution of 21a (200 mg, 0.40 mmol) and Ac$_2$O (230 µL, 2.38 mmol) in dry THF (5 mL) was stirred overnight at rt in presence of polymer-supported triphenylphosphine (820 mg, 2.38 mmol). The suspension was filtered off and the resulting solution was then diluted with EtOAc (100 mL), dried over sodium sulfate, filtered and concentrated in vacuo to yield a solid residue (150 mg). Purification by flash chromatography (silica gel, pure EtOAc as eluant) afforded the pure target compound (35 mg, yield 16.8%).

$^1$H-NMR (300 MHz, DMSO-d$_6$): δ 1.44 (3H, s, C$\underline{H}_3$—CH$_2$), 1.91 (3H, s, C$\underline{H}_3$—C=O), 2.44–2.59 (2H, m, C$\underline{H}_2$), 4.50 (2H, q, CH$_3$—C$\underline{H}_2$), 5.32 (1H, bm, C$\underline{H}$—NHAc), 6.31 (1H, bs, C$\underline{H}$=CH—CH—NHAc), 6.38 (1H, bd, CH=C$\underline{H}$—CH—NHAc), 6.77 (1H, m, C$\underline{H}$—N), 7.32–7.41 (2H, m, indole H$\underline{s}$), 7.46–7.65 (31H, m, indole H$\underline{s}$+H-7), 7.80 (1H, m, indole H-7), 8.25 (1H, bd N$\underline{H}$Ac), 9.16 (1H, d, indole H-4), 9.25 (1H, d, indole H-4), 12.24 (1H, bs, indole N$\underline{H}$). MS (ESI) m/z 521 [M+H]$^+$.

Example 22

NAD 049

22a)

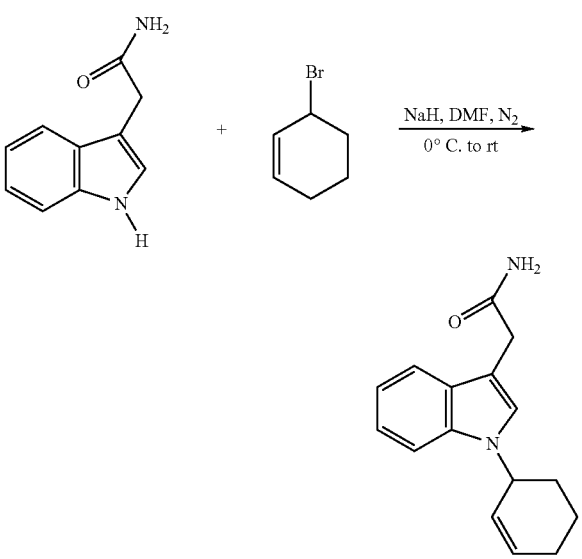

A suspension of sodium hydride (1.6 g, 60% paraffin, 40 mmol) in dry DMF (25 mL) was treated dropwise with 1f (5 g, 28.7 mmol) in dry DMF (25 mL) at rt under nitrogen atmosphere. The resulting mixture was stirred for 30 minutes at rt and then cooled to 0° C. A solution of 3-bromocyclohexene (5.64 g, 35 mmol) in dry DMF (50 mL) was then added dropwise. The solution was then warmed to rt and stirred for 18 hours, diluted with EtOAc (1 L), washed with water (2×500 mL) and brine (500 mL). The organic phase was dried over sodium sulfate, filtered and concentrated in vacuo to give a brown oily residue (6.8 g). The crude was purified by flash chromatography (silica gel, EtOAc as eluant) to give the pure target compound (1.9 g, yield 26.1%).

$^1$H-NMR (300 MHz, DMSO-d$_6$): δ 1.60–1.84 (3H, m, C$\underline{H}_2$—C$\underline{H}_2$—C$\underline{H}_2$), 1.94–2.24 (3H, m, C$\underline{H}_2$—C$\underline{H}_2$—C$\underline{H}_2$), 5.12 (1H, bs, C$\underline{H}$—N), 5.77 (1H, bd, C$\underline{H}$=CH—CH$_2$), 6.10 (1H, bd, CH=C$\underline{H}$—CH$_2$), 6.87 (1H, bs, NH$_2$), 7.03 (1H, bt, indole H$\underline{s}$), 7.12 (1H, bt, indole H$\underline{s}$), 7.19 (1H, s, indole H-2), 7.38 (1H, bs, NH₂), 7.48 (1H, d, indole H-7), 7.58 (1H, d, indole H-4). MS (ESI) m/z 255 [M+H]⁺.

22b)

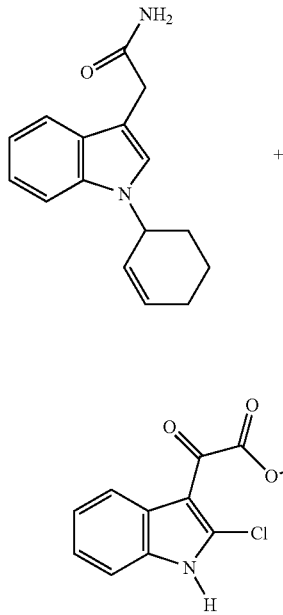

+

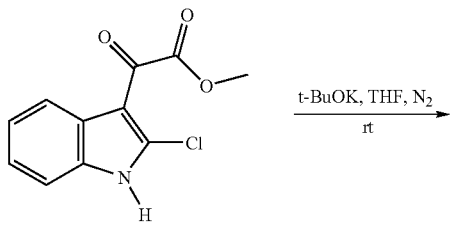

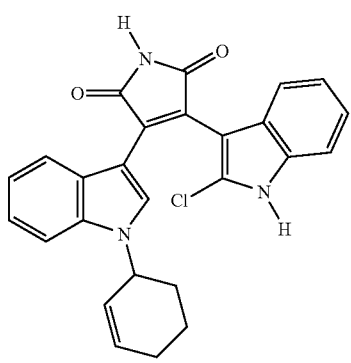

KOtBu (1M in THF, 45 mL, 45 mmol) was added dropwise to a vigorously stirred suspension of 22a (1.9 g, 7.9 mmol) and 1h (2.67 g, 11.3 mmol) in THF (20 mL) at rt under nitrogen atmosphere. The resulting slurry was stirred at rt for 48 hours, then poured into 4/1 water/brine (100 mL) and extracted with EtOAc (2×50 mL). The organic layer was washed with 2M NaOH (25 mL), water (25 mL) and brine (25 mL), then dried over sodium sulfate, filtered and concentrated in vacuo to give a crude oil (4.1 g). Purification by flash chromatography (silica gel, PE/EtOAc 2/1 as eluant mixture) afforded the pure target compound (3.0 g, yield 90.0%).

¹H-NMR (300 MHz, DMSO-d₆): δ 1.64–2.30 (6H, m, CH₂—CH₂—CH₂), 5.67 (1H, bt, CH—N), 6.17 (1H, d, CH=CH—N), 6.54 (1H, dt, CH=CH—N), 6.96–7.65 (8H, m, indole Hs), 8.11 (1H, d, indole H-2, 11.08 (1H, bs, imide NH), 11.92 (1H, bs, Cl-indole NH). MS (ESI) m/z 442 [M+H]⁺.

22) NAD 049

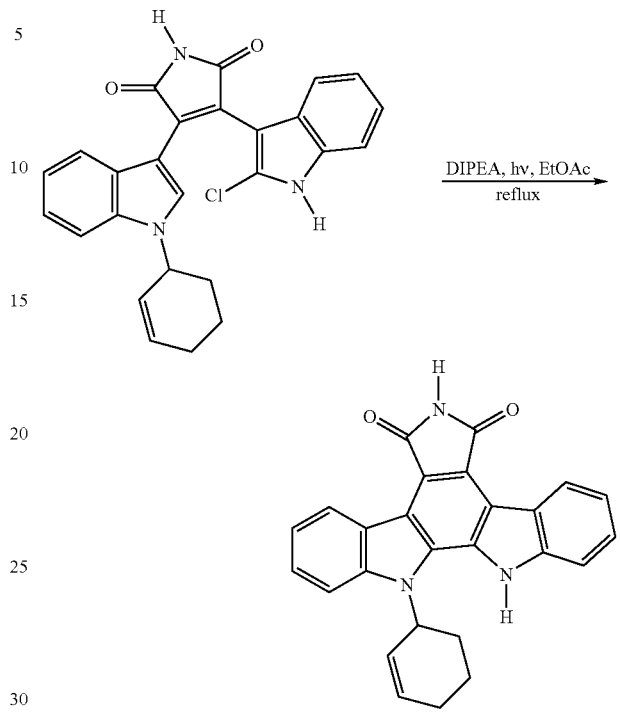

A solution of 22b (3 g, 6.8 mmol) and DIPEA (400 μL, 6.8 mmol) in EtOAc (50 mL) was irradiated with a halogen lamp. After 2 hours of irradiation the solution was cooled to rt, washed with water (25 mL), dried with sodium sulfate and concentrated in vacuo to give a solid residue (2.15 g). Purification by trituration with MeOH afforded the pure target compound (1.51 g, yield 55.7%).

¹H-NMR (300 MHz, DMSO-d₆): δ 1.92–2.48 (6H, m, CH, —CH₂CH₂—CH₂), 6.04–6.28 (3H, m, CH—N+CH=CH—CH₂), 7.36 (2H, dt, indole Hs), 7.50–7.62 (2H, m, indole Hs), 7.80 (1H, d, indole H-7), 7.89 (1H, d, indole H-7), 9.14 (1H, d, indole H-4), 9.23 (1H, d, indole H-4), 11.08 (1H, bs, imide NH), 12.06 (1H, bs, indole NH). MS (ESI) m/z 406 [M+H]⁺.

Example 23

NAD 085

23a)

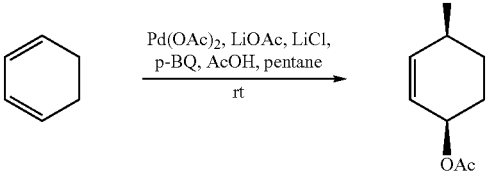

LiOAc.2H₂O (12.2 g, 200 mmol), LiCl (5.1 g, 120 mmol), p-benzoquinone (12.9 g, 120 mmol) and Pd(OAc)₂ (0.67 g, 3 mmol) were dissolved in AcOH (200 mL). Pentane (300 mL) and subsequently 1,3-cyclohexadiene (5.7 mL, 60 mmol) were added and the reaction mixture was stirred overnight at rt. Saturated NH₄Cl (70 mL) was added, the organic phase was separated and the aqueous layer was extracted with pentane (2×150 mL). The combined organic layers were washed with saturated NaHCO₃ (120 mL), 2N NaOH (2×120 mL), water (2×120 mL), dried over sodium sulfate and concentrated in vacuo to give the pure target compound (6.75 g, yield 63.8%).

¹H-NMR (300 MHz, CDCl₃): δ 1.73–2.20 (4H, m, C$\underline{H_2}$—C$\underline{H_2}$), 2.03 (3H, s, OCOC$\underline{H_3}$), 4.79 (1H, m, C$\underline{H}$—Cl), 5.18–5.25 (1H, m, C$\underline{H}$—OCOCH₃), 5.78 (1H, dd, AcO—CH—C$\underline{H}$=CH), 5.97 (1H, ddd, Cl—CH—C$\underline{H}$=CH). MS (ESI) m/z 192 [M+NH₄]⁺.

23b)

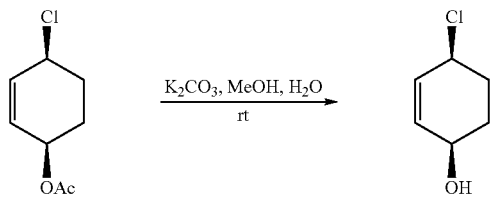

A solution of K₂CO₃ (4.84 g, 35 mmol) in water (3 mL) was added rapidly to a solution of 23a (11.77 g, 67.4 mmol) in MeOH (100 mL) and stirring at rt was continued for 1 hour. The solvent was removed in vacuo and the residue was purified by flash chromatography (silica gel, PE/EtOAc 5/1 to 2/1 as eluant mixture) to afford the pure target compound (6.34 g, yield 71.1%).

¹H-NMR (300 MHz, CDCl₃): δ 1.85 (1H, s, O$\underline{H}$), 1.90–2.15 (4H, m, C$\underline{H_2}$—C$\underline{H_2}$), 4.27 (1H, m, C$\underline{H}$—Cl), 4.56 (1H, m, C$\underline{H}$—OH), 5.91 (2H, s, C$\underline{H}$=C$\underline{H}$).

23c)

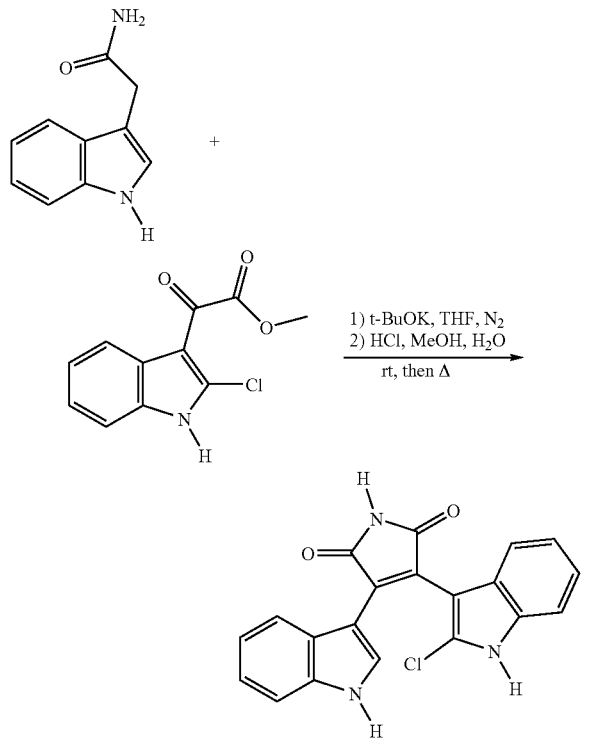

A 1M solution of KOtBu in THF (610 mL, 610 mmol) was added dropwise to a vigorously stirred suspension of 1f (18 g, 103 mmol) and 1h (36 g, 151 mmol) in THF (130 mL) at rt under nitrogen atmosphere. The resulting slurry was stirred at rt for 48 hours, then poured into 4/1 water/brine mixture (1 L) and extracted with EtOAc (2×500 mL). The organic layer was washed with water (250 mL) and brine (250 mL), then was dried over sodium sulfate, filtered and concentrated in vacuo to give a crude oil (26 g). This was dissolved in MeOH (200 mL) and treated with 37% HCl (100 mL), then refluxed for 1 hour. The resulting mixture was cooled to rt, poured in water (1 L) and extracted with EtOAc (3×200 mL). After washing with saturated NaHCO₃ (200 mL), drying over sodium sulfate, filtering and concentrating in vacuo a crude (20 g) was obtained. Purification by flash chromatography (silica gel, PE/EtOAc 1/1 as eluant mixture) afforded the pure target compound (15.8 g, yield 42.4%).

¹H-NMR (300 MHz, DMSO-d₆): δ 6.42 (1H, d, indole H$\underline{s}$), 6.57 (1H, t, indole H$\underline{s}$), 6.94–7.02 (2H, m, indole H$\underline{s}$), 7.14 (1H, t, indole H$\underline{s}$), 7.28–7.41 (3H, m, indole H$\underline{s}$), 8.01 (1H, d, indole H-2), 11.03 (1H, s, imide N$\underline{H}$), 11.84 (1H, d, indole N$\underline{H}$), 12.19 (1H, bs, Cl-indole N$\underline{H}$). MS (ESI) m/z 362 [M+H]⁺.

23d)

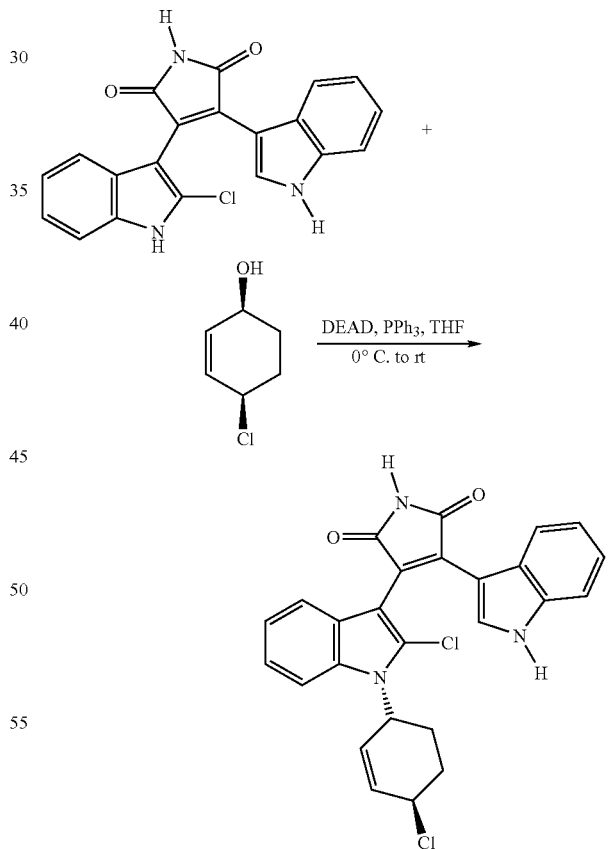

A solution of 23c (2 g, 5.5 mmol), 23b (0.73 g, 5.5 mmol) and triphenylphosphine (1.57 g, 6 mmol) in THF (40 mL) was cooled to 0° C. DEAD (0.95 mL, 6 mmol) was added within 5 minutes and the reaction mixture was warmed and stirred overnight at rt. The solvent was removed in vacuo and the residue was dissolved in Et₂O, washed with 5N HCl (2×30 mL) and saturated NaHCO₃ (30 mL), dried over sodium sulfate and concentrated in vacuo. Purification by flash chromatography of the residue (silica gel, PE/EtOAc 2/1 as eluant mixture) gave the pure target compound (1.28 g, yield 49.1%).

¹H-NMR (300 MHz, DMSO-d₆): δ 1.75–1.95 (1H, m, C$\underline{H}$₂), (1.98–2.14 (2H, m, H 2.37 (1H, m, C$\underline{H}$₂), 5.07 (1H, m, C$\underline{H}$—Cl), 5.32 (1H, m, C$\underline{H}$—N), 5.74–5.90 (1H, m, CH═C$\underline{H}$—CH—N), 6.04 (1H, bd, CH═C$\underline{H}$—CH—Cl), 6.16 (1H, m, indole H$\underline{s}$), 6.53 (1H, m, indole H$\underline{s}$), 6.97–7.08 (2H, m, indole H$\underline{s}$), 7.14–7.18 (1H, m, indole H$\underline{s}$), 7.37–7.43 (2H, m, indole H$\underline{s}$), 7.58 (1H, d, indole H$\underline{s}$), 8.09 (1H, d, indole H-2), 11.05 (1H, s, imide N$\underline{H}$), 11.90 (1H, bs, indole N$\underline{H}$) MS (ESI) m/z 476 [M+H]⁺.

23) NAD 085

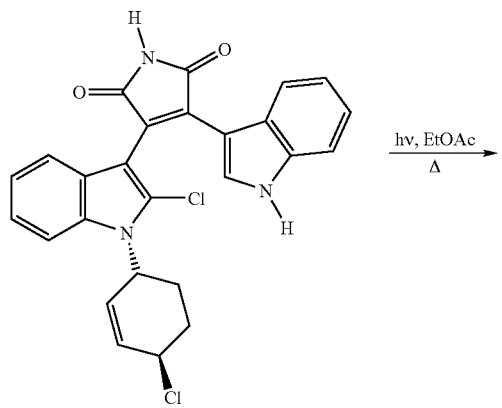

A solution of 23d (0.21 g, 0.44 mmol) in EtOAc (20 mL) was irradiated with a halogen lamp for 1 hour. The solvent was then removed in vacuo and the brownish residue was triturated in hot EtOAc (2×1 mL), filtered and dried in vacuo to give the pure target compound (0.14 g, yield 72.0%).

¹H-NMR (300 MHz, DMSO-d₆): δ 2.29–2.35 (2H, m, C$\underline{H}$₂), 2.40–2.50 (2H, m, C$\underline{H}$₂), 5.29 (1H, m, C$\underline{H}$—Cl), 6.20 (1H, m, C$\underline{H}$—N), 6.25 (2H, s, C$\underline{H}$═C$\underline{H}$), 7.35–7.40 (1H, t, indole H$\underline{s}$), 7.49–7.62 (4H, m, indole H$\underline{s}$), 7.78–7.83 (1H, t, indole H$\underline{s}$), 9.15 (1H, d, indole H-4), 9.24 (1H, d, indole H-4), 11.09 (1H, s, imide N$\underline{H}$), 12.09 (1H, s, indole N$\underline{H}$). MS (EST) m/z 440 [M+H]⁺.

Example 24

NAD 135

24a)

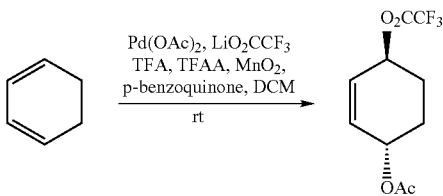

Palladium diacetate (1.4 g, 6.2 mmol), lithium trifluoroacetate (15 g, 125 mmol), p-benzoquinone (2.3 g, 21.3 mmol), and manganese dioxide were dissolved in acetic acid (170 mL). Trifluoroacetic acid (28.5 g, 0.25 mol) followed by trifluoroacetic anhydride (39.4 g, 0.188 mol) and DCM (420 mL) were added. 1,3-cyclohexadiene (11.9 mL, 125 mmol) was added portionwise within 4 hours and the reaction mixture was stirred at rt for 19 hours. The solvent was removed and a mixture pentane/Et₂O 1/1 (mL) was added. The precipitate was filtered off and the filtrate was washed with water (2×600 mL), saturated solution of NaHCO₃ (2×200 mL), and brine (200 mL). The organic phase was dried over sodium sulfate and the solvent was removed in vacuo to yield the pure target compound (26 g, yield 81.9%).

¹H-NMR (300 MHz, CDCl₃): δ 1.68–1.90 (2H, m, C$\underline{H}$₂), 2.04 (3H, s, OCOC$\underline{H}$₃), 2.08–2.26 (2H, m, C$\underline{H}$₂), 5.27–5.33 (1H, m, C$\underline{H}$—OAc), 5.44–5.49 (1H, m, C$\underline{H}$—O₂CCF₃), 5.92 (1H, ddd, C$\underline{H}$═), 6.03 (1H, ddd, C$\underline{H}$). MS (ESI) m/z 270 [M+NH₄]⁺.

24b)

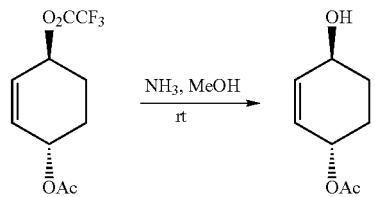

Ammonia (7 M in MeOH, 15 mL, 100 mmol) was added portionwise to a solution of 24a (25.2 g, 100 mmol) in MeOH (200 mL). The solution was stirred for 45 minutes at rt and AcOH (2 mL) was added. The solvent was removed in vacuo and the dark oily residue was purified by flash chromatography (silica gel, PE/AcOEt 2/1 as eluant mixture) to yield the pure target compound (13.2 g, yield 85.4%).

¹H-NMR (300 MHz, DMSO-d₆): δ 1.36–1.55 (2H, m, C$\underline{H}$₂), 1.98 (3H, s, OCOC$\underline{H}$₃), 1.87–2.06 (2H, m, C$\underline{H}$₂), 4.03–4.09 (1H, m, C$\underline{H}$—OH), 4.88 (1H, d, O$\underline{H}$), 5.14–19 (1H, m C$\underline{H}$—OAc), 5.56–5.61 (1H, m, C$\underline{H}$, 5.79–5.84 (1H, m, C$\underline{H}$). MS (ESI) m/z 157 [M+H]⁺.

24c)

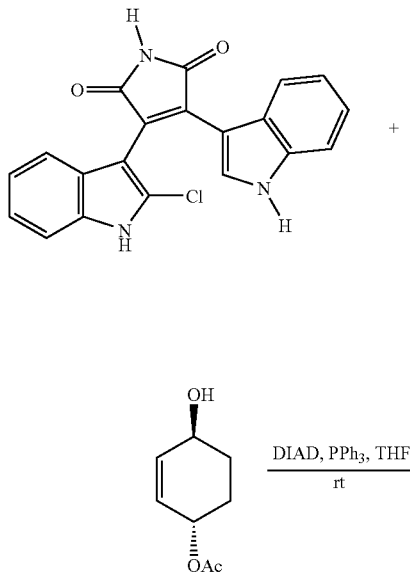

+

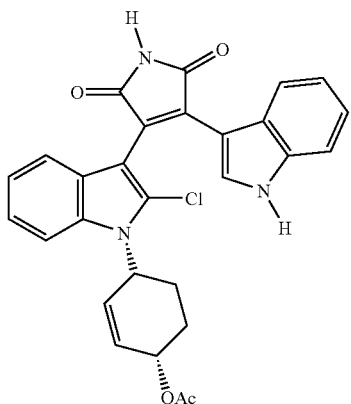

$\xrightarrow{\text{DIAD, PPh}_3\text{, THF}}{\text{rt}}$

A solution containing 23c (1.43 g, 3.95 mmol), 24b (1.25 g, 8 mmol) and triphenylphosphine in THF (10 mL) was cooled to 0° C. DIAD (1.75 mL, 9 mmol) was added dropwise within 10 minutes. The cooling bath was removed and the reaction mixture was stirred at rt for 2 hours. A few drops of water were added before removing the solvent in vacuo, producing a red oily residue (7 g). Double purification by flash chromatography (silica gel, PE/EtOAc/Et$_3$N 5/5/1 and DCM/EtOAc 5/1 as eluant mixtures) yielded the pure target compound (0.54 g, yield 27.6%).

$^1$H-NMR (300 MHz, DMSO-d$_6$): δ 1.80–2.15 (4H, m, CH$_2$), 2.10 (3H, bs, OCOCH$_3$), 5.14–5.19 (1H, m, CH—OAc), 5.90–6.10 (1H, m, CH—N), 6.18 (1H, m, CH=), 6.50–6.59 (1H, m, CH=), 6.97–7.09 (2H, m, indole Hs), 7.17–7.24 (1H, m, indole Hs), 7.33–7.45 (2H, m, indole Hs), 7.54–7.59 (1H, m, indole Hs), 8.08 (1H, m, indole H-2), 11.06 (1H, bs, imide NH, 11.90 (1H, bs, indol NH). MS (ESI) m/z 500 [M+H]$^+$.

24) NAD 135

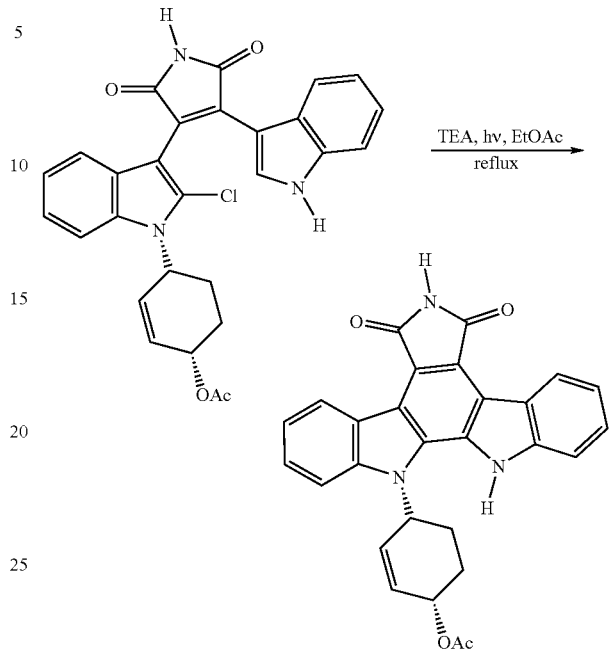

TEA, hv, EtOAc, reflux

A solution of 24c (0.52 g, 1.04 mmol) and TEA (4 mL) in EtOAc (20 mL) was irradiated with a halogen lamp. After 2 hours of irradiation the solution was cooled to rt. EtOAc (20 mL) and water (10 mL) were added, the organic layer was dried over sodium sulfate, filtered and concentrated to give a solid residue (0.52 g). Purification by flash chromatography (silica gel, PE/EtOAc 1/1 as eluant mixture) afforded the pure target compound (0.4 g, yield 83.1%).

$^1$H-NMR (300 MHz, DMSO-d$_6$): δ 2.06–2.17 (2H, m, CH$_2$), 2.16 (3H, s, OCOCH$_3$), 2.33–2.45 (2H, m, CH$_2$), 5.39 (1H, bs, CH—OAc), 6.10–6.14 (1H, m, CH—N), 6.27 (1H, bd, CH=), 6.42 (1H, bd, CH) 7.35–7.40 (2H, m, indole Hs), 7.57 (2H, q, indole Hs), 7.77 (1H, d, indole H-7), 7.90 (1H, d, indole H-7), 9.13 (1H, d, indole H-4), 9.22 (1H, d, indole H-4), 11.07 (1H, bs, imide NH) 12.09 (1H, bs, indole NH). MS (ESI) m/z 464 [M+H]$^+$.

Example 25

NAD 138

25)

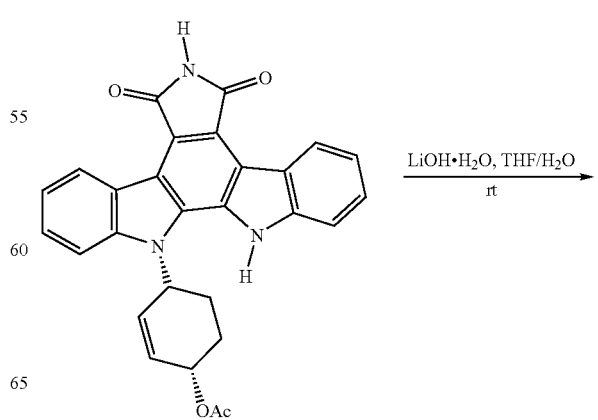

$\xrightarrow{\text{LiOH·H}_2\text{O, THF/H}_2\text{O}}{\text{rt}}$

-continued

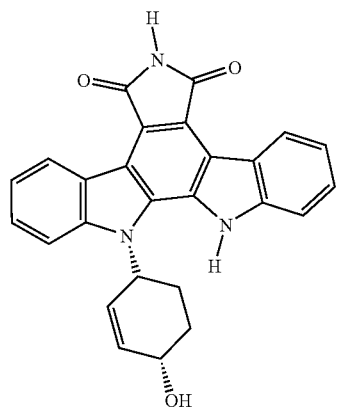

A solution of LiOH.H₂O (0.24 g, 5.6 mmol) in water (2 mL) was added dropwise to a stirred solution of 24 (0.13 g, 0.28 mmol) in THF (10 mL). The solution was stirred at rt for 16 hours, then neutralised with 37% HCl. The mixture was diluted with EtOAc (50 mL), then washed with a saturated solution of NaHCO₃ (20 mL) and water (10 mL). The organic layer was then dried over sodium sulfate and concentrated to give a residue (120 mg). This was dissolved in THF/EtOAc (1 mL) and precipitated by addition of Et₂O. Filtration and drying produced the pure target compound (70 mg, yield 58.9%).

¹H-NMR (300 MHz, DMSO-d₆, T=83° C.): δ 2.04–2.30 (3H, m, CH₂), 2.59–2.72 (1H, m CH₂), 4.41 (1H, bs, CH—OH), 5.98 (1H, m, CH—N), 6.11 (1H, bd, CH=), 6.29 (1H, m, CH=), 7.36 (2H, q, indole Hs), 7.56 (2H, t, indole Hs), 7.75 (1H, d, indole H-7), 8.04 (1H, d, indole H-7), 9.15 (1H, d, indole H-4), 9.25 (1H, d, indole H-4), 10.75 (1H, bs, imide NH), 11.53 (1H, bs, indole NH). MS (ESI) m/z 422 [M+H]⁺.

Example 26

NAD 106

26a)

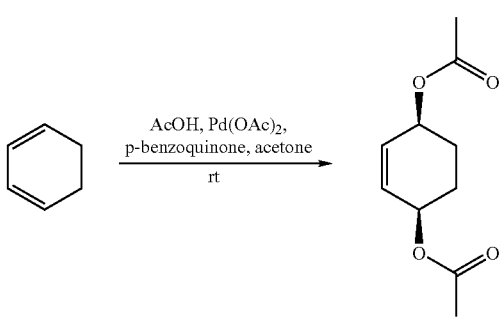

p-Benzoquinone (70.8 g, 665 mmol), Pd(OAc)₂ (3.5 g, 15.6 mmol) and AcOH (178 mL, 3.12 mol) were dissolved in acetone (950 mL). 1,3-cyclohexadiene (25 g, 312 mmol) was added dropwise during 6 hours. The reaction mixture was stirred at rt for 20 hours, then the solvent was removed in vacuo. The residue was poured into brine (1 L) and extracted with a 1/1 mixture pentane/Et₂O (3×500 mL) and filtered. The combined organic layers were washed carefully with 1M NaOCl until the aqueous layer became colourless (ca. 2 L), then with water (2×500 mL). The combined aqueous layers were extracted with 1/1 pentane/Et₂O (2×500 mL). The combined organic layers were dried over sodium sulfate and concentrated in vacuo to give an oily residue (44 g). The crude product was distilled at reduce pressure (Bp₂₀ ₘₘHg=140–152° C.) to yield the pure target compound (32 g, yield 51.9%).

¹H-NMR (300 MHz, CDCl₃): δ 1.85–2.00 (4H, m, CH₂), 2.20 (6H, s, CH₃), 5.20 (2H, dt, CH—OAc), 5.85 (2H, s, CH=). MS (ESI) m/z 199 [M+H]⁺.

26b)

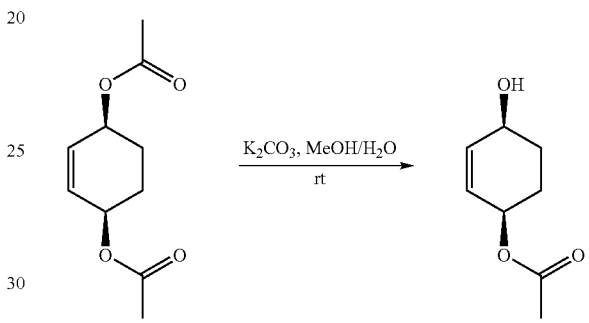

Potassium carbonate (0.7 g, 2.5 mmol) in water (20 mL) was added in two portions over 30 minutes to a stirred solution of 26a (9.88 g, 49.8 mmol) in MeOH (80 mL) at rt. After 90 minutes AcOH (1 mL) was added and MeOH was removed in vacuo. The aqueous layer was saturated with NaCl and extracted with EtOAc (2×80 mL). The organic layer was dried over sodium sulfate, filtered and concentrated in vacuo to yield a crude dark brown oil (7 g). Purification by flash chromatography (silica gel, PE/EtOAc 1/1 as eluant mixture) afforded the pure target compound (3.3 g, 42.3%).

¹H-NMR (300 MHz, CDCl₃): δ 1.82–2.07 (4H, m, CH₂—CH₂), 2.18 (3H, s, CH₃), 4.28–4.34 (1H, m, CH—OH), 5.31 (1H, dt, CH—OAc), 5.93 (1H, ddd, CH=CH—CH—OAc), 6.09 (1H, ddd, CH=CH—CH—OAc). MS (ESI) m/z 157 [M+H]⁺.

26c)

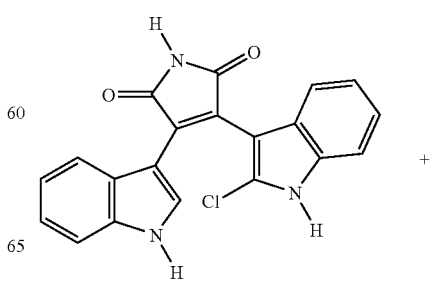

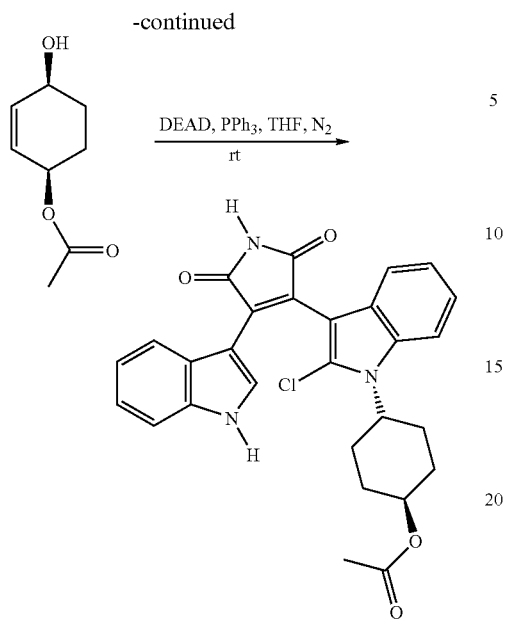

A solution of 26b (1.95 g, 12.5 mmol), 23c (3.78 g, 10.4 mmol) and PPh₃ (3.41 g, 13 mmol) in dry THF (80 mL) was cooled to 0° C., then DEAD (2.26 g, 13 mmol) was added portionwise over 10 minutes under nitrogen atmosphere. The solution was warmed to rt and stirred for 17 hours. The solvent was removed in vacuo, the residue was taken up with Et₂O (150 mL), washed with 3N HCl (2×50 mL) and with saturated NaHCO₃ (100 mL). The organic layer was dried over sodium sulfate, filtered and concentrated in vacuo to yield a crude orange foam (8.9 g). Purification by flash chromatography (silica gel, PE/EtOAc 3/2 as eluant mixture) afforded the pure target compound (2.44 g, yield 47.5%).

¹H-NMR (300 MHz, DMSO-d₆): δ 1.76–1.91 (4H, m, CH₂—CH₂), 2.08 (3H, s, CH₃) 2.13–2.28 (4H, m, CH₂—CH₂), 5.56 (1H, bt, CH—OAc), 5.95 (1H, bm, CH—N), 6.20 (1H, t, CH=CH—CH—OAc), 6.55 (1H, dt, CH=CH—CH—OAc), 6.95–7.15 (3H, m, indole Hs), 7.22 (1H, t, indole Hs), 7.30–7.65 (4H, m, indole Hs), 8.12 (1H, d, indole H-2), 11.08 (1H, s, imide NH), 11.92 (1H, d, indole NH). MS (ESI) m/z 500 [M+H]⁺.

26) NAD 106

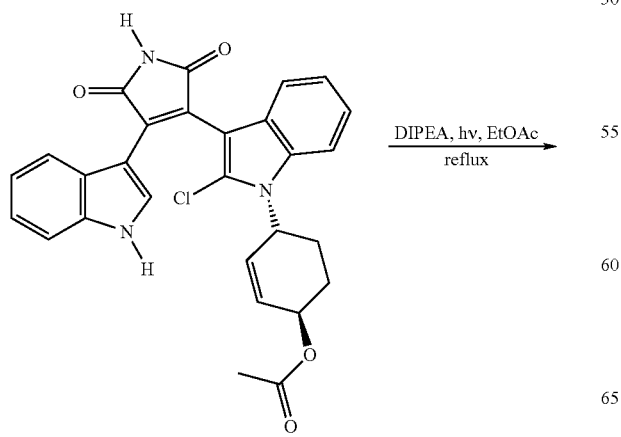

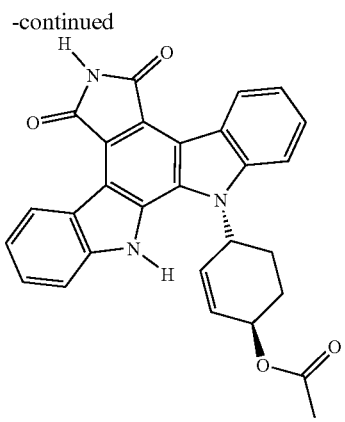

A solution of 26c (2 g, 4 mmol) and DIPEA (740 μL, 12 mmol) in EtOAc (100 mL) was irradiated with a halogen lamp. After 2 hours of irradiation the solution was cooled to rt, washed with water (50 mL), dried over sodium sulfate and concentrated in vacuo to give a solid residue (2.15 g). Purification by flash chromatography (silica gel, PE/EtOAc 3/2 as eluant mixture) afforded the pure target compound (950 mg, yield 51.2%).

¹H-NMR (300 MHz, DMSO-d₆): δ 2.14 (3H, s, CH₃), 2.20–2.43 (4H, m, CH₂—CH₂), 5.72 (1H, bt, CH—O), 6.09 (1H, d, CH=CH—CH—OAc), 6.17–6.30 (2H, m, CH—N+CH=CH—CH—OAc), 7.38 (2H, t, indole Hs), 7.51–7.63 (2H, m, indole Hs), 7.79 (1H, d, indole H-7), 7.83 (1H, d, indole H-7), 9.13 (1H, d, indole H-4), 9.22 (1H, d, indole H-4), 11.08 (1H, bs, imide NH), 12.08 (1H, bs, indole h. MS (ESI) m/z 464 [M+H]⁺.

Example 27

NAD 109

27)

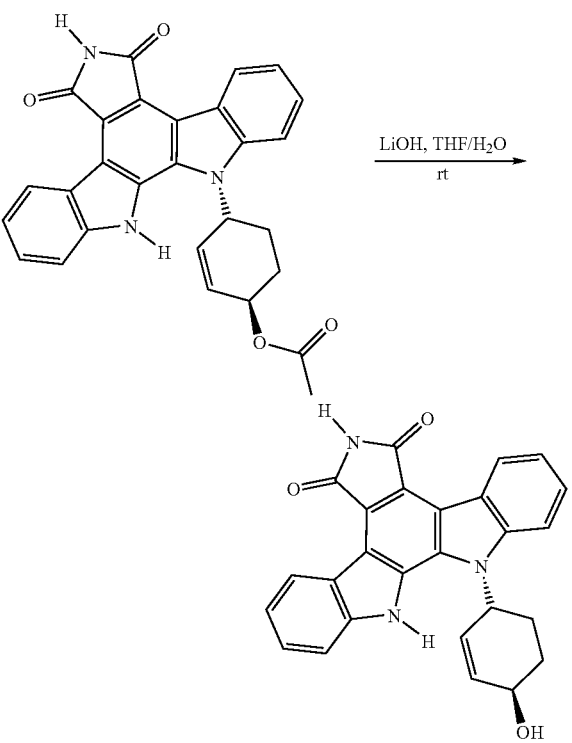

A solution of LiOH.H₂O (0.15 g, 3.6 mmol) in water (0.5 mL) was added dropwise to a stirred suspension of 26 (0.11 g, 0.24 mmol) in THF (5 mL) at rt. The solution was stirred for 24 hours, then neutralised with 1N HCl. THF was removed in vacuo, the resulting residue was suspended in boiling water (5 mL) and filtered. The solid was washed with boiling water (1 mL), MeOH (1 mL) and then Et₂O (1 mL). After drying in vacuo the pure target compound (75 mg, yield 74.1%) was obtained.

¹H-NMR (300 MHz, DMSO-d₆): δ 2.02–2.40 (4H, m, C$\underline{H_2}$—C$\underline{H_2}$), 4.55 (1H, bs, C$\underline{H}$—OH), 5.21 (1H, bs, O$\underline{H}$), 6.02 (1H, d, C$\underline{H}$=CH—CH—OH), 6.10–6.21 (2H, m, CH—N+CH=C$\underline{H}$—CH—OH), 7.37 (2H, t, indole $\underline{Hs}$), 7.55 (2H, dt, indole $\underline{Hs}$), 7.78–7.86 (2H, m, indole $\underline{H-7}$), 9.14 (1H, d, indole $\underline{H-4}$); 9.23 (1H, d, indole $\underline{H-4}$), 11.07 (1H, bs, imide N$\underline{H}$), 12.11 (1H, bs, indole N$\underline{H}$). MS (ESI) m/z 422 [M+H]⁺.

Example 28

NAD 148

28a)

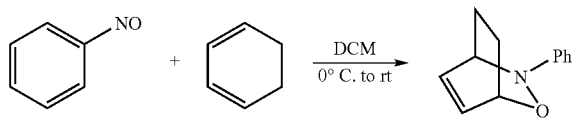

1,3-cyclohexadiene (12.4 g, 155 mmol) was added within 30 minutes at 0° C. to a solution of nitrosobenzene (13.9 g, 130 mmol) in DCM (220 mL). After warming to rt the reaction mixture was stirred for 2 hours. After concentration in vacuo the solid residue was recrystallized from ethanol (40 mL) to afford the pure target compound (18.4 g, yield 76.1%).

¹H-NMR (300 MHz, CDCl₃): δ 1.32–1.41 (1H, m, C$\underline{H_2}$), 1.54–1.63 (1H, m, C$\underline{H_2}$), 2.18–2.35 (2H, m, C$\underline{H_2}$), 4.43 (1H, m, C$\underline{H}$—O), 4.70 (1H, 1H, C$\underline{H}$—N), 6.14 (1H, ddd, C$\underline{H}$=), 6.58 (1H, ddd, C$\underline{H}$=), 6.92 (1H, t, phenyl $\underline{H-4}$), 7.01 (1H, d, phenyl $\underline{H-2,H-6}$), 7.18–7.26 (2H, m, phenyl $\underline{H-3,H-5}$). MS (ESI) m/z 188 [M+H]⁺.

28b)

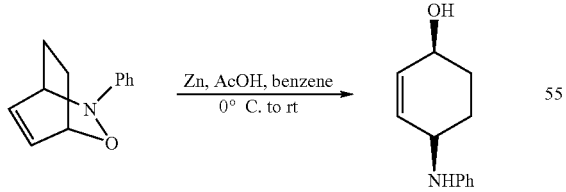

Zinc powder (45 g, mmol) was added portionwise within 45 minutes at 0° C. to a vigorously stirred solution of 28a (18.4 g, 98.3 mmol) in a 3/2 AcOH/benzene mixture (250 mL). The suspension was warmed to rt and stirred for 22 hours, then filtered over celite and washed with hot EtOH (3×100 mL). The filtrate was concentrated in vacuo to dryness by azeotopic distillation with toluene. The residue was suspended in hot EtOAc (40 mL), filtered and washed with hot EtOAc (40 mL). The filtrate was concentrated in vacuo to give a solid residue (18 g). Purification by flash chromatography (silica gel, PE/EtOAc 1/1 as eluant mixture) afforded an oil which was triturated with Et₂O to give the pure target compound (17 g, yield 91.2%).

¹H-NMR (300 MHz, DMSO-d₆): δ 1.58–1.74 (4H, m, C$\underline{H_2}$), 3.81 (1H, bd, C$\underline{H}$—OH), 4.01 (1H, bm, C$\underline{H}$—NH), 4.79 (1H, d, O$\underline{H}$), 5.54 (1H, bd, N$\underline{H}$), 5.68 (1H, ddd, C$\underline{H}$=), 5.77 (1H, ddd, C$\underline{H}$=), 6.50 (1H, t, phenyl $\underline{H-4}$), 6.60 (2H, d, phenyl $\underline{H-2,H-6}$), 7.05 (2H, dt, $\underline{H-3,H-5}$). MS (ESI) m/z 190 [M+H]⁺.

28c)

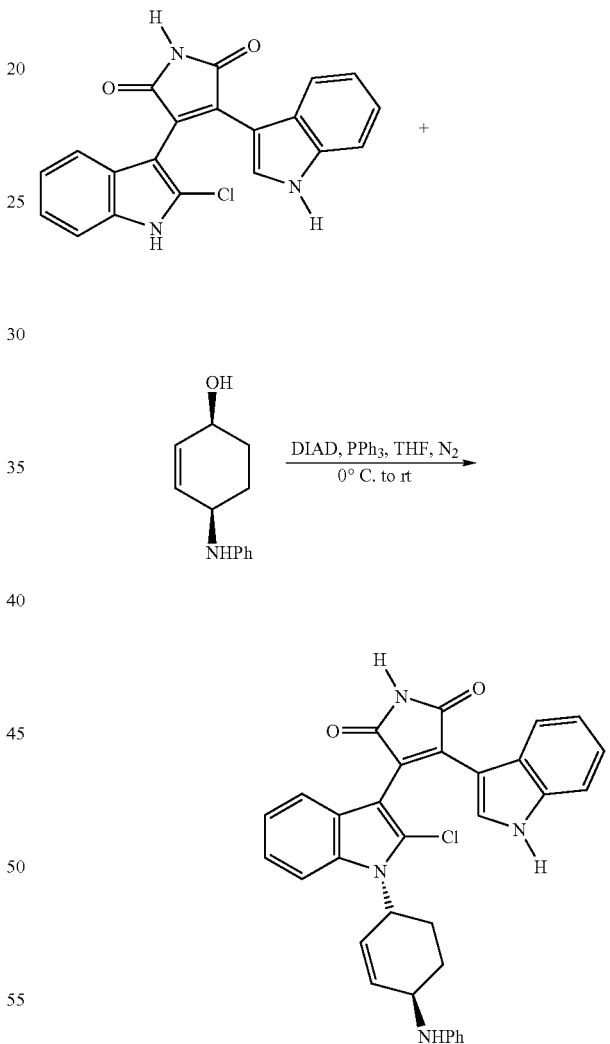

A solution of 28b (0.95 g, 5 mmol), 23c (1.74 g, 4.8 mmol) and PPh₃ (1.44 g, 5.5 mmol) in dry THF (15 mL) was cooled to 0° C. under nitrogen atmosphere, then DIAD (1.11 g, 5.5 mmol) was added portionwise in 5 minutes. The solution was warmed to rt and stirred for 19 hours, then the solvent was removed in vacuo. Purification by flash chromatography (silica gel, DCM/EtOAc 10/1 as eluant mixture) afforded the target compound (0.94 g) as a crude which was directly submitted to the final cyclization conditions.

28) NAD 148

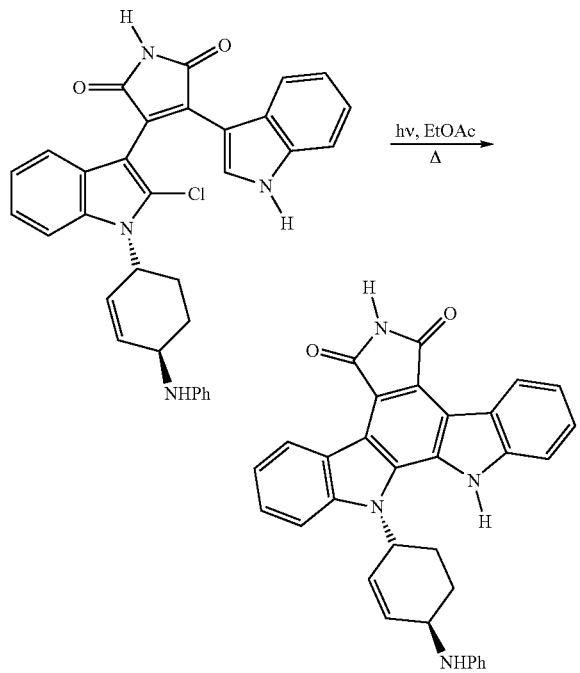

A solution of 28c (0.92 g, theoretically 1.73 mmol) in EtOAc (50 mL) was irradiated with a halogen lamp for 1.5 hours. The solution was cooled to rt and the precipitate was filtered, washed with EtOAc (10 mL) and Et₂O (10 mL), and dried in vacuo to give a first crop of the pure target compound (0.3 g). The filtrate was irradiated for additional 2 hours and treated as above to give a second crop of the pure target compound (0.21 g, total yield 55.0%).

¹H-NMR (300 MHz, DMSO-d₆): δ 2.36 (1H, m, CH₂), δ 2.40–2.65 (3H, m, CH₂) 4.77 (1H, bs, CH—N), 6.26 (1H, d, CH=), 6.48 (2H, d, CH=+CH—NH), 7.32 (2H, m, aromatic Hs) 7.49–7.57 (4H, m, aromatic Hs), 7.64–7.74 (3H, m, aromatic Hs), 8.03 (1H, d, aromatic Hs) 8.12 (1H, d, aromatic Hs), 9.58 (1H, d, indole H-4), 9.66 (1H, d, indole H-4), 11.41 (1H, s, imide NH), 12.58 (1H, bs, indole NH). MS (ESI) m/z 397 [M+H]⁺.

Example 29

NAD 073

29)

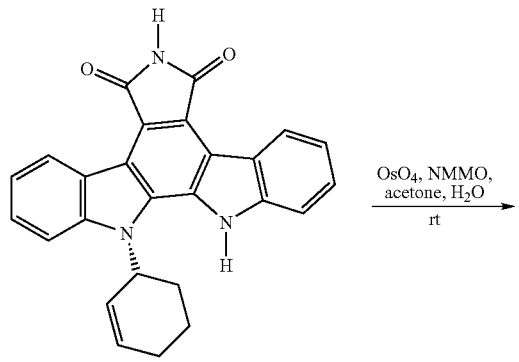

-continued

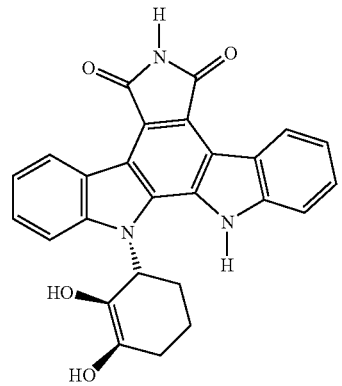

22 (0.2 g, 0.49 mmol) in acetone (60 mL) was treated sequentially with solutions of NMMO (90 mg, 0.75 mmol) in acetone (5 mL) and OsO₄ (2.5% in tBuOH, 250 μL, catalytic) at rt. The mixture was stirred for 72 hours, then concentrated in vacuo to a volume of about 10 mL and cooled at −5° C. After filtration the solid residue was washed with cold acetone, then with Et₂O and dried in vacuo to yield the pure target compound (0.19 g, yield 88.1%).

¹H-NMR (300 MHz, DMSO-d₆): δ 1.60–1.71 (1H, m, CH₂), 1.76–2.24 (4H, m, CH₂), 2.66–2.78 (1H, m, CH₂), 4.21 (1H, bs, OH), 4.36 (1H, bd, OH), 5.33–5.62 (3H, m, CH—N+CH—OH), 7.38 (2H, t, indole Hs), 7.52–7.63 (2H, m, indole Hs), 7.79 (1H, d, indole H-7), 8.04 (1H, d, indole 1–7), 9.11 (1H, d, indole H-4), 9.20 (1H, d, indole H-4), 11.06 (1H, bs, imide NH), 11.18 (1H, bs, indole NH). MS (ESI) m/z 440 [M+H]⁺.

Example 30

NAD 140

30)

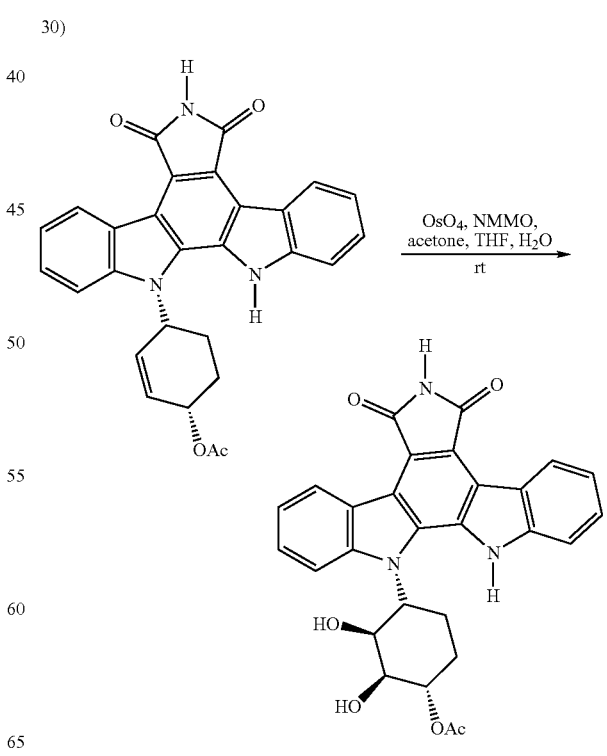

A solution of 24 (0.1 g, 0.22 mmol) in a mixture acetone/THF 2/1 (30 mL) was treated sequentially with NMMO (60 mg, 0.51 mmol) in acetone (4 mL) and OsO$_4$ (2.5% in tBuOH, 100 μL, catalytic) at rt. The mixture was stirred for 3 days, then concentrated in vacuo. The residue was dissolved in a mixture THF/EtOAc 1/1 (60 mL), washed with 1M HCl (2×30 mL), then with water (20 mL). The organic phase was dried over sodium sulfate and concentrated. The crude product (0.12 g) was triturated in hot EtOAc (2 ml), filtered and washed with Et$_2$O to yield the pure target compound (30 mg, yield 73.0%).

$^1$H-NMR (300 MHz, DMSO-d$_6$): δ 1.86 (1H, bs, C<u>H</u>$_2$), 2.06 (1H, m, C<u>H</u>$_2$), 2.25 (3H, s, OCOC<u>H</u>$_3$), 2.35 (1H, t, C<u>H</u>$_2$), 2.88 (1H, dq, C<u>H</u>$_2$), 4.02–4.06 (1H, m, C<u>H</u>—OH), 4.51–4.58 (1H, m, C<u>H</u>—OH), 5.07 (1H, d, C<u>H</u>—OAc), 5.26 (1H, d, O<u>H</u>) 5.38 (1H, dt, C<u>H</u>—N), 5.96 (1H, d, O<u>H</u>), 7.38 (2H, q, indole <u>H</u>s), 7.60 (2H, t, indole <u>H</u>s), 7.78 (1H, d, indole <u>H-7</u>), 7.87 (1H, d, indole <u>H-7</u>), 9.11 (1H, d, indole <u>H-4</u>), 9.23 (1H, d, indole <u>H-4</u>), 11.04 (1H, bs, imide N<u>H</u>), 11.29 (1H, bs, indole N<u>H</u>). MS (ESI) m/z 498 [M+H]$^+$.

Example 31

NAD 149

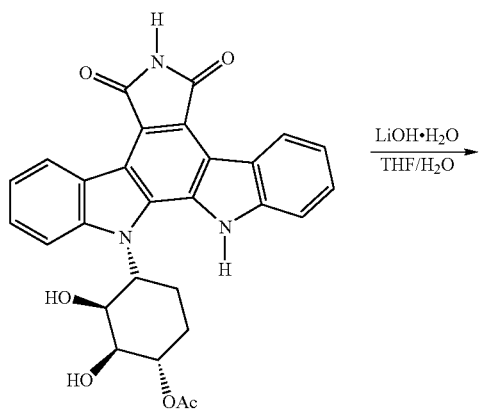

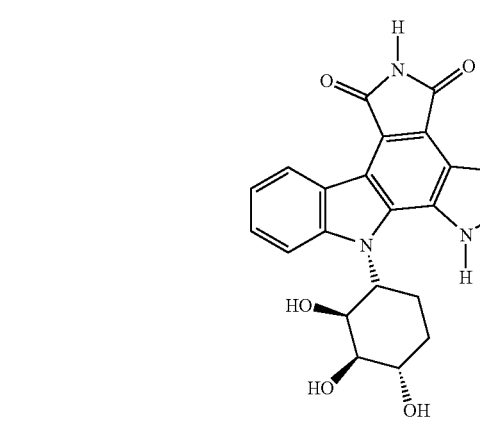

A solution of LiOH.H$_2$O (390 mg, 9.2 mmol) in water (2 mL) was added dropwise to a stirred suspension of 30 (230 mg, 0.46 mmol) in THF (6 mL) at rt. The solution was stirred for 2 hours, then neutralised with HCl and diluted by addition of THF (4 mL) and EtOAc (20 mL). The mixture was washed with water (15 mL) and brine (10 mL). The organic layer was dried over sodium sulfate and concentrated in vacuo. The crude (0.22 g) was triturated in hot EtOAc (2 mL) and Et$_2$O (2 mL) to give the pure target compound (200 mg, yield 94.8%).

$^1$H-NMR (300 MHz, DMSO-d$_6$): δ 1.75–1.90 (1H, m, C<u>H</u>$_2$), 2.00–2.40 (2H, m, C<u>H</u>$_2$) 3.21–3.32 (1H, m, C<u>H</u>$_2$) 4.25 (1H, m, C<u>H</u>—OH), 4.60–4.67 (1H, m, C<u>H</u>—OH), 4.90 (1H, d, O<u>H</u>), 5.05–5.22 (3H, m, C<u>H</u>—OH+O<u>H</u>), 5.60 (1H, bs, O<u>H</u>) 7.15–7.39 (2H, m, indole <u>H</u>s), 7.59–7.65 (2H, m, indole <u>H</u>s), 7.79 (1H, m, indole <u>H</u>s) 7.90 (H, d, indole <u>H</u>s), 9.08–9.26 (2H, m, indole <u>H-4</u>), 11.26 (1H, bs, imide N<u>H</u>), 12.20 (1H, bs, indole MS (ESI) z/Z 456 [M+H]$^+$.

Example 32

NAD 190

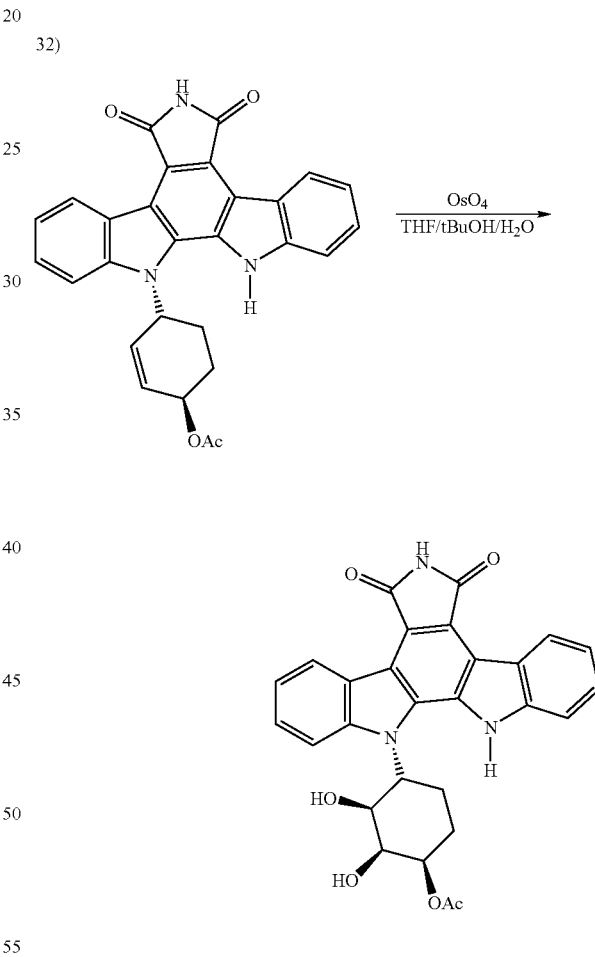

OsO$_4$ (2.5% in tBuOH, 6.8 ml, 0.54 mmol) and water (few drops) were added to a solution of 26 (0.25 g, 0.54 mmol) in THF (25 mL) at rt and under nitrogen atmosphere. Pyridine was added (90 μL, 1.08 mmol) and the reaction mixture was stirred for 18 hours. EtOAc (50 mL) and a 10% solution of NaHSO$_3$ (25 mL) were added and phases were separated. The aqueous layer was extracted with EtOAc (20 mL), the combined organic layers were washed with SN HCl (30 mL) and dried over sodium sulfate. After concentration in vacuo, the solid residue (0.32 g) was dissolved in THF (2 mL) and precipitated by addition of MeOH (10 mL) to give the pure target compound e (0.14 g, yield 52.0%).

¹H-NMR (300 MHz, DMSO-d₆): δ 1.79–1.85 (1H, m, C$\underline{H}_2$), 2.00–2.04 (1H, m, C$\underline{H}_2$), 2.10 (3H, s, OCOC$\underline{H}_3$), 2.16–2.31 (1H, m, C$\underline{H}_2$), 2.73–2.88 (1H, m, C$\underline{H}_2$), 4.25 (1H, bs, C$\underline{H}$—OH), 4.46 (1H, m, C$\underline{H}$—OH), 5.08–5.13 (1H, m, C$\underline{H}$—OAc), 5.34–5.41 (1H, m, C$\underline{H}$—N), 5.80–6.00 (2H, bs, O$\underline{H}$), 7.37 (2H, t, indole $\underline{H}$s), 7.50 (1H, dt, indole $\underline{H}$s), 7.60 (1H, dt, indole $\underline{H}$s), 7.75 (1H, d, indole $\underline{H}$-7), 8.12 (1H, d, indole $\underline{H}$-7), 9.10 (1H, d, indole $\underline{H}$-4), 9.18 (1H, d, indole $\underline{H}$-4), 11.05 (1H, bs, imide N$\underline{H}$), 11.17 (1H, bs, indole N$\underline{H}$). MS (ESI) m/z 498 [M+H]⁺.

Example 33

NAD 181

33)

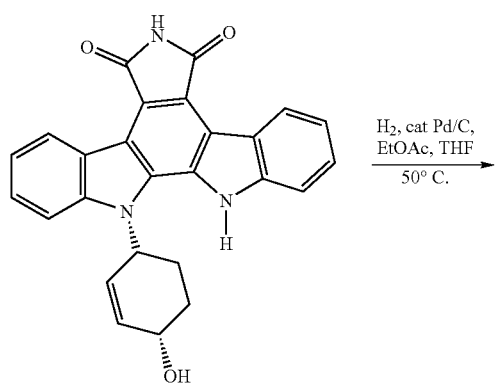

H₂, cat Pd/C,
EtOAc, THF
50° C.

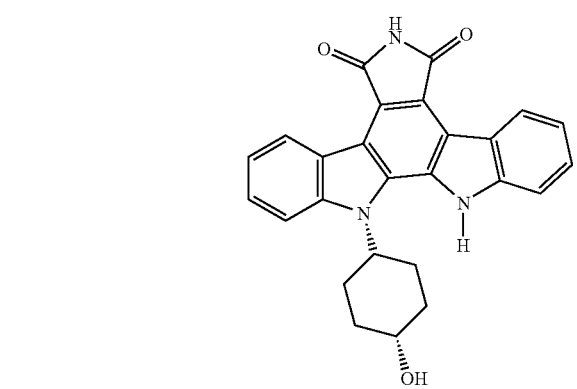

Hydrogen gas was bubbled into a vigorously stirred suspension of 25 (160 mg, 0.38 mmol) and 10% Pd/C (0.16 g, catalyst) in a 8/12 TBF/EtOAc mixture (20 mL). The suspension was then heated to 50° C. for 1.5 hours and after cooling for 1 hour at rt. Hydrogen was removed by a stream of nitrogen, then the catalyst was filtered off through a short pad of silica gel. The silica gel was rinsed with EtOAc and the combined organic layer was concentrated under vacuum. Purification by flash chromatography (silica gel, PE/EtOAc 1/1 as eluant mixture) afforded the pure target compound (40 mg, yield 25.2%).

¹H-NMR (300 MHz, DMSO-d₆): δ 1.70–2.20 (6H, m, C$\underline{H}_2$), 2.40–2.80 (2H, m, C$\underline{H}_2$), 4.31 (1H, bs, C$\underline{H}$—OH), 5.32 (1H, m, C$\underline{H}$—N), 6.74 (1H, bs, O$\underline{H}$), 7.38 (2H, t, indole $\underline{H}$s), 7.54–7.63 (2H, m, indole $\underline{H}$s), 7.69 (1H, m, indole $\underline{H}$s), 8.01 (1H, bd, indole $\underline{H}$s), 9.16 (1H, d, indole $\underline{H}$-4), 9.26 (1H, d, indole $\underline{H}$-4), 11.08 (1H, s, imide N$\underline{H}$), 12.59 (1H, bs, indole N$\underline{H}$) MS(ESI) m/z 424 [M+H]⁺.

Example 34

NAN 174

34a)

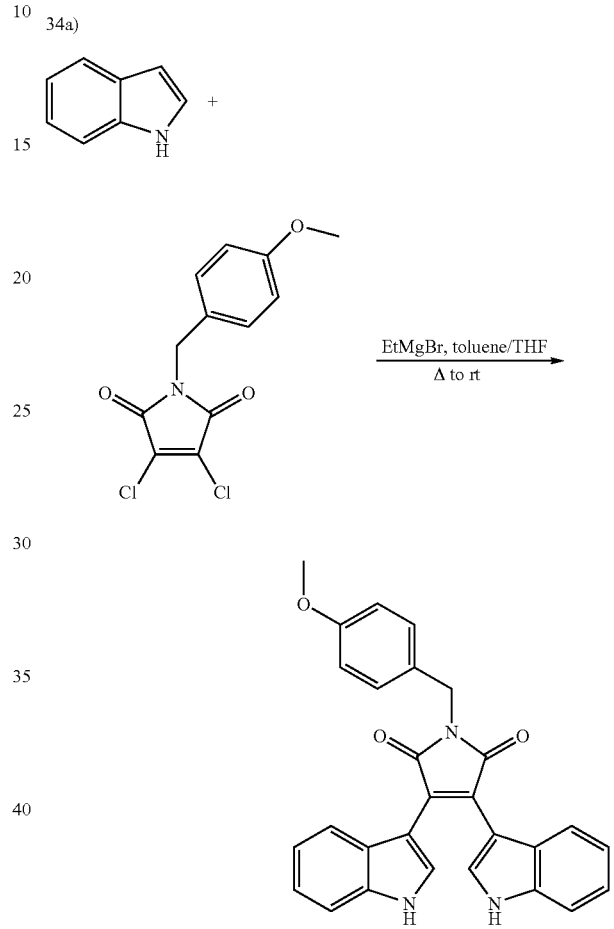

EtMgBr, toluene/THF
Δ to rt

Ehylmagnesiumbromide (3 M in Et₂O, 100 mL, 0.3 mol) was added dropwise to a solution of indole (35.1 g, 0.3 mol) in a 10/1 mixture of toluene/THF (660 mL) while stirring under nitrogen atmosphere. The solution was stirred for 1 additional hour at rt before adding a solution of compound 19a (39 g, 0.136 mol) in toluene (250 mL) within 1 hour. The reaction mixture was then refluxed for 4 hours and stirred at rt overnight. The solvent was concentrated in vacuo and the residue dissolved in EtOAc (800 mL), treated with a saturated solution of NH₄Cl (150 mL), then washed with water (2×100 mL). The organic phase was then dried over sodium sulfate, and concentrated. The crude residue was refluxed in CH₂Cl₂ (200 mL), cooled to −20° C., filtered and washed twice with cold CH₂Cl₂ to afford after drying the pure target compound (40.5 g, yield 67.2%).

¹H-NMR (300 MHz, DMSO-d₆): δ 3.72 (3H, s, OC$\underline{H}_3$), 4.69 (2H, s, C$\underline{H}_2$—N), 6.62–7.00 (8H, m, aromatic $\underline{H}$s), 7.30 (2H, d, aromatic $\underline{H}$s), 7.35 (2H, d, aromatic $\underline{H}$s), 7.89 (2H, s, indole $\underline{H}$-2), 11.70 (2H, bs, indole N$\underline{H}$). MS (ESI) m/z 448 [M+H]⁺.

34b)

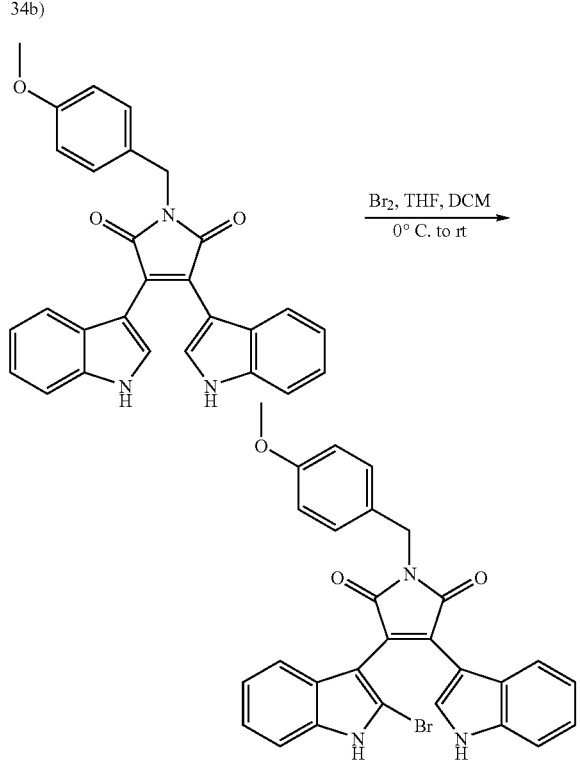

A solution of 34a (35 g, 78.2 mmol) in DCM/THF 7/6 (1300 mL) was cooled to 0° C. A solution of bromine (12.5 g, 78.2 mmol) in DCM (50 mL) was added dropwise within 1 hour. The resulting solution was stirred for 1 hour at 0° C., the cooling bath was removed, the solution was stirred for additional 30 minutes at rt and was washed with a saturated solution of NaHCO$_3$ (200 ml). Drying over sodium sulfate and concentration in vacuo yielded a solid residue (49.7 g). The crude product was recrystallized from acetonitrile (55 mL) to give a first crop of the pure target compound (14.4 g). The mother liquors were concentrated to dryness and crystallized from DCM to give a second crop of the pure target compound (16.7 g, total yield 76.0%).

$^1$H-NMR (300 MHz, DMSO-d$_6$): δ 3.70 (3H, s, OC<u>H</u>$_3$), 4.65 (2H, s, C<u>H</u>$_2$—N), 6.35 (2H, d, phenyl <u>H</u>s), 6.50–6.60 (2H, m, phenyl <u>H</u>s), 6.90–7.20 (4H, m, indole <u>H</u>s), 7.30–7.40 (4H, d, indole <u>H</u>s), 8.10 (1H, s, indole <u>H-2</u>), 11.90 (1H, bs, indole N<u>H</u>), 12.45 (1H, bs, indole N<u>H</u>). MS (ESI) m/z 526 [M+H]$^+$.

34c)

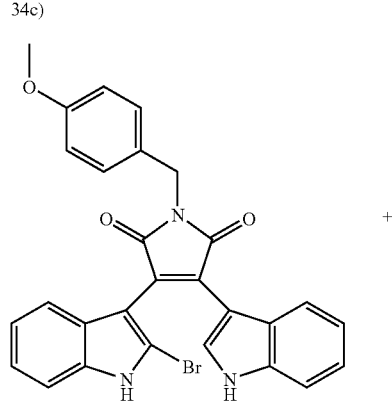

+

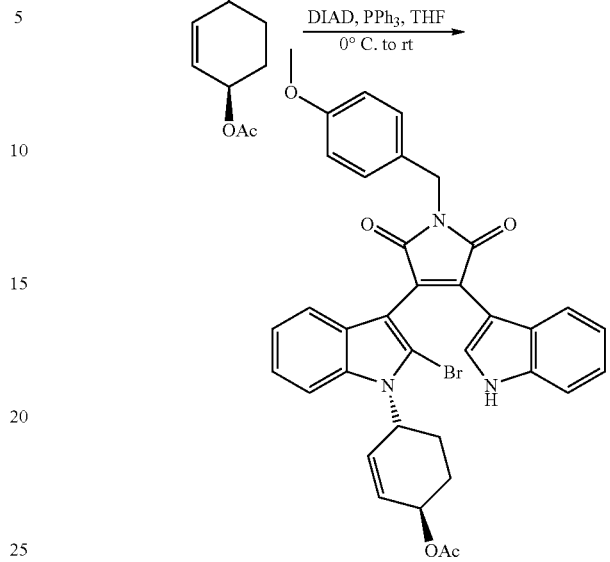

34b (2.14 g, 4.07 mmol), 26b (1.02 g, 6.05 mmol) and triphenylphosphine (2.10 g, 8 mmol) were dissolved in THF (20 mL). The solution was cooled to 0° C. and DIAD (1.62 g, 8 mmol) was added dropwise. At the end of addition the solution was warmed to rt and stirred for 1 hour. Two drops of water were then added before removing the solvent in vacuo to give an oily residue which was further purified by double flash chromatography (silica gel, PE/EtOAc/NEt$_3$ 1/1/10 and DCM/EtOAc 20/1 as eluant mixtures) to give the pure target product (1.17 g, 43.4%).

$^1$H-NMR (300 MHz, DMSO-d$_6$): δ 1.72–1.90 (2H, m, C<u>H</u>$_2$) 1.99 (3H, s, OCOC<u>H</u>$_3$), 2.00–2.20 (2H, m, C<u>H</u>$_2$) 3.70 (3H, s, OC<u>H</u>$_3$), 4.65 (2H, s, C<u>H</u>—N), 5.30 (1H, m, C<u>H</u>—OAc), 5.55 (1H, m, C<u>H</u>—N), 5.80 (1H, m, C<u>H</u>=), 5.95 (1H, m, C<u>H</u>=), 6.25 (1H, d, aromatic <u>H</u>s), 6.45–6.55 (1H, m, aromatic <u>H</u>s), 6.90–7.10 (5H, m, aromatic <u>H</u>s), 7.15–7.20 (2H, m, aromatic <u>H</u>s), 7.27–7.55 (2H, m, aromatic <u>H</u>s), 7.65 (1H, m, aromatic <u>H</u>s), 8.15 (1H, s, indole <u>H-2</u>), 11.90 (1H, bs, indole N<u>H</u>) MS (ESI) m/z 665 [M+H]$^+$.

34d)

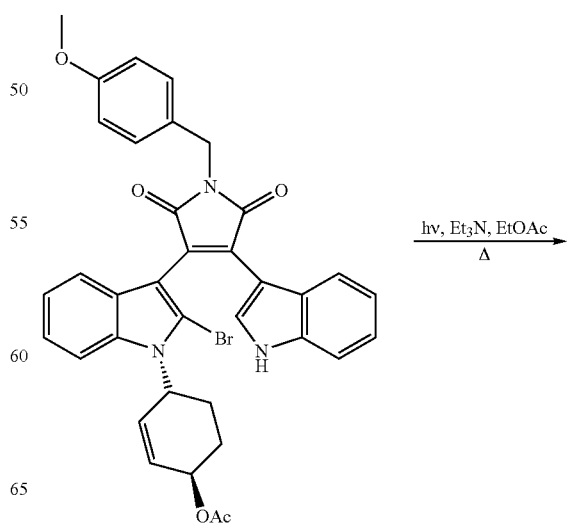

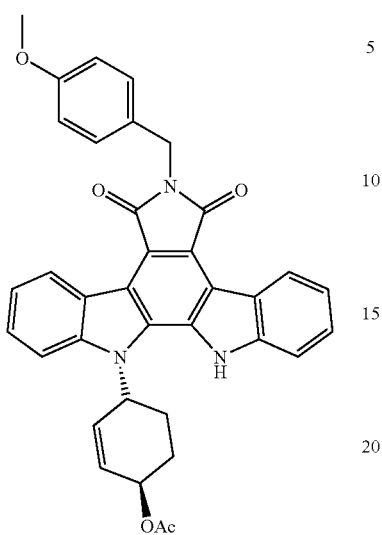

A solution of 33c (1;10 g, 1.66 mmol) and Et$_3$N (8 mL, 551 mmol) in EtOAc (30 mL) was irradiated with an halogen lamp. After 3 hours of irradiation the solution was cooled to rt and filtered. The solution was washed with water (2×. 20 mL), dried over sodium sulfate and concentrated in vacuo (1.06 g). The crude was then recrystallized from EtOAc (3 mL) to yield the pure target compound (0.36 g, yield 36.8%).

$^1$H-NMR (300 MHz, DMSO-d$_6$): δ 2.00 (3H, s, OCO CH$_3$), 2.10–2.30 (3H, m, indole CH$_2$), 2.40–2.50 (1H, m, CH$_2$), 3.65 (3H, s, OCH$_3$), 4.75 (2H, s, CH$_2$NCO), 5.60–5.80 (1H, bs, CH—OH), 6.15 (1H, d, CH=), 6.22 (1H, bs, CH—N), 6.30 (1H, d, CH=), 6.70 (2H, d, aromatic Hs), 7.35–7.40 (4H, m, aromatic Hs), 7.45–7.60 (2H, m, aromatic Hs), 7.75 (2H, m, aromatic Hs), 9.10 (1H, d, indole H-4), 9.20 (1H, d, indole H-4), 11.95 (1H, bs, indole NH). MS (ESI) m/z 584 [M+H]$^+$.

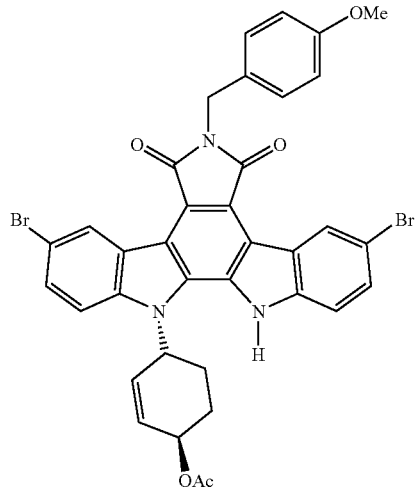

Bromine (0.38 g, 2.4 mmol) was added dropwise at rt to a solution of 33d (0.47 g, 0.81 mmol) in DCM (100 mL). The solution was stirred for 3 hours and the resulting suspension was filtered. The filtrate was washed with aqueous sodium sulfite (30 mL) then dried over sodium sulfate. After filtration and evaporation the solid residue was recrystallised from EtOAc (2 mL). The precipitate was filtered, washed with EtOAc (1 mL) and Et$_2$O (3×2 mL), and dried in vacuo to give the pure target compound (0.37 g, yield 62.7%).

$^1$H-NMR (300 MHz, DMSO-d$_6$): δ 2.13 (3H, s, OCO CH$_3$), 2.17–2.48 (4H, m, CH$_2$), 3.68 (3H, s, OCH$_3$), 4.53 (2H, s, CH$_2$—N), 5.69 (1H, m, CH—OAc), 6.10 (2H, d, CH=), 6.22 (1H, d, CH—N), 6.87 (2H, d, aromatic Hs), 7.26 (2H, d, aromatic Hs), 7.56–7.72 (4H, m, aromatic Hs), 9.08 (1H, s, indole 14), 9.15 (1H, d, indole H-4), 12.19 (1H, bs, indole NH). MS (ESI) m/z 740 [M+H]$^+$.

Example 35

NAD 176

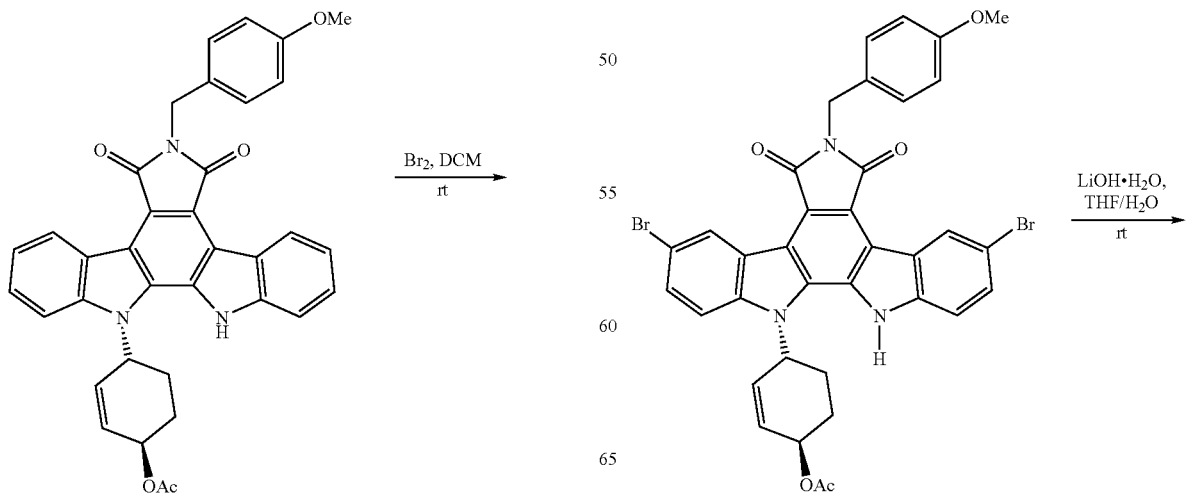

34) NAD 174

35)

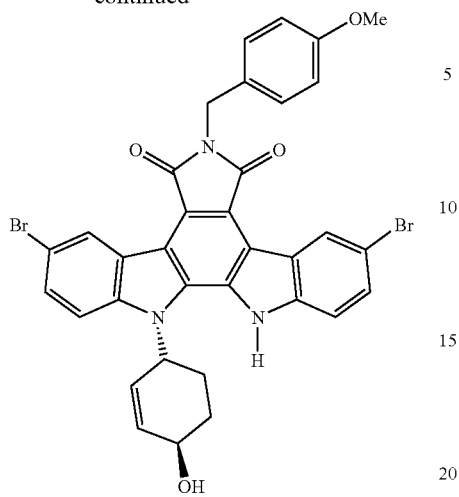

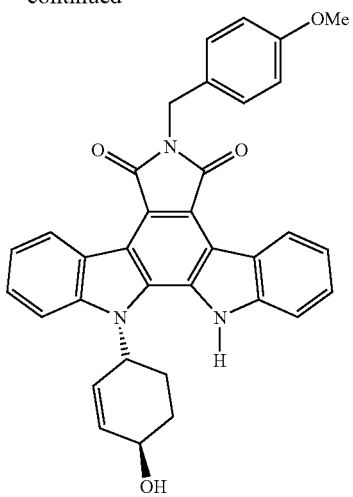

LiOH.H$_2$O (0.13 g, 3 mmol) in water (1 mL) was added dropwise to a stirred solution of 34 (0.11 g, 0.15 mmol) in THF. (6 mL). The solution was stirred overnight at rt, then neutralised with 1N HCl. The mixture was diluted with EtOAc (30 mL) and water (20 mL). The organic layer was washed with water (20 mL), then dried over sodium sulfate. After concentration the crude product (0.11 g) was triturated in hot EtOAc (2 mL) to afford after filtration and drying in vacuo the pure target compound (70 mg, yield 67.0%).

$^1$H-NMR (300 MHz, DMSO-d$_6$): δ 1.90–2.3 (4H, m, CH$_2$), 3.69 (3H, s, OCH$_3$), 4.49 (1H, m, H), 4.63 (2H, s, CH$_2$—N), 5.21 (1H, d, CH—OH), 5.97 (1H, d, CH—N), 6.06 (1H, m, CH=), 6.13 (1H, d, CH=), 6.88 (2H, d, aromatic Hs), 7.3 (2H, d, aromatic Hs), 7.59–7.73 (4H, m, aromatic Hs), 9.14 (1H, s, indole H-4), 9.21 (1H, d, indole H-4), 12.26 (1H, s, indole NH). MS (ESI) m/z 698 [M+H]$^+$.

LiOH.H$_2$O (0.84 g, 20 mmol) dissolved in hot water (3 mL) was added dropwise to a stirred solution of 34d (0.59 g, 1.1 mmol) in THF (6 mL). The solution was stirred 2 hours at 50° C. and 2 hours at rt, then neutralised with a few drops of 37% HCl. The mixture was diluted with EtOAc (30 mL) and water (20 mL). The organic layer was separated and washed with water (20 mL), then dried over sodium sulfate. After concentration in vacuo the crude product (0.57 g) was purified by flash chromatography (silica gel, PE/EtOAc 1/1 as eluant mixture). The solid obtained was recrystallized from EtOAc to give after filtration and drying in vacuo the pure target compound (0.28 g, yield 51.3%).

$^1$H-NMR (300 MHz, DMSO-d$_6$): δ 2.01–2.19 (3H, m, CH$_2$), 2.26–2.34 (1H, m, CH$_2$), 3.69 (3H, s, OCH$_3$), 4.52 (1H, bs, OH), 4.76 (2H, s, CH$_2$—NCO), 5.19 (1H, d, CH—N), 5.99 (1H, d, CH—OH), 6.11 (2H, d, CH=), 6.89 (2H, d, aromatic Hs), 7.32–7.36 (4H, m, aromatic Hs), 7.54 (2H, dt, aromatic Hs), 7.78 (2H, t, aromatic Hs), 9.09 (1H, d, indole H-4), 9.17 (1H, d, indole H-4), 12.09 (1H, bs, indole NH) MS (ESI) m/z 698 [M+H]$^+$.

Example 36

NAD 133

36a)

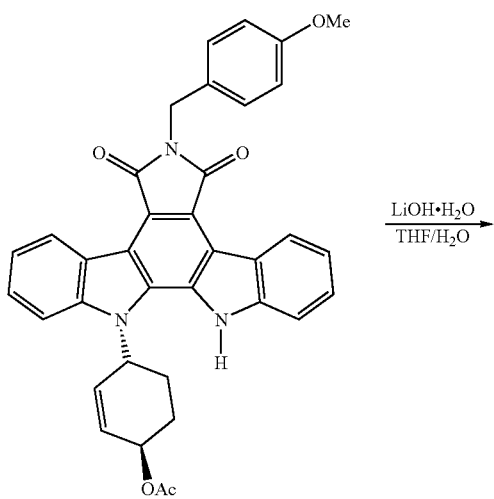

LiOH·H$_2$O
THF/H$_2$O

36) NAD 133

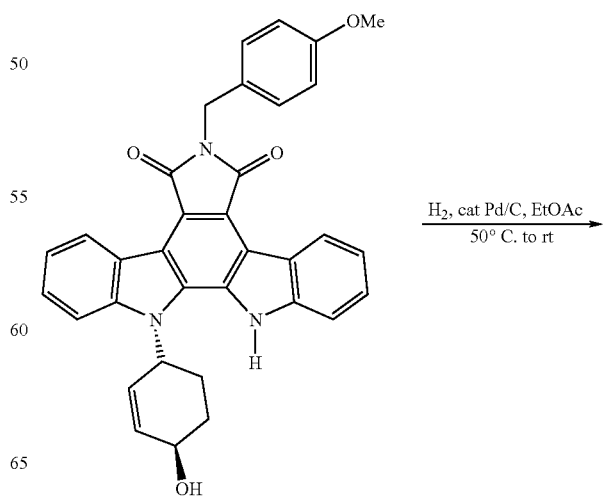

H$_2$, cat Pd/C, EtOAc
50° C. to rt

-continued

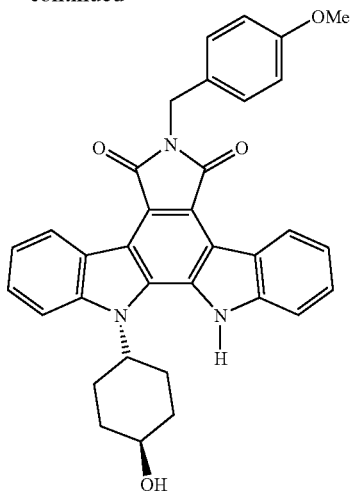

Hydrogen was bubbled into a vigourously stirred suspension of 36a (280 mg, 0.52 mmol) and 10% Pd/C (0.15 g, catalyst) in EtOAc (10 mL). The suspension was heated to 50° C. for 4 hours, then stirred overnight at rt. Hydrogen was flushed away with a nitrogen stream, the catalyst was filtered off through a short pad of silica gel and the eluate was concentrated. Purification by flash chromatography (silica-gel, pure EtOAc as eluant) followed by crystallisation from MeOH (2 mL) afforded the pure target compound (0.6 g, 46.7%).

Example 37

NAD 244

37a)

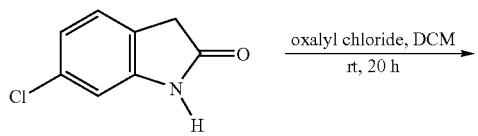

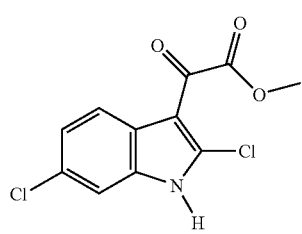

6-chlorooxindole (6.3 g, 97.3 mmol) was added portionwise within 5 minutes to a vigorously stirred solution of oxalyl chloride (16.7 mL, 195 mmol) in DCM (60 mL) at rt. After 20 hours the suspension was filtered and the solid washed with DCM (4×10 mL). After drying in vacuo at 80° C. for 2 hours the residue was suspended in Et$_2$O (80 mL) and dry methanol (7.7 mL, 190 mmol) was added as a single portion to the vigorously stirred mixture at rt. The suspension was stirred for 30 minutes, filtered, the solid was washed with Et$_2$O (3×10 mL) and dried in vacuo to give the pure target compound (14.7 g, yield 56.0%).

$^1$H-NMR (300 MHz, DMSO-d$_6$): δ 3.92 (3H, s, CH$_3$—O), 7.35 (1H, dd, indole H-5), 7.50 (1H, s, indole H-7), 8.05 (1H, bd, indole H-4), 3.60 (1H, bs, NH). MS (APCI) m/z 272 [M+H]$^+$.

37b)

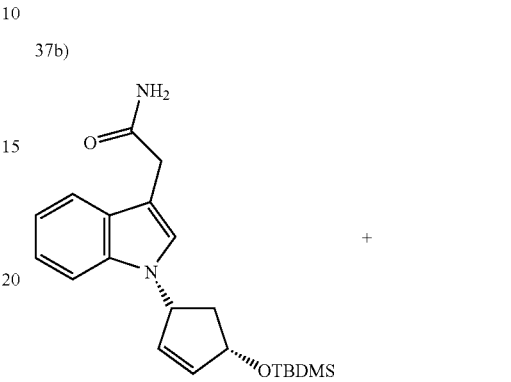

+

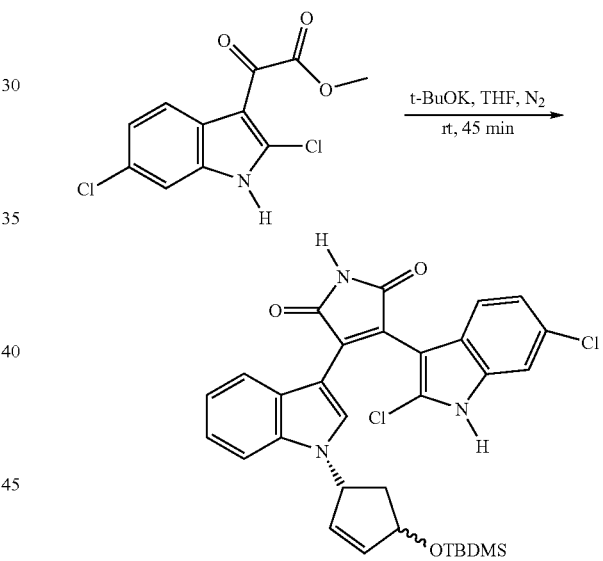

Potassium t-butoxide (1M in THF, 28 mL, 28 mmol) was added dropwise to a stirred solution of 37a (2.5 g, 9.18 mmol) and 1g (1.7 g, 4.59 mmol) in dry THF (20 mL) at rt under nitrogen atmosphere. After 45 minutes the reaction was diluted with EtOAc (200 mL), washed with water (100 mL) and brine (50 mL), dried over sodium sulfate, filtered and concentrated in vacuo. The crude residue (2.92 g, quantitative yield) was considered pure enough for the next step.

$^1$H-NMR (300 MHz, DMSO-d$_6$): δ 0.14 (3H, s, CH$_3$—Si), 0.21 (3H, s, CH$_3$—Si), 0.95 (9H, tBu), 1.60 (1H, dt, CH$_2$), 3.05 (1H, m, CH$_2$) 5.15 (1H, bt, CH—O), 6.30 (2H, m, CH=CH), 6.40 (1H, bt, CH—N), 7.38 (4H, m, indole Harom), 7.75 (1H, d, indole H-7), 8.05 (1H, d, indole H-7), 9.13 (1H, d, indole H-4), 9.23 (1H, d, indole H-4), 11.10 (1H, bs, imide NH), 12.10 (1H, bs, indole NH. MS (ESI) m/z 556 [M+H]$^+$.

37c)

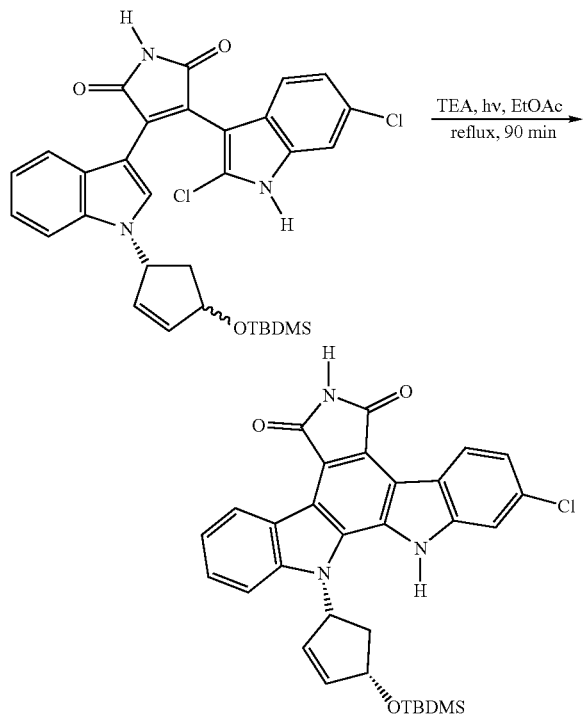

A solution of 37b (2.9 g, 4.89 mmol) and triethylamine (1.39 mL, 10 mmol) in EtOAc (50 mL) was irradiated with a halogen lamp. After irradiation for 90 minutes the solution was cooled to rt, washed with water (2×50 mL), dried with sodium sulfate and concentrated in vacuo to give a solid residue (2.5 g). Purification by flash chromatography (silica gel, PE/EtOAc 85/15 to 1/1 as eluant mixture) afforded the pure target compound (1.3 g, yield 47.8%) together with other products.

$^1$H-NMR (300 MHz, DMSO-d$_6$): δ 0.14 (3H, s, CH$_3$—Si), 0.21 (3H, s, CH$_3$Si), 0.95 (9H, tBu), 2.20 (1H, dt, CH$_2$), 3.30 (1H, m, CH$_2$), 4.90 (1H, bt, CH—O), 6.10–6.20 (2H, m, CH=CH), 6.40 (1H, bt, CH—N), 6.60 (1H, m, Harom), 7.05 (2H, m, Harom), 7.40 (2H, m, indole Harom), 7.75 (1H, d, indole H-7), 8.05 (1H, s, Harom), 11.10 (1H, bs, imide NH), 12.35 (1H, bs, indole NH). S (ESI) m/z 592 [M+H]$^+$.

37d)

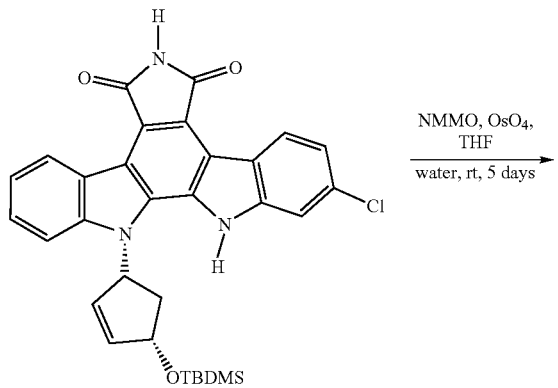

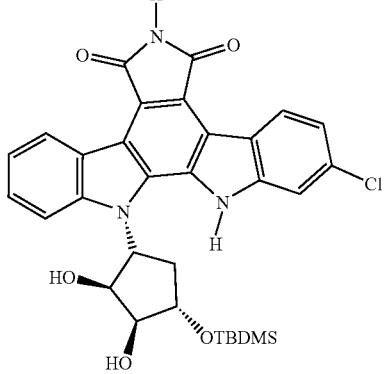

N-Methylmorpholine N-oxide (120 mg, 1 mmol) in acetone (10 mL) was added dropwise to a solution of 37c (280 mg, 0.5 mmol) in acetone (5 mL) at rt. Then osmium tetroxide (2.5% w/w solution in t-BuOH, 0.45 mL, catalytic) and water (a few drops, catalytic) were added and stirring at rt was continued for 5 days. The resulting suspension was filtered, the solid was washed repeatedly with acetone and dried to give the pure target compound (240 mg, yield 81.1%).

$^1$H-NMR (300 MHz, DMSO-d$_6$): δ 0.25 (6H, s, CH$_3$—Si), 1.05 (9H, tBu), 2.45 (1H, dt, CH$_2$), 3.10 (1H, m, CH$_2$), 3.40 (2H, m, 2-CH—OH+3-CH—OH), 3.80 (1H, d, OH), 4.35 (1H, d, OH), 5.05 (1H, bt, CH—OSi), 5.65 (1H, bt, CH—N), 7.55 (3H, m, Harom), 7.85 (1H, d, indole H-7), 8.45 (1H, d, indole H-7), 9.15 (1H, d, indole H-4), 9.25 (1H, d, indole H-4), 11.10 (1H, bs, imide NH), 11.80 (1H, bs, indole NH). MS (ESI) m/z 590 [M+H]$^+$.

37) NAD 244

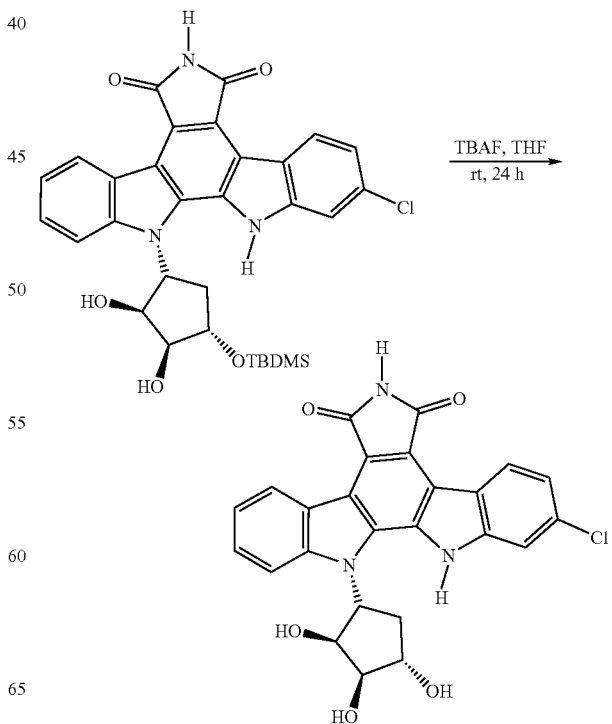

Tetrabutylammonium fluoride (1M in THF, 0.67 mL, 0.67 mmol) was added dropwise to a stirred solution of 37d (195 mg, 0.33 mmol) in dry THF (5 mL) under nitrogen atmosphere at rt. After 24 hours the solution was diluted with EtOAc (50 mL), washed with 1N HCl (20 mL) and water (2×20 mL). The organic layer was dried over sodium sulfate filtered and concentrated in vacuo to yield a crude (180 mg). Preparative chromatoghraphy (silica gel, EtOAc as eluant) afforded the pure target compound as an orange solid (55 mg, yield 35.1%).

$^1$H-NMR (300 MHz, DMSO-d$_6$): δ 2.45 (1H, dt, C$\underline{H}_2$), 3.10 (1H, m, C$\underline{H}_2$), 3.95 (1H, d, O$\underline{H}$), 4.20 (1H, d, O$\underline{H}$), 5.05 (4-C$\underline{H}$—OH), 5.15 (1H, m, 2-C$\underline{H}$—OH), 5.25 (2H, m, 3-C$\underline{H}$—OH), 5.65 (1H, bt, C$\underline{H}$—N), 7.45 (2H, m, Harom), 7.65 (1H, d, indole Harom), 7.75 (1H, bs, indole Harom), 8.20 (1H, m, Harom), 9.15 (1H, d, indole H-4), 9.25 (1H, d, indole H-4), 11.15 (1H, bs, imide N$\underline{H}$), 11.80 (1H, bs, indole N$\underline{H}$). MS (ESI) m/z 476 [M+H]$^+$.

Example 38

NAD 245

38)

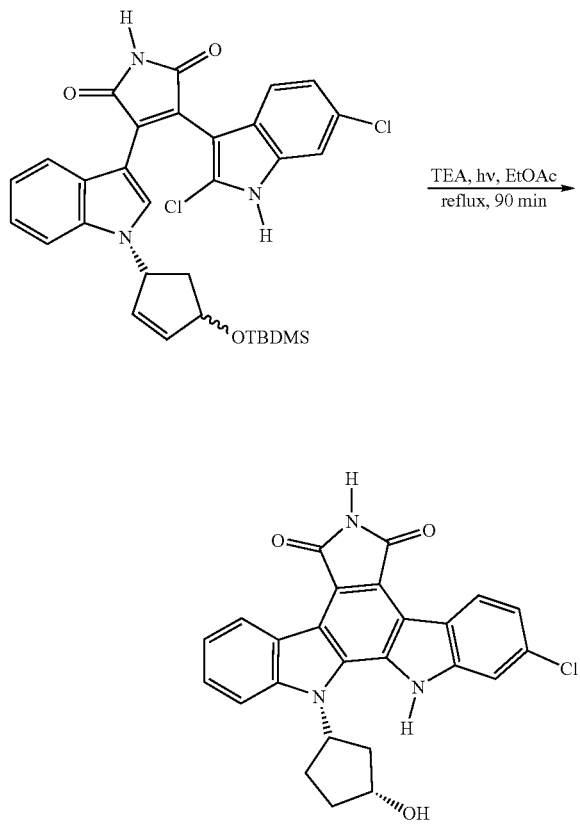

A solution of 37b (2.9 g, 4.89 mmol) and triethylamine (1.39 mL, 10 mmol) in EtOAc (50 mL) was irradiated with a halogen lamp. After irradiation for 90 minutes the solution was cooled to rt, washed with water (2×50 mL), dried with sodium sulfate and concentrated in vacuo to give a solid residue (2.5 g). Purification by flash chromatography (silica gel, PE/EtOAc 85/15 to 1/1 as eluant mixture), followed by a preparative TLC (silica gel, PE/EtOAc 1/1 as eluant mixture) of a slightly impure fraction (150 mg) afforded the pure target compound (85 mg, yield 3.15%) as a minor component together with other products.

$^1$H-NMR (300 MHz, DMSO-d$_6$): δ 2.20 (1H, dt, C$\underline{H}_2$), 3.25 (1H, m, C$\underline{H}_2$), 5.05 (1H, bt, C$\underline{H}$—O), 5.55 (1H, d, O$\underline{H}$), 6.30 (2H, m, C$\underline{H}$=C$\underline{H}$), 6.40 (1H, bt, C$\underline{H}$—N), 7.45 (3H, m, Harom), 7.75 (1H, d, indole H-7), 8.05 (1H, d, indole H-7), 9.15 (1H, d, indole H-4), 9.25 (1H, d, indole H-4), 11.15 (1H, s, imide N$\underline{H}$), 12.10 (1H, s, indole N$\underline{H}$). MS (ESI) m/z 442 [M+H]$^+$.

Example 39

39a)

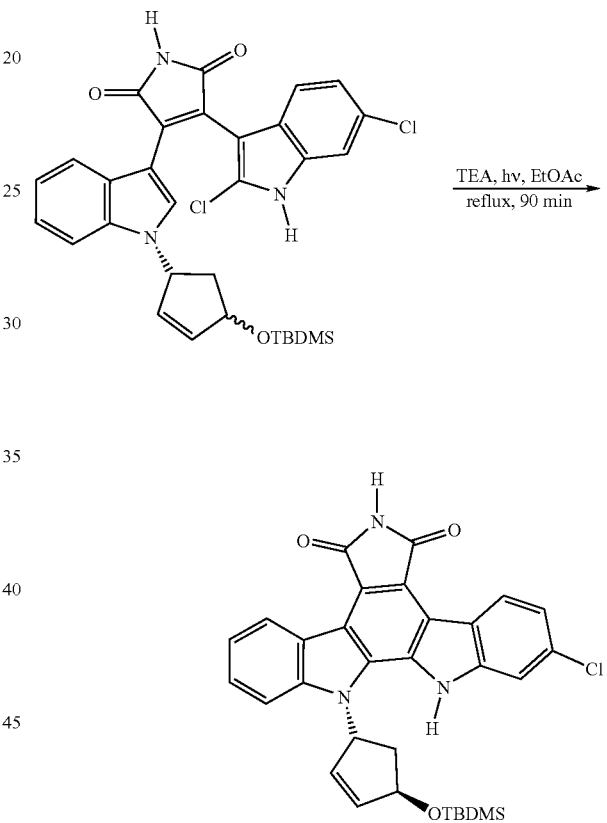

A solution of 37b (2.9 g, 4.89 mmol) and trithylamine (1.39 mL, 10 mmol) in EtOAc (50 mL) was irradiated with a halogen lamp. After irradiation for 90 minutes the solution was cooled to rt, washed with water (2×50 mL), dried with sodium sulfate and concentrated in vacuo to give a solid residue (2.5 g). Purification by flash chromatography (silica gel, PE/EtOAc 85/15 to 1/1 as eluant mixture) afforded the pure target compound (125 mg, yield 5.8%) as a minor component together with other products.

$^1$H-NMR (300 MHz, DMSO-d$_6$): δ 0.21 (6H, s, C$\underline{H}$—Si), 0.95 (9H, tBu), 2.55 (2H, m, H, 5.50 (1H, bt, C$\underline{H}$—O), 6.30 (2H, m, CH=CB, 6.80 (1H, bt, C$\underline{H}$—N), 7.40 (2H, m, indole Harom), 7.55 (2H, m, Harom), 7.75 (1H, d, indole H-7), 9.13 (1H, d, indole H-4), 9.23 (1H, d, indole H-4), 11.10 (1H, bs, imide N$\underline{H}$), 12.30 (1H, bs, indole i). MS (ESI) m/z 556 [M+H]$^+$.

39) NAD 265

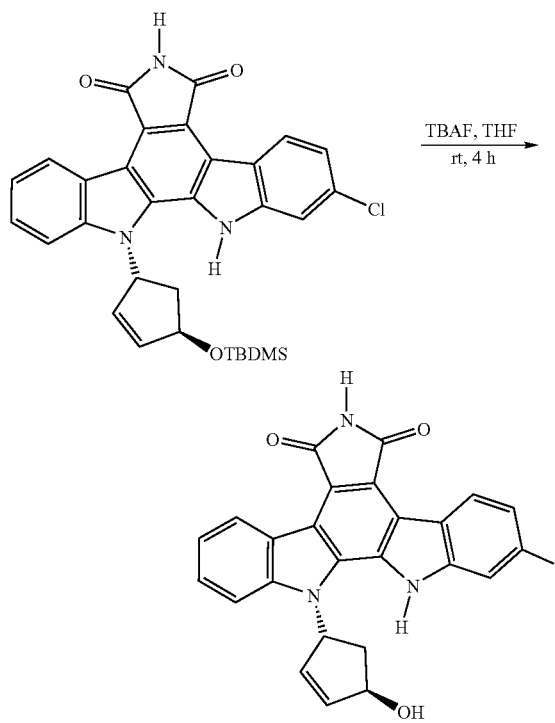

Tetrabutylammonium fluoride (1M in THF, 0.44 mL, 0.44 mmol) was added dropwise to a stirred solution of 39a (120 mg, 0.22 mmol) in dry THF (5 mL) under nitrogen atmosphere at rt. After 4 hours the solution was diluted with EtOAc (50 mL), washed with 1N HCl (20 mL) and water (2×20 mL). The organic layer was dried over sodium sulfate, filtered and concentrated in vacuo to yield the pure target compound (73 mg, yield 75.0%).

$^1$H-NMR (300 MHz, DMSO-$d_6$): δ 2.55 (2H, m, CH), 5.30 (1H, bt, C$\underline{H}$—O), 6.30 (2H, m, C$\underline{H}$=C$\underline{H}$), 6.80 (1H, bt, C$\underline{H}$—N), 7.40 (2H, m, indole $\underline{H}$arom), 7.55 (2H, m, $\underline{H}$arom), 7.75 (1H, d, indole $\underline{H}$-7), 9.13 (1H, d, indole $\underline{H}$-4), 9.23 (1H, d, indole $\underline{H}$-4), 11.10 (1H, bs, imide $\underline{NH}$), 12.30 (1H, bs, indole $\underline{NH}$). MS (ESI) m/z 442 [M+H]$^+$.

Example 40

NAD 247

40a)

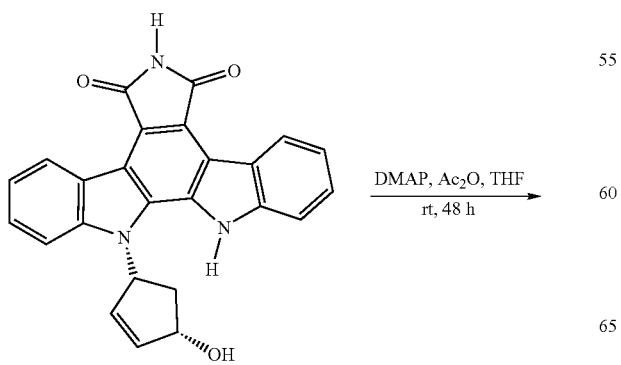

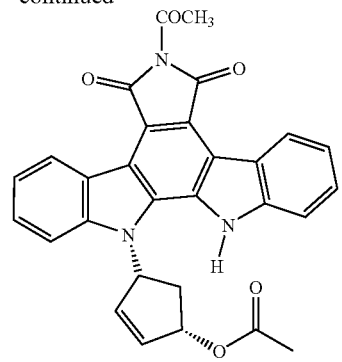

Dimethylaminopyridine (72 g, 60.0 mmol) was added to a stirred solution of 1 (4.2 g, 10.3 mmol) and acetic anhydride (10 mL) in THF (120 mL) at rt. Stirring was continued for 48 hours, then the suspension was poured into 2N HCl (200 mL) under stirring at 0° C. The precipitate was filtered and thoroughly washed with water. The dried solid was characterized as the pure target compound (4.6 g, yield 90.7%).

$^1$H-NMR (300 MHz, DMSO-$d_6$): δ 2.14 (3H, s, C$\underline{H_3}$—COO), 2.25 (1H, m, C$\underline{H_2}$), 2.65 (3H, s, C$\underline{H}$—CON), 3.40 (1H, m, C$\underline{H_2}$) 5.85 (1H, bt, CH—OAc), 6.40 (1H, dt, C$\underline{H}$=), 6.50 (1H, bt, C$\underline{H}$—N), 6.60 (1H, bd, C$\underline{H}$=), 7.45 (4H, m, indole $\underline{H}$arom), 7.80 (1H, d, indole $\underline{H}$-7), 7.85 (1H; d, indole $\underline{H}$-7), 9.15 (1H, d, indole $\underline{H}$-4), 9.25 (1H, d, indole $\underline{H}$-4, 12.20 (1H, bs, indole $\underline{NH}$). MS (ESI) m/z 492 [M+H]$^+$.

40b)

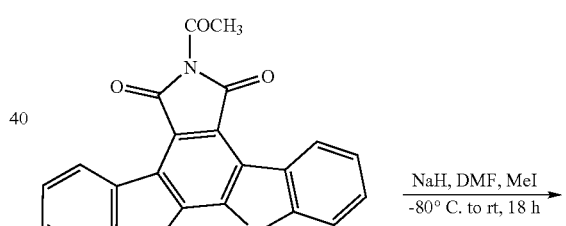

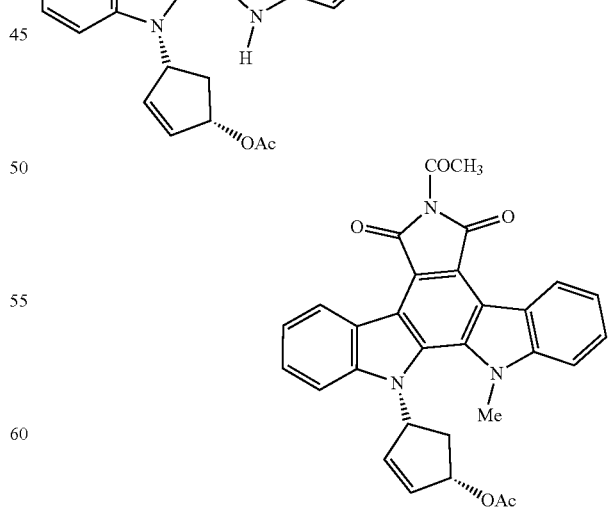

A solution of 40a (250 mg, 0.5 mmol) in dry DMF (5 mL) was added dropwise to a suspension of sodium hydride (60% mineral oil suspension, 40 mg, 1 mmol) in dry DMF (5 mL) at rt under nitrogen atmosphere. After stirring for 30 minutes the suspension was cooled to −80° C. and a solution of MeI (0.315 mL, 5 mmol) in dry DMF (5 mL) was added dropwise. After 2 hours the reaction mixture was warmed to rt and stirred for 16 hours. After dilution (EtOAc, 100 mL), washings (0.1N HCl, 50 mL, and water, 2×50 mL), drying and concentration a crude (300 mg) was obtained. Flash chromatography (silica gel, 2/3 EtOAc/PE as eluant mixture) afforded the pure title compound (75 mg, yield 29.8%).

$^1$H-NMR (300 MHz, DMSO-d$_6$): δ 1.35 (3H, s, N—CH$_3$), 2.15 (3H, s, CH$_3$—COO), 2.25 (1H, m, CH$_2$), 2.68 (3H, s, CH$_3$CON), 3.15 (1H, m, CH$_2$), 5.75 (1H, bt, CH—OAc), 6.15 (1H, dt, CH=), 6.30 (2H, m, CH—N+CH=), 7.45 (1H, m, indole Harom), 7.55 (1H, d, indole Harom), 7.85 (4H, md, indole Harom), 9.15 (2H, dd, indole H-4). MS (ESI) m/z 506 [M+H]$^+$.

40) NAD 247

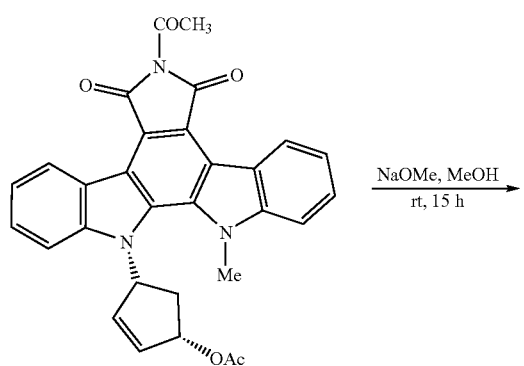

A solution of 40b (70 mg, 13.8 mmol) and sodium methoxide (2 mg, catalytic) in MeOH (5 mL) was stirred for 16 hours at rt. The resulting suspension was filtered, the solid was washed with cold MeOH and dried under vacuum to afford the pure target compound (30 mg, yield 51.7%).

$^1$H-NMR (300 MHz, DMSO-d$_6$): δ 1.25 (3H, s, N—CH$_3$, 2.30 (1H, dt, CH$_2$), 3.05 (1H, m, CH$_2$), 4.85 (1H, bq, CH—OH), 5.58 (1H, s, OH), 6.30 (2H, s, CH=CH), 6.41 (1H, bt, CH—N), 7.39 (2H, dt, indole Hs), 7.53 (1H, dt, indole Hs), 7.60 (1H, dt, indole Hs), 7.79 (1H, d, indole H-7), 8.04 (1H, d, indole H-7), 9.14 (1H, d, indole H-4), 9.23 (1H, d, indole H-4), 11.10 (1H, bs, imide NH). MS (ESI) m/z 422 [M+H]$^+$.

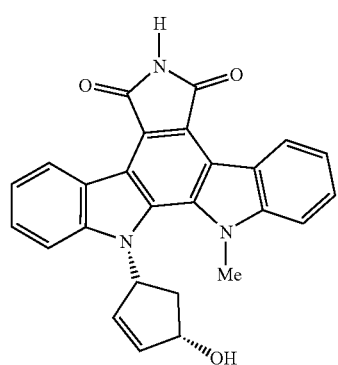

Example 41

NAD 254

41)

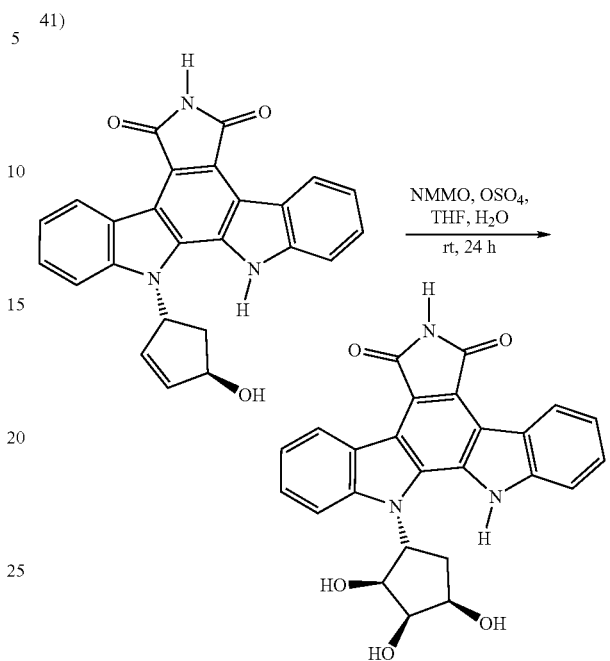

N-Methylmorpholine N-oxide (240 mg, 2 mmol) in acetone (20 mL) was added dropwise to a solution of 4 (408 mg, 1 mmol) in acetone (10 mL) at rt. Then osmium tetroxide (2.5% w/w solution in t-BuOH, 0.9 mL, catalytic) and water (a few drops, catalytic) were added and stirring at rt was continued for 24 hours. The solution was concentrated and taken up with EtOAc (100 mL), washed (sat. sodium bisulfite, 2×50 mL, and water, 2×50 mL), dried and concentrated to give a residue (500 mg). Flash chromatography (silica gel, EtOAc as eluant) afforded the pure title compound (75 mg, yield 17.0%).

$^1$H-NMR (300 MHz, DMSO-d$_6$): δ 2.80 (2H, dt, CH$_2$), 4.05 (1H, m, CH—OH), 4.70 (2H, m, CH—OH), 4.85 (1H, d, OH), 5.00 (1H, d, OH), 5.25 (1H, d, OH), 5.75 (1H, bt, CH—N), 7.45 (2H, m, Harom), 7.65 (2H, m, Harom), 7.75 (1H, d, indole H-7), 7.85 (1H, d, indole H-7), 9.15 (1H, d, indole H-4), 9.25 (1H, d, indole H-4), 1.1.15 (1H, bs, imide NH), 11.65 (1H, bs, indole NH). MS (ESI) m/z 442 [M+H]$^+$.

Example 42

NAD 294

42a)

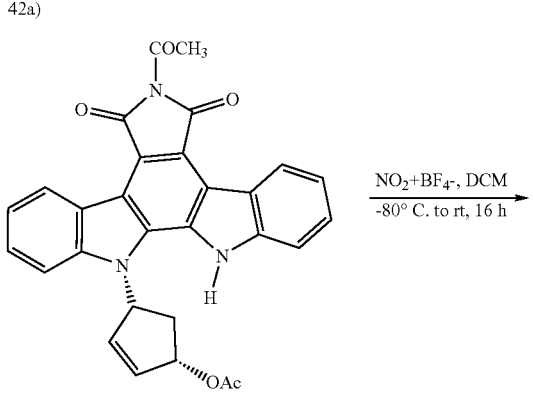

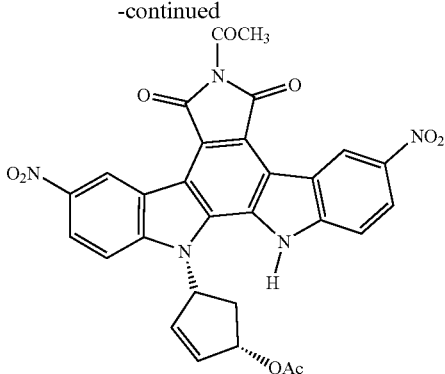

Nitronium tetrafluoroborate (0.5M in sulfzlane, 3 mL, 1.5 mmol) was added dropwise to a solution of 40a (250 mg, 0.5=mol) in dry DCM (10 mL) at −30° C. under nitrogen atmosphere. After warming to rt and stirring for 16 hours the brown suspension was filtered and washed repeatedly with DCM. The solid was dried and characterized as the pure target compound (210 mg, yield 72.4%).

$^1$H-NMR (300 MHz, DMSO-$d_6$): δ 2.15 (3H, s, N$\underline{CH_3}$), 2.20 (1H, dt, $\underline{CH_2}$), 2.35 (3H, s, OCO$\underline{CH_3}$), 3.25 (1H, m, $\underline{CH_2}$), 5.90 (1H, m, $\underline{CH}$—O), 6.15 (1H, m, $\underline{CH}$—N), 6.45 (1H, bd, $\underline{CH}$=), 6.60 (1H, bd, $\underline{CH}$=), 7.45 (1H, m, $\underline{Harom}$), 7.75 (1H, m, $\underline{Harom}$), 7.95 (1H, m, $\underline{Harom}$), 8.25 (1H, m, $\underline{Harom}$), 8.75 (1H, d, $\underline{Harom}$), 9.25 (1H, d, $\underline{Harom}$), 12.50 (1H, s, indole $\underline{NH}$). MS (ESI) molecular ion not detectable.

42) NAD 294

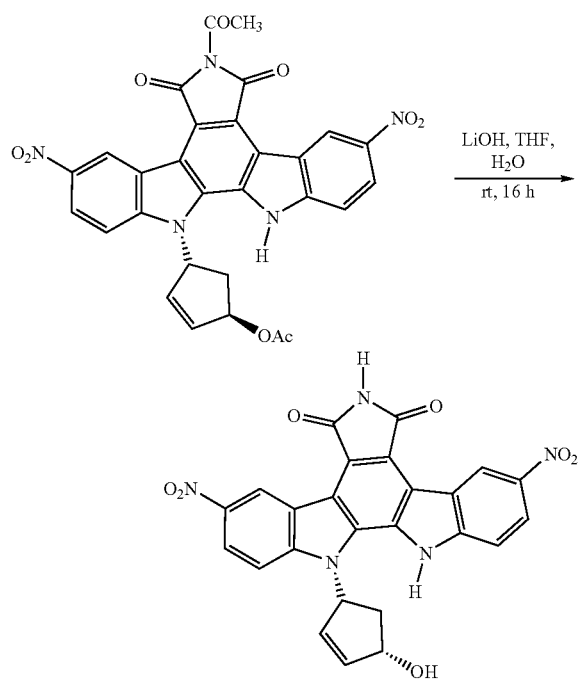

42a (205 mg, 0.35 mmol) in 4/1 THF/water (5 mL) was treated with lithium hydroxide monohydrate (84 mg, 2 mmol) and stirred at rt for 16 hours. The mixture was diluted with EtOAc (50 mL), washed (water, 50 mL) and dried to give the pure title compound (70 mg, yield 40.2%).

$^1$H-NMR (300 MHz, DMSO-$d_6$): δ 2.30 (1H, dt, $\underline{CH_2}$), 3.25 (1H, m, $\underline{CH_2}$), 5.05 (1H, bt, $\underline{CH}$—O), 5.55 (1H, d, $\underline{OH}$), 6.30 (3H, m, $\underline{CH}$=$\underline{CH}$+$\underline{CH}$—N), 7.45 (3H, m, $\underline{Harom}$), 7.75 (1H, d, indole $\underline{H-7}$), 8.05 (1H, d, indole $\underline{H-7}$), 8.50 (1H, d, indole $\underline{H-4}$), 8.85 (1H, d, indole $\underline{H-4}$), 11.05 (1H, s, imide $\underline{NH}$), 12.10 (1H, s, indole $\underline{NH}$). MS (ESI) 498 [M+H]$^+$.

Example 43

NAD 402

43a)

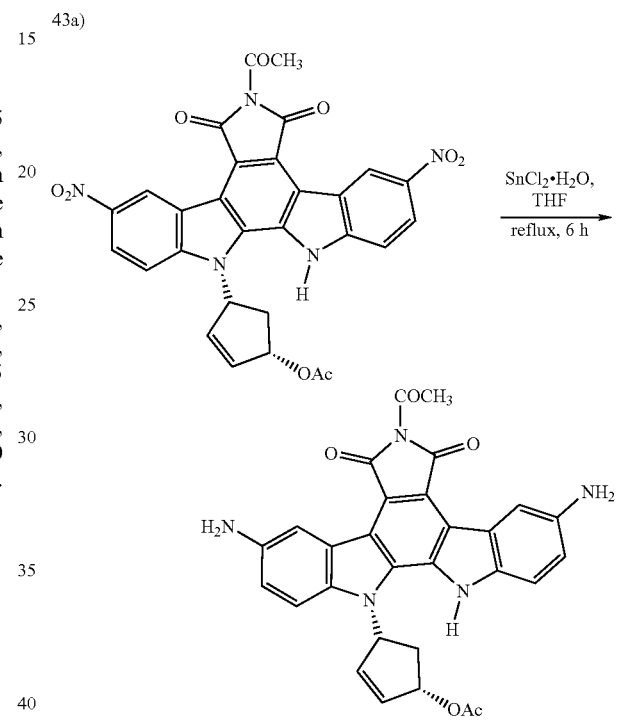

A suspension of 42a (290 mg, 0.5 mmol) and tin (II) chloride monohydrate (2.26 g, 9.9 mmol) in THF (30 mL) was refluxed for 6 hours. The mixture was poured into water/ice (200 mL) and extracted twice (2×100 mL, EtOAc). The aqueous layer was treated with solid NaHCO$_3$ and extracted (2×100 mL, EtOAc). The organic layer was dried and filtered to give, after evaporation, a residue (165 mg, yield 49.6%) which was directly used in the following step.

43) NAD 402

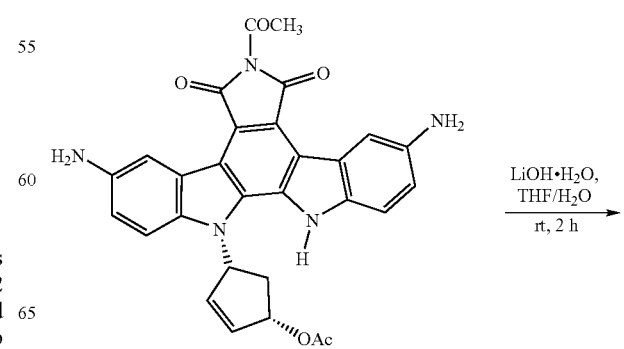

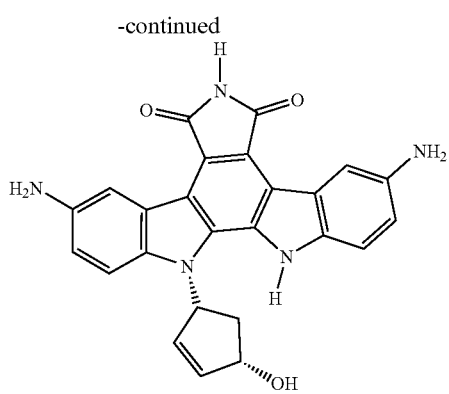

A solution of 43a (165 mg, 0.25 mmol) and lithium hydroxide monohydrate (42 mg, 10 mmol) in 4/1 THF/water (5 mL) was stirred for 2 hours at rt. The resulting solution was diluted (20 mL, H₂O) and extracted (2×25 mL, EtOAc). The solid obtained after drying, filtering and concentration resulted to be the target compound (85 mg, 85% pure by HPLC, yield 66.9%).

¹H-NMR (300 MHz, DMSO-d₆): δ 2.25 (1H, dt, CH₂), 3.20 (1H, m, CH₂), 5.05 (5H, m, CH—O+NH₂), 5.55 (1H, d, OH), 6.30 (3H, m, CH=CH+CH—N), 6.90 (2H, m, Harom) 7.45 (1H, d, Harom), 7.65 (1H, d, indole H-7), 8.35 (1H, d, indole H-7), 8.50 (1H, s, indole H-4), 8.85 (1H, s, indole H-4), 10.75 (1H, s, imide NH), 11.5 (1H, s, indole NH). MS (ESI) 438 [M+H]⁺.

Example 44

NAD 306

44a)

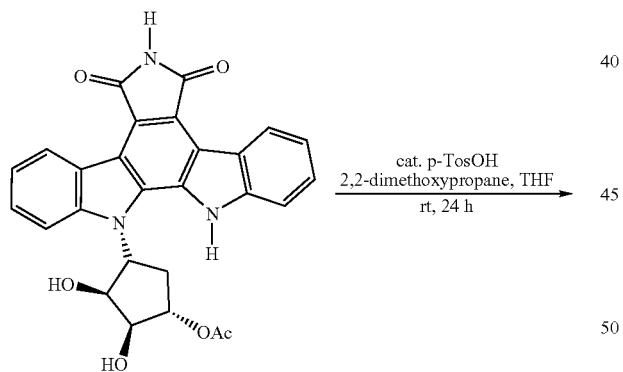

A solution of 9 (280 mg, 5.8 mmol), p-toluenesulfonic acid (5 mg, catalytic) and 2,2-dimethoxypropane (4 mL, large excess) in THF (10 mL) was stirred at rt for 24 hours. The resulting suspension was filtered to give, after drying, a first crop of pure target compound (65 mg). The solution was concentrated to 2 mL, taken up with EtOAc (30 mL), washed (water, 20 mL) and dried to give a second crop of pure target compound (240 mg, total yield 79.2%).

¹H-NMR (300 MHz, DMSO-d₆): δ 1.15 (3H, s, OC(CH₃)₂), 1.50 (3H, s, OC(CH₃)₂), 2.15 (3H, s, COCH₃), 2.85 (1H, dt, CH₂), 3.15 (1H, m, CH₂) 5.15 (1H, m, CH—OC), 5.35 (1H, m, CH—OC), 5.55 (1H, m, CH—OAc), 5.75 (1H, m, CH—N), 7.45 (2H, m, indole Harom), 7.55 (2H, m, Harom), 7.85 (2H, m, Harom), 9.15 (1H, d, indole H-4), 9.25 (1H, d, indole H-4), 11.10 (1H, s, imide NH), 12.20 (1H, bs, indole NH). MS (ESI) 524 [M+H]⁺.

44) NAD 306

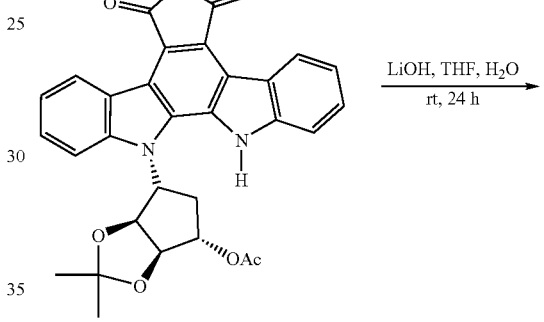

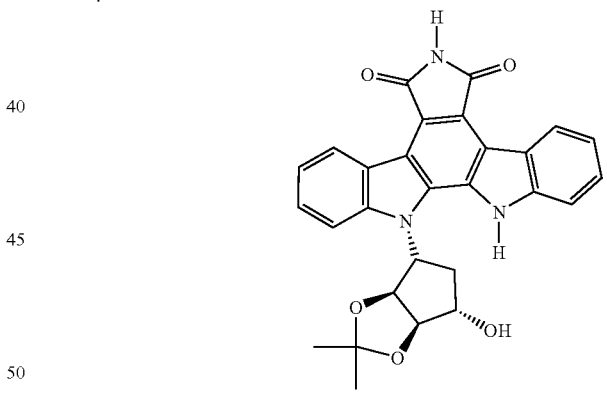

A solution of 44a (275 mg, 0.52 mmol) in 4/1 THF/water (20 mL) was treated with lithium hydroxide monohydrate (84 mg, 2 mmol) and stirred at rt for 24 hours. The mixture was diluted with EtOAc (50 mL), washed (water, 50 mL) and dried to give the pure title compound (195 mg, yield 77.1%).

¹H-NMR (300 MHz, DMSO-d₆): δ 1.25 (3H, s, OC(CH₃)₂), 1.50 (3H, s, OC(CH₃)₂), 2.90 (2H, m, H₂), 4.50 (1H, m, CH—OH), 4.85 (1H, m, CH—OC), 5.25 (1H, m, CH—OC), 5.65 (2H, m, CH—N+CH), 7.45 (2H, m, indole Harom), 7.55 (2H, m, Harom), 7.85 (2H, m, Harom), 9.15 (1H, d, indole H-4), 9.25 (1H, d, indole H-4), 11.05 (1H, s, imide NH), 12.20 (1H, bs, indole NH). MS (ESI) 482 [M+H]⁺.

Example 45

NAD 352

45a)

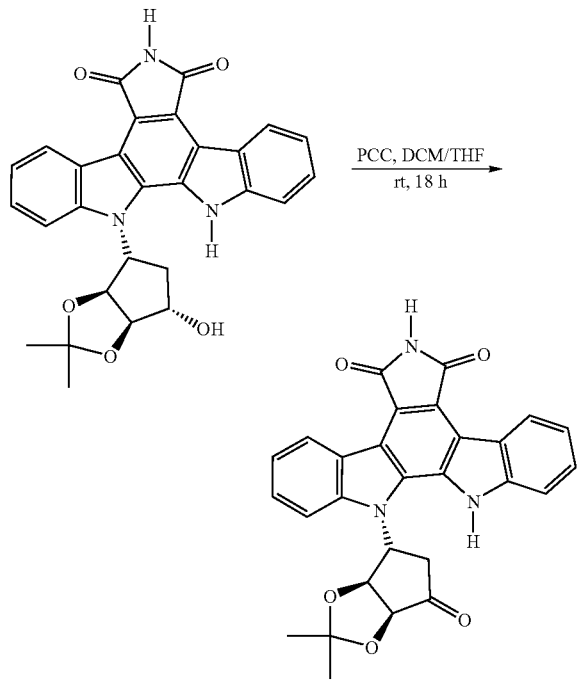

Pyridinium chlorochromate (670 mg, 3.2 mmol) was added to a solution of 44 (750 mg, 1.6 mmol) in 5/1 DCM/THF (60 mL) under stirring at rt. Filtration on celite and concentration after overnight stirring gave a residue (890 mg). Flash chromatography (silica gel, EtOAc/PE 1/1 to pure EtOAc as eluant mixture) produced the pure title compound (240 mg, yield 33.0%).

$^1$H-NMR (300 MHz, DMSO-d$_6$): δ 1.25 (3H, s, OC(CH$_3$)$_2$), 1.55 (3H, s, OC(CH$_3$)), 2.95 (1H, d, CH$_2$), 3.20 (1H, m, CH), 4.50 (1H, m, CH—OC), 4.65 (1H, m, CH—OC), 5.45 (1H, bt, CH—N), 7.45 (2H, m, indole Harom), 7.55 (2H, m, Harom), 7.85 (2H, m, Harom), 9.15 (1H, d, indole H-4), 9.25 (1H, d, indole H-4), 11.10 (H, s, imide J. MS (APCI) 480 [M+H]$^+$.

45) NAD 352

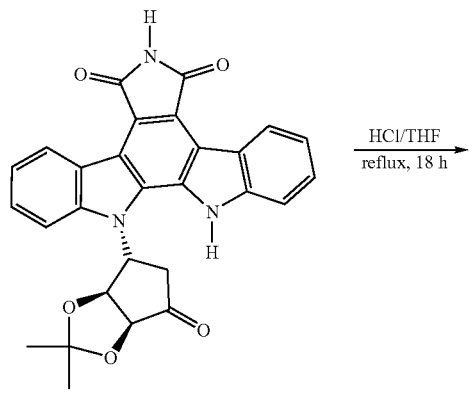

-continued

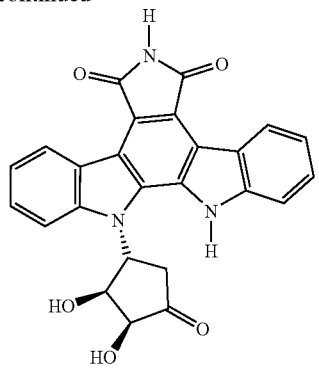

A solution of 45a (230 mg, 0.48 mmol) in 1/1 2N HCl/TH (30 mL) was refluxed for 18 hours. Extraction (EtOAc, 100 mL), washing (water, 2×50 mL) and drying produced a crude (460 mg). Purification by flash chromatography (silica gel, EtOAc/PE 3/2 as eluant mixture) produced the pure title compound (130 mg, yield 61.6%).

$^1$H-NMR (300 MHz, DMSO-d$_6$): δ 2.45 (1H, dt, CH$_2$), 3.10 (1H, m, CH$_2$), 4.15 (1H, m, 2-CH—OH), 4.20 (1H, bt, CH—N) 5.35 (1H, dd, 3-CH—OH), 5.55 (1H, d, OH), 5.75 (1H, d, OH), 7.45 (2H, m, Harom), 7.55 (1H, bt, indole Harom), 7.65 (1H, bt, indole Harom), 7.85 (1H, d, Harom), 8.40 (1H, d, Harom), 9.15 (1H, d, indole H-4), 9.25 (1H, d, indole H-4), 11.15 (1H, bs, imide H-4), 11.8 (1H, bs, indole NH). MS (ESI) m/z 476 [M+H]$^+$.

Example 46

NAD 405

46)

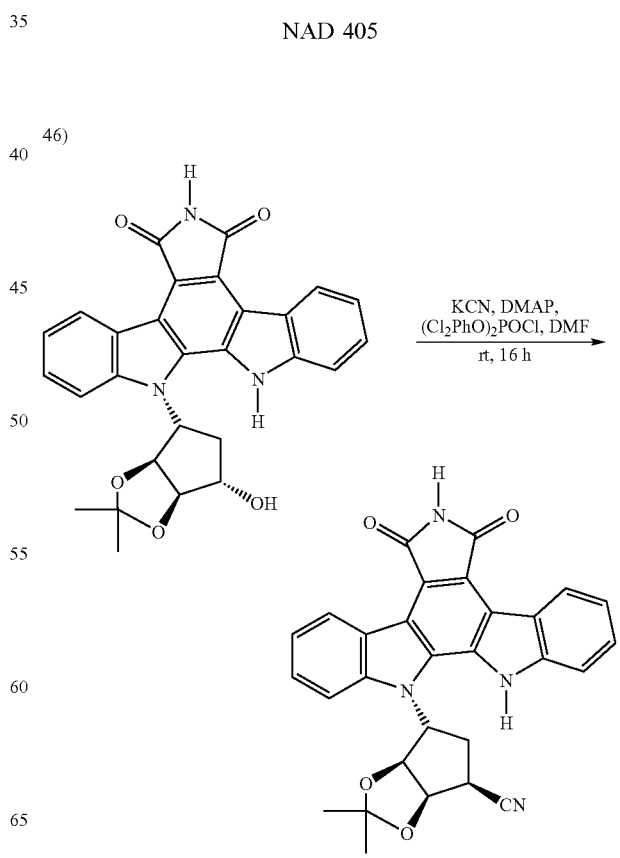

A stirred solution of 44 (480 mg, 1 mmol) in dry DMF (10 ml) was treated under nitrogen atmosphere sequentially with potassium cyanide (260 mg, 4 mmol), dimethylaminopyridine (150 mg, mmol) and (Cl$_2$PhO)$_2$POCl (430 mg, mmol) at rt. After stirring for 16 hours the solution was diluted by addition of EtOAc (100 ml), washed with water (25 mL) and brine (25 mL), 32% aqueous NaOH (20 mL) and brine (2×20 mL). The organic layer was then dried over sodium sulfate, filtered and concentrated in vacuo to give a solid residue (900 mg). Purification by flash chromatography (silica gel, PE/EtOAc 1/1 as eluant mixture) afforded the pure target compound (65 mg, 13.3 yield %).

$^1$H-NMR (300 MHz, DMSO-d$_6$): δ 1.25 (3H, s, OC(CH$_3$)$_2$), 1.50 (3H, s, OC(CH$_3$)$_2$), 2.85–2.95 (2H, m, CH$_2$), 5.20 (1H, m, CH—OC), 5.30 (1H, m, CH—OC), 5.55 (1H, m, CH—CN), 5.80 (1H, m, CH—N), 7.45 (2H, m, indole Harom), 7.55 (2H, m, Harom), 7.85 (2H, m, Harom), 9.15 (1H, d, indole H-4), 9.25 (1H, d, indole H-4), 11.05 (1H, s, imide NH), 12.20 (1H, bs, indole NH). MS (ESI) 464 [M+H—HCN]$^+$.

Example 47

NAD 349

47)

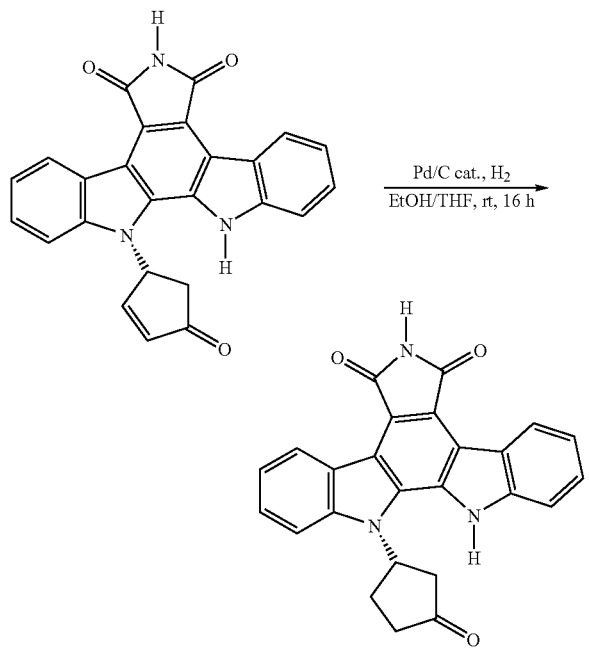

A suspension of 8 (800 mg, 1.97 mmol) and Pd/C (10%, 100 mg) in 9/1 THF/EtOH (100 mL) was stirred for 16 hours under hydrogen atmosphere. After nitrogen purging, filtration of the catalyst and concentration a residue (900 mg) was recovered. Flash chromatography (silica gel, EtOAc/PE 3/7 to pure EtOAc as eluant mixture) produced the pure title compound (400 mg, yield 49.7%).

$^1$H-NMR (300 MHz, DMSO-d$_6$): δ 1.75 (2H, m, CH$_2$), 2.30 (1H, m, CH$_2$), 2.45 (1H, m, CH$_2$), 2.70 (1H, m, CH$_2$), 2.95 (1H, dt, CH$_2$), 5.70 (1H, m, CH—N), 7.40 (2H, m, Harom), 7.55 (2H, m, Harom), 7.85 (1H, d, Harom), 8.40 (1H, dd, Harom), 9.15 (1H, d, indole H-4), 9.25 (1H, d, indole H-4), 11.12 (1H, bs, imide NH). MS (ESI) m/z 408 [M+H]$^+$.

Example 48

NAD 427

48)

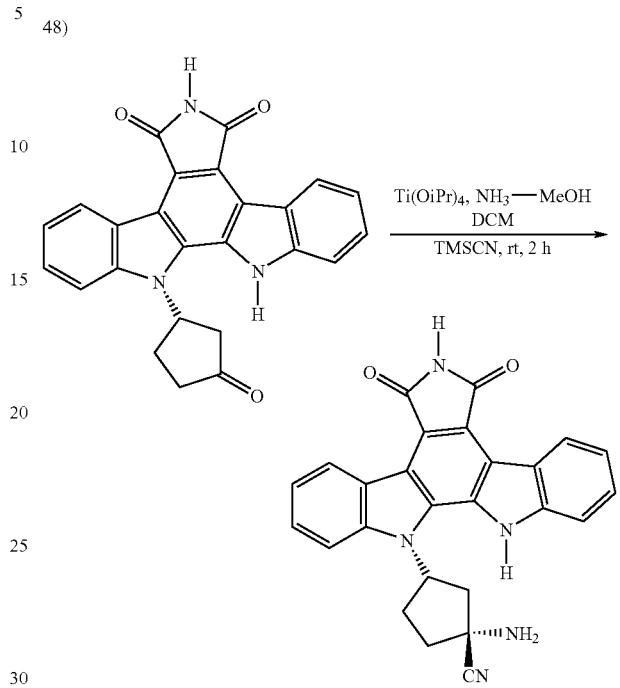

Titanium isopropoxide (1.26 mL. 7 mmoles) was added to a stirred solution of 47 (140 mg, 0.35 mmoles) in 1/1 7M methanolic ammonia/DCM (20 mL) at rt. Trimethylsilyl cyanide (540 μL, 5.45 mmoles) was added fter 2 hours and stirring was continued for 16 hours. A precipitate was filtered and washed with DCM (2×5 mL) to afford after drying the pure title compound (50 mg, yield 33.0%).

$^1$H-NMR (300 MHz, DMSO-d$_6$): δ 2.20 (1H, m, CH$_2$), 2.35 (1H, m, CH$_2$) 2.50 (1H, m, CH$_2$), 2.80 (1H, m, CH$_2$), 3.00 (1H, dt, CH$_2$), 3.30 (1H, dt, CH, 6.10 (1H, bt, CH—N), 7.30 (2H, m, Harom), 7.55 (2H, m, Harom), 7.70 (1H, d, Harom), 8.35 (1H, m, Harom), 9.10 (1H, d, indole H-4), 9.25 (1H, d, indole H-4) MS (APCI) m/z 434 [M+H]$^+$.

Example 49

NAD 419

49a)

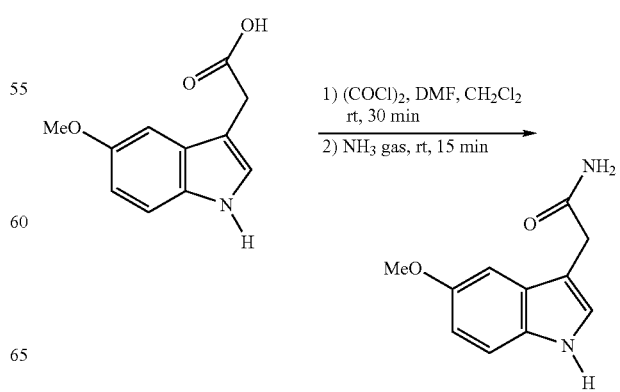

Oxalyl chloride (6.5 mL, 75.6 mmol) was added portionwise at rt to a stirred suspension of commercially available 5-methoxy-indolyl-3-acetic acid (14.1 g, 68.7 mmol) and DMF (0.5 mL, 6.4 mmol) in DCM (100 mL). After 0.30 minutes ammonia was bubbled through the solution for 15 min, the reaction mixture was diluted with EtOAc (200 mL) and washed with water (100 mL). The precipitate was filtered, washed with water (20 mL) and EtOAc (2×20 mL). The solid was dried in vacuo to give a first crop of the expected compound (7.4 g). The organic layer was washed (water, 80 mL), dried over sodium sulfate, filtered and concentrated to yield a solid residue (6.6 g). Flash chromatography (silica gel, EtOac/MeOH 40/1 as eluant mixture) afforded additional 1.2 g of the pure target compound (total yield 71.2%).

$^1$H-NMR (300 MHz, DMSO-$d_6$): δ 3.55 (2H, s, C$\underline{H}_2$—CO), 3.74 (3H, s, OC$\underline{H}_3$), 6.72 (1H, dd, indole $\underline{H}$-6), 6.82 (1H, bs, CON$\underline{H}_2$), 7.05 (1H, d, indole $\underline{H}$-4), 7.14 (1H, d, indole $\underline{H}$-2), 7.23 (1H, d, indole $\underline{H}$-7), 7.28 (1H, bs, N$\underline{H}_2$), 10.70 (1H, bs, indole N$\underline{H}$). MS (APCI) m/z 205 [M+H]$^+$.

49b)

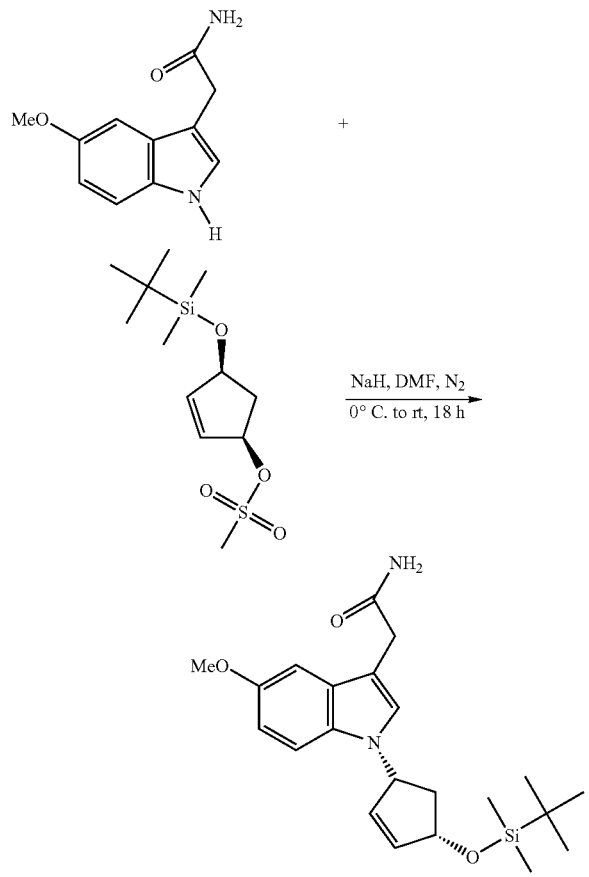

A suspension of sodium hydride (1.48 g, 60% paraffin oil, 37.0 mmol) in dry DMF (25 mL) was treated dropwise with 49a (5 g, 25.5 mmol) in dry DMF (25 mL) at rt under nitrogen atmosphere. The resulting mixture was stirred for 30 minutes at rt and then cooled to 0° C. A solution of 1e in dry DMF (50 mL) was then added dropwise. The solution was stirred at rt for 18 hours, diluted with EtOAc (1 L), washed with water (2×500 mL) and brine (500 mL). The organic phase was dried over sodium sulfate, filtered and concentrated in vacuo to give a dark red oily residue (12 g). The crude was purified by flash chromatography (silica gel, EtOAc/PE 8/2 as eluant mixture) to give the pure target compound (4.9 g, yield 48.1%).

$^1$H-NMR (300 MHz, DMSO-$d_6$): δ 0.14 (3H, s, C$\underline{H}_3$—Si), 0.21 (3H, s, C$\underline{H}_3$—Si), 0.95 (9H, tBu), 1.55 (1H, dt, C$\underline{H}_2$), 2.85 (1H, dt, C$\underline{H}_2$), 3.40 (2H, s, CO—), 3.75 (3H, s, OC$\underline{H}_3$), 4.90 (1H, m, C$\underline{H}$—O), 5.40 (1H, bt, C$\underline{H}$—N), 5.90 (1H, dt, H=), 6.10 (1H, dt, CH), 6.70 (1H, dd, indole $\underline{H}$-6), 7.00 (1H, d, indole $\underline{H}$-7), 7.10 (1H, s, indole $\underline{H}$-2), 7.4 (1H, d, indole $\underline{H}$-4). MS (APCI) m/z 401 [M+H]$^+$.

49c)

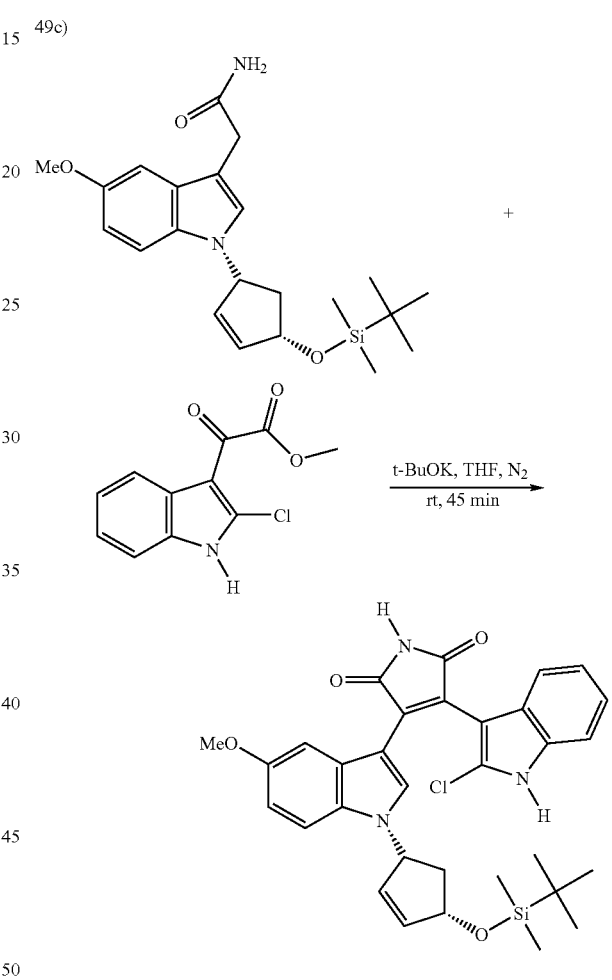

Potassium t-butoxide (1M in THF, 75 mL, 75 mmol) was added dropwise to a stirred solution of 1h (5.9 g, 40 mmol) and 49b (4.9 g, 20 mmol) in dr THF (50 ml) at rt under nitrogen atmosphere. After 45 minutes the reaction was diluted with EtOAc (500 mL), washed with water (2×250 mL), dried over sodium sulfate, filtered and concentrated in vacuo. The crude residue (7.49 g) was purified by flash chromatography (silica gel, PE/EtOAc 4/1 to 1/4 as eluant mixture) to afford the pure target compound (2.42 g, yield 21.0%).

$^1$H-NMR (300 MHz, DMSO-$d_6$): δ 0.14 (3H, s, C$\underline{H}_3$—Si), 0.21 (3H, s, C$\underline{H}_3$—Si), 0.95 (9H, tBu), 1.85 (1H, m, C$\underline{H}_2$) 2.85 (1H, m, C$\underline{H}_2$), 3.20 (3H, s, O$\underline{H}$), 4.80 (1H, m, C$\underline{H}$—O), 5.80 (1H, d, C$\underline{H}$=), 6.10 (2H, m, C$\underline{H}$=+C$\underline{H}$—N), 6.40 (1H, d, $\underline{H}$arom), 6.90 (1H, m, $\underline{H}$arom), 7.05 (1H, m, $\underline{H}$arom), 7.25 (2H, m, indole $\underline{H}$arom), 7.45 (2H, d, indole Harom), 8.05 (1H, s, indole H-2), 11.10 (1H, bs, imide NH), 12.35 (1H, bs, indole NH). MS (APCI) m/z 588 [M+H]+.

49d)

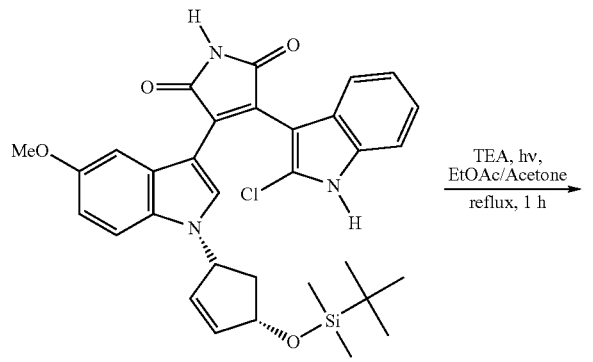

A solution of 49c (2.4 g, 4.08 mmol) and triethylamine (1.15 mL, 8.6 mmol) in EtOAc/acetone 4/1 (250 mL) was irradiated at reflux with a halogen lamp. After 1 h the solution was cooled to rt, washed with water (120 mL), dried with sodium sulfate and concentrated in vacuo to give the pure target compound (2.32 g, quantitative yield).

1H-NMR (300 MHz, DMSO-d6): δ 0.15 (6H, s, Si(CH3)2), 0.85 (9H, s, tBu), 2.05 (1H, m, CH2), 3.25 (1H, m, CH2) 3.95 (3H, s, OCH3), 5.05 (1H bt, CH—O), 6.30 (3H, m, CH=CH+CH—N), 7.05 (1H, m, Harom), 7.35 (1H, m, indole Harom), 7.55 (1H, dt, Harom), 7.75 (1H, dt, Harom), 7.95 (1H, d, indole Harom), 8.80 (1H, d, Harom), 9.15 (1H, d, indole Harom), 11.15 (1H, s, imide NH), 12.10 (1H, s, indole NH). MS (ESI) m/z 552 [M+H]+.

49e)

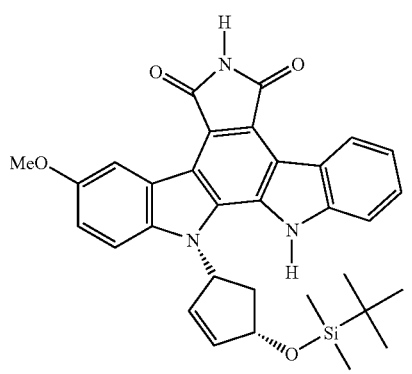

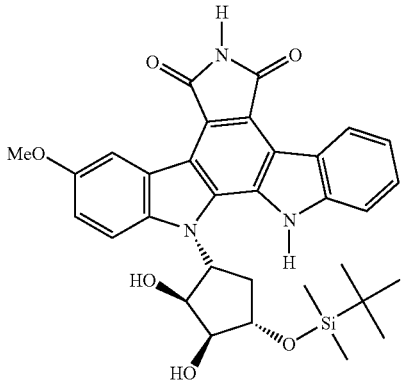

N-Methylmorpholine N-oxide (365 mg, 3.44 mmol) in acetone (30 mL) was added dropwise to a solution of 49d (585 mg, 1.06 mmol) in acetone (20 mL) at rt. Then osmium tetroxide (2.5% w/w solution in t-BuOH, 2 mL, catalytic) and water (a few drops, catalytic) were added and stirring at rt was continued for 72 hours. The resulting suspension was filtered, the solid was washed repeatedly with acetone and dried to give the pure target compound crude (250 mg). The solution was diluted with AcOEt (250 mL), washed with aqueous bisulfite (100 mL) and water (2×100 mL) and dried. After concentration a second crop of the pure target compound (330 mg, total yield 91.0%) was obtained.

1H-NMR (300 MHz, DMSO-d6): δ 0.15 (6H, s, Si(CH3)2), 0.85 (9H, s, tBu), 2.25 (1H, m, CH2), 3.05 (1H, m, CH2), 3.85 (1H, d, OH), 3.95 (3H, s, OCH3), 4.25 (1H, d, OH), 4.90 (1H, m, CH—O), 5.30 (2H, m, CH—O), 5.60 (1H, m, CH—N), 7.05 (1H, m, Harom), 7.35 (1H, dt, Harom), 7.55 (1H, dt, Harom), 7.75 (1H, d, indole Harom), 8.30 (1H, d, Harom), 8.80 (1H, d, Harom), 9.15 (1H, d, indole Harom), 11.15 (1H, s, imide NH), 12.10 (1H, s, indole NH). MS (APCI) m/z 586 [M+H]+.

49) NAD 419

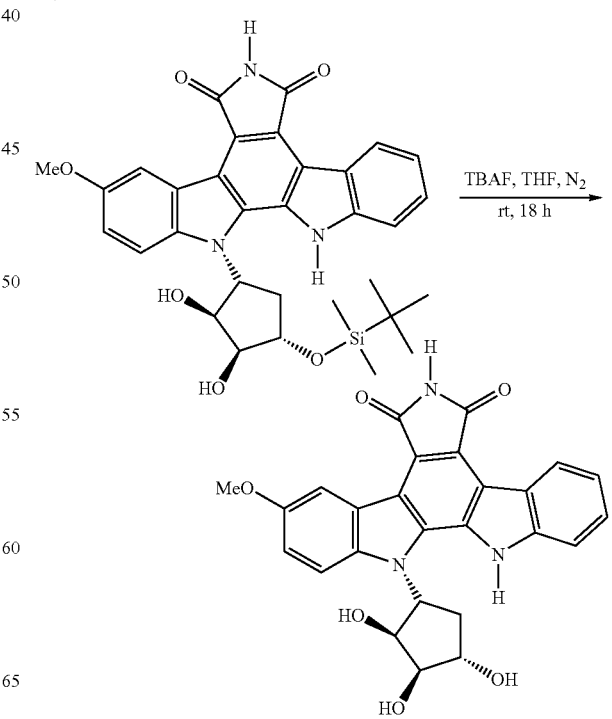

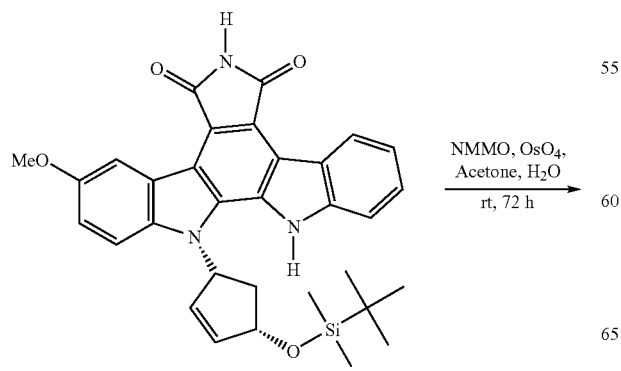

Tetrabutylammonium fluoride (1M in THF, 2 mL, 2 mmol) was added dropwise to a stirred solution of 49e (235 mg, 0.40 mmol) in dry THF (10 mL) under nitrogen atmosphere at rt. After 18 hours the solution was diluted with EtOAc (50 mL) and washed with 1N HCl (20 mL) and water (2×20 mL). The organic layer was dried over sodium sulfate, filtered and concentrated in vacuo to yield the pure target compound as an orange solid (190 mg, quantitative yield).

$^1$H-NMR (300 MHz, DMSO-$d_6$): δ 2.30 (1H, m, C$\underline{H}_2$), 2.95 (1H, m, C$\underline{H}_2$), 3.85 (1H, d, O$\underline{H}$), 3.95 (3H, s, O$\underline{H}$), 4.20 (2H, m, O$\underline{H}$), 4.90 (1H, m, C$\underline{H}$—O), 5.15 (2H, m, C$\underline{H}$—O), 5.55 (1H, m, C$\underline{H}$—N), 7.20 (1H, m, $\underline{H}$arom), 7.35 (1H, dt, $\underline{H}$arom), 7.55 (1H, dt, $\underline{H}$arom), 7.75 (1H, d, indole $\underline{H}$arom), 8.20 (1H, m, $\underline{H}$arom), 8.80 (1H, d, $\underline{H}$arom), 9.15 (1H, d, indole $\underline{H}$arom), 11.15 (1H, s, imide N$\underline{H}$), 12.10 (1H, bs, indole N$\underline{H}$). MS (APCI) m/z 472 [M+H]$^+$.

Example 50

NAD 415

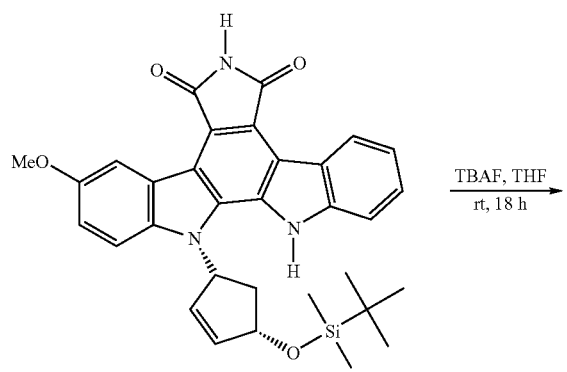

Tetrabutylammonium fluoride (1M in THF, 1 mL, 1 mmol) was added dropwise to a stirred solution of 49d (265 mg, 0.48 mmol) in dry THF (10 mL) under nitrogen atmosphere at rt. After 18 hours the solution was diluted with EtOAc (50 mL), washed with 1N HCl (20 mL) and water (2×20 mL). The organic layer was dried over sodium sulfate, filtered and concentrated in vacuo to yield the pure target compound as a yellow solid (200 mg, yield 95.2%).

$^1$H-NMR (300 MHz, DMSO-$d_6$): δ 2.20 (1H, dt, C$\underline{H}_2$), 3.25 (1H, m, C$\underline{H}_2$) 3.95 (3H, s, O), 5.05 (1H, bt, C$\underline{H}$—O), 5.55 (1H, d, O$\underline{H}$), 6.30 (3H, m, C$\underline{H}$=C$\underline{H}$+C$\underline{H}$—N), 7.20 (1H, m, $\underline{H}$arom), 7.35 (1H, d, indole $\underline{H}$-7), 7.55 (1H, dt, $\underline{H}$arom), 7.75 (1H, dt, $\underline{H}$arom), 7.95 (1H, d, indole $\underline{H}$-7), 8.80 (1H, s, indole $\underline{H}$-4), 9.15 (1H, d, indole $\underline{H}$a-4), 11.15 (1H, s, imide N$\underline{H}$), 12.10 (1H, s, indole N$\underline{H}$). MS (ESI) m/z 438 [M+H]$^+$.

Example 51

NAD 422

51)

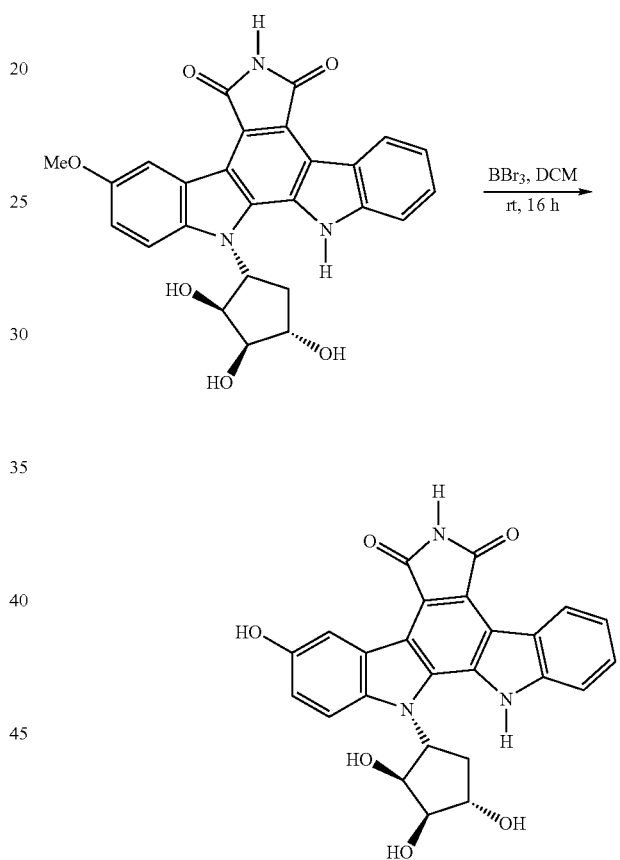

Boron tribromide (1M in DCM, 10 mL, 10 mmoles) was added to a suspension of 49 (200 mg, 0.42 mmol) in DCM (40 mL) under stirring at rt. After 16 hours the mixture was diluted with EtOAc (300 mL) and poured into water/ice (150 mL). The organic layer was washed (2×100 mL, water), dried with sodium sulfate and concentrated to give the pure target compound (180 mg, yield 92.3%).

$^1$H-NMR (300 MHz, DMSO-$d_6$): δ 2.35 (1H, m, C$\underline{H}_2$), 3.00 (1H, m, C$\underline{H}_2$), 3.60 (2H, m, C$\underline{H}$—O), 3.90 (1H, d, O$\underline{H}$), 4.20 (2H, m, O$\underline{H}$), 4.90 (1H, m, C$\underline{H}$—O), 5.55 (1H, dt, C$\underline{H}$—N), 7.10 (1H, dd, $\underline{H}$arom), 7.40 (1H, dt, $\underline{H}$arom), 7.60 (1H, dt, $\underline{H}$arom), 7.75 (1H, bd, indole $\underline{H}$arom), 8.00 (1H, s, indole O$\underline{H}$), 8.10 (1H, m, $\underline{H}$arom), 8.75 (1H, d, $\underline{H}$arom), 9.15 (1H, d, indole $\underline{H}$arom), 11.05 (1H, s, imide N$\underline{H}$), 12.00 (1H, bs, indole N$\underline{H}$). MS (APCI) ma/z 458 [M+H]$^+$.

Example 52

NAD 449

52a)

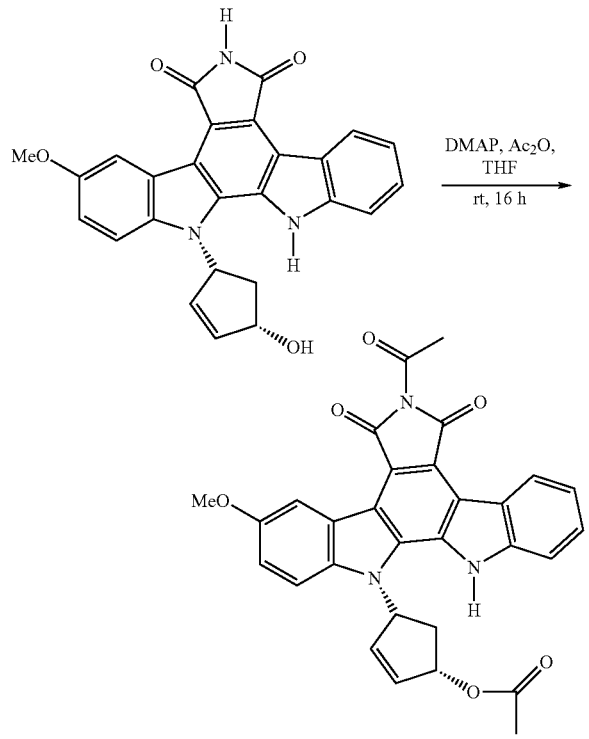

Dimethylaminopyridine (1.58 g, 14.4 mmol) was added to a stirred solution of 50 (1.01 g, 2.30 mmol) and acetic anhydride (2.2 mL, 2.15 mmol) in THF (30 mL) at rt. Stirring was continued for 16 hours, then the precipitate was filtered and thoroughly washed with THF and water. The dried solid was characterized as the pure target compound (1.04 g, 83.1 yield %).

$^1$H-NMR (300 MHz, DMSO-$d_6$): 3, 2.15 (3H, OCOC$\underline{H}_3$), 2.20 (1H, m, C$\underline{H}_2$), 2.70 (3H, s, NCOC$\underline{H}_3$), 3.25 (1H, m, C$\underline{H}_2$), 3.90 (3H, s, O$\underline{H}$), 5.80 (1H, m, C$\underline{H}$—O), 6.40 (1H, m, C$\underline{H}$=), 6.55 (2H, m, C$\underline{H}$=+C$\underline{H}$—N), 7.40 (1H, dt, H$\underline{arom}$), 7.65 (3H, m, H$\underline{arom}$), 7.85 (1H, d, indole $\underline{H}$-7), 8.10 (1H, d, indole $\underline{H}$-7), 9.15 (1H, d, indole $\underline{H}$-4), 12.20 (1H, s, indole N$\underline{H}$). MS (APCI) m/z 522 [M+H]$^+$.

52b)

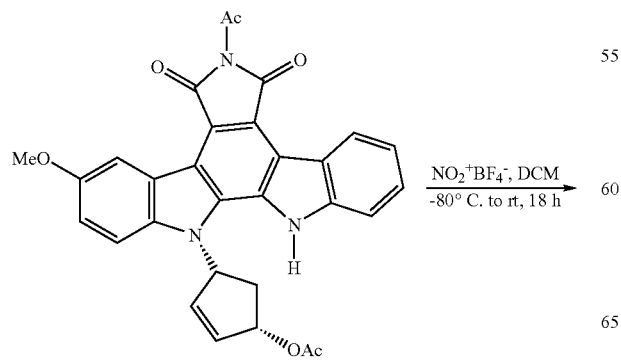

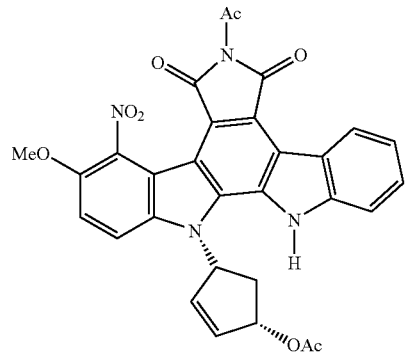

Nitronium tetrafluoroborate (0.5M in sulfolane, 4.9 mL, 2.45 mmoles) was added dropwise to a solution of 52a (800 mg, 1.50 mmol) in dry DCM (30 mL) at −80° C. under stirring and nitrogen atmosphere. After warming, to rt and stirring for 18 hours the suspension was filtered and a first crop of the pure target compound (280 mg) was obtained. The solution was taken up with EtOAc (30 mL) and filtered to obtain a second crop of pure target compound (400 mg, total yield 50.0%).

$^1$H-NMR (300 MHz, DMSO-$d_6$): δ 2.05 (3H, s, OCOC$\underline{H}_3$), 2.15 (1H, m, C$\underline{H}_2$), 2.70 (3H, s, NCOC$\underline{H}_3$), 3.25 (1H, m, C$\underline{H}_2$), 3.90 (3H, s, O$\underline{H}$), 5.80 (1H, m, C$\underline{H}$—O), 6.40 (1H, m, C$\underline{H}$=), 6.55 (2H, m, C$\underline{H}$=+C$\underline{H}$—N), 7.40 (1H, dt, H$\underline{arom}$), 7.65 (2H, m, H$\underline{arom}$), 7.85 (1H, d, indole $\underline{H}$-7), 8.1–0 (1H, d, indole $\underline{H}$-7), 9.15 (1H, d, indole $\underline{H}$-4), 12.20 (1H, s, indole N$\underline{H}$). MS (APCI) m/z 525 [M+H—COCH$_3$]$^+$.

52) NAD 449

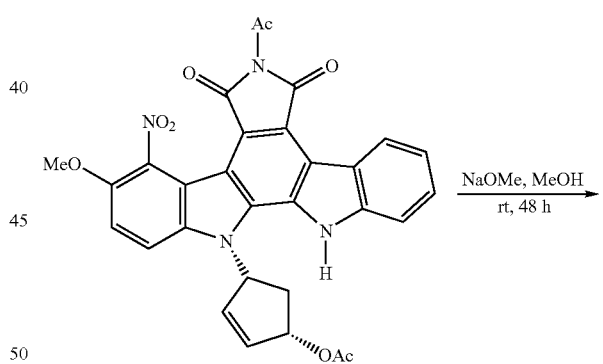

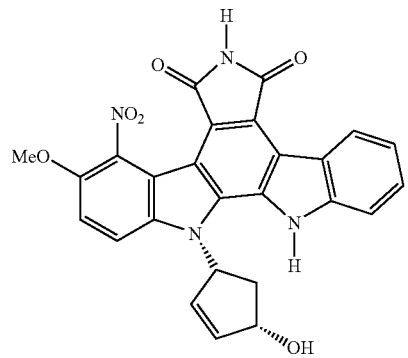

A solution of 52b (90 mg, 0.17 mmol) and sodium methoxide (2 mg, catalytic) in MeOH (5 mL) was stirred for 48 hours at rt. The solution was concentrated to a residue. (95 mg) which was chromatographed (2/3 THF/toluene as eluant mixture) to afford the pure target compound (60 mg, yield 82.1%).

$^1$H-NMR (300 MHz, DMSO-d$_6$): δ 2.10 (1H, m, CH$_2$), 3.25 (1H, m, CH$_2$), 3.95 (3H, s, OCH$_3$), 5.00 (1H, m, CH—O), 5.60 (1H, d, OH), 6.25 (2H, m, CH═H), 6.40 (1H, m, CH—N), 7.40 (1H, dt, Harom), 7.60 (2H, m, Harom), 7.80 (1H, d, indole H-7), 8.35 (1H, d, indole H-7), 9.15 (1H, d, indole H-4), 10.95 (1H, s, imide NH), 12.20 (1H, s, indole NH). MS (APCI) m/z 483 [M+H]$^+$.

Example 53

NAD 450

53a)

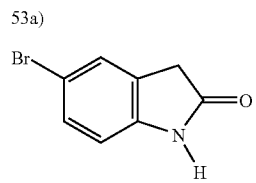

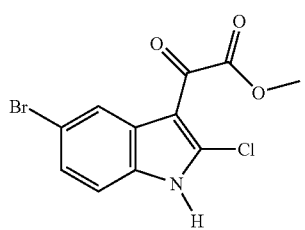

A solution of 5-bromo-oxindole (24.8 g, 117 mmol, prepared according to the procedure described in *J. Am. Chem. Soc.*, 1947, 67, 1656) was added to a stirred solution of oxalyl chloride (25.3 mL, 293 mmol) in DCM (60 mL) at rt. The reaction mixture was stirred for 21 hours, the precipitate was filtered, washed with DCM (2×20 mL) and dried in vacuo to give a crude yellow powder (17.7 g).

The residue was suspended in Et$_2$O (45 mL) and MeOH (6.6 mL, 164 mmol) was added at rt. The reaction mixture was stirred at rt for 30 minutes, the precipitate was filtered, washed with Et$_2$O (2×25 mL) and dried in vacuo to yield the pure target compound (13.9 g, yield 37.8%).

$^1$H-NMR (300 MHz, DMSO-d$_6$): δ 3.92 (3H, s, CH$_3$—O), 7.45 (2H, m, indole H-6+H-7), 8.19 (1H, s, indole H-4), 13.70 (1H, bs, N. MS (APCI) m/z 316 [M+H]$^+$.

53b)

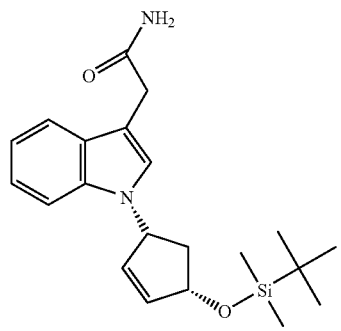

+

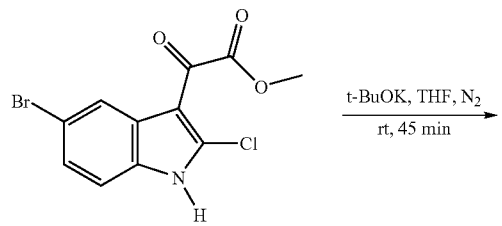

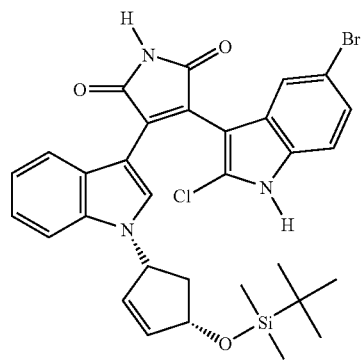

Potassium t-butoxide (1M in THF, 80 mL, 80 mmol) was added dropwise to a stirred solution of 53a (6.6 g, 16.2 mmol) and 1g (5.15 g, 17.8 mmol) in dry THF (50 ml) at rt under nitrogen atmosphere. After 45 minutes the reaction was diluted with EtOAc (500 mL), washed with water (2×250 mL), dried over sodium sulfate, filtered and concentrated in vacuo. The crude residue (8.71 g) was purified by flash chromatography (silica gel, PE/EtOAc 8/2 to pure AcOEt as eluant mixture) to afford the pure target compound (5.06 g, yield 49.0%).

$^1$H-NMR (300 MHz, DMSO-d$_6$): δ 0.14 (6H, d, CH$_3$—Si), 0.95 (9H, tBu), 1.55 (1H, m, CH$_2$), 2.85 (1H, m, CH$_2$), 4.75 (1H, bt, CH—O), 5.55 (1H, bt, CH—N) 6.05 (1H, dd, CH═), 6.15 (1H, dd, CH═), 6.40 (1H, m, indole Harom), 6.50 (1H, t, indole Harom), 6.90 (1H, t, indole Harom), 7.20 (2H, m, indole Harom), 7.45 (1H, m, indole Harom), 7.55 (1H, d, indole Harom), 7.80 (1H, s, indole H-2), 10.80 (1H, s, imide NH), 12.30 (1H, bs, indole NH. MS (APCI) m/z 636 [M+H]$^+$.

53c)

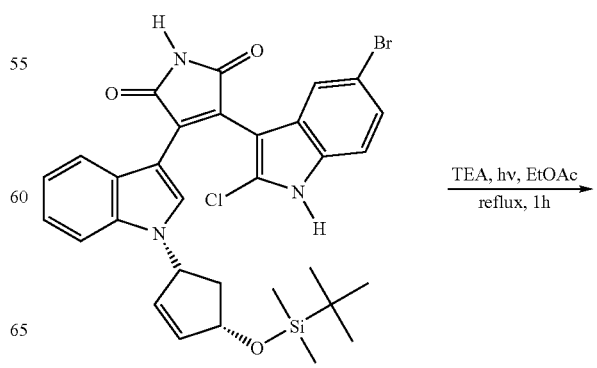

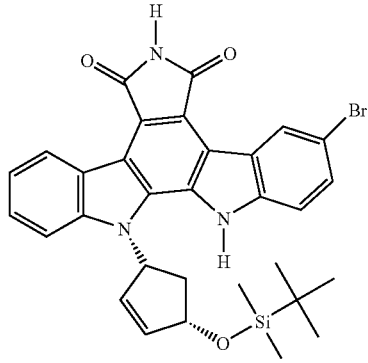

A solution of 53b (5.06 g, 7.9 mmol) and triethylamine (3 mL, excess) in EtOAc (200 mL) was irradiated at reflux with a halogen lamp. After 1 h the solution was cooled to rt, washed with water (120 mL), dried over sodium sulfate and concentrated in vacuo to give the pure target compound (4.69 g, yield 97.0%).

$^1$H-NMR (300 MHz, DMSO-d$_6$): δ 0.15 (6H, s, CH$_3$—Si), 0.95 (9H, tBu), 2.20 (1H, m, CH$_2$), 3.30 (1H, m, CH$_2$), 5.10 (1H, bt, CH—O), 6.20 (2H, m, CH=), 6.40 (1H, bt, CH—N), 7.40 (2H, m, indole Harom), 7.65 (2H, d, indole Harom), 8.05 (1H, d, Harom), 9.15 (1H, d, indole Harom), 9.25 (1H, s, indole Harom), 11.10 (1H, bs, imide NH), 12.35 (1H, bs, indole NH). MS (APCI) m/z 600 [M+H]$^+$.

53d)

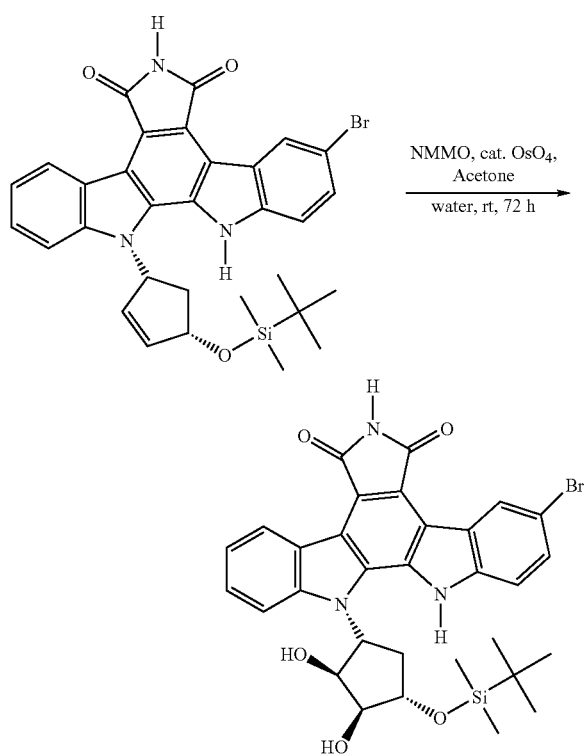

N-Methylmorpholine N-oxide (1.41 g, 11.8 mmol) in acetone (130 mL) was added dropwise to a solution of 53c (2.4 g, 4.0 mmol) in acetone (70 mL) at rt. Then osmium tetroxide (2.5% w/w solution in t-BuOH, 6 mL, catalytic) and water (a few drops, catalytic) were added and stirring at rt was continued for 72 hours. The resulting suspension was filtered, the solid was washed repeatedly with acetone and dried to give a first crop of the pure target compound (1.65 g). The solution was diluted with AcOEt (500 mL), washed with aqueous bisulfite (200 mL) and water (2×200 mL) and dried. After concentration a second crop of the pure target compound (630 mg, total yield 75.2%) was obtained.

$^1$H-NMR (300 MHz, DMSO-d$_6$): δ 0.15 (6H, s, CH$_3$Si), 0.95 (9H, tBu), 2.40 (1H, m, OH), 3.15 (1H, m, CH$_2$), 3.65 (1H, dt, CH—OH), 3.85 (1H, d, OH), 4.10 (1H, dt, CH—OH), 4.30 (1H, d, OH), 5.00 (1H, m, CH—OSi), 5.65 (1H, mt, CH—N), 7.40 (2H, m, indole Harom), 7.65 (2H, m, indole Harom), 8.40 (1H, d, Harom), 9.15 (1H, d, indole Harom), 9.20 (1H, s, indole Harom), 1.10 (1H, bs, imide NH). MS (APCI) m/z 634 [M+H]$^+$.

53) NAD 450

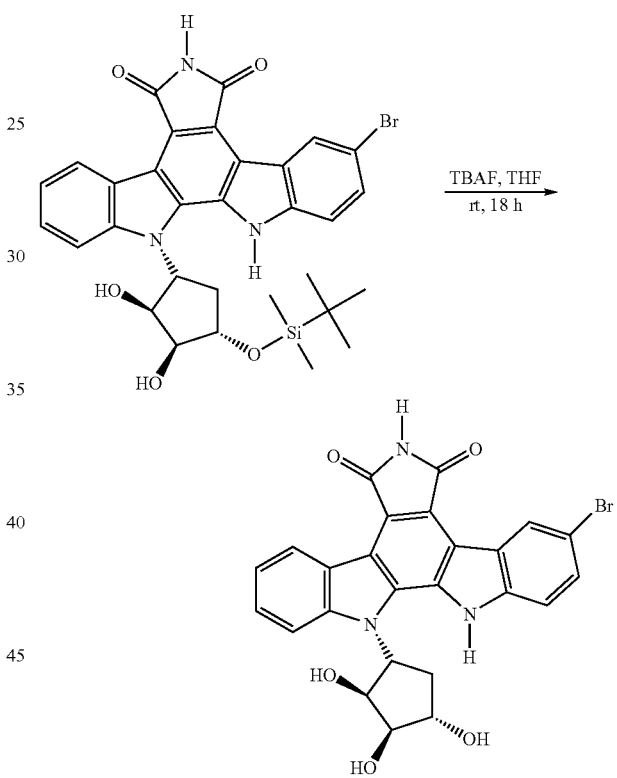

Tetrabutylammonium fluoride (1M in THF, 2 mL, 2 mmol) was added dropwise to a stirred solution of 53d (630 mg, 1.0 mmol) in dry THF (20 mL) under nitrogen atmosphere at rt. After 18 hours the solution was diluted with EtOAc (100 mL) and washed with 1N HCl (30 mL) and water (2×50 mL). The organic layer was dried over sodium sulfate, filtered and concentrated in vacuo to yield the pure target compound as an orange solid (490 mg, yield 87.8%).

$^1$H-NMR (300 MHz, DMSO-d$_6$): δ 2.35 (1H, m, CH$_2$), 3.05 (1H, m, CH$_2$), 4.05 (1H, bs, OH), 4.35 (1H, m, CH—OH), 5.05 (2H, m, CH—OH), 5.20 (1H, m, CH—OH), 5.30 (1H, d, M, 5.65 (1H, mt, CH—N), 7.55 (1H, m, indole Harom), 7.70 (1H, m, indole Harom), 7.75 (2H, m, Harom), 8.40 (1H, d, Harom), 9.35 (1H, d, indole Harom), 9.40 (1H, s, indole Harom), 11.10 (1H, s, imide NH), 12.10 (1H, bs, indole NH). MS (APCI) m/z 520 [M+H]$^+$.

Example 54

NAD 234

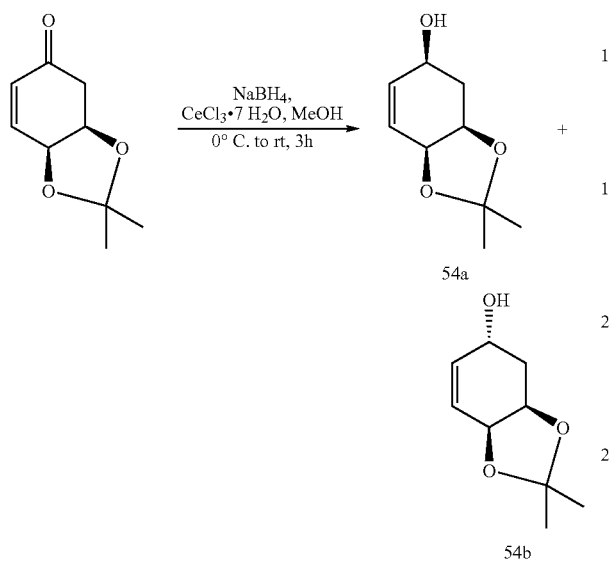

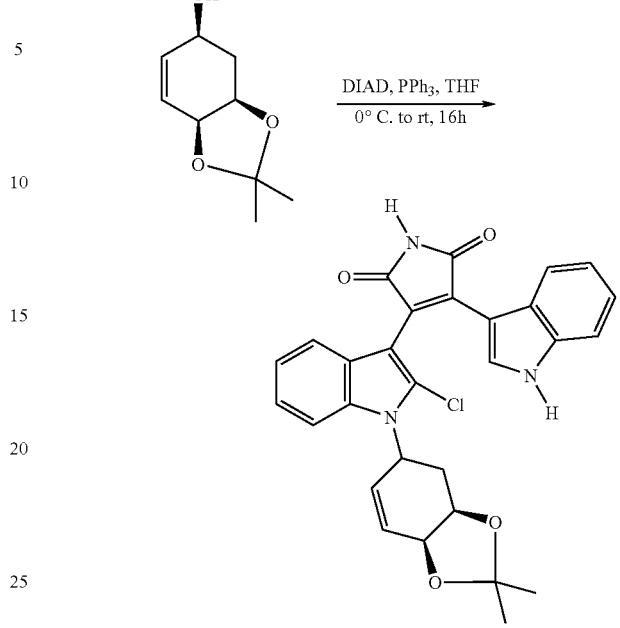

Sodium borohydride (1.05 g, 27.8 mmol) was added portionwise within 10 minutes to a solution of 2,2-dimethyl-3,7-dihydro-4-benzo-[1,3]dioxol-5-one (3.9 g, 23.2 mmol, prepared as in JOC, 1989, 54, 3738–3740) and CeCl$_3$ (13 g, 34.8 mmol) in MeOH (100 mL) at 0° C. The reaction mixture was stirred at rt for 3 hours and was quenched by addition of ice-water (150 mL). MeOH was removed in vacuo and the aqueous layer was extracted with EtOAc (2×100 mL). The combined organic layer were dried over sodium sulfate, filtered and concentrated in vacuo to give a crude (3.5 g). Purification by flash chromatography (silica gel, PE/EtOAc 1/1 as eluant mixture) gave the two pure diastereoisomers in a 2/1 ratio. (3.01 g, total yield 76%).

Cis-isomer 54a: $^1$H-NMR (300 MHz, CDCl$_3$): δ 1.33 (3H, s, C(CH$_3$)$_2$), 1.34 (3H, s, C(CH$_3$)$_2$), 1.65 (1H, m, CH$_2$), 2.45 (1H, m, CH$_2$), 4.40 (3H, m, CH—OH+CH—OC), 5.65 (1H, d, CH═), 5.85 (1H, dd, CH═). (MS (ESI) m/z 171 [M+H].

Trans-isomer 54b: $^1$H-NMR (300 MHz, CDCl$_3$): δ 1.34 (3H, s, C(CH$_3$)$_2$), 1.44 (3H, s, C(CH$_3$)$_2$), 2.0 (1H, m, CH$_2$), 2.30 (1H, m, CH$_2$), 4.05 (1H, d, CH—OH), 4.40 (2H, bt, CH—OC), 5.70 (1H, d, CH═), 6.0 (1H, dd, CH═). MS (ESI) m/z 171 [M+H].

A solution of 23c (2.71 g, 7.5 mmol), 54a (1.41 g, 8.3 mmol) and triphenylphosphine (2.62 g, 10 mmol) in THF (10 mL) was cooled to 0° C. Diisopropyl azodicarboxylate (1.94 mL, 10 mmol) was added within 15 minutes and the reaction mixture was warmed and stirred overnight at rt. The solvent was removed in vacuo and the residue purified by flash chromatography (silica gel, PE/EtOAc/NEt$_3$ 1/1/0.02 as eluant mixture) to give an orange foam (5 g). A second purification by flash chromatography (silica gel, DCM/EtOAc 10/1 as eluant mixture) gave the pure title compound as an orange foam (2.06 g, yield 53.0%).

$^1$H-NMR (300 MHz, DMSO-d$_6$): δ 1.25–1.35 (6H, bs, CH$_3$)$_2$), 2.25–2.45 (2H, m, CH$_2$), 4.47 (1H, m, CH—O), 4.71 (1H, m, CH—O) 5.15 (1H, m, CH—N), 6.13 (1H, m, CH═), 6.57 (1H, m, CH═), 7.00–7.20 (3H, m, Harom), 7.35–7.55 (3H, m, Harom), 8.11 (1H, bt, indole H-2), 11.07 (1H, bs, imide NH), 11.92 (1H, bs, indole NH). MS (APCI) m/z 514 [M+H]$^+$.

54) NAD 234

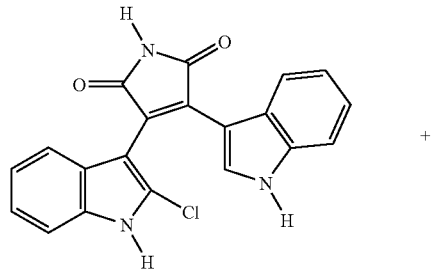

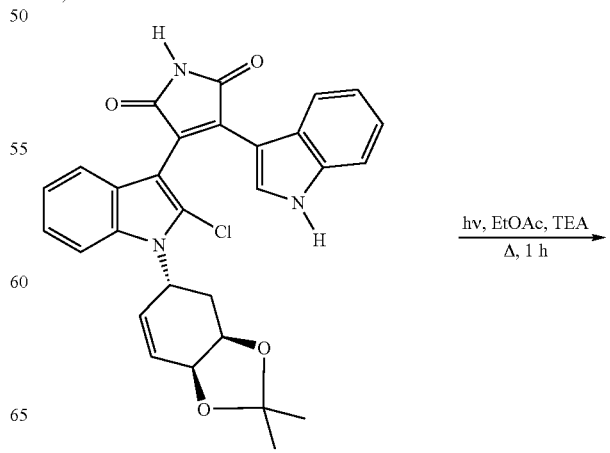

-continued

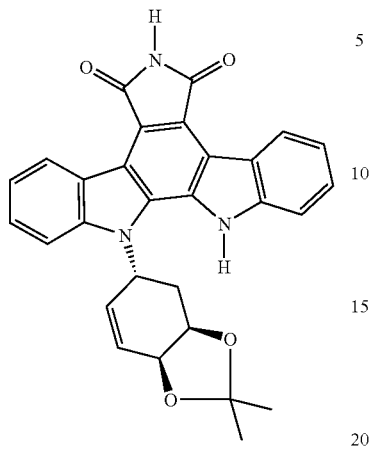

A solution of 54c (2.03 g, 3.95 mmol) and triethylamine (30 mL) in EtOAc (300 mL) was irradiated with a halogen lamp. After 1 hour the solution was cooled to rt, washed with water (2×100 mL), dried with sodium sulfate and concentrated in vacuo to give a solid residue (2.0 g). Purification by trituration with hot 3/2 MeOH/Acetone (10 mL) afforded the pure target compound (1.52 g, yield 81.0%).

$^1$H-NMR (300 MHz, DMSO-d$_6$): δ 1.36 (3H, s, C(CH$_3$)$_2$), 1.56 (3H, s, C(CH$_3$)$_2$), 2.29 (1H, m, CH$_2$), 2.43 (1H, m, CH$_2$), 4.53 (1H, m, CH—O), 4.85 (1H, m, CH—O), 6.06 (2H, m, CH=+CH—N), 6.45 (1H, m, CH=), 7.38 (2H, m, indole Harom), 7.54 (1H, t, indole Harom), 7.59 (1H, dt, Harom), 7.75 (1H, d, indole H), 7.77 (1H, d, indole H-7), 9.11 (1H, d, indole H-4), 9.20 (1H, d, indole H-4), 11.10 (1H, bs, imide NH), 12.10 (1H, bs, indole NH). MS (APCI) m/z 478 [M+H]$^+$.

Example 55

NAD 238

55)

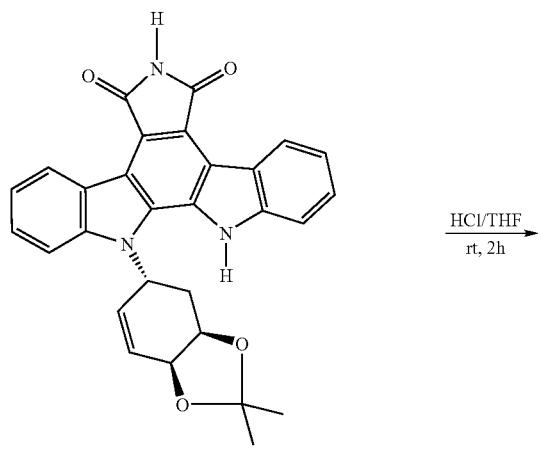

HCl/THF
rt, 2h

-continued

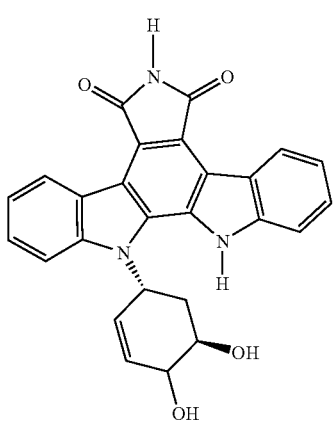

Concentrated HCl (1 mL) was added to a solution of 54 (300 mg, 0.63 mmol) in THF (2 mL). The reaction was stirred for 2 hours at rt and water (2 mL) was added. The orange precipitate was filtered, washed with water (1 mL), then Et$_2$O (3 mL) and dried in vacuo to give the pure title compound (230 mg, yield 83.0%).

$^1$H-NMR (300 MHz, DMSO-d$_6$): δ 2.25 (2H, m, CH$_2$), 4.56 (1H, bs, CH—OH), 4.88 (1H, bs, CH—OH), 4.97 (2H, bs, OH), 6.00 (1H, d, CH=), 6.19 (2H, m, CH=+CH—N), 7.37 (2H, t, indole Harom), 7.53 (1H, t, indole Harom), 7.58 (1H, dt, Harom), 7.78 (1H, d, indole H-7), 7.83 (1H, d, indole H-7), 9.12 (1H, d, indole H-4), 9.20 (1H, d, indole H-4), 11.08 (1H, bs, imide NH), 11.95 (1H, bs, indole NH). MS (APCI) m/z 438 [M+H]$^+$.

Example 56

NAD 223

56a)

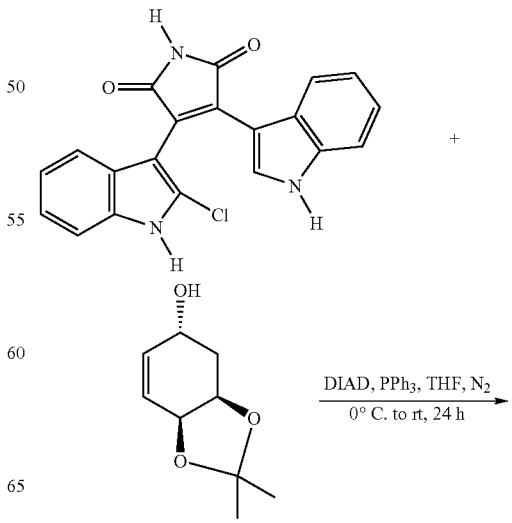

+

DIAD, PPh$_3$, THF, N$_2$
0° C. to rt, 24 h

-continued

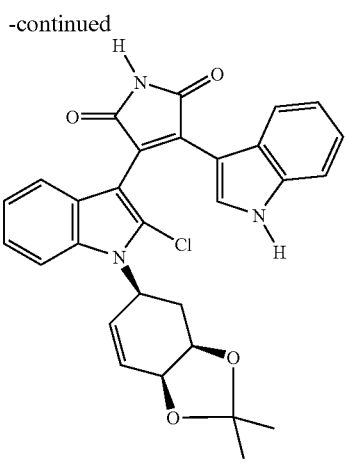

A solution of 23c (0.83 g, 2.3 mmol), 54b (0.43 g, 2.53 mmol) and triphenylphosphine (0.71 g, 2.7 mmol) in THF (10 mL) was cooled to 0° C. Diisopropyl azodicarboxylate (0.53 mL, 2.7 mmol) was added within 5 minutes and the reaction mixture was warmed and stirred for 24 hours at rt. The solvent was removed in vacuo and the residue purified by flash chromatography (silica gel, PE/EtOAc/NEt₃ 1/1/0.02 as eluant mixture) to give an orange foam (0.96 g). A second purification by flash chromatography (silica gel, DCM/EtOAc 10/1 as eluant mixture) gave the pure compound as an orange foam (0.27 g, yield 23.0%).

56) NAD 223

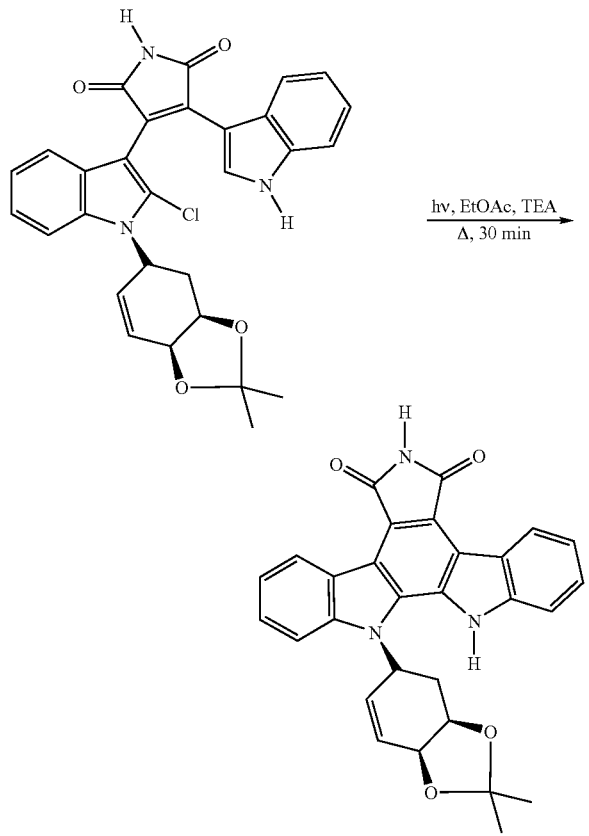

A solution of 56a (0.25 g, 0.49 mmol) and triethylamine (30 mL, excess) in EtOAc (150 mL) was irradiated with a halogen lamp. After 30 minutes the solution was cooled to rt, washed with water (2×50 mL), dried with sodium sulfate and concentrated in vacuo to give a solid residue (0.23 g). Purification by trituration with boiling MeOH (2 mL), filtration, washing with MeOH (1 mL) and drying in vacuo afforded the pure target compound (0.16 g, yield 68.0%).

¹H-NMR (300 MHz, DMSO-d₆): δ 1.41 (3H, s, C(CH₃)₂), 1.45 (3H, s, C(CH₃)₂), 2.28 (2H, m, CH₂), 4.75 (2H, m, CH—O), 6.11 (1H, m, CH═), 6.33 (1H, d, CH—N), 6.47 (1H, m, CH═), 7.39 (2H, m, indole Harom), 7.53 (2H, m, indole Harom), 7.75 (1H, d, indole H-7), 7.78 (1H, d, indole H-7), 9.13 (1H, d, indole H-4), 9.23 (1H, d, indole H-4), 11.10 (1H, bs, imide NH), 12.06 (1H, bs, indole NH). MS (APCI) m/z 478 [M+H]⁺.

Example 57

NAD 292

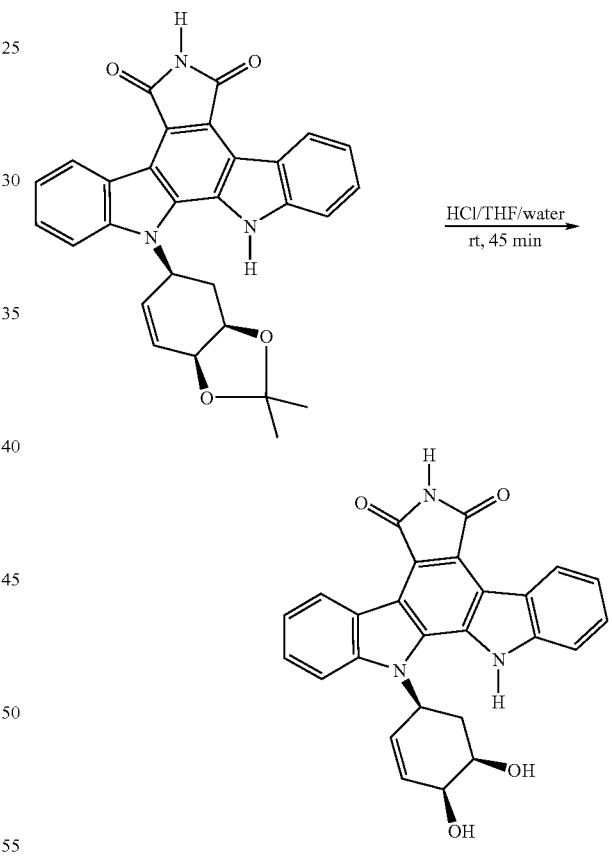

Concentrated HCl (1 mL) was added to a solution of 56 (240 mg, 0.50 mmol) in THF (2 mL). The reaction mixture was stirred for 45 minutes at rt and water (5 mL) was added. The orange precipitate was filtered, washed with water (2 mL), MeOH (2 mL), boiling acetone (3 mL) and dried in vacuo to give the pure title compound (110 mg, yield 50.0%).

¹H-NMR (300 MHz, DMSO-d₆, T=80° C.): δ 2.27 (1H, m, CH₂), 2.64 (1H, m, CH₂), 4.13 (1H, bs, CH—OH), 4.34 (1H, bs, CH—OH), 6.06 (1H, m, CH═+CH—N), 6.27 (1H, m, CH═), 7.37 (2H, q, indole Harom), 7.56 (2H, dt, indole Harom), 7.76 (1H, d, indole H-7), 8.05 (1H, d, indole H-7), 9.15 (1H, d, indole H-7), 9.25 (1H, d, indole H-4), 10.76 (1H, bs, imide NH), 11.60 (1H, bs, indole NH). MS (APCI) m/z 438 [M+H]+.

Example 58

NAD 226

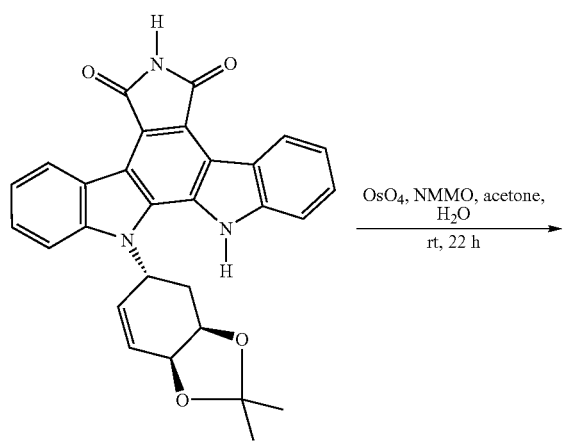

56 (0.11 g, 0.23 mmol) in THF (3 mL) was treated sequentially with N-methylmorpholine N-oxide (54 mg, 0.46 mmol) in acetone (6 mL) and osmium tetroxide (2.5% in tBuOH, 0.5 mL, catalytic) at rt. The mixture was stirred for 22 hours, the reaction mixture was poured onto 5% NaHSO$_3$ (40 mL) and extracted with EtOAc (60 mL). The organic layer was washed with water (40 mL), brine (25 mL), dried over magnesium sulfate, filtered and concentrated in vacuo. Trituration in 1/1 EtOH/MeOH (5 mL), filtration and drying in vacuo gave the pure target compound (0.13 g, yield 41.9%).

$^1$H-NMR (300 MHz, DMSO-d$_6$): δ 1.38 (3H, s, C(CH$_3$)$_2$), 1.66 (3H, s, C(CH$_3$)$_2$), 2.54 (1H, m, CH$_2$), 2.76 (1H, m, CH$_2$), 4.28 (1H, bs, CH—OH), 4.36 (1H, bs, CH—OH), 4.58 (1H, m, CH—OC), 4.70 (1H, m, CH—OC), 5.45 (2H, m, OH+CH—N), 6.27 (1H, m, O), 7.38 (2H, q, indole Harom), 7.59 (2H, dt, indole Harom), 7.73 (1H, d, indole H-7), 7.97 (1H, d, indole H-7), 9.10 (1H, d, indole H-4), 9.22 (1H, d, indole H-4), 11.06 (1H, bs, imide NH), 11.40 (1H, bs, indole NH). MS (APCI) m/z 512 [M+H]+.

Example 59

NAD 284

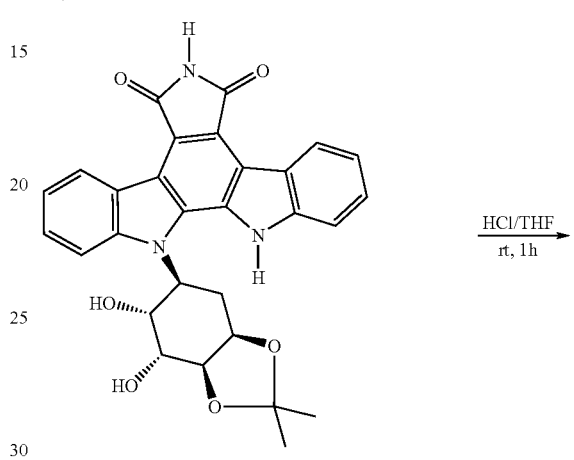

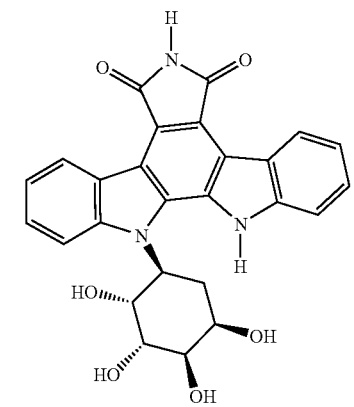

Concentrated HCl (1 mL) was added to a solution of 58 (130 mg, 0.25 mmol) in THF (2 mL). The reaction mixture was stirred for 1 hour at rt and water (5 mL) was added. The orange precipitate was filtered, washed with water (2 mL), MeOH (2 mL), boiling acetone (3 mL) and dried in vacuo to give the pure title compound (110 mg, yield 50.2%).

$^1$H-NMR (300 MHz, DMSO-d$_6$): δ 2.10–2.20 (2H, m, CH$_2$) 3.96 (1H, d, CH—OH), 4.06–4.15 (1H, m, CH—OH), 4.28–4.40 (1H, m, CH—OH), 4.87 (1H, d, CH—OH), 5.05 (1H, m, OH), 5.08–5.21 (1H, m, OH), 5.23–5.33 (1H, m, OH), 5.43 (1H, m, OH), 7.38 (2H, q, indole Harom), 7.59 (2H, dt, indole Harom), 7.73 (1H, d, indole H-7), 7.97 (1H, d, indole H-7), 9.10 (1H, d, indole H-4), 9.22 (1H, d, indole H-4), 11.06 (1H, bs, imide NH), 11.40 (1H, bs, indole NH). MS (APCI) m/z 472 [M+H]+.

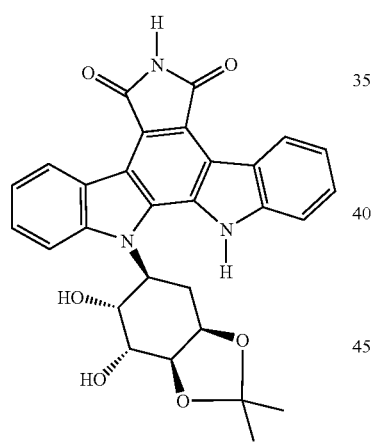

Example 60

NAD 296

60)

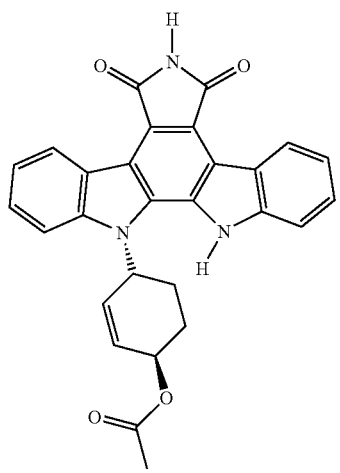

NO2-BF4+, THF, N2
-78° C. to rt, 2h
50° C., 2.5h
→

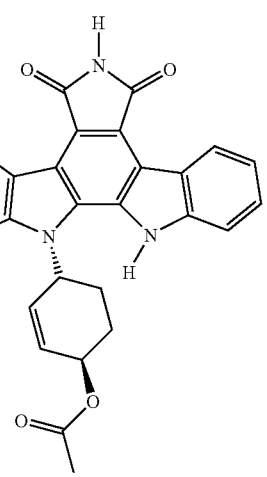

Nitronium tetrafluoborate (0.5M solution in sulfolane, 1.1 mL, 0.55 mmol) was added dropwise to a solution of 26 (120 mg, 0.26 mmol) in dry THF (5 mL) at −78° C. under nitrogen atmosphere. After 2 hours the reaction mixture was warmed and stirred at 50° C. for 2.5 hours. The precipitate was filtered, washed repeatedly with THF (6×1 mL) and Et$_2$O (3 mL), and dried in vacuo to give the pure target compound (70 mg, 53.0% yield).

$^1$H-NMR (300 MHz, DMSO-d$_6$): δ 2.14 (3H, s, CH$_3$), 2.30 (4H, m, CH$_2$13 CH$_2$), 5.72 (1H, m, CH—O), 6.00 (1H, d, CH=), 6.16 (1H, m, CH—N), 6.29 (1H, d, CH=), 7.37 (1H, t, indole Hs), 7.56 (1H, t, indole Hs), 7.83 (1H, d, indole H-7), 7.84 (1H, d, indole H-7), 9.13 (1H, d, indole H-4), 9.22 (1H, d, indole H-4), 9.88 (1H, d, H-6), 11.17 (1H, bs, imide NH), 12.62 (1H, bs, indole NH). MS (APCI): molecular ion not detectable.

Example 61

NAD240

61a)

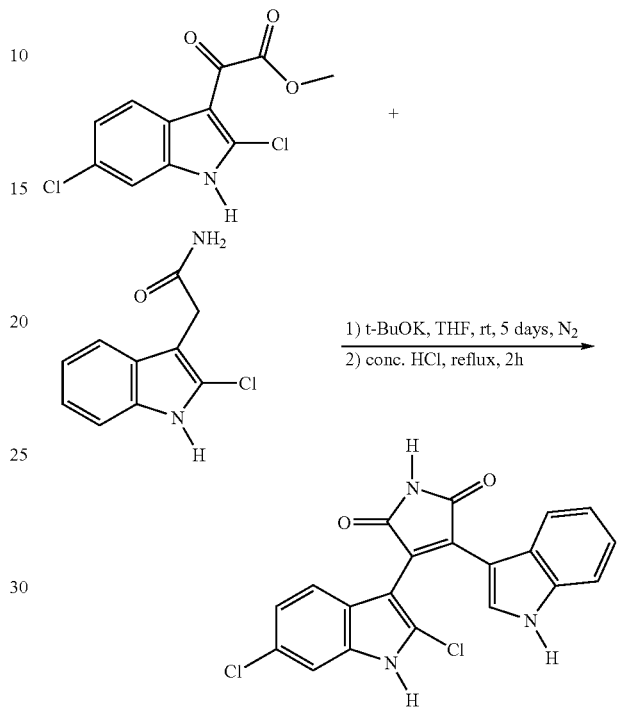

1) t-BuOK, THF, rt, 5 days, N$_2$
2) conc. HCl, reflux, 2h
→

Potassium t-butoxide (1M in THF, 102 mL, 102 mmol) was added dropwise to a stirred solution of 37a (6.80 g, 25 mmol) and commercially available 3-indolecarboxamide (2.96 g, 17 mmol) in dry THF (20 mL) at rt under nitrogen atmosphere. After 5 days concentrated HCl (10 mL) was added and the reaction mixture was stirred at reflux for 2 h. After cooling to rt the reaction mixture was diluted with EtOAc (500 mL), washed with water (2×300 mL) and brine (300 mL), dried over sodium sulfate, filtered and concentrated in vacuo to give the pure target compound (3.54 g, yield 53.0%).

$^1$H-NMR (300 MHz, DMSO-d$_6$): δ 6.37 (1H, d, Harom), 6.59 (1H, bt, Harom), 7.00 (2H, m, Harom), 7.29 (1H, d, Harom), 7.39 (2H, m, indole Harom), 8.01 (1H, d, indole Harom), 11.06 (1H, s, imide NH), 12.23 (1H, bs, indole NH). MS (APCI) m/z 396 [M+H]$^+$.

61b)

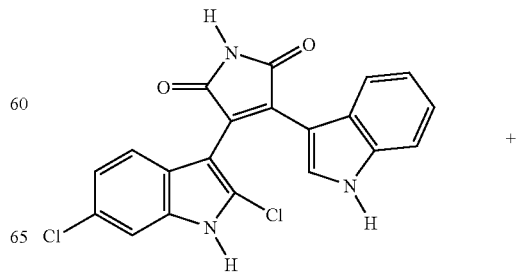

-continued

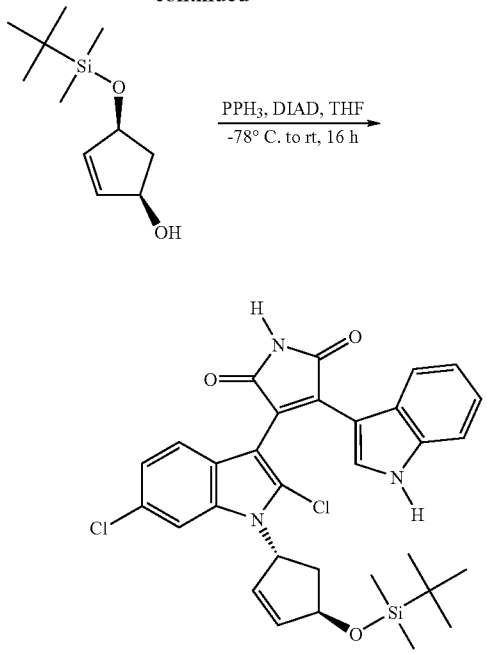

A solution of 1d (2.25 g, 10.5 mmol), 61a (3.18 g, 8.03 mmol) and triphenylphosphine (3.59 g, 13.7 mmol) in THF (10 mL) was cooled to −78° C. Diisopropyl azodicarboxylate (2.7 mL, 13.7 mmol) was added within 30 minutes, the reaction mixture was warmed slowly to rt and stirred overnight. The solvent was removed in vacuo and the residue purified by flash chromatography (silica gel, PE/EtOAc/NEt$_3$ 1/1/0.02 as eluant mixture) to give an orange foam (3.2 g). A second purification by flash chromatography (silica gel, DCM/EtOAc 10/1 as eluant mixture) gave the pure title compound as an orange foam (2.13 g, yield 45.1%).

$^1$H-NMR (300 MHz, DMSO-d$_6$): δ 0.11 (6H, s, CH$_3$—Si), 0.89 (9H, s, tBu), 2.05 (1H, m, CH$_2$), 2.20 (1H, m, CH$_2$), 5.20 (1H, bdd, CH—N), 5.95 (2H, m, CH=+CH—O) 6.15 (2H, m, Harom+CH=), 6.60 (1H, bq, Harom) 7.05 (2H, m, Harom), 7.40 (2H, m, Harom), 7.55 (1H, dd, Harom), 8.08 (1H, dd, indole Harom), 11.05 (1H, s, imide NH), 11.85 (1H, bs, indole NH). MS (APCI) m/z 592 [M+H]$^+$.

61c)

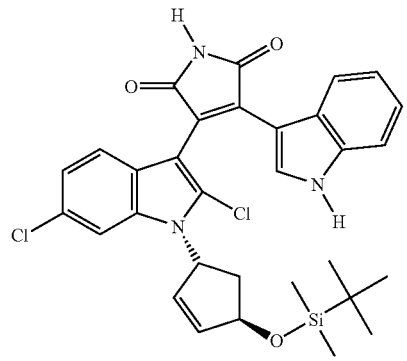

-continued

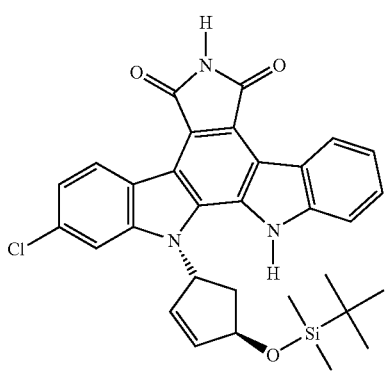

A solution of 61b (2.10 g, 3.54 mmol) and triethylamine (30 mL) in EtOAc (300 mL) was irradiated with a halogen lamp. After 1 hour the solution was cooled to rt, washed with water (2×100 mL), dried with sodium sulfate and concentrated in vacuo to give a solid residue (2.02 g). Trituration in hot MeOH (5 mL), filtration and washing with MeOH (3 mL) afforded after drying in vacuo the pure target compound (1.95 g, yield 98.9%).

$^1$H-NMR (300 MHz, DMSO-d$_6$): δ 0.15 (6H, s, CH$_3$—Si), 0.93 (9H, tBu), 2.50 (2H, m, CH$_2$), 5.42 (1H, m, CH—O), 6.34–6.39 (2H, m, CH=CH), 6.78 (1H, bt, CH—N), 7.34 (1H, dt, Harom), 7.38 (1H, dd, Harom), 7.52 (1H, d, indole Harom), 7.56 (1H, dt, indole Harom), 7.76 (1H, d, indole Harom), 9.07 (1H, d, indole H-4), 9.14 (1H, d, indole H-4), 11.08 (1H, bs, imide NH), 12.20 (1H, bs, indole NH. MS (APCI) m/z 556 [M+H]$^+$.

61) NAD 240

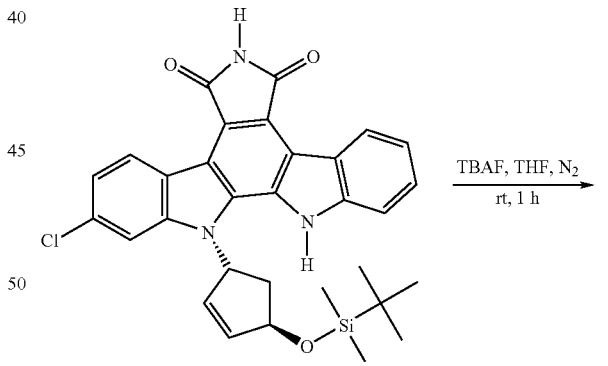

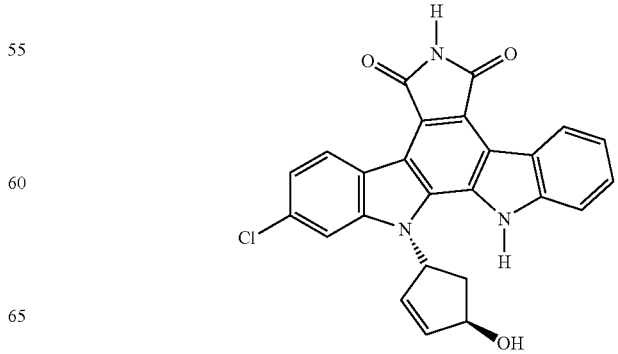

Tetrabutylammonium fluoride (1M in THF, 1 mL, 1 mmol) was added dropwise to a stirred solution of 61c (0;27 g, 0.49 mmol) in dry THF (8 mL) under nitrogen atmosphere at rt. After 1 hour AcOH (10 drops) and EtOAc (50 mL) were added. The solution was washed with sat. NaHCO₃ (10 mL), water (10 mL) and brine (10 mL). The organic layer was dried over sodium sulfate, filtered and concentrated in vacuo to yield the pure target compound as an orange solid (170, mg, yield 79.0%).

¹H-NMR (300 MHz, DMSO-d₆): δ 2.47 (2H, m, CH₂), 5.22 (1H, m, CH—O), 5.26 (1H, bs, OH), 6.36 (2H, m, CH=CH), 6.79 (1H, bt, CH—N), 7.35 (1H, dt, Harom), 7.39 (1H, d, Harom), 7.55 (1H, d, Harom), 7.57 (1H, dt, Harom), 7.78 (1H, d, Harom), 9.09 (1H, d, indole H-4), 9.16 (1H, d, indole H-4), 11.10 (1H, bs, imide NH), 12.30 (1H, bs, indole NH). MS (APCI) m/z 442 [M+H]⁺.

Example 62

NAD 340

62a)

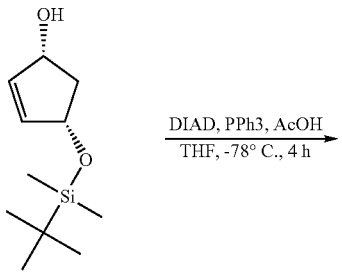

Diisopropyl azodicarboxylate (23 mL, 118 mmol) was added dropwise to a stirred solution of 1d (12.6 g, 59 mmol), triphenylphosphine (31 g, 118 mmol) and AcOH (7 mL, 118 mmol) in THF (300 mL) at −78° C. under nitrogen atmosphere. The reaction mixture was stirred for 4 hours at −780C, then 10% NaHCO₃ (100 mL) was added, the mixture was warmed to rt and extracted with Et₂O (2×300 mL). The combined organic layers were dried over sodium sulfate, filtered and concentrated in vacuo. Purification by flash chromatography (silica gel, PE/EtOAc 4/1 as eluant mixture) gave the pure expected compound (15.0 g, quantitative yield) used in the next step.

¹H-NMR (300 MHz, DMSO-d₆): d 0.03 (6H, s, Si(CH₃)₂), 0.82 (9H, s, tBu), 1.95 (4H, m, OCOCH₃+CH₂), 2.15 (1H, m, CH) 5.00 (1H, m, CH—OAc), 5.60 (1H, m, CH—OSi), 5.85 (1H, dd, CH=), 6.10 (1H, dd, CH=). MS (APCI) m/z 257 [M+H]⁺.

62b)

Potassium hydroxide (0.75 g, 13.4 mmol) was added to a solution of 62a (15 g, 58.5 mmol) in MeOH (100 mL) and the reaction mixture was stirred for 1 hour at rt. 1N HCl (50 mL) was added and the reaction mixture was extracted with Et₂O (2×250 mL). The combined organic layers were dried over sodium sulfate and concentrated in vacuo. Purification by flash chromatography (silica gel, PE/EtOAc 6/1 as eluant mixture) gave the pure expected compound as a colorless oil (11.0 g, yield 87.0%).

¹H-NMR (300 MHz, DMSO-d₆): d 0.03 (6H, s, Si(CH₃)₂), 0.82 (9H, s, tBu), 1.85 (2H, m, CH₂), 4.75 (2H, m, CH—OH), 4.90 (1H, m, CH—OSi), 5.75 (1H, dd, CH=), 5.85 (1H, dd, CH=). MS (APCI) m/z 215 [M+H]⁺.

62c)

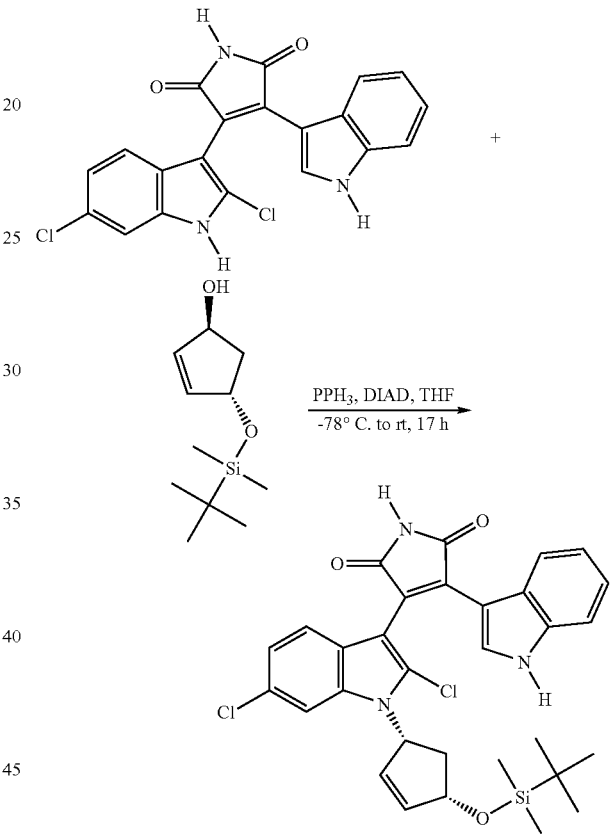

A solution of 62b (1.63 g, 7.6 mmol), 61a (2.0 g, 5.05 mmol) and triphenylphosphine (2.62 g, 10 mmol) in THF (20 mL) was cooled to −78° C. Diisopropyl azodicarboxylate (1.94 mL, 10 mmol) was added within 10 minutes, the reaction mixture was warmed slowly to rt and stirred overnight. The solvent was removed in vacuo and the residue purified by flash chromatography (silica gel, PE/EtOAc/ NEt₃ 1/1/0.02 as eluant mixture) to give an orange foam (3.5 g). A second purification by flash chromatography (silica gel, DCM/EtOAc 10/1 as eluant mixture) gave the pure target compound (0.81 g, yield 27.0%).

¹H-NMR (300 MHz, DMSO-d₆): δ 0.11 (6H, d, CH₃—Si), 0.89 (9H, d, tBu), 1.75–1.85 (1H, dm, CH₂), 2.80–3.00 (1H, dm, CH₂), 4.90 and 5.45 (1H, dm, CH—N), 5.85 and 6.10 (3H, dm, CH=CH+CH—O), 6.55 and 6.65 (2H, bq, Harom) 7.05 (2H, m, Harom), 7.40 (2H, m, Harom), 7.80 (1H, dd, Harom), 8.08 (1H, dd, indole Harom), 11.05 (1H, s, imide H), 11.85 (1H, bs, indole NH). MS (APCI) m/z 592 [M+H]⁺.

62d)

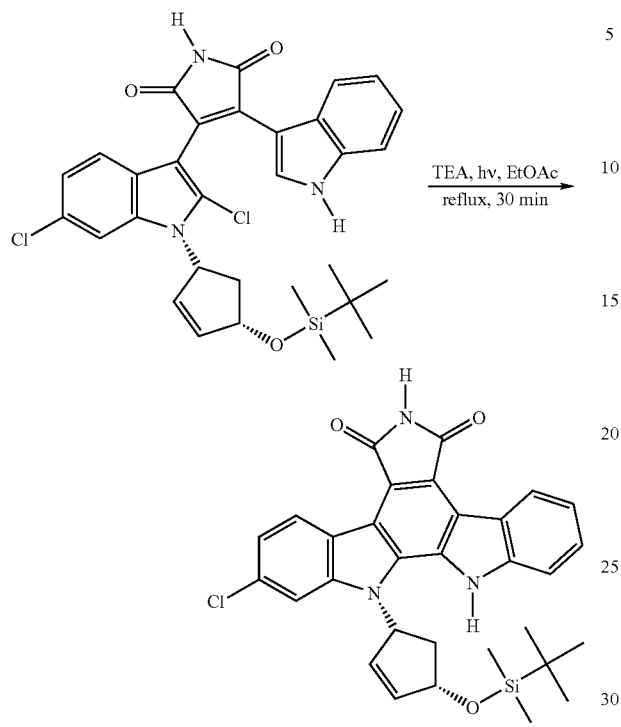

TEA, hv, EtOAc
reflux, 30 min
→

A solution of 62c (0.79 g, 1.33 mmol) and triethylamine (10 mL) in EtOAc (150 mL) was irradiated with a halogen lamp. After 30 min the solution was cooled to rt, washed with water (2×50 mL), dried with sodium sulfate and concentrated in vacuo to give a solid residue (0.74 g). Trituration in hot MeOH (2 mL), filtration and washing with MeOH (1 mL) afforded after drying in vacuo the pure target compound (9.65 g, yield 88.0%).

$^1$H-NMR (300 MHz, DMSO-$d_6$): δ 0.14 (3H, s, C$\underline{H_3}$—Si), 0.21 (3H, s, C$\underline{H_3}$—Si), 0.93 (9H, s, t$\underline{Bu}$), 2.13 (1H, dt, C$\underline{H_2}$), 3.32 (1H, m, C$\underline{H_2}$) 5.11 (1H, m, C$\underline{H}$—O), 6.30 (2H, m, C$\underline{H}$=C$\underline{H}$), 6.40 (1H, mt, C$\underline{H}$—N), 7.34 (1H, dt, $\underline{H}$arom), 7.38 (1H, m, $\underline{H}$arom), 7.58 (1H, t, $\underline{H}$arom), 7.76 (1H, d, $\underline{H}$arom), 8.05 (1H, d, $\underline{H}$arom), 9.10 (1H, d, indole $\underline{H}$-4), 9.16 (1H, d, indole $\underline{H}$-4), 11.13 (1H, bs, imide N$\underline{H}$), 12.12 (1H, bs, indole N$\underline{H}$). MS (APCI) m/z 556 [M+H]$^+$.

62) NAD 340

Tetrabutylammonium fluoride (1M in THF, 1 mL, 1 mmol) was added dropwise to a stirred solution of 62d (0.27 g, 0.49 mmol) in dry THF (8 mL) under nitrogen atmosphere at reflux. The reaction mixture was cooled to rt and was stirred for 2 hours at rt. Then AcOH (10 drops) and EtOAc (40 mL) were added. The solution was washed with sat. NaHCO$_3$ (10 mL), water (10 mL) and brine (10 mL). The organic layer was dried over sodium sulfate, filtered and concentrated in vacuo. The residue was triturated in hot MeOH (2 mL), filtered and dried in vacuo to yield the pure target compound as a yellow solid (130 mg, yield 87.0%).

$^1$H-NMR (300 MHz, DMSO-$d_6$): δ 2.09 (1H, m, C$\underline{H_2}$), 3.22 (1H, m, C$\underline{H_2}$), 4.97 (1H, m, C$\underline{H}$—O), 5.64 (1H, d, O$\underline{H}$), 6.30 (2H, m, C$\underline{H}$=C$\underline{H}$), 6.37 (1H, m, C$\underline{H}$—N), 7.37 (1H, t, $\underline{H}$arom), 7.42 (1H, m, $\underline{H}$arom), 7.59 (1H, dt, indole $\underline{H}$arom), 7.77 (1H, d, indole $\underline{H}$arom), 8.09 (1H, d, indole $\underline{H}$arom), 9.11 (1H, d, indole $\underline{H}$-4), 9.17 (1H, d, indole $\underline{H}$-4), 11.13 (1H, bs, imide N$\underline{H}$), 12.10 (1H, bs, indole N$\underline{H}$). MS (APCI) m/z 442 [M+H]$^+$.

Example 63

NAD 338

63a)

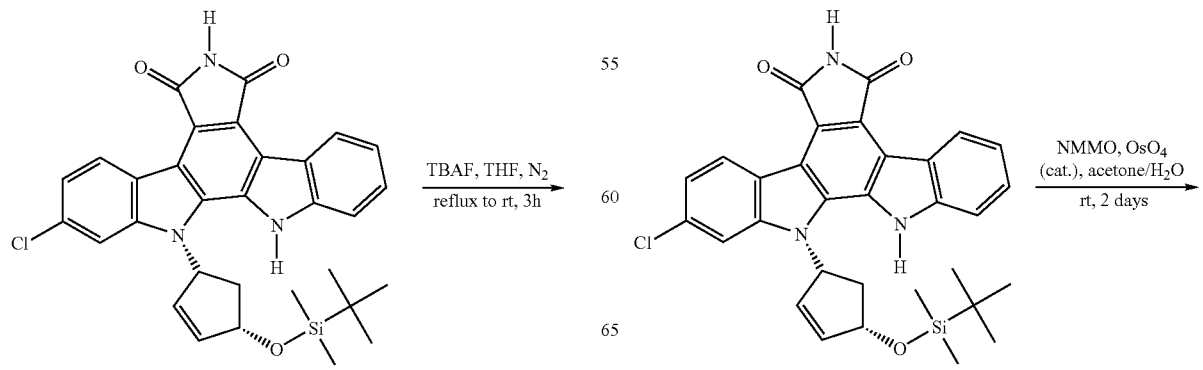

TBAF, THF, N$_2$
reflux to rt, 3h
→

NMMO, OsO$_4$ (cat.), acetone/H$_2$O
rt, 2 days
→

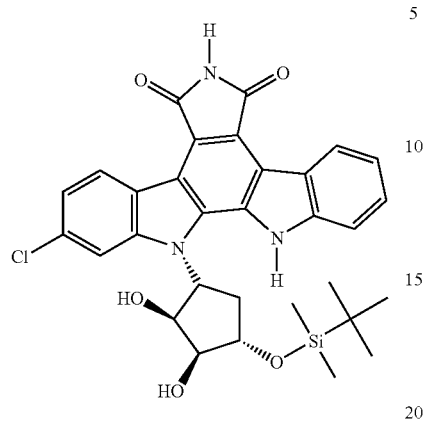

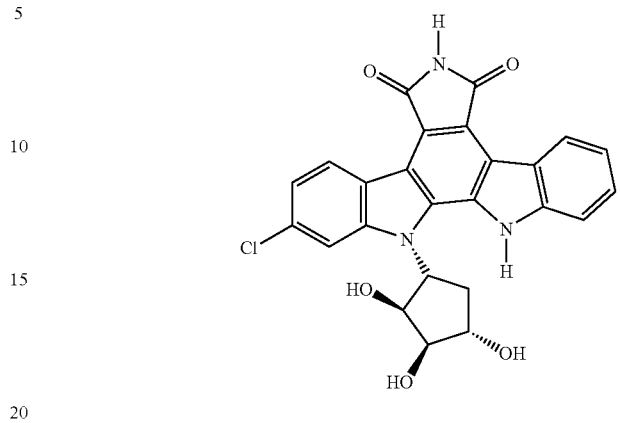

A suspension of 62d (250 mg, 0.45 mmol) in acetone (5 mL) was treated sequentially with N-methylmorpholine N-oxide (110 mg, 0.94 mmol) and osmium tetroxide (2.5% in tBuOH, 0.5 mL, catalytic). The suspension was vigorously stirred for 48 hours at rt. EtOAc (50 mL) was added and the reaction mixture was washed with 10% NaHSO$_3$ (40 mL), then 1N HCl (40 mL) and water (40 mL). The organic layer was dried over sodium sulfate, filtered and concentrated to give a crude solid residue (260 mg). Trituration in hot MeOH (2 mL), filtration and drying in vacuo gave the pure target compound as an orange powder (200 mg, yield 75.0%).

$^1$H-NMR (300 MHz, DMSO-d$_6$): δ 0.25 (6H, s, Si(CH$_3$)$_2$), 1.01 (9H, s, tBu), 2.37 (1H, dd, CH$_2$), 3.12 (1H, dd, CH$_2$), 3.85 (1H, d, OH), 4.29 (1H, bs, OH), 4.97 (1H, bs, CH—OSi), 5.32 (2H, m, CH—OH), 5.63 (1H, q, CH—N), 7.37 (1H, dt, Harom), 7.45 (1H, dd, Harom), 7.60 (1H, dt, Harom), 7.81 (1H, d, Harom), 8.33 (1H, bd, Harom), 9.10 (1H, d, indole H-4), 9.22 (1H, d, indole H-4), 11.13 (1H, bs, imide NH), 11.72 (1H, bs, indole NH). MS (APCI) m/z 590 [M+H]$^+$.

Tetrabutylammonium fluoride (1M in THF, 0.6 mL, 0.6 mmol) was added dropwise to a stirred solution of 63a (160 mg, 0.27 mmol) in dry THF (16 mL) under nitrogen atmosphere at reflux. The reaction was stirred at reflux for 3 hours. The reaction mixture was cooled to rt, AcOH (10 drops) and EtOAc (100 mL) were added. The solution was washed with sat. NaHCO$_3$ (50 mL), water (50 mL) and brine (50 mL). The organic layer was dried over sodium sulfate, filtered and concentrated in vacuo. The residue (160 mg) was triturated in hot MeOH(2 mL), filtered and dried in vacuo to yield the pure target compound as a yellow solid (110 mg, yield 85.9%).

$^1$H-NMR (300 MHz, DMSO-d$_6$): δ 2.28 (1H, m, CH), 3.05 (1H, m, CH), 3.94 (1H, bs, OH), 4.23 (1H, d, OH), 4.94 (1H, m, CH—OH), 5.17 (1H, bs, OH), 5.23 (2H, m, CH—OH), 5.58 (1H, q, CH—N), 7.37 (1H, dt, Harom), 7.44 (1H, dd, Harom), 7.59 (1H, dt, Harom), 7.73 (1H, d, Harom), 8.44 (1H, bs, Harom), 9.11 (1H, d, indole H-4), 9.21 (1H, d, indole H-4), 11.14 (1H, bs, imide NH), 12.10 (1H, bs, indole NH). MS (APCI) m/z 476 [M+H]$^+$.

Example 64

NAD 336

63) NAD 338

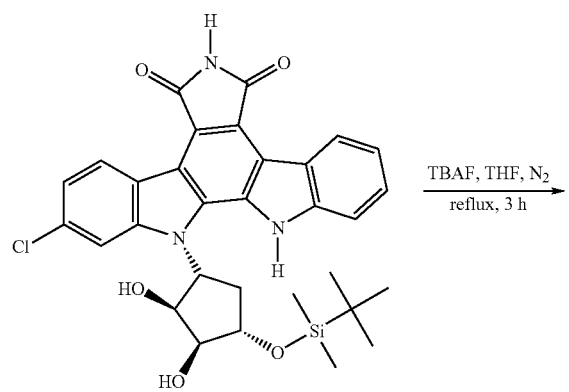

64a)

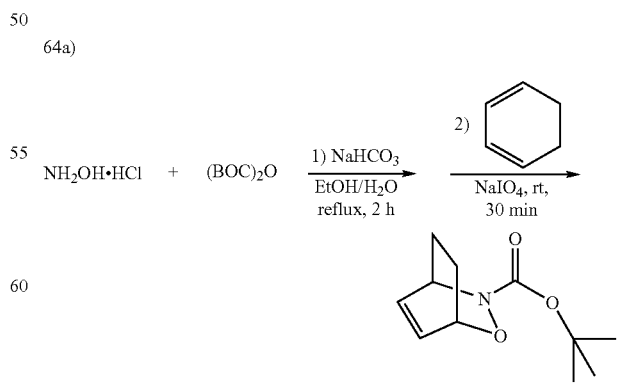

Sodium hydrogen carbonate (6.26 g, 74.5 mmol) was added portionwise to a stirred solution of hydroxylamine hydrochloride (5.22 g, 75 mmol) in a 2/1 mixture EtOH/H₂O (90 mL) at rt. The solution was stirred for 15 minutes, then neat t-butyloxycarbonate (16.24 g, 74.5 mmol) was added portionwise within 30 minutes and the reaction mixture was heated to reflux for 2 hours. The colorless solution was cooled to rt and saturated NH₄Cl (40 mL) was added. The pH was set to ca. 5.5 by addition of 5 N HCl and the the reaction mixture was treated sequentially with 1,3-cyclohexadiene (7.1 mL, 74.5 mmol) and sodium periodate (16 g, 74.8 mmol). The slurry was stirred for 30 minutes at rt before being filtered and washed with EtOH (20 mL). The filtrate was poured onto H₂O (100 mL) and extracted with DCM (2×100 mL). The combined organic layers were washed with saturated Na₂SO₃ (2×50 mL) and H₂O (2×100 mL), dried over sodium sulfate, filtered and concentrated in vacuo at low temperature to yield a crude (13.4 g). Purification by flash chromatography (silica gel, PE/EtOAc 2/1 as eluant mixture) gave the pure expected compound as an orange oil (11.8 g, yield 75.1%).

¹H-NMR (300 MHz, CDCl₃): δ 1.35 (1H, m, C$\underline{H}_2$) 1.40 (9H, s, C(C$\underline{H}_3$)₃), 2.35 (3H, m, C$\underline{H}_2$), 4.70 (2H, m, C$\underline{H}$—N+ C$\underline{H}$—O), 6.14 (1H, ddd, C$\underline{H}$═), 6.55 (1H, ddd, C$\underline{H}$═). MS (ESI) m/z 212 [M+H]⁺.

64b)

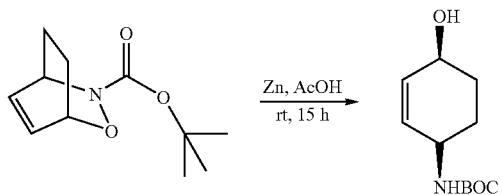

Zinc powder (45 g, mmol) was added portionwise within 30 minutes to a vigorously stirred solution of 64a (7.2 g, 34.5 mmol) in 10N AcOH (100 mL) at rt. The suspension was stirred at rt for 15 hours, then filtered over celite and washed with hot EtOH (3×100 mL). The filtrate was concentrated in vacuo to dryness by azeotropic distillation with toluene. The residue was suspended in hot EtOAc (40 mL), filtered and washed with hot EtOAc (40 mL). The filtrate was concentrated in vacuo to give a solid residue (4.47 g). Purification by flash chromatography (silica gel, PE/EtOAc 1/1 as eluant mixture) afforded the pure target compound as an oil (3.67 g, yield 50.0%).

¹H-NMR (300 MHz, DMSO-d₆): δ 1.35 (9H, s, C(C$\underline{H}_3$)₃), 1.6 (4H, m, C$\underline{H}_2$), 3.8 (1H, bs, C$\underline{H}$—OH), 3.95 (1H, m, CH—N$\underline{H}$), 4.75 (1H, d, O$\underline{H}$, 5.55 (1H, ddd, C$\underline{H}$═), 5.65 (1H, ddd, C$\underline{H}$═), 6.90 (1H, bd, N$\underline{H}$). MS (ESI) m/z 212 [M+H]⁺.

64c)

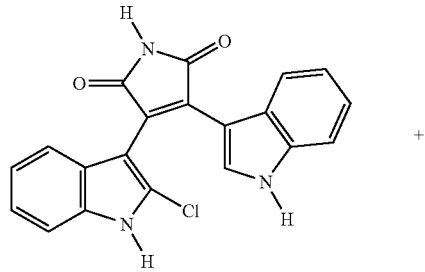

+

-continued

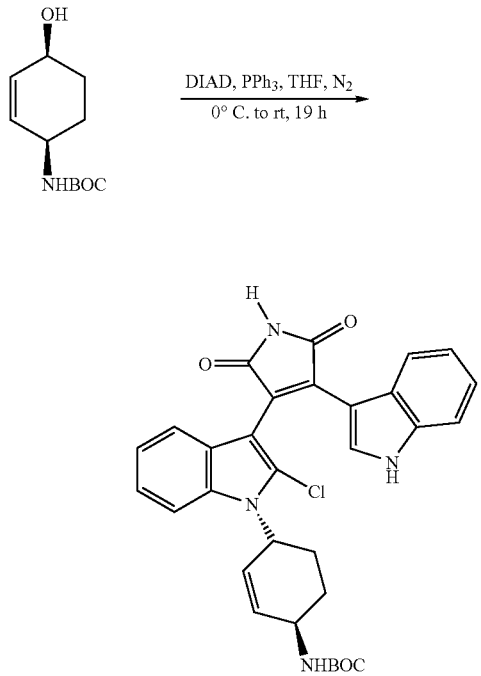

A solution of 64b (0.73 g, 3.4 mmol), 23c (0.82 g, 2.27 mmol) and triphenylphosphine (1.18 g, 4.5 mmol) in THF (20 mL) was cooled to 0° C. Diisopropyl azodicarboxylate (0.9 mL, 4.6 mmol) was added within 5 minutes, the reaction mixture was warmed to rt and stirred for 19 hours. The solvent was removed in vacuo and the residue purified by flash chromatography (silica gel, PE/EtOAc/NEt₃ 1/1/0.02 as eluant mixture) to give an orange foam (1.25 g). A second purification by flash chromatography (silica gel, DCM/EtOAc 10/1 as eluant mixture) gave the pure target compound (0.40 g, yield 32.0%).

¹H-NMR (300 MHz, DMSO-d₆): δ 1.35 (9H, s, tBu), 1.65 (2H, m, C$\underline{H}_2$), 2.25 (2H, m, C$\underline{H}_2$), 4.25 (1H, bs, N$\underline{H}$-Boc), 5.15 (1H, bs, C$\underline{H}$—N), 5.65–5.85 (2H, bm, C$\underline{H}$—N-Boc+ C$\underline{H}$═), 6.20 (1H, t, C$\underline{H}$═), 6.55 (1H, m, Harom), 7.15 (4H, m, Harom), 7.25 (2H, m, Harom), 7.60 (1H, m, Harom), 8.12 (1H, d, indole $\underline{H}$-2), 11.05 (1H, s, imide N$\underline{H}$), 11.85 (1H, s, indole N$\underline{H}$). MS (APCI) m/z 557 [M+H]⁺.

64d)

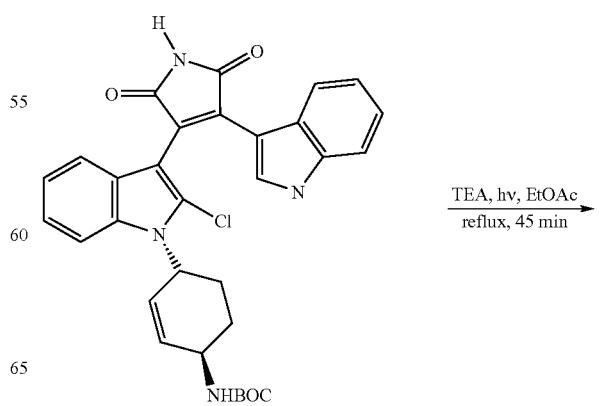

-continued

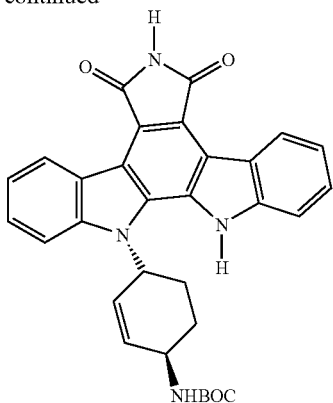

A solution of 64c (0.38 g, 0.68 mmol) and triethylaamine (1 mL) in EtOAc (250 mL) was irradiated with a halogen lamp. After 45 minutes the solution was cooled to rt, washed with water (2×100 mL), dried with sodium sulfate and concentrated in vacuo to give a solid residue (0.34 g). Trituration in hot MeOH (2 mL), filtration and washing with MeOH (1 mL) afforded after drying in vacuo the pure target compound (0.30 g, yield 85.0%).

$^1$H-NMR (300 MHz, DMSO-d$_6$): δ 1.46 (9H, s, tBu), 2.09 (2H, m, CH$_2$), 2.33 (2H, m, CH$_2$), 4.40 (1H, m, CH—N), 6.00 (2H, m, CH=CH), 6.13 (1H d, CH—NBoc), 7.37 (2H, t, Harom), 7.55 (2H, dt, Harom), 7.59 (1H, dt, Harom), 7.80 (1H, d, indole H-7), 7.84 (1H, d, indole H-7), 9.13 (1H, d, indole H-4), 9.22 (1H, d, indole H-4), 11.07 (1H, bs, imide NH), 12.19 (1H, bs, indole NH). MS (APCI) m/z 521 [M+H]$^+$.

62) NAD 336

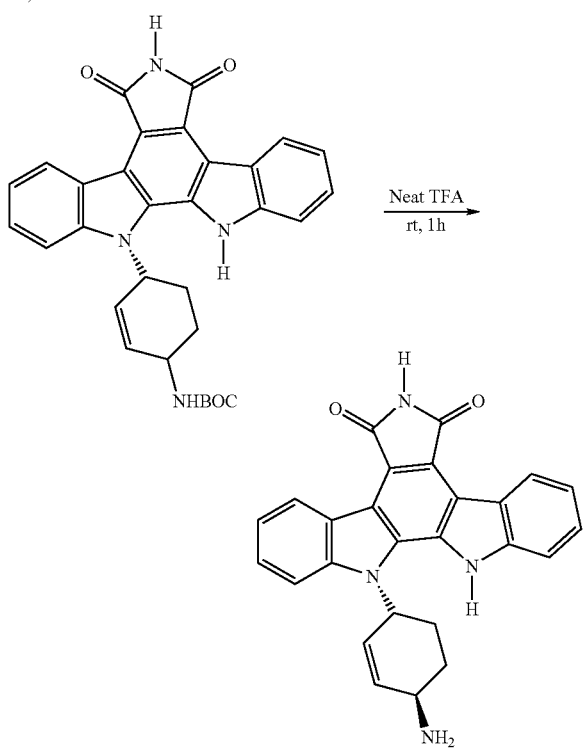

A solution of 64d (90 mg, 0.17 mmol) in TFA (1 mL) was stirred at rt for 1 hour. The reaction mixture was then diluted with EtOAc (40 mL), washed with 0.5N NaOH (40 mL) and water (40' mL). Drying over sodium sulfate, filtration and concentration in vacuo yielded the pure target compound (70 mg, yield 98.4%).

$^1$H-NMR (300 MHz, DMSO-d$_6$): δ 1.93 (1H, m, CH$_2$), 2.19 (2H, m, CH$_2$), 2.35 (1H, m, CH$_2$), 3.72 (1H, m, CH—NH$_2$), 5.97 (1H, d, CH=), 6.06 (1H, d, CH=), 6.13 (1H, d, CH—N), 7.36 (1H, t, Harom), 7.52 (2H, dt, Harom), 7.58 (1H, dt, Harom), 7.79 (1H, d, indole H-7), 7.84 (1H, d, indole NH, 9.13 (1H, d, indole H-4), 9.21 (1H, d, indole H-4), 12.10 (1H, bs, indole h. MS (APCI) m/z 421[M+H]$^+$.

Example 65

NAD 401

65a)

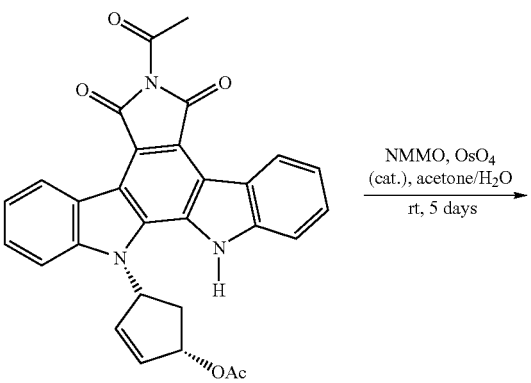

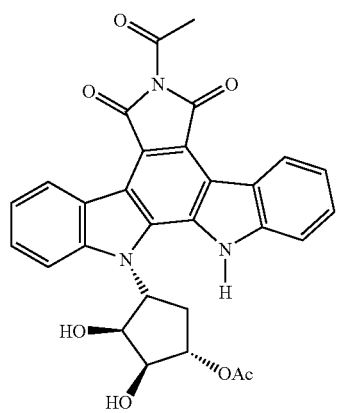

A suspension of 40a (2.0 g, 4.07 mmol) in a 11/4 mixture acetone/THF (140 mL) was treated sequentially with N-methylmorpholine N-oxide monohydrate (1.1 g, 8.15 mmol), osmium tetroxide (2.5% in tBuOH, 5.1 mL, 0.41 mmol) and water (20 mL). The suspension was vigorously stirred for 5 days at rt. The reaction mixture was poured onto sat. NaHSO$_3$ (500 mL) and extracted with EtOAc (2×500 mL). The combined organic layers were dried over sodium sulfate, filtered and concentrated in vacuo. Purification by flash chromatography (silica gel, DCM/THF 10/1 to 2/1 as eluant mixture) gave the pure target compound as a yellow powder (1.45 g, yield 68.0%).

¹H-NMR (300 MHz, DMSO-d$_6$): δ 1.35 (3H, s, C<u>H$_3$</u>—CON), 2.24 (3H, s, C<u>H$_3$</u>—COO), 2.25 (1H, m, C<u>H$_2$</u>), 3.10 (1H, m, C<u>H$_2$</u>), 4.07 (1H, bs, O<u>H</u>), 4.88 (1H, m, C<u>H</u>—OAc), 5.45 (2H, m, C<u>H</u>—OH), 5.80 (1H, bt, C<u>H</u>—N), 7.40 (2H, m, <u>H</u>arom), 7.60 (2H, m, <u>H</u>arom), 7.80 (1H, d, indole <u>H-7</u>), 7.85 (1H, d, indole <u>H-7</u>), 9.10 (1H, d, indole <u>H-4</u>), 9.28 (1H, d, indole <u>H-4</u>), 11.80 (1H, bs, indole N<u>H</u>). MS (APCI) m/z 525 [M+H]⁺.

65b)

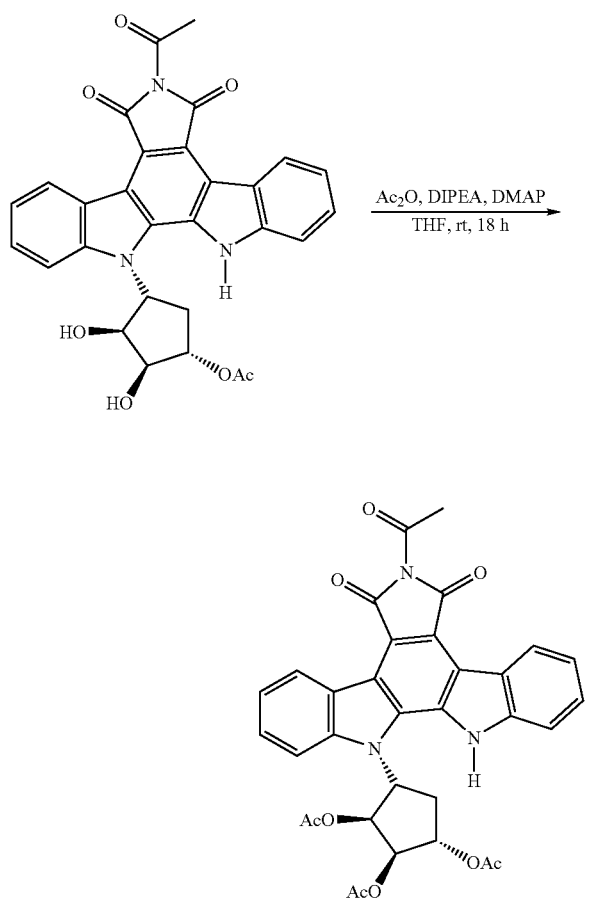

Ac$_2$O, DIPEA, DMAP
THF, rt, 18 h

A solution of 65a (960 mg, 1.99 mmol) in THF (20 mL) was treated sequentially with diisopropylethyl amine (2.03 mL, 11.9 mmol), acetic anhydride (1.13 mL, 1.9 mmol) and dimethylamino pyridine (242 mg, 1.99 mmol). The reaction mixture was stirred overnight at rt and the solvent was removed under reduced pressure. The crude residue was purified by flash chromatography (silica gel, DCM/THF 20/1 to 15/1 as eluant mixture) to afford the pure target compound as a yellow solid (960 mg, 80.0% yield).

¹H-NMR (300 MHz, DMSO-d$_6$): δ 1.35 (3H, s, C<u>H$_3$</u>—COO), 2.15 (3H, s, C<u>H$_3$</u>—COO), 2.24 (3H, s, C<u>H</u>—COO), 2.65 (3H, s, C<u>H</u>—CON), 2.75 (1H, m, C<u>H$_2$</u>), 3.10 (1H, m, C<u>H$_2$</u>), 5.71 (2H, m, C<u>H</u>—OAc), 6.05 (2H, m, C<u>H</u>—OAc+C<u>H</u>—N), 7.40 (2H, m, <u>H</u>arom), 7.65 (2H, m, <u>H</u>arom), 7.85 (1H, d, indole <u>H-7</u>), 8.05 (1H, d, indole <u>H-7</u>), 9.12 (1H, d, indole <u>H-4</u>), 9.23 (1H, d, indole <u>H-4</u>), 12.30 (1H, bs, indole N<u>H</u>). MS (APCI) m/z 610 [M+H]⁺.

65c)

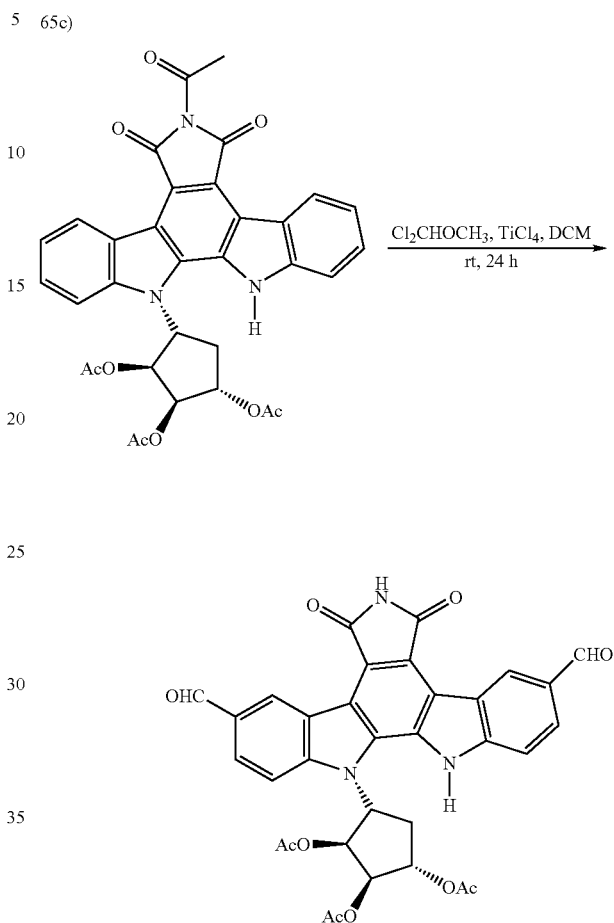

Cl$_2$CHOCH$_3$, TiCl$_4$, DCM
rt, 24 h

A solution of 65b (500 mg, 0.82 mmol) and 1,1-dichloromethyl methylether (3 mL, 32.8 mmol) was cooled to 0° C. Titanium tetrachloride (1M in DCM, 16.4 mL, 16.4 mmol) was added dropwise within 30 minutes, the reaction mixture was warmed to rt and stirred for 20 hours. The reaction mixture was then cooled to 0° C. and more 1,1-dichloromethyl-methylether (3 mL, 32.8 mmol) and titanium tetrachloride (1M in DCM, 16.4 mL, 16.4 mmol) were added. The reaction mixture was stirred for further 3, hours at rt and was poured onto saturated NaHCO$_3$ (500 mL). After 30 minutes the reaction mixture was extracted with EtOAc (3×500 mL). The combined organic layers were dried over sodium sulfate, filtered and concentrated in vacuo. Purification by flash chromatography (silica gel, DCM/THF 15/1 to 10/1 as eluant mixture) gave the pure target compound as a yellow powder (322 mg, yield 63.0%).

¹H-NMR (300 MHz, DMSO-d$_6$): δ 1.35 (3H, s, C<u>H$_3$</u>—COO), 2.15 (3H, s, C<u>H$_3$</u>—COO), 2.24 (3H, s, C<u>H$_3$</u>—COO), 2.75 (1H, m, C<u>H$_2$</u>), 3.10 (1H, m, C<u>H$_2$</u>), 5.70 (2H, m, C<u>H</u>—OAc), 5.95 (2H, m, C<u>H</u>—OAc+C<u>H</u>—N), 7.95 (1H, m, <u>H</u>arom), 8.15 (2H, m, <u>H</u>arom), 8.27 (1H, d, indole <u>H-7</u>), 9;56 (1H, d, indole <u>H-4</u>), 9.69 (1H, d, indole <u>H-4</u>), 10.19 (2H, d, C<u>HO</u>), 11.35 (1H, s, imide N<u>H</u>), 12.69 (1H, bs, indole NH). MS (APCI) m/z 624 [M+H]⁺.

65) NAD 401

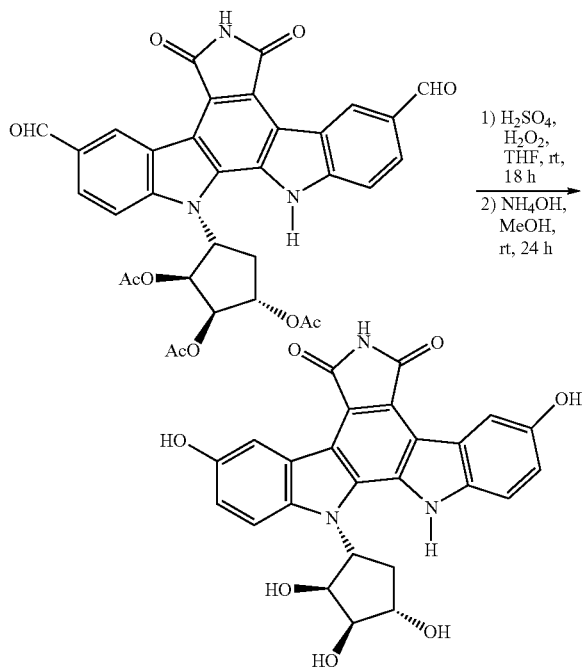

Hydrogen peroxyde (30% aqueous solution, 10 mL) and concentrated sulfuric acid were added to a solution of 65c (680 mg, 1.09 mmol) in THF (100 mL) at rt and the reaction mixture was stirred overnight. Water (100 mL) was added and the reaction mixture was extracted with EtOAc (2×500 mL). The organic layer was washed with water (300 mL), dried over sodium sulfate, filtered and concentrated in vacuo. The crude residue was dissolved in MeOH (40 mL), and 0.30% aqueous ammonia (10 mL) was added at rt. The resulting solution was stirred at rt for 24 hours and the solvent was eliminated in vacuo. The residue was taken up in EtOAc (500 mL), washed with water (2×500 mL) and brine (200 mL), then dried over sodium sulfate, filtered and concentrated in vacuo. Purification by flash chromatography (silica gel, DCM/EtOAc 2/1 to 1/1 as eluent mixture) gave the pure target compound as a brown solid (209 mg, yield 41.2%).

$^1$H-NMR (300 MHz, DMSO-d$_6$): δ 2.27 (1H, m, CH$_2$), 2.90 (1H, m, CH$_2$), 3.92 (2H, bs, OH), 4.17 (1H, d, OH), 4.89 (1H, m, CH—OH), 5.10 (2H, m, CH—OH), 5.49 (1H, q, CH—N), 7.04 (2H, m, Harom), 7.50 (1H, d, Harom), 7.98 (1H, bs, Harom), 8.51 (1H, d, Harom), 8.64 (1H, d, Harom), 9.23 (1H, bs, phenolic OF), 9.23 (1H, bs, phenolic OH), 10.91 (1H, bs, imide NH), 11.53 (1H, bs, indole NH). MS (ESI) m/z 472 [M−H]$^-$.

Example 66

NAD 370

66a)

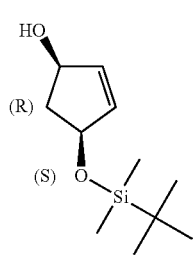

A solution of enantiopure 4R-(t-butyl-dimethyl-silanoxy)-cyclopent-1S-enol (3.8 g, 17.7 mmol, prepared according to *Tetrahedron*, 197, 1983–6) and triphenylphosphine (6.98 g, 26.6 mmol) in dry THF (60 mL) was cooled to 0° C. Acetic acid (1.21 mL, 21.2 mmol) and diisopropyl azodicarboxylate (5.3 mL, 27.5 mmol) were added within 20 minutes. The reaction mixture was warmed at rt and stirred for 3 hours. Purification by flash chromatography (silica gel, PE/EtOAc 10/1 as eluent mixture) after concentration in vacuo afforded a light yellow oil (1.67 g). The oil was dissolved in MeOH (16 mL) and K$_2$CO$_3$ (0.97 g, 7 mmol) in H$_2$O (4 mL) was added at rt. The resulting suspension was stirred for 90 minutes, then the reaction mixture was diluted with Et$_2$O (100 mL) and washed with water (2×75 mL). The organic layer was dried over sodium sulfate, filtered and concentrated in vacuo. Purification by flash chromatography (silica gel, PE/EtOAc 6/1 as eluant mixture) gave the pure target compound as a colorless oil (1.16 g, yield 31.0%).

$^1$H-NMR (300 MHz, CDCl$_3$): δ 0.03 (6H, s, Si(CH$_3$)$_2$), 0.81 (9H, s, tBu), 1.50 (1H, bs, OH), 1.97 (2H, m, CH$_2$), 4.93 (1H, m, CH—OH), 5.02 (1H, m, CH—OSi), 5.85 (2H, dq, CH=CH). MS (ESI) m/z 215 [M+H]$^+$. ee≧98%.

66b)

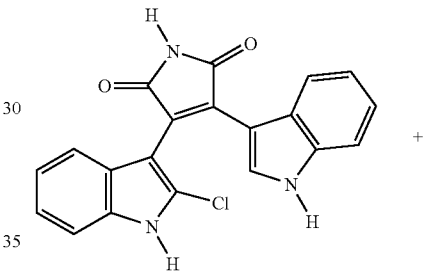

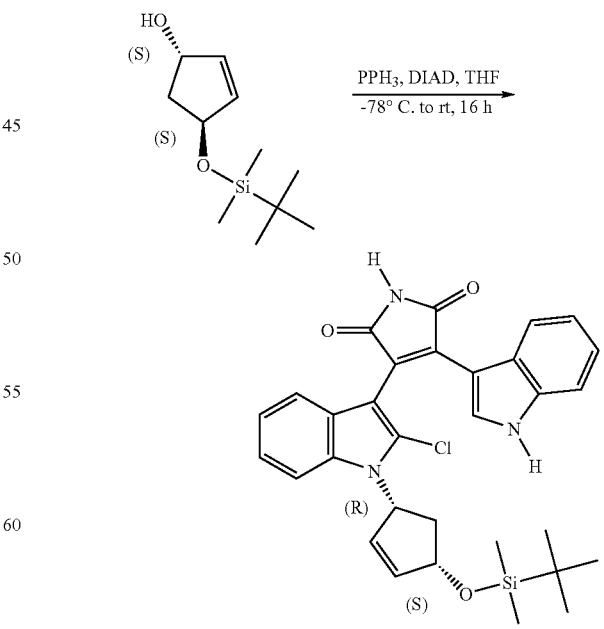

A solution of 66a (1.09 g, 5.08 mmol), 23c (1.41 g, 3.91 mmol) and triphenylphosphine (1.84 g, 7 mmol) in THF (15 mL) was cooled to 0° C. Diisopropyl azodicarboxylate (1.36 mL, 7 mmol) was added within 10 minutes, the reaction mixture was warmed to rt and stirred for 16 h. The solvent was removed in vacuo and the residue purified by flash chromatography (silica gel, PE/EtOAc/NEt₃ 1/1/0.02 as eluant mixture) to give an orange foam (2.8 g). A second purification by flash chromatography (silica gel, DCM/EtOAc 10/1 as eluant mixture) gave the pure target compound (0.67 g, yield 31.0%).

¹H-NMR (300 MHz, DMSO-d₆): δ 0.10 (6H, s, CH₃—Si), 0.90 (9H, tBu), 1.90 (1H, m, CH₂), 2.80 (1H, m, CH₂), 4.95 and 5.45 (1H, bt, CH—N), 5.80 and 6.05 (1H, bt, CH—O), 6.10 (2H, dm, CH=CH), 6.45 and 6.55 (1H, bt, Harom), 7.10 (3H, m, Harom), 7.38 (3H, m, Harom), 7.75 (1H, dd, Harom), 8.15 (1H, bt, indole H-2) 11.05 (1H, s, imide NH), 11.88 (1H, bs, indole NH). MS (ESI) m/z 558 [M+H]⁺.

66c)

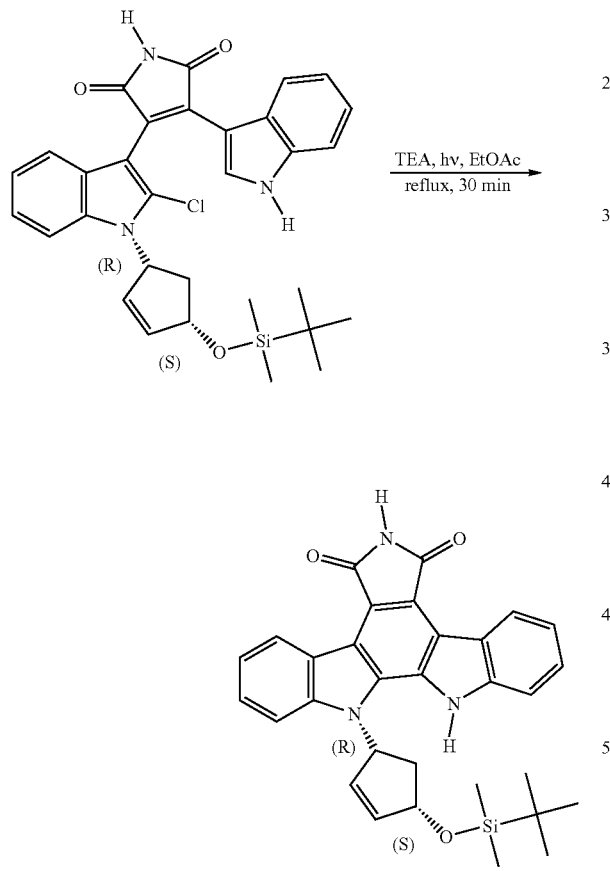

TEA, hv, EtOAc
reflux, 30 min

A solution of 60b (0.38 g, 1.16 mmol) and triethylamine (10 mL) in EtOAc (150 mL) was irradiated with a halogen lamp. After 30 minutes the solution was cooled to rt, washed with water (2×100 mL), dried with sodium sulfate and concentrated in vacuo to give a solid residue (0.61 g). Trituration in hot MeOH (1.5 mL), filtration and washing with MeOH (1 mL) afforded after drying in vacuo an orange solid (0.62 g). Recrystallization in acetone (2 mL) gave the enantiopure compound (0.36 g, yield 52.8%).

¹H-NMR (300 MHz, DMSO-d₆): δ 0.13 (3H, s, CH₃—Si), 0.20 (3H, s, CH₃Si), 0.93 (9H, tBu), 2.18 (1H, dt, CH₂), 3.28 (1H, m, CH₂), 5.12 (1H, bt, CH—O), 6.28 (2H, q, CH=CH), 6.42 (1H, bt, CH—N), 7.34 (2H, t, Harom), 7.45 (1H, dt, Harom), 7.58 (1H, dt, Harom), 7.77 (1H, d, indole H-7), 8.03 (1H, d, indole H-7), 9.12 (1H, d, indole H-4), 9.21 (1H, d, indole H-4), 11.07 (1H, bs, imide NH, 12.06 (1H, bs, indole NH). MS (ESI) m/z 522 [M+H]⁺.

66d)

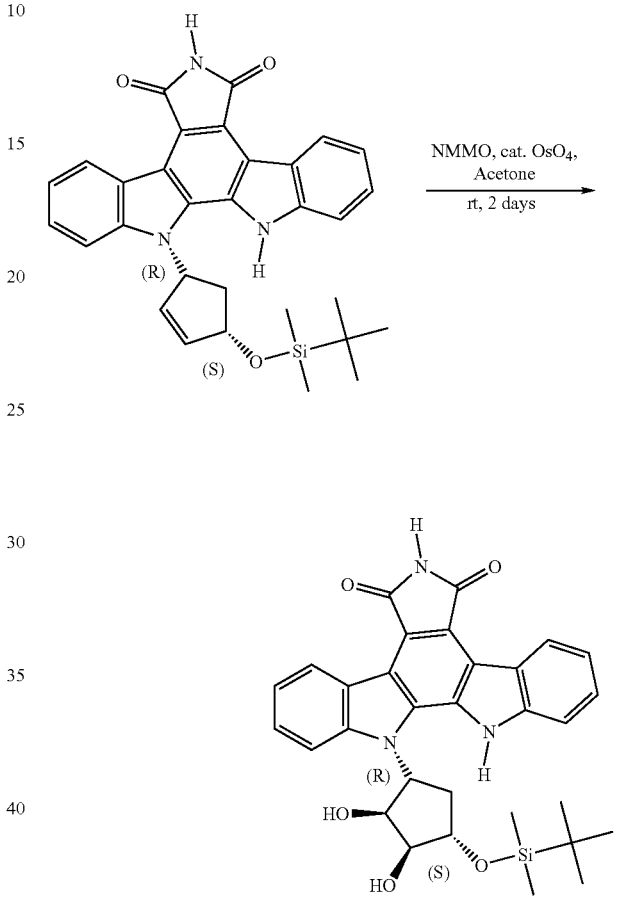

NMMO, cat. OsO₄,
Acetone
rt, 2 days

A solution of 66c (260 mg, 0.5 mmol) in acetone (5 mL) was treated sequentially with N-methylmorpholine N-oxide monohydrate (120 mg, 1 mmol) and osmium tetroxide (2.5% in tBuOH, 0.5 mL, catalytic). The solution was stirred for 48 hours at rt. EtOAc (70 mL) was added and the reaction mixture was washed with 10% o NaHSO₃ (30 mL), then with 1N HCl (30 mL). The organic layer was dried over sodium sulfate, filtered and concentrated to about 5 mL. Filtration over a short pad of silica gel using EtOAc as eluant gave, after concentration in vacuo, a solid residue (0.23 g).

Trituration in hot MeOH (1 mL), filtration and drying in vacuo gave the pure target compound as an orange powder (190 mg, yield 68.0%).

¹H-NMR (300 MHz, DMSO-d₆): δ 0.22 (6H, s, (CH₃)₂—Si), 1.02 (9H, tBu), 2.45 (1H, m, CH₂), 3.06 (1H, m, CH₂), 3.87 (1H, m, CH—OH), 4.30 (1H, m, CH—OH), 5.00 (1H, m, CH—OSi), 5.25 (1H, d, OH), 5.35 (2H, d, OH), 5.65 (1H, q, CH—N), 7.40 (3H, m, Harom), 7.59 (1H, dt, Harom), 7.81 (1H, d, indole H-7), 8.41 (1H, d, indole H-7), 9.12 (1H, d, indole H-4), 9.25 (1H, dd, indole H-4), 11.07 (1H, bs, imide NH), 11.64 (1H, bs, indole NH). MS (APCI) m/z 556 [M+H]⁺.

66) NAD 370

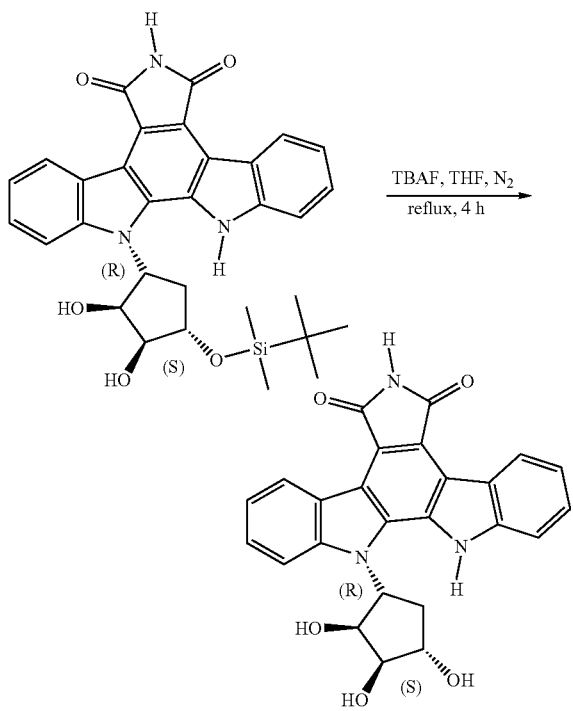

Tetrabutylammonium fluoride (1M in THF, 0.6 mL, 0.6 mmol) was added dropwise to a stirred solution of 66d (0.14 g, 0.25 mmol) in dry THF (15 mL) under nitrogen atmosphere. The reaction mixture was stirred at reflux for 4 hours. After cooling AcOH (20 drops) and EtOAc (100 mL) were added. The solution was washed with sat. NaHCO$_3$ (50 mL) and water (50 mL). The organic layer was dried over sodium sulfate, filtered and concentrated in vacuo. The residue was triturated in hot MeOH (2×1 mL), filtered and dried in vacuo to yield the pure target compound as an orange solid (0.06 g, yield 54.0%).

$^1$H-NMR (300 MHz, DMSO-d$_6$): δ 2.34 (1H, m, CH$_2$), 3.01 (1H, m, CH$_2$), 3.94 (1H, m, CH—OH), 4.24 (1H, m, CH—OH), 4.98 (1H, m, CH—OH), 5.12 (1H, d, OH), 5.21 (2H, m, OH), 5.62 (1H, m, CH—N), 7.38 (2H, q, Harom), 7.58 (2H, t, Harom), 7.73 (1H, d, indole H-7), 8.21 (1H, d, indole H-7), 9.13 (1H, d, indole H-4), 9.25 (1H, dd, indole H-4), 11.08 (1H, bs, imide NH). MS (ESI) m/z 442 [M+H]$^+$.

Example 67

67)

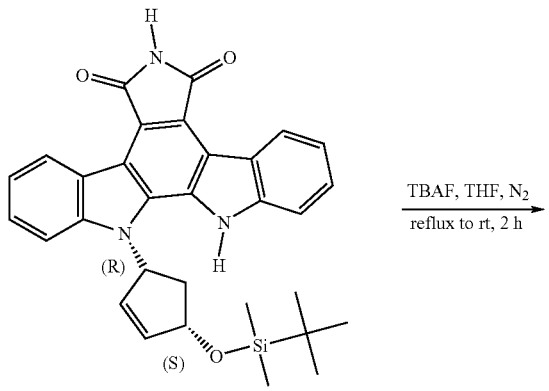

Example 68

NAD 368

68a)

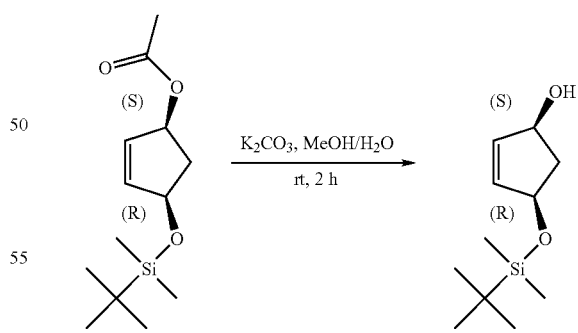

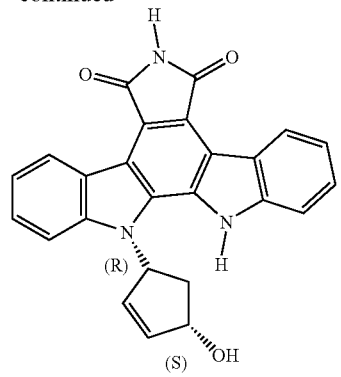

Tetrabutylammonium fluoride (1M in THF, 0.6 mL, 0.6 mmol) was added dropwise to a stirred solution of 66c (0.14 g, 0.27 mmol) in dry THF (3 mL) under nitrogen atmosphere at rt. The reaction mixture was heated to reflux for 10 minutes and stirred at rt for 2 hours. The solution was diluted with EtOAc (40 mL), washed with NaHCO$_3$ (400 mL) and water (50 mL). The organic layer was dried over sodium sulfate, filtered and concentrated in vacuo to yield a crude orange solid (0.14 g). Trituration in hot MeOH (2×1 mL), filtration and drying in vacuo afforded the pure target compound (90 mg, yield 81.9%).

$^1$H-NMR (300 MHz, DMSO-d$_6$): δ 2.15 (1H, dt, CH$_2$), 3.18 (1H, dt, CH$_2$), 4.97 (1H, bq, CH—OH), 5.56 (1H, s, OH), 6.28 (2H, s, CH=CH), 6.41 (1H, bt, CH—N), 7.37 (2H, dt, Harom), 7.50 (1H, dt, Harom), 7.58 (1H, dt, Harom), 7.77 (1H, d, indole H-7), 8.02 (1H, d, indole H-7), 9.12 (1H, d, indole H-4), 9.21 (1H, d, indole H-4), 11.06 (1H, bs, imide NH), 12.04 (1H, bs, indole NH). MS (ESI) m/z 408 [M+H]$^+$.

Potassium carbonate (2.76 g, 20 mmol) in water (10 mL) was added to a solution of acetic acid 4R-(tert-butyl-dimethyl-silanoxy)-cyclopent-2S-enyl ester (4.62 g, 18 mmol, prepared according to *Tetrahedron*, 1997, 1983) in MeOH (40 mL) at rt. The reaction mixture was stirred for 2 hours, was, diluted with H$_2$O (100 mL) and extracted with Et$_2$O (2×75 mL). The combined organic layers were dried over sodium sulfate, filtered and concentrated in vacuo. Purification by flash chromatography (silica gel, PE/EtOAc 4/1 as eluant mixture) gave the pure target compound as a colorless oil (3.51 g, yield 91.0%).

¹H-NMR (300 MHz, CDCl₃): δ 0.03 (6H, s, Si(C$\underline{H_3}$)₂), 0.81 (9H, s, t$\underline{Bu}$), 1.60 (1H, m, CHC$\underline{H_2}$), 1.80 (1H, bs, O$\underline{H}$), 2.65 (1H, m, C$\underline{H_2}$), 4.55 (1H, bt, C$\underline{H}$—OH), 4.65 (1H, bt, C$\underline{H}$—OSi), 5.85 (2H, dq, C$\underline{H}$=C$\underline{H}$). MS (ESI) m/z 215 [M+H]⁺. ee≧98%.

68b)

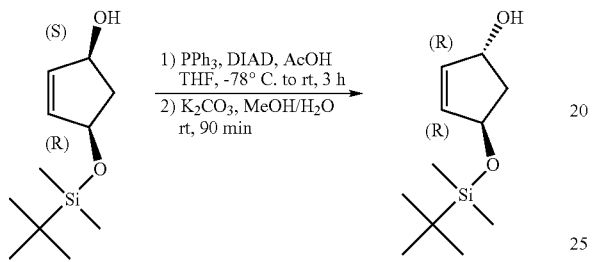

A solution of 68a (3.45 g, 16.1 mmol) and triphenylphosphine (6.3 g, 24.0 mmol) in dry THF (50 mL) was cooled to −78° C. Acetic acid (1.16 g, 19.3 mmol) and diisopropyl azodicarboxylate (4.8 mL, 24.5 mmol) were added within 20 minutes. The reaction mixture was warmed to rt and was stirred for 3 hours. Purification by flash chromatography (silica gel, PE/EtOAc 15/1 as eluant mixture) after concentration in vacuo afforded a light yellow oil (2.62 g). The oil was dissolved in MeOH (25 mL) and potassium carbonate (1.52 g, 11 mmol) in H₂O (5 mL) was added at rt. The resulting suspension was stirred for 90 minutes, then the reaction mixture was diluted with Et₂O (150 mL) and washed with water (2×100 mL). The organic layer was dried over sodium sulfate, filtered and concentrated in vacuo. Purification by flash chromatography (silica gel, PE/EtOAc 6/1 as eluant mixture) gave the pure target compound as a colorless oil (1.81 g, yield 52.0%).

¹H-NMR (300 MHz, CDCl₃): δ 0.03 (6H, s, Si(C$\underline{H_3}$)₂, 0.81 (9H, s, t$\underline{Bu}$), 1.55 (1H, d, O$\underline{H}$), 2.05 (2H, m, C$\underline{H_2}$, 4.95 (1H, m, C$\underline{H}$—OH), 5.02 (1H, m, C$\underline{H}$—OSi), 5.90 (2H, dq, C$\underline{H}$=C$\underline{H}$). MS (ESI) m/z 215 [M+H]⁺. ee≧98%.

68c)

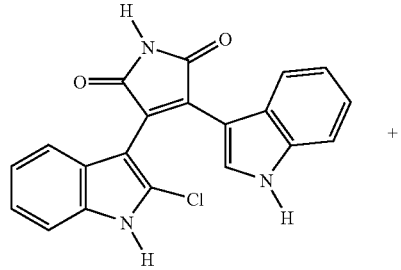

+

-continued

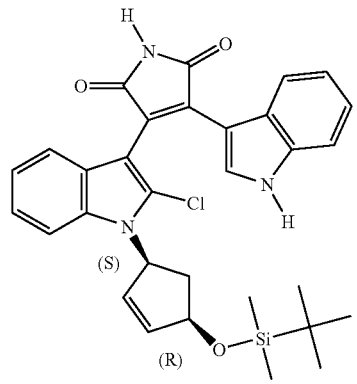

68c was prepared as seen for 66b starting from 68b (1.75 g, 8.16 mmol), 23c (2.27 g, 6.28 mmol), triphenylphosphine (2.62 g, 10 mmol), diisopropyl azodicarboxylate (1.95 mL, 10 mmol) and THF (30 mL) to give the pure title compound (1.05 g, yield 30.0%).

¹H-NMR (300 MHz, DMSO-d₆): δ 0.10 (6H, s, C$\underline{H_3}$—Si), 0.90 (9H, s, t$\underline{Bu}$), 1.80–1.90 (1H, m, C$\underline{H_2}$, 2.75–2.90 (1H, m, C$\underline{H_2}$), 4.95–5.45 (1H, bt, C$\underline{H}$—N), 5.80–6.05 (1H, bt, C$\underline{H}$—O), 6.10 (2H, dm, C$\underline{H}$=C$\underline{H}$), 6.45–6.55 (1H, bt, $\underline{H}$arom), 7.10 (3H, m, $\underline{H}$arom), 7.38 (3H, m, $\underline{H}$arom), 7.75 (1H, dd, $\underline{H}$arom), 8.15 (1H, s, indole $\underline{H}$-2)) 11.05 (1H, s, imide N$\underline{H}$, 11.85 (1H, bs, indole N$\underline{H}$). MS (ESI) m/z 558 [M+H]⁺.

68d)

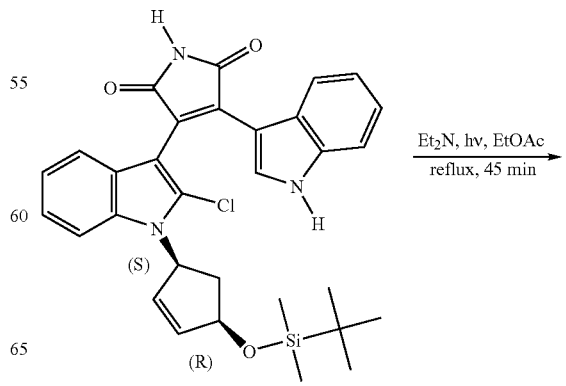

-continued

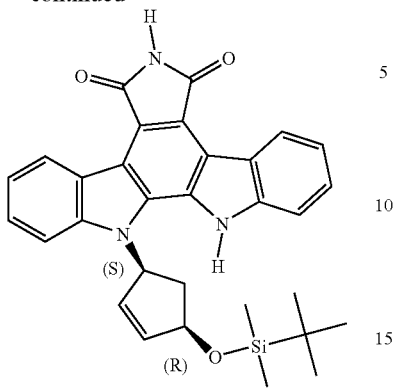

68d was prepared as seen for 66c starting from 68c (1.03 g, 1.85 mmol), triethylamine (10 mL) and EtOAc (150 mL) to give the enantiopure target compound (0.59 g, yield 60.8%).

$^1$H-NMR (300 MHz, DMSO-d$_6$): δ 0.12 (3H, s, CH$_3$—Si), 0.20 (3H, s, CH$_3$—Si), 0.93 (9H, s, u), 2.17 (1H, dt, CH$_2$), 3.26 (1H, m, CH$_2$), 5.12 (1H, bt, CH—O), 6.28 (2H, q, CH=CH), 6.42 (1H, bt, CH—N), 7.36 (2H, t, Harom), 7.45 (1H, dt, Harom), 7.58 (1H, t, Harom), 7.76 (1H, d, indole H-7), 8.03 (1H, d, indole H-7), 9.12 (1H, d, indole H-4), 9.21 (1H, d, indole H-4), 11.07 (1H, bs, imide NH), 12.05 (1H, bs, indole NH). MS (ESI) m/z 522 [M+H]$^+$.

68) NAD 368

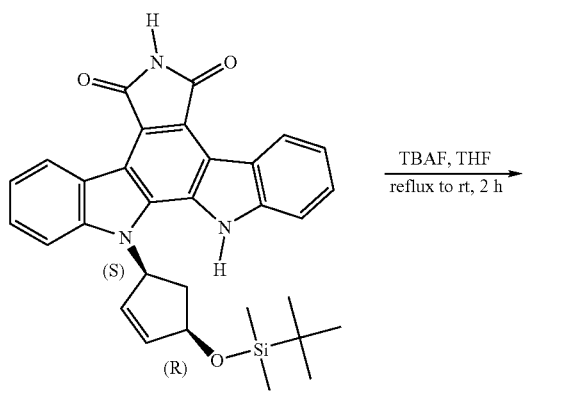

TBAF, THF
reflux to rt, 2 h

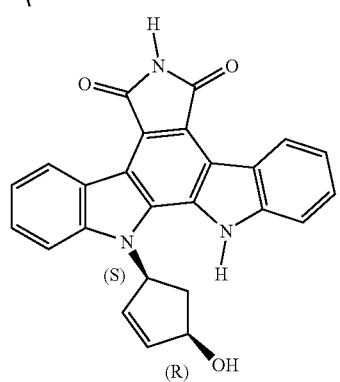

68 was prepared as compound 67 starting from tetrabutylammonium fluoride (1M in THF, 0.6 mL, 0.6 mmol), 68d (0.15 g, 0.29 mmol) and dry THF (2 mL) to afford the pure target compound (110 mg, yield 93.1%).

$^1$H-NMR (300 MHz, DMSO-d$_6$): δ 2.15 (1H, m, CH), 3.19 (1H, m, CH$_2$), 4.97 (1H, m, CH—OH), 5.55 (1H, s, H, 6.28 (2H, s, CH=CH), 6.39 (1H, bt, CH—N), 7.37 (2H, dt, Harom), 7.51 (1H, dt-Harom), 7.58 (1H, dt, Harom), 7.77 (1H, d, indole H-7), 8.02 (1H, d, indole H-7), 9.12 (1H, d, indole H-4), 9.21 (1H, d, indole H-4), 11.06 (1H, bs, imide NH), 12.04 (1H, bs, indole NH). MS (ESI) m/z 408 [M+H]$^+$.

Example 69

NAD 319

69a)

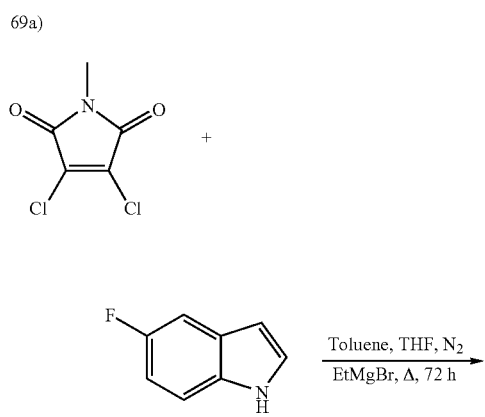

Ethylmagnesium bromide (3M in Et$_2$O, 62 mL, 185 mmol) was added dropwise to a solution of 5-fluoroindole (25 g, 185 mmol) in dry toluene (200 mL) under nitrogen atmosphere at rt. The solution was warmed to 40° C. and stirred at this temperature for 1 hour. A solution of 12a (15.2 g, 84 mmol) in dry THF (30 mL) was then added and the reaction mixture was refluxed for 72 hours. After cooling to rt the reaction mixture was poured onto sat. NH$_4$Cl (800 mL) and extracted with EtOAc (3×1 L). The combined organic layers were washed with water (750 mL), dried over magnesium sulfate, filtered and concentrated in vacuo to give a crude orange solid. Purification by flash chromatography (silica gel, PE/EtOAc 6/1 to 1/1 as eluant mixture) gave the pure target compound as an orange powder (20.1 g, yield 63.0%).

$^1$H-NMR (300 MHz, DMSO-d$_6$): δ 3.04 (3H, s, N—CH$_3$), 6.40 (2H, dd, Harom), 6.86 (2H, dt, indole H-6), 7.40 (2H, dd, Harom), 7.86 (2H, s, indole H-2), 11.64 (2H, s, indole NH). MS (APCI) m/z 378 [M+H]$^+$.

69b)

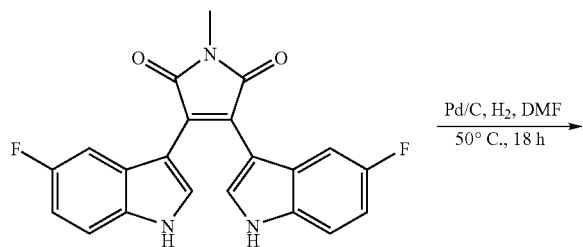

Pd/C, H₂, DMF
―――――――→
50° C., 18 h

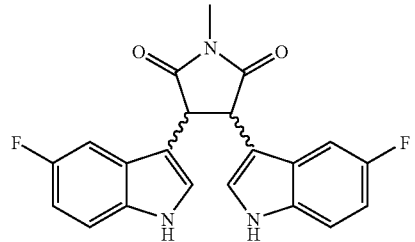

A solution of 69a (4.1 g, 10.9 mmol) in dry DMF (30 mL) was added to 10% Pd/C (173 mg, 1.63 mmol). Nitrogen was exchanged against hydrogen and the reaction mixture was stirred at 50° C. overnight. After cooling to rt the reaction mixture was filtered over a short pad of celite which was then rinsed with EtOAc (500 mL). The organic layer was washed with water (4×1 L), dried over magnesium sulfate, filtered and concentrated in vacuo to give the pure target compound as an orange solid (4.4 g, quantitative yield).

$^1$H-NMR (300 MHz, DMSO-$d_6$): δ 3.11 (3H, s, N—CH₃, 4.90 (2H, s, CH—CH), 6.75 (2H, dt, Harom), 7.10 (4H, m. Harom), 7.20 (2H, dd, Harom), 10.80 (2H, s, indole NH). MS (APCI) m/z 380 [M+H]⁺.

69c)

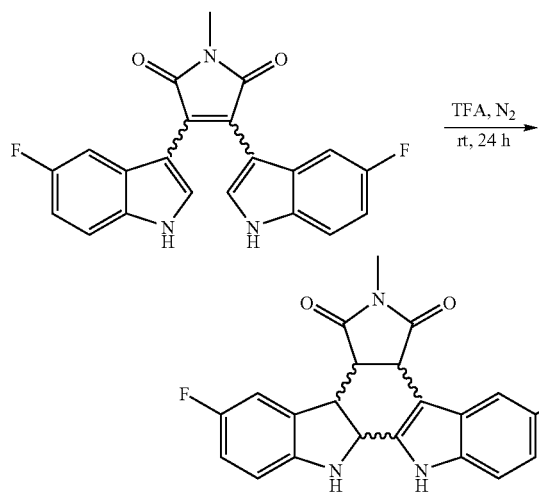

TFA, N₂
―――――→
rt, 24 h

A solution of 69b (1.29 g, 3.4 mmol) in trifluoroacetic acid (30 mL) was stirred at rt for 24 hours under nitrogen atmosphere. TFA was concentrated in vacuo and the residue was diluted with toluene (300 mL). The white colorless precipitate was filtered, taken up in EtOAc (500 mL) and washed with sat. NaHCO₃ (200 mL). The organic layer was dried over magnesium sulfate, filtered, and concentrated in vacuo to give the pure target compound as a light brown powder (1.3 g, quantitative yield).

$^1$H-NMR (300 MHz, DMSO-$d_6$): δ 2.81 (3H, s, N—CH₃), 4.17 (2H, m, indoline H-2), 4.29 (1H, dd, indoline H-3), 4.75 (1H, dd, indoline NH—CH—CH—CH), 4.75 (1H, d, indole NH—CH=CH—CH), 5.85 (1H, s, indoline NH, 6.50 (1H, dd, Harom), 6.72 (1H, dt, Harom), 6.92 (1H, dt, Harom), 7.20 (2H, m, Harom), 7.32 (1H, dd, Harom), 7.45 (1H, dd, Harom), 11.10 (1H, s, indole NH). MS (ESI) m/z 380 [M+H]⁺.

69d)

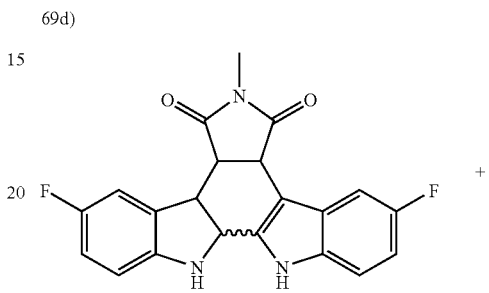

+

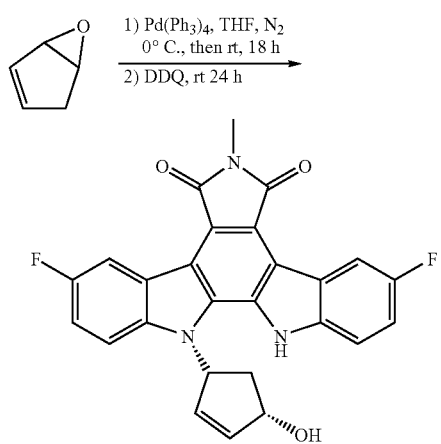

1) Pd(Ph₃)₄, THF, N₂
0° C., then rt, 18 h
―――――――――→
2) DDQ, rt 24 h 1a (3.4 g, 41 mmol) was added to a solution of 69c (3.1 g, 8.18 mmol) and palladium tetrakis (346 mg, 0.82 mmol) in dry THF (50 mL) at 0° C. under nitrogen atmosphere. The reaction mixture was warmed to rt and stirred for t 8 hours. The solvent was concentrated to about 5 mL and was filtered over a short pad of silica gel using EtOAc as eluant mixture. The solvent was eliminated in vacuo, the crude residue (1.4 g) was dissolved in THF and a solution of DDQ (1.4 g, 6.07 mmol) in THF (10 mL) was added at rt. The reaction mixture was stirred for 24 hours and the solvent was removed in vacuo. The residue was taken up in EtOAc (50 mL), washed with sat. NaHCO₃ (25 mL), dried over sodium sulfate, filtered and concentrated in vacuo. Purification by flash chromatography (silica gel, PE/EtOAc 2/1 to 1/1 as eluant mixture) gave the pure target compound as an orange solid (261 mg, yield 19.0%).

$^1$H-NMR (300 MHz, DMSO-$d_6$): δ 2.10 (1H, dt, CH₂), 3.05 (3H, s, NCH₃) 3.18 (1H, dt, CH₂), 4.97 (1H, bq, CH—OH), 5.58 (1H; s, OH), 6.28 (2H, m, CH=CH), 6.41 (1H, bt, CH—N), 7.37 (1H, dt, Harom), 7.50 (1H, dt, Harom), 7.55 (1H, dt, Harom), 8.00 (1H, dd, indole H-7), 8.71 (1H, dd, indole H-4), 8.85 (1H, dd, indole H-4), 12.04 (1H, bs, indole NH). MS (ESI) m/z 458 [M+H]⁺.

69e)

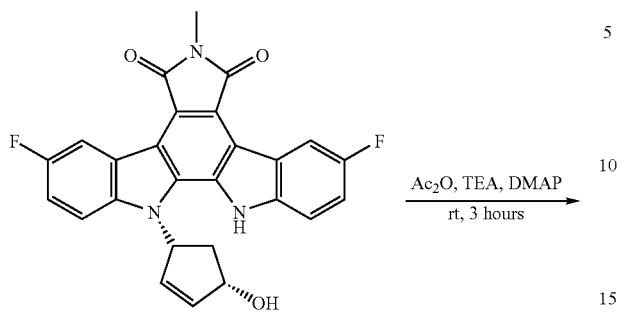

Ac₂O, TEA, DMAP
rt, 3 hours
→

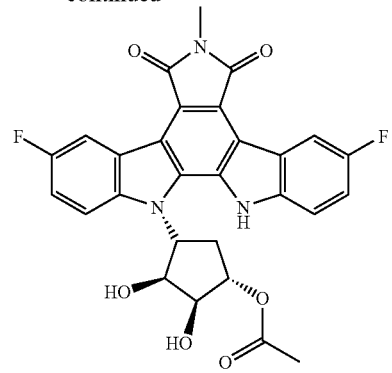

NMMO, cat. OsO₄
acetone/water
rt, 18 h
→

-continued

A solution of 69e (280 mg, 0.56 mmol) in acetone (30 mL) was treated with N-methylmorpholine N-oxide (152 mg, 1.12 mmol), osmium tetroxide (2.5% in tBuOH, 0.7 mL, catalytic) and water (1 mL). The solution was stirred for 18 hours at rt. The reaction mixture was diluted with AcOt (800 mL), washed with 10% NaHSO₃ (500 mL), then 1N HCl (100 mL). The organic layer was dried over sodium sulfate, filtered and concentrated to give a crude. Purification by flash chromatography (silica gel, DCM/THF 4/1 to 1/1 as eluant mixture) afforded the pure target compound as a yellow solid (245 mg, yield 81.7%).

$^1$H-NMR (300 MHz, DMSO-d₆): δ 2.35 (1H, m, C$\underline{H}_2$), 2.25 (3H, s, OCOC$\underline{H}_3$), 3.20 (3H, s, NC, 3.25 (1H, m, C$\underline{H}_2$) 4.10 (1H, m, C$\underline{H}$—OH), 4.82 (1H, m, C$\underline{H}$—OH), 5.19 (1H, s, CH—OAc), 5.32 (1H, d, O$\underline{H}$), 5.44 (1H, d, O$\underline{H}$), 5.60 (1H, bt, C$\underline{H}$—N), 7.45 (2H, dt, $\underline{H}$arom), 7.82 (1H, dd, $\underline{H}$arom), 7.98 (1H, dd, $\underline{H}$arom), 8.79 (1H, dd, indole $\underline{H}$-4), 8.95 (1H, dd, indole $\underline{H}$-4), 11.90 (1H, bs, indole N$\underline{H}$). MS (APCI) m/z 534 [M+H]⁺.

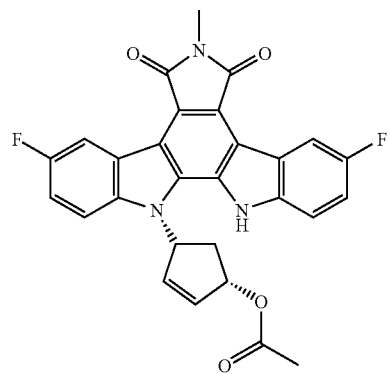

Triethylamine (0.11 mL, 0.87 mmol) and acetic anhydride (88 mg, 0:87 mmol) were added to a solution of 69d (330 mg, 0.72 mmol) and dimethylamino pyridine (9 mg, 0.07 mmol) in acetonitrile (25 mL) at rt. The reaction mixture was stirred for 3 hours and the solvent was removed in vacuo to yield a crude. Purification by flash chromatography (silica gel, DCM/THF 5/1 as eluant mixture) afforded the pure target compound as a yellow solid (310 mg, yield 86.2%).

$^1$H-NMR (300 MHz, DMSO-d₆): δ 2.10 (1H, dt, C$\underline{H}_2$), 2.18 (3H, s, OCOC$\underline{H}_3$), 2.96 (3H, s, NC$\underline{H}_3$, 3.30 (1H, dt, C$\underline{H}_2$), 5.85 (1H, s, C$\underline{H}$—OAc), 6.37 (2H, m, C$\underline{H}$═C$\underline{H}$), 6.56 (1H, bt, C$\underline{H}$—N), 7.39 (2H, dt, $\underline{H}$arom), 7.70 (2H, m, $\underline{H}$arom), 8.61 (1H, dd, indole $\underline{H}$-4), 8.75 (1H, dd, indole $\underline{H}$-4), 12.04 (1H, bs, indole N$\underline{H}$). MS (APCI) m/z 500 [M+H]⁺.

69f)

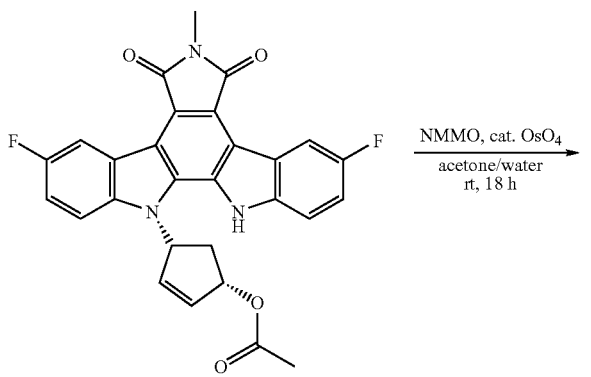

69g)

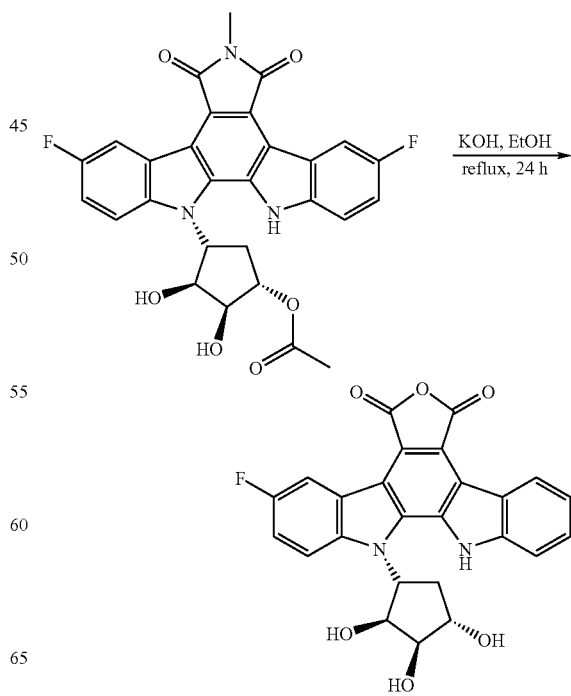

KOH, EtOH
reflux, 24 h
→

A solution of potassium hydroxide (630 mg, 11.3 mmol) and 69f (200 mg, 0.38 mmol) in EtOH (30 mL) was stirred at reflux for 24 hours. The reaction mixture was cooled to rt, poured onto 20% aqueous citric acid (500 mL) and extracted with EtOAc (2×300 mL). The organic layers were washed with water (2×500 mL), dried over sodium sulfate, filtered and concentrated in vacuo to give a crude residue (192 mg) which was directly used in the next step.

$^{1}$H-NMR (300 MHz, DMSO-d$_6$): δ 2.35 (1H, m, C<u>H</u>$_2$), 3.15 (1H, m, C<u>H</u>$_2$), 3.95 (1H, m, C<u>H</u>—OH), 4.20 (1H, d, O<u>H</u>), 4.85 (2H, m, O<u>H</u>), 5.15 (2H, m, C<u>H</u>—OH), 5.60 (1H, bt, C<u>H</u>—N), 7.45 (2H, dt, <u>H</u>arom), 7.75 (1H, m, <u>H</u>arom), 8.25 (1H, m, <u>H</u>arom), 8.50 (1H, dd, indole <u>H</u>-4), 8.65 (1H, dd, indole <u>H</u>-4), 11.90 (1H, bs, indole N<u>H</u>). MS (APCI) m/z 479 [M+H]$^+$.

69) NAD 319

A mixture of 69f (179 mg, 0.37 mmol) and ammonium acetate (5 g, large excess) was heated to 120° C. for 3 hours. The reaction mixture was cooled to rt, dissolved in water (400 mL) and extracted with EtOAc (2×500 mL). The combined organic layers were dried over sodium sulfate, filtered and concentrated in vacuo. Purification by preparative TLC (silica gel, DCM/THF 1/1 as eluant mixture) gave the pure target compound as a brown yellow solid (136 mg, yield 76.4%).

$^{1}$H-NMR (300 MHz, DMSO-d$_6$): δ 2.30 (1H, m, C<u>H</u>$_2$), 3.08 (1H, m, C<u>H</u>$_2$), 3.96 (2H, bs, O<u>H</u>), 4.22 (1H, d, O<u>H</u>), 4.95 (1H, m, C<u>H</u>$_2$), 5.15 (2H, m, C<u>H</u>—OH), 5.60 (1H, bt, C<u>H</u>—N), 7.48 (2H, m, <u>H</u>arom), 7.71 (1H, m, <u>H</u>arom), 8.29 (1H, m, <u>H</u>arom), 8.80 (1H, dd, indole <u>H</u>-4), 8.95 (1H, dd, indole <u>H</u>-4), 11.05 (1H, s, imide N<u>H</u>), 11.95 (1H, bs, indole N<u>H</u>. MS (APCI) m/z 478 [M+H]$^+$.

Example 70

NAD 439

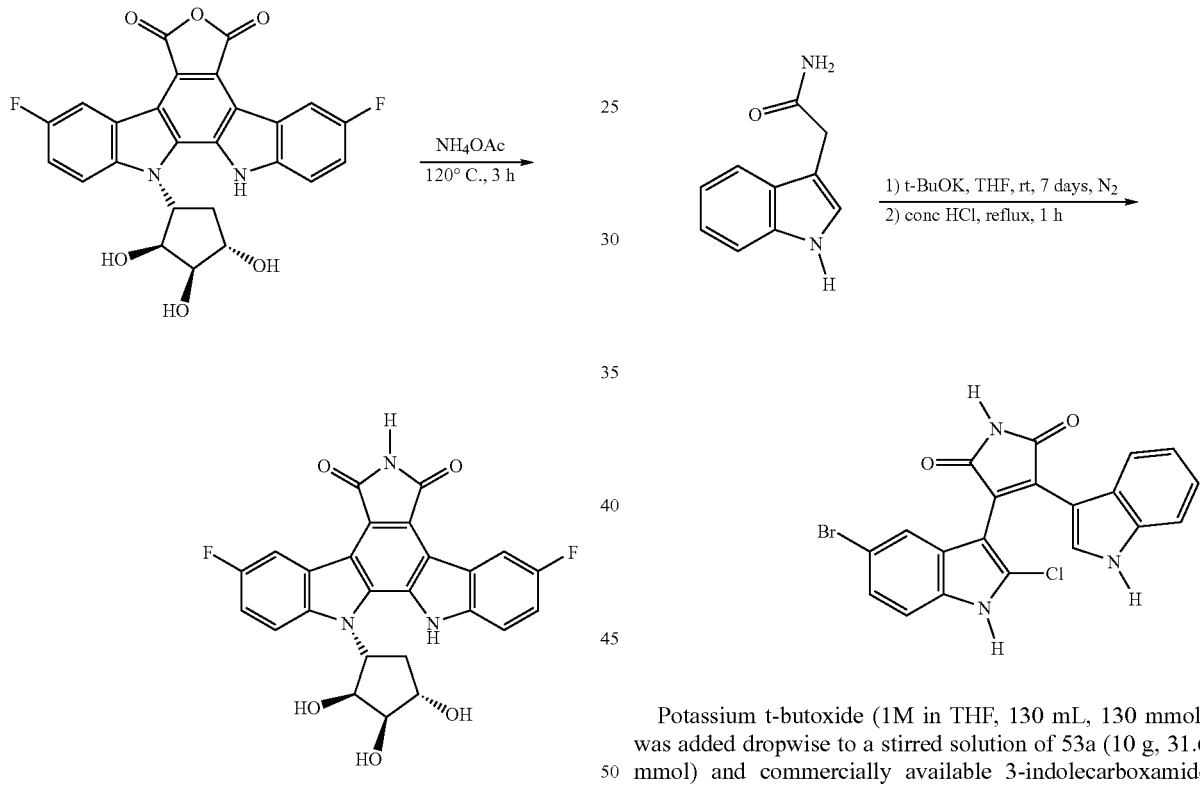

70a)

Potassium t-butoxide (1M in THF, 130 mL, 130 mmol) was added dropwise to a stirred solution of 53a (10 g, 31.6 mmol) and commercially available 3-indolecarboxamide (3.68 g, 21.1 mmol) in dry THF (25 mL) at rt under nitrogen atmosphere. After 7 days the violet solution was poured in a 2/1 mixture water/EtOAc (450 mL). The organic layer was washed with water (200 mL) and brine (100 mL), dried over sodium sulfate, filtered and concentrated in vacuo to give a red foam (9.7 g). The residue was dissolved in MeOH (100 mL), and concentrated HCl (50 mL) was added. The reaction mixture was stirred at reflux for 1 hour. After cooling to rt the reaction mixture was diluted with EtOAc (300 mL) and washed with water (2×250 mL) to give, after concentration in vacuo, a crude (9.3 g). Purification by flash chromatography (silica gel, PE/EtOAc 3/2 as eluant mixture) gave the pure target compound as a red foam (7.9 g, yield 85.2%).

$^{1}$H-NMR (300 MHz, DMSO-d$_6$): δ 6.35 (1H, d, <u>H</u>arom), 6.58 (1H, bt, <u>H</u>arom), 7.02 (1H, bt, <u>H</u>arom), 7.20 (2H, bq, <u>H</u>arom), 7.39 (1H, d, <u>H</u>arom), 7.52 (1H, s, indole a), 8.01

(1H, d, Harom), 11.03 (1H, s, imide NH), 11.86 (1H, s, indole NH), 12.41 (1H, bs, indole NH). MS (APCI) m/z 440 [M+H]⁺.

70b)

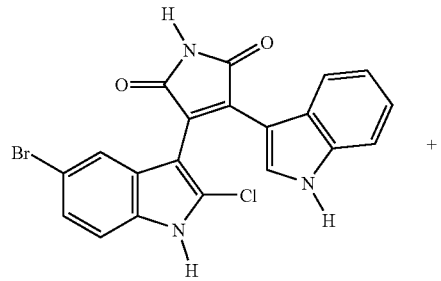

+

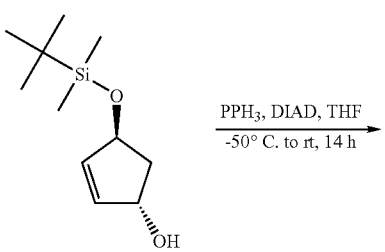

PPh₃, DIAD, THF
-50° C. to rt, 14 h

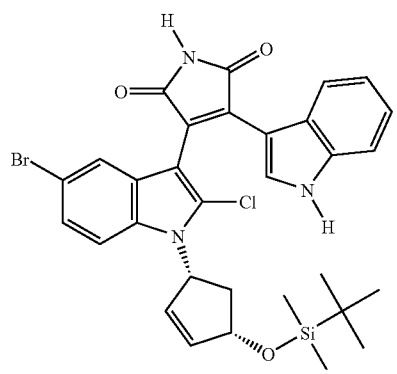

A solution of 70a (4.4 g, 10 mmol), 62b (2.79 g, 13 mmol) and triphenylphosphine (3.93 g, 15 mmol) in THF (50 mL) was cooled to −50° C. Diisopropyl azodicarboxylate (2.9 mL, 15 mmol) was added, the reaction mixture was warmed slowly to rt and stirred overnight. The solvent was removed in vacuo and the residue purified by flash chromatography (silica gel, PE/EtOAc/NEt₃ 1/1/0.02 as eluant mixture) to give an orange foam (7.3 g). A second purification by flash chromatography (silica gel, DCM/EtOAc 10/1 as eluant mixture) gave the pure title compound (2.44 g, yield 38.3%).

¹H-NMR (300 MHz, DMSO-d₆): δ 0.11 (6H, s, CH₃—Si), 0.89 (9H, s, tBu), 1.75–1.85 (1H, dm, CH₂), 2.75–2.95 (1H, dm, CH₂), 4.91–5.46 (1H, dm, CH—N), 5.85 (1H, m, CH—O, 6.10 (2H, m, CH=CH), 6.55–6.65 (1H, dt, Harom) 7.05–7.25 (2H, m, Harom), 7.40 (1H, m, Harom), 7.35 (1H, s, indole H-4), 7.75 (1H, dd, Harom), 8.10 (1H, d, Harom), 11.06 (1H, s, imide NH), 11.93 (1H, bs, indole NH). MS (APCI) m/z 636 [M+H]⁺.

70c)

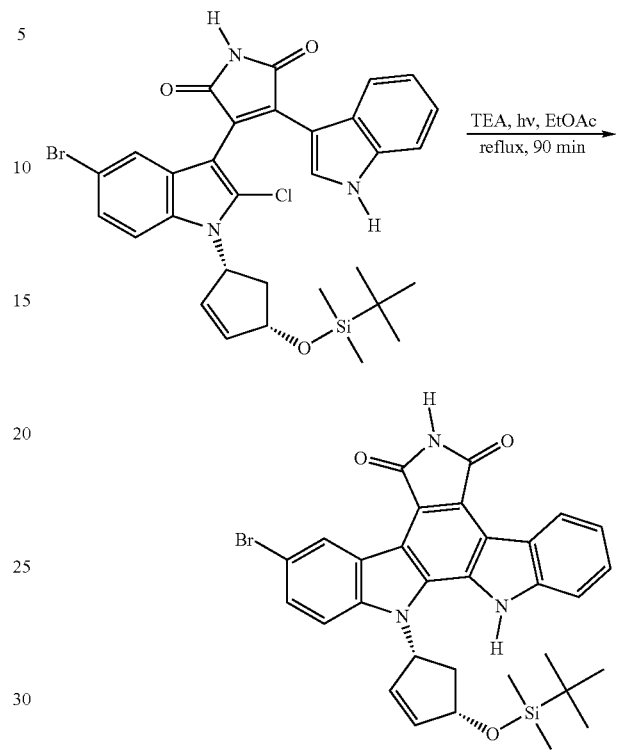

TEA, hv, EtOAc
reflux, 90 min

A solution of 70b (2.42 g, 3.8 mmol) and triethylamine (30 mL) in EtOAc (300 mL) was irradiated with a halogen lamp. After 90 minutes the solution was cooled to rt, washed with water (2×200 mL), dried with sodium sulfate and concentrated in vacuo to give a solid residue (2.27 g). Trituration in hot MeOH (2 mL), filtration and washing with MeOH (1 mL) afforded after drying in vacuo the pure target compound (1.95 g, yield 88.0%).

¹H-NMR (300 MHz, DMSO-d₆): δ 0.14 (3H, s, CH₃—Si), 0.21 (3H, s, CH₃—Si), 0.93 (9H, s, tBu), 2.14 (1H, m, CH₂) 3.32 (1H, m, H, 5.10 (1H, m, CH—O), 6.30 (2H, m, CH=CH), 6.38 (1H, mt, CH—N), 7.34 (1H, bt, Harom), 7.50 (1H, m, Harom), 7.77 (1H, bt, Harom), 7.98 (1H, d, Harom), 8.05 (1H, d, Harom), 9.10 (1H, d, indole H-4, 9.35 (1H, d, indole H-4), 11.12 (1H, bs, imide NH), 12.10 (1H, bs, indole NH). MS (APCI) m/z 600 [M+H]⁺.

70d)

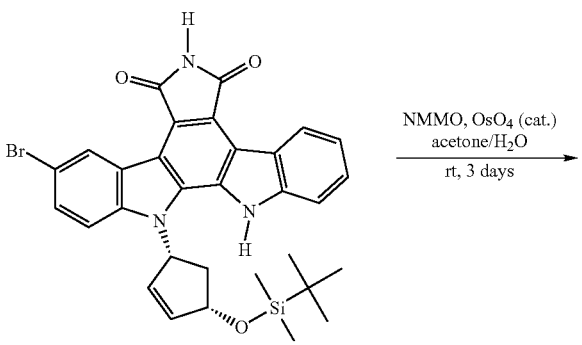

NMMO, OsO₄ (cat.)
acetone/H₂O
rt, 3 days

-continued

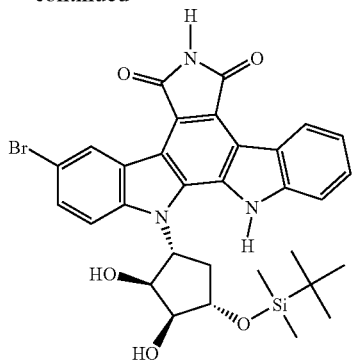

A solution of 70c (300 mg, 0.5 mmol) in acetone (2 mL) was treated with N-methylmorpholine N-oxide (180 mg, 1.5 mmol), osmium tetroxide (2.5% in tBuOH, 0.2 mL, catalytic) and water (5 drops). The suspension was vigorously stirred for 3 days at rt. Hot THF (70 mL) was added and the reaction mixture was diluted with EtOAc (70 mL), washed with 10% NaHSO₃ (50 mL), then 1N HCl (100 mL). The organic layer was dried over sodium sulfate, filtered and concentrated to give a crude solid residue (320 mg). Trituration in hot MeOH (2 mL), filtration and drying in vacuo gave the pure target compound as an orange powder (280 mg, yield 88.0%).

$^1$H-NMR (300 MHz, DMSO-d₆): δ 0.25 (6H, s, Si(CH₃)₂), 1.01 (9H, s, tBu), 2.37 (1H, dd, CH₂), 3.10 (1H, dd, CH₂), 3.85 (1H, d, OH), 4.29 (1H, bs, OH), 4.90 (1H, m, CH—OSi), 5.32 (2H, m, CH—OH), 5.63 (1H, m, CH—N), 7.38 (1H, bt, Harom), 7.55 (1H, dd, Harom), 7.60 (1H, bt, Harom), 7.81 (1H, d, Harom), 8.38 (1H, bd, Harom), 9.11 (1H, d, indole H-4), 9.41 (1H, d, indole H-4), 11.13 (1H, bs, imide NH), 11.75 (1H, bs, indole NH). MS (APCI) m/z 634 [M+H]⁺.

70) NAD 429

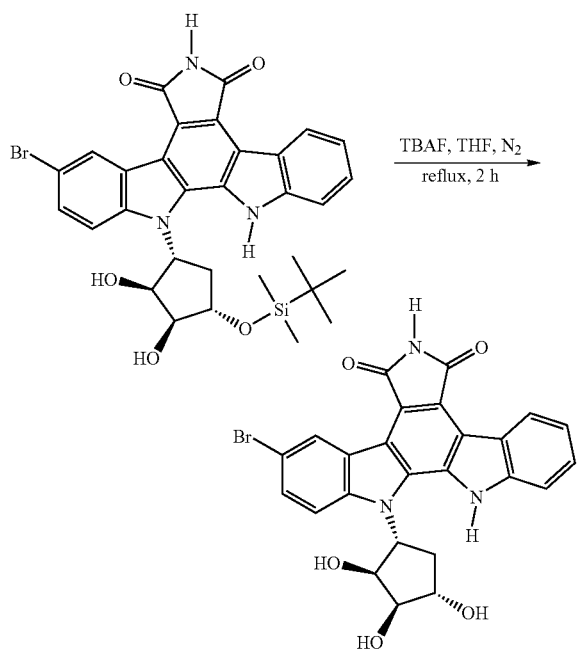

Tetrabutylammonium fluoride (1M in THF, 1 mL, 1 mmol) was added dropwise to a stirred solution of 70d (250 mg, 0.39 mmol) in dry THF (15 mL) under nitrogen atmosphere. The reaction was stirred at reflux for 2 hours. The reaction mixture was cooled to rt and AcOH (10 drops) and EtOAc (100 mL) were added. The solution was washed with sat. NaHCO₃ (50 mL), water (50 mL) and brine (50 mL). The organic layer was dried over sodium sulfate, filtered and concentrated in vacuo. The residue (250 mg) was recrystallized in MeOH (1.5 mL), filtered and dried in vacuo to yield the pure target compound as a yellow solid (130 mg, yield 64.1%).

$^1$H-NMR (300 MHz, DMSO-d₆): δ 2.31 (1H, m, CH₂), 3.05 (1H, m, CH₂), 3.94 (1H, bs, OH), 4.24 (1H, d, OH), 4.94 (1H, m, CH—OH), 5.16 (1H, bs, OH), 5.23 (2H, m, CH—OH), 5.60 (1H, bq, CH—N), 7.37 (1H, dt, Harom), 7.59 (1H, dt, Harom), 7.73 (2H, m, Harom), 8.44 (1H, bs, Harom), 9.12 (1H, d, indole H-4), 9.40 (1H, d, indole H-4), 11.14 (1H, bs, imide NH), 12.1 (1H, bs, indole NH). MS (APCI) m/z 520 [M+H]⁺.

Example 71

NAD 433

71a)

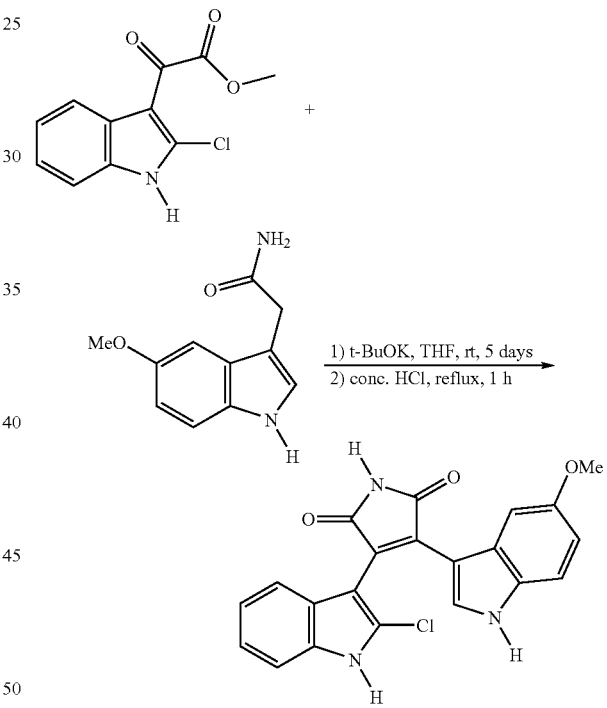

Potassium t-butoxide (1M in THF, 150 mL, 150 mmol) was added dropwise to a stirred solution of 1h (8.6 g, 36 mmol) and 49a (4.9 g, 24 mmol) in dry THF (40 mL) at rt under nitrogen atmosphere. The reaction mixture was stirred for 5 days and the solvent was removed in vacuo. The residue was dissolved in EtOAc (200 mL) and washed with water (200 mL). The aqueous layer was extracted with EtOAc (100 mL) and the combined organic layers were washed with water (100 mL), brine (100 mL), dried over sodium sulfate, filtered and concentrated in vacuo. The crude (5.9 g) was dissolved in MeOH (50 mL) and concentrated HCl (25 mL) was added. The reaction mixture was heated at reflux for 1 hour, then cooled to rt, poured onto water (100 mL) and extracted with EtOAc (200 mL). The organic layer was dried over sodium sulfate, filtered and concentrated in vacuo to give a residue (4 g). Purification by flash chromatography (silica gel, PE/EtOAc 1/1 as eluant mixture) afforded the pure target compound (1.35 g, yield 14.0%).

¹H-NMR (300 MHz, DMSO-d₆): δ 2.75 (3H, s, O$CH_3$), 5.79 (1H, d, Harom), 6.55 (1H, dd, Harom), 7.00 (1H, dt, Harom), 7.15 (1H, dt, Harom), 7.25 (1H, d, Harom), 7.32 (1H, d, Harom), 7.39 (1H, d, Harom), 8.01 (1H, s, indole H-4), 10.99 (1H, s, imide NH), 11.73 (1H, s, indole NH), 12.17 (1H, bs, 2-Cl indole NH). MS (APCI) m/z 392 [M+H]⁺.

71b)

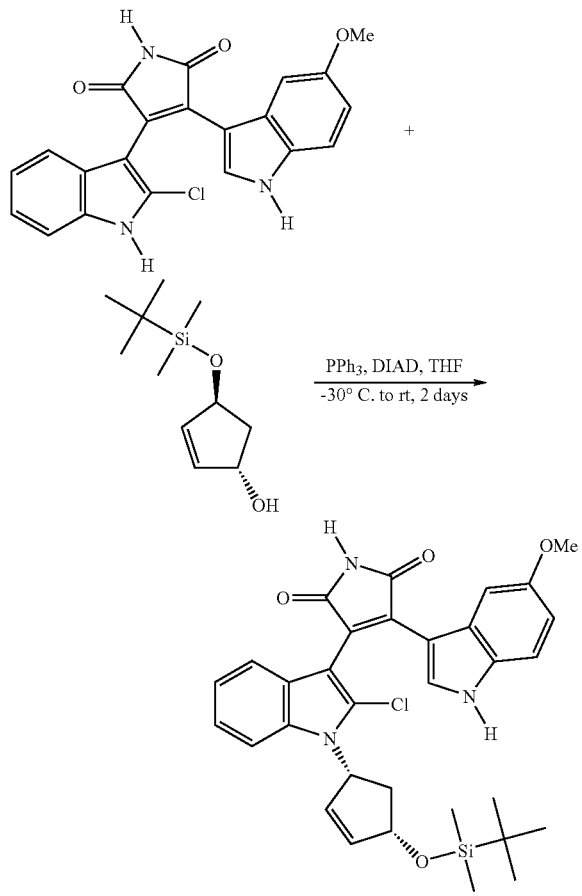

A solution of 71a (1 g, 2.55 mmol), 62b (0.82 g, 3.82 mmol) and triphenylphosphine (1.31 g, 5 mmol) in THF (22 mL) was cooled to −30° C. Diisopropyl azodicarboxylate (0.97 mL, 5 mmol) was added, the reaction mixture was warmed slowly to rt and stirred overnight. The solvent was removed in vacuo and the residue purified by flash chromatography (silica gel, PE/EtOAc/NEt₃ 1/1/0.02 as eluant mixture) to give an orange foam (2.2 g). A second purification by flash chromatography (silica gel, DCM/EtOAc 10/1 as eluant mixture) gave the pure title compound (0.52 g, yield 35%).

¹H-NMR (300 MHz, DMSO-d₆): δ 0.11 (6H, t, $CH_3$—Si), 0.89 (9H, d, tBu), 1.75–1.90 (1H, dm, $CH_2$), 2.65–2.70 (3H, s, O$CH_3$), 2.65–2.95 (1H, dm, CH), 4.91–5.46 (1H, dm, $CH$—N), 5.65 (1H, m, $CH$—O), 5.98 (1H, bd, $CH$=), 6.10 (1H, bd, $CH$=), 6.60 (1H, dt, Harom) 7.12 (2H, m, Harom), 7.25 (1H, dd, Harom), 7.50 (2H, m, Harom), 7.70 (1H, m, Harom), 8.10 (1H, d, Harom), 11.02 (1H, s, imide NH), 11.78 (1H, bs, indole NH). MS (APCI) m/z 588 [M+H]⁺.

71c)

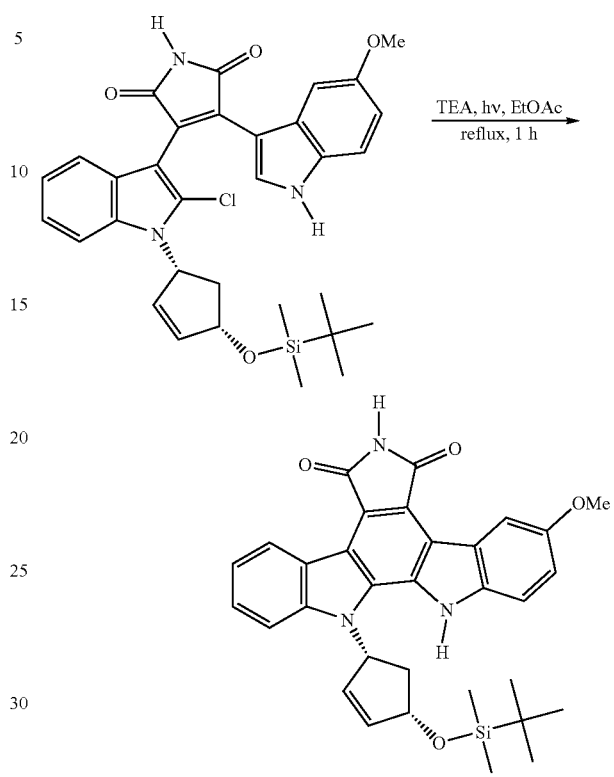

A solution of 71b (0.5 g, 0.85 mmol) and triethylamine (10 mL) in EtOAc (150 mL) was irradiated with a halogen lamp. After 1 hour the solution was cooled to rt, washed with water (2×100 mL), dried with sodium sulfate and concentrated in vacuo to give a solid residue (0.48 g). Trituration in hot MeOH (2 mL), filtration and washing with MeOH (1 mL) afforded after drying in vacuo the pure target compound (0.43 g, yield 92.0%).

¹H-NMR (300 MHz, DMSO-d₆): δ 0.14 (3H, s, $CH_3$—Si), 0.21 (3H, s, $CH_3$—Si), 0.93 (9H, s, tBu), 2.19 (1H, m, $CH_2$), 3.20 (1H, m, $CH_2$), 3.90 (3H, s, O$CH_3$), 5.10 (1H, m, $CH$—O), 6.30 (2H, m, $CH$=$CH$), 6.40 (1H, mt, $CH$—N), 7.25 (1H, dd, Harom), 7.40 (2H, m, Harom), 7.69 (1H, d, Harom), 8.03 (1H, d, Harom), 8.71 (H, d, indole H-4), 9.18 (1H, d, indole H-4), 11.05 (1H, bs, imide NH), 11.90 (1H, bs, indole NH). MS (APCI) m/z 552 [M+H]⁺.

71d)

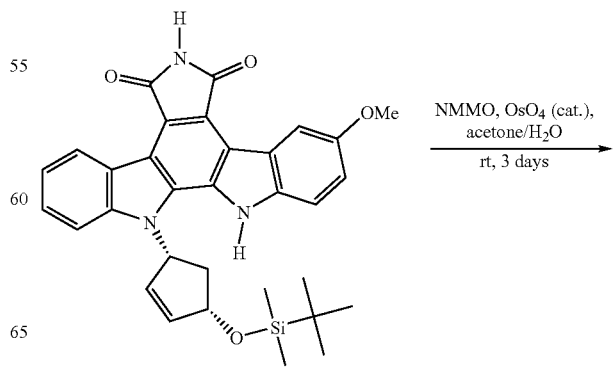

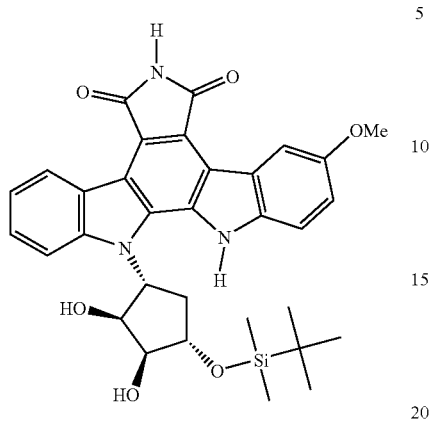

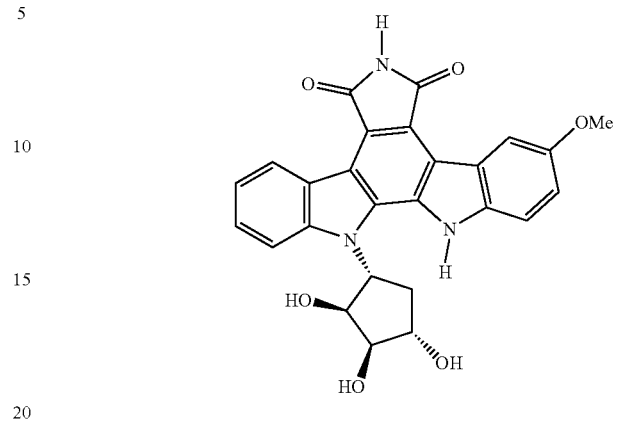

A solution of 71c (390 mg, 0.71 mmol) in acetone (4 mL) was treated with N-methylmorpholine N-oxide (180 mg, 1.5 mmol), osmium tetroxide (2.5% in tBuOH, 0.5 mL, catalytic) and water (5 drops). The suspension was vigorously stirred for 3 days at rt. The solvent was removed in vacuo and the residue diluted with THF (50 mL) and AcOEt (100 mL), washed with 10% NaHSO₃ (100 mL), then with 1N HCl (100 mL). The organic layer was dried over sodium sulfate, filtered and concentrated to give a crude residue (420 mg). Trituration in hot MeOH (2 mL), filtration and drying in vacuo gave the pure target compound as an orange powder (320 mg, yield 77.0%).

¹H-NMR (300 MHz, DMSO-d₆): δ 0.21 (6H, s, Si(CH₃)₂), 1.01 (9H, s, tBu), 2.40 (1H, dd, CH₂, 3.10 (1H, m, CH₂), 3.85 (1H, d, OH), 3.90 (3H, s, OCH₃), 4.30 (1H, d, OH), 4.95 (1H, m, CH—OSi), 5.25 (1H, m, CH—OH), 5.32 (1H, m, CH—OH), 5.63 (1H, m, CH—N), 7.25 (1H, dd, Harom), 7.45 (2H, m, Harom), 7.70 (1H, d, Harom), 8.40 (1H, d, Harom), 8.70 (1H, d, indole H-4), 9.24 (1H, d, indole H-4), 11.03 (1H, bs, imide NH), 11.47 (1H, bs, indole NH). MS (APCI) m/z 552 [M+H]⁺.

Tetrabutylammonium fluoride (1M in THF, 1.2 mL, 1.2 mmol) was added dropwise to a stirred solution of 71d (300 mg, 0.51 mmol) in dry THF (30 mL) under nitrogen atmosphere. The reaction was stirred at reflux for 2.5 hours. The reaction mixture was cooled to rt and AcOH (40 drops) and EtOAc (100 mL) were added. The solution was washed with sat. NaHCO₃ (60 mL). The organic layer was dried over sodium sulfate, filtered and concentrated in vacuo. The residue (290 mg) was triturated in hot MeOH (2 mL), filtered and dried in vacuo to yield the pure target compound as a yellow solid (200 mg, yield 83.2%).

¹H-NMR (300 MHz, DMSO-d₆): δ 2.30 (1H, m, CH₂), 3.05 (1H, m, CH₂), 3.90 (3H, s, OCH₃), 3.94 (1H, bs, OH), 4.22 (1H, d, OH), 4.95 (1H, m, CH—OH), 5.15 (1H, s, OH), 5.23 (2H, dd, CH—OH), 5.60 (1H, bq, CH—N), 7.25 (1H, dd, Harom), 7.40 (2H, t, Harom), 7.59 (1H, t, Harom), 7.63 (1H, d, Harom), 8.72 (1H, d, indole H-4), 9.25 (1H, d, indole H-4), 11.05 (1H, bs, imide NH), 11.90 (1H, bs, indole NH). MS (APCI) m/z 472 [M+H]⁺.

Example 72

NAD214

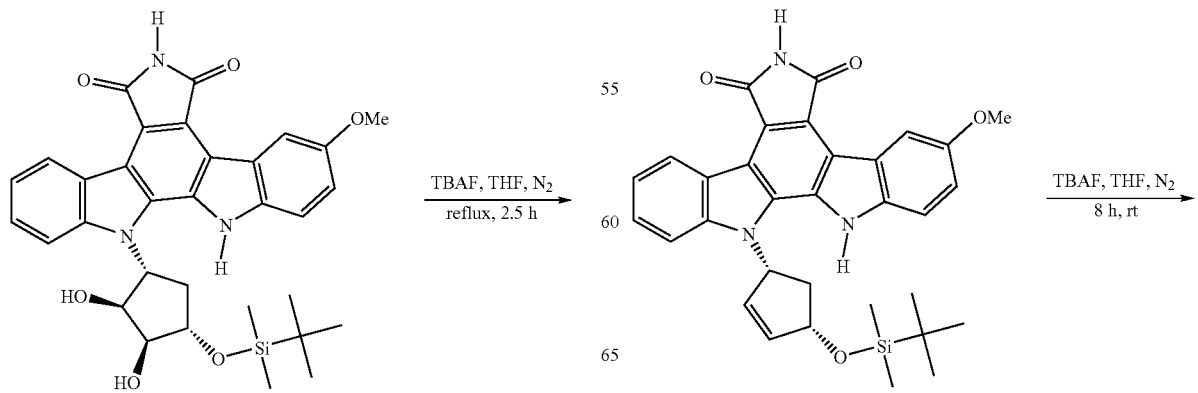

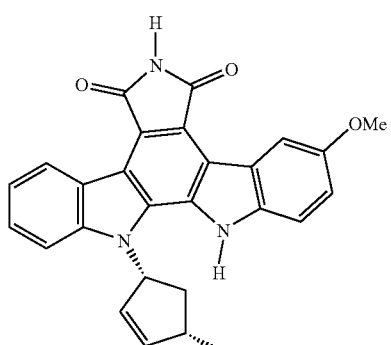

Tetrabutylammonium fluoride (1M in THF, 0.36 mL, 0.36 mmol) was added dropwise to a stirred solution of 71c (100 mg, 0.18 mmol) in dry THF (10 mL) under nitrogen atmosphere at rt. The reaction was stirred for 8 hours, then AcOH (40 drops) and EtOAc (100 mL) were added. The solution was washed with sat. NaHCO$_3$ (20 mL). The organic layer was dried over sodium sulfate, filtered and concentrated in vacuo. The residue (95 mg) was triturated in hot MeOH (2 mL), filtered and dried in vacuo to yield the pure target compound as a yellow solid (70 mg, yield 89.7%).

$^1$H-NMR (300 MHz, DMSO-d$_6$): δ 2.10 (1H, dd, CH$_2$), 3.15 (1H, m, CH$_2$), 3.90 (3H, s, OCH$_3$), 4.90 (1H, m, CH—OH), 5.55 (1H, bs, OH), 6.35 (3H, m, CH—N+CH═CH), 7.25 (1H, dd, Harom), 7.50 (2H, m, Harom), 7.70 (1H, d, Harom), 8.00 (1H, d, Harom), 3.71 (1H, d, indole H-4), 9.20 (1H, d, indole H-4), 11.03 (1H, bs, imide NH), 11.95 (1H, bs, indole NH). MS (APCI) m/z 438 [M+H]$^+$.

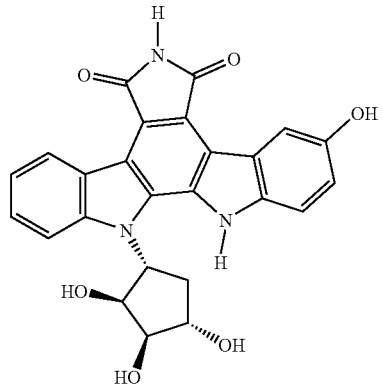

A solution of 71 (0.16 g, 0.34 mmol) and boron tribromide (1M in DCM, 13.6 mL, 13.6 mmol) in DCM (40 mL) was stirred at rt for 17 hours. The reaction mixture was poured into water (150 mL) and extracted with 1/1 EtOAc/THF (200 mL). The organic layer was washed with water (100 mL) and brine (100 mL), dried over sodium sulfate, filtered and concentrated in vacuo to yield a residue (0.22 g). The residue was dissolved in THF (3 mL) and filtered over a short pad of silica gel using EtOAc as eluant. After evaporation in vacuo the residue (0.19 g) was triturated in hot EtOAc (2 mL), filtered and washed with EtOAc (1 mL) to give after drying in vacuo the pure target compound (100 mg, yield 63.7%).

$^1$H-NMR (300 MHz, DMSO-d$_6$): δ 2.30 (1H, m, CH$_2$), 3.05 (1H, m, CH$_2$), 3.94 (1H, bs, OH), 4.22 (1H, d, OH), 5.15 (1H, s, OH), 5.23 (2H, dd, CH—OH), 5.37 (1H, m, CH—OH), 5.60 (1H, bq, CH—N), 7.08 (1H, dd, Harom), 7.37 (2H, t, Harom), 7.59 (1H, m, Harom), 7.63 (1H, m, Harom), 8.53 (1H, d, indole H-4), 9.25 (1H, d, indole H-4), 11.05 (1H, bs, imide NH), 11.90 (1H, bs, indole NH). MS (APCI) m/z 472 [M+H]$^+$.

Example 73

NAD 440

72)

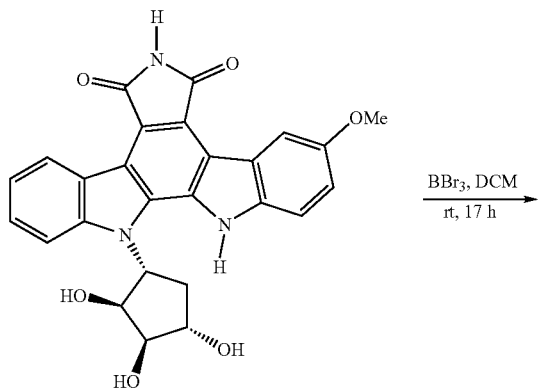

Example 74

NAD 471

74a)

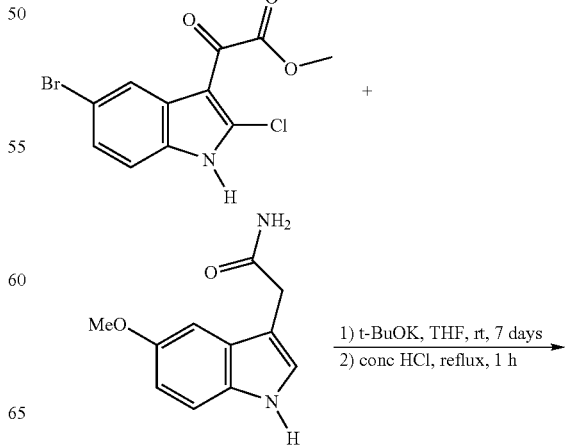

-continued

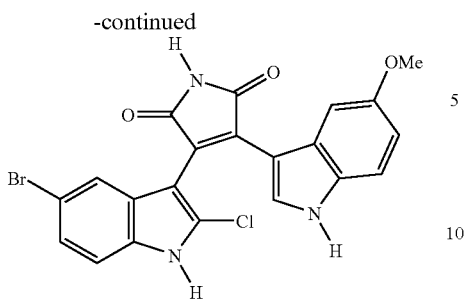

Potassium t-butoxide (1M in THF, 150 mL, 150 mmol) was added dropwise to a stirred solution of 53a (10.22 g, 32.3 mmol) and 49a (4.4 g, 21.5 mmol) in dry THF (25 mL) at rt under nitrogen atmosphere. The reaction mixture was stirred for 7 days, was poured into water (400 mL) and extracted with EtOAc (400 mL). The organic layer was dried over sodium sulfate, filtered and concentrated in vacuo to give a crude (8 g). The residue was dissolved in MeOH (80 mL) and concentrated HCl (40 mL) was added. The reaction mixture was heated at reflux for 1 hour, was then cooled to rt, poured onto water (500 mL) and extracted with EtOAc (400 mL). The organic layer was dried over sodium sulfate, filtered and concentrated in vacuo to give a solid residue which was triturated in hot AcOEt (15 mL). Filtration and drying in vacuo afforded a first crop of the pure target compound (2.1 g). The mother liquors were concentrated and the residue was purified by flash chromatography (silica gel, PE/EtOAc 2/1 as eluant mixture) to give a second crop of the pure target compound (2.8 g, total yield 48.1%).

$^1$H-NMR (300 MHz, DMSO-d$_6$): δ 2.80 (3H, s, OC$\underline{H_3}$), 6.50 (1H, dd, $\underline{Harom}$), 7.30 (2H, d, $\underline{Harom}$), 7.60 (1H, s, $\underline{Harom}$), 7.39 (1H, d, $\underline{Harom}$), 8.01 (1H, s, indole $\underline{H-2}$), 10.909 (1H, s, imide $\underline{NH}$) 11.73 (1H, s, indole $\underline{NH}$), 12.25 (1H, bs, 2-Cl indole $\underline{NH}$). MS (APCI) m/z 470 [M+H]$^+$.

74b)

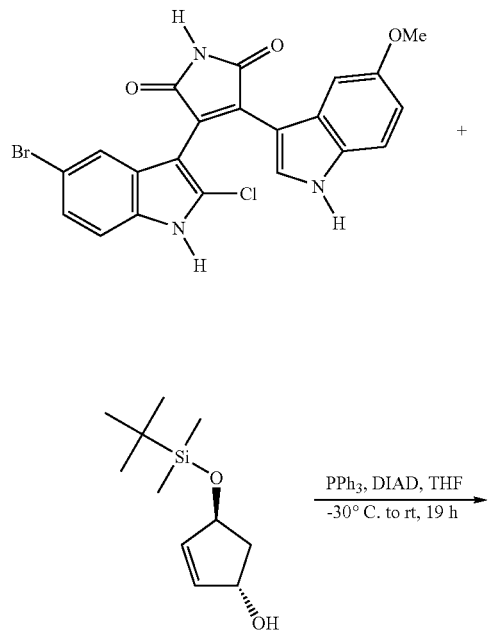

-continued

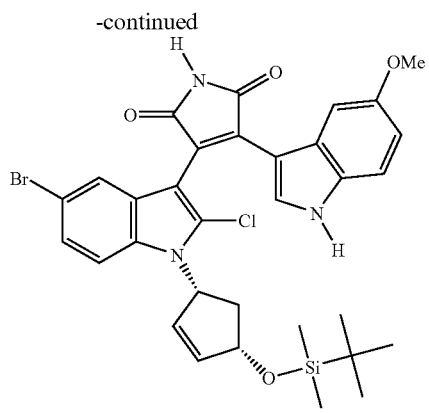

A solution of 74a (4.17 g, 8.86 mmol), 62b (2.85 g, 13.3 mmol) and triphenylphosphine (3.93 g, 15 mmol) in THF (80 mL) was cooled to −30° C. Diisopropyl azodicarboxylate (2.9 mL, 15 mmol) was added, the reaction mixture was warmed slowly to rt and stirred overnight. The solvent was removed in vacuo and the residue purified by flash chromatography (silica gel, PE/EtOAc/NEt$_3$ 1/1/0.02 as eluant mixture) to give an orange foam (6.5 g). A second purification by flash chromatography (silica gel, DCM/EtOAc 10/1 as eluant mixture) gave the pure title compound (2.05 g, yield 35.0%).

$^1$H-NMR (300 MHz, DMSO-d$_6$): δ 0.11 (6H, s, C$\underline{H_3}$—Si), 0.89 (9H, s, t$\underline{Bu}$), 1.75 (1H, m, C$\underline{H_2}$) 2.75 (3H, s, OC$\underline{H_3}$), 2.65–2.95 (1H, dm, C$\underline{H_2}$), 4.85 (1H, m, C$\underline{H}$—O), 5.45 (1H, dm, C$\underline{H}$—N), 5.60 (1H, dd, C$\underline{H}$=), 6.10 (1H, dd, C$\underline{H}$=), 6.60 (1H, m, $\underline{Harom}$) 7.25 (2H, m, $\underline{Harom}$), 7.70 (2H, m, $\underline{Harom}$), 8.10 (1H, d, indole $\underline{Harom}$), 10.95 (1H, s, imide $\underline{NH}$), 11.75 (1H, bs, indole $\underline{NH}$). MS (APCI) m/z 666 [M+H]$^+$.

74c)

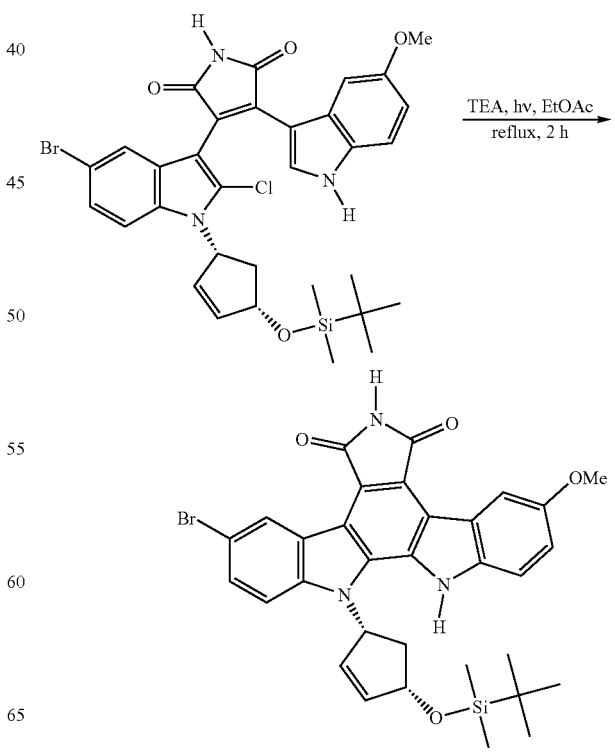

A solution of 74b (2.02 g, 3.03 mmol) and triethylamine (30 mL) in EtOAc (350 mL) was irradiated with a halogen lamp. After 2 hour the solution was cooled to rt, washed with water (2×200 mL), dried with sodium sulfate and concentrated in vacuo to give a solid residue (1.91 g). Trituration in hot MeOH (7 mL), filtration and washing with MeOH (1 mL) afforded after drying in vacuo the pure target compound (1.73 g, yield 91.0%).

$^1$H-NMR (300 MHz, DMSO-d$_6$): δ 0.14 (3H, s, CH$_3$—Si), 0.21 (3H, s, CH$_3$—Si), 0.93 (9H, s, tBu), 2.15 (1H, m, CH$_2$, 3.25 (1H, m, CH$_2$), 3.90 (3H, s, OCH$_3$), 5.10 (1H, m, CH—O), 6.35 (3H, m, CH=CH+CH—N), 7.20 (1H, dd, Harom), 7.50 (1H, dd, Harom), 7.70 (1H, d, Harom), 7.95 (1H, d, Harom), 8.60 (1H, s, indole H-4), 9.30 (1H, s, indole H-4, 11.05 (1H, bs, imide NH), 11.90 (1H, bs, indole NH). MS (APCI) m/z 630 [M+H]$^+$.

74) NAD 471

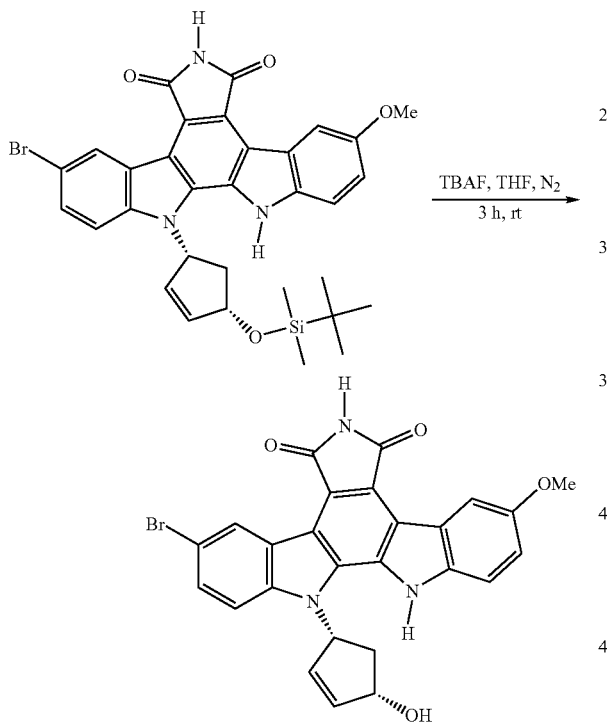

Tetrabutylammonium fluoride (1M in THF, 0.6 mL, 0.6 mmol) was added dropwise to a stirred solution of 74c (140 mg, 0.22 mmol) in dry THF (3 mL) under nitrogen atmosphere at rt. The reaction was stirred for 3 hours, then AcOH (15 drops) and EtOAc (50 mL) were added. The solution was washed with sat. NaHCO$_3$ (20 mL). The organic layer was dried over sodium sulfate, filtered and concentrated in vacuo. The residue (120 mg) was triturated in hot MeOH (2×1 mL), filtered and dried in vacuo to yield the pure target compound as a yellow solid (100 mg, yield 88%).

$^1$H-NMR (300 MHz, DMSO-d$_6$): δ 2.05 (1H, dd, CH$_2$), 3.15 (1H, m, CH$_2$), 3.90 (3H, s, OCH$_3$), 4.90 (1H, m, CH—OH), 5.55 (1H, bs, OH), 6.35 (3H, m, CH—N+CH=CH), 7.20 (1H, dd, Harom), 7.60 (2H, m, Harom), 7.70 (1H, d, Harom), 7.95 (1H, d, Harom), 8.65 (1H, s, indole H-4), 9.30 (1H, s, indole H-4), 11.05 (1H, bs, imide NH), 11.90 (1H, bs, indole NH). MS (APCI) m/z 516 [M+H]$^+$.

Example 75

NAD 460

75a)

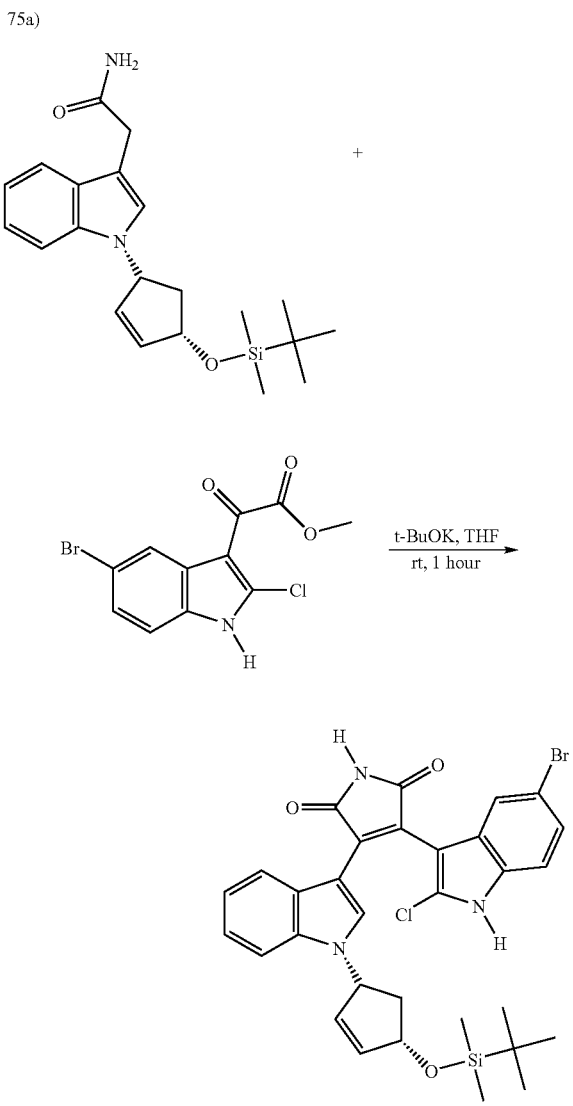

Potassium t-butoxide (1M in THF, 80 mL, 80 mmol) was added dropwise to a stirred solution of 1g (5.15 g, 13.9 mmol) and 53a (6.6 g, 20.8 mmol) in dry THF (50 mL) at rt under nitrogen atmosphere. After 45 minutes the reaction was diluted with EtOAc (2 L), washed with water (1 L) and brine. (500 mL), dried over sodium sulfate, filtered and concentrated in vacuo. The crude residue was purified by flash chromatography (silica gel, PE/EtOAc 2/1 as eluant mixture) to afford the pure target compound (5.06 g, yield 62.9%).

$^1$H-NMR (300 MHz, DMSO-d$_6$): δ 0.14 (3H, s, Si(CH$_3$)$_2$), 0.21 (3H, s, Si(CH$_3$)$_2$), 0.85 (9H, s, tBu), 1.60 (1H, m, CH$_2$), 3.0 (1H, m, CH$_2$), 4.90 (1H, bs, CH—OSi), 6.10 (1H, d, CH=), 6.25 (1H, d, CH=), 6.40 (1H, bt, CH—N), 6.65 (1H, t, Harom), 7.00 (2H, t, Harom), 7.25 (3H, m, Harom), 7.70 (1H, d, Harom), 8.10 (1H, s, Harom), 11.05 (1H, s, imide NH), 12.40 (1H, bs, indole NH). MS (APCI) 636 [M+H]$^+$.

75b)

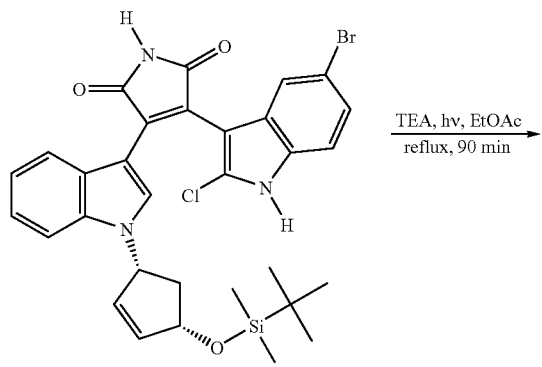

TEA, hv, EtOAc
reflux, 90 min
→

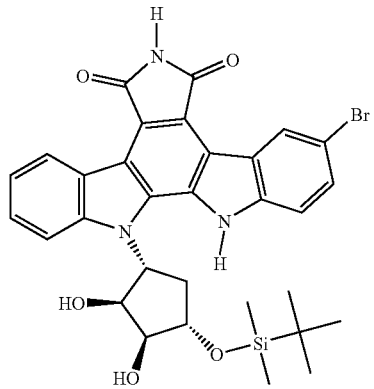

-continued

A solution of 75a (5.06 g, 7.97 mmol) and triethylamine (2.3 mL, large excess) in EtOAc (250 mL) was irradiated with a halogen lamp. After 1 hour the solution was cooled to rt, washed with water (2×100 mL), dried with sodium sulfate and concentrated in vacuo to give the pure target compound (4.69 g, yield 97.9%).

¹H-NMR (300 MHz, DMSO-d₆): δ 0.14 (3H, s, Si(CH₃)₂), 0.21 (3H, s, Si(CH₃)₂), 0.90 (9H, s, tBu), 2.20 (1H, m, CH₂), 3.25 (1H, m, CH₂), 5.15 (1H, bs, CH—OSi), 6.30 (2H, bt, CH=CH), 6.40 (1H, bt, CH—N), 7.40 (2H, m, Harom), 7.80 (2H, m, Harom), 8.10 (1H, d, Harom), 9.15 (1H, d, indole H-4), 9.30 (1H, s, indole H-4) 11.05 (1H, s, imide NH), 12.30 (1H, bs, indole NH). MS (APCI) 600 [M+H]₊.

A solution of 75b (2.4 mg, 4 mmol) in acetone (200 mL) was treated with N-methylmorpholine N-oxide (1.41 g, 12 mmol), osmium tetroxide (2.5% in tBuOH, 5 mL, catalytic) and water (5 drops). The suspension was vigorously stirred for 2 days at rt. Hot THF (70 mL) was added and the reaction mixture was diluted with EtOAc (70 mL), washed with 10% NaHSO₃ (50 mL), then 1N HCl (100 mL). The organic layer was dried over sodium sulfate, filtered and concentrated to give a crude. Trituration in hot MeOH (25 mL), filtration and drying in vacuo gave the pure target compound as an orange powder (1.65 g, yield 66.0%).

¹H-NMR (300 MHz, DMSO-d₆): δ 0.21 (6H, s, Si(CH₃)₂), 0.90 (9H, s, tBu), 2.45 (1H, m, CH₂), 3.15 (1H, m, CH₂), 3.65 (1H, dd, CH—OH), 3.85 (1H, d, OH), 4.10 (1H, bt, CH—OH), 4.35 (1H, d, OH), 4.95 (1H, m, CH—OSi), 5.65 (1H, bt, CH—N), 7.40 (2H, m, Harom), 7.70 (1H, d, Harom), 7.80 (1H, d, Harom), 8.40 (1H, d, Harom), 9.25 (2H, m, Harom) 11.05 (1H, bs, imide NH). MS (APCI) 634 [M+H]⁺.

75c)

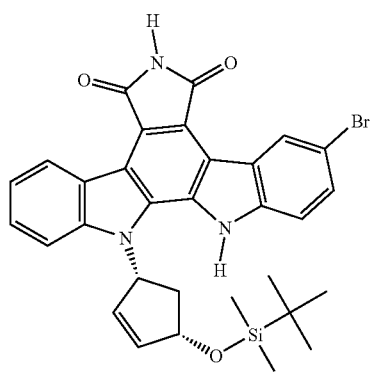

NMMO, OsO₄ (cat.),
acetone/H₂O
rt, 2 days
→

75d)

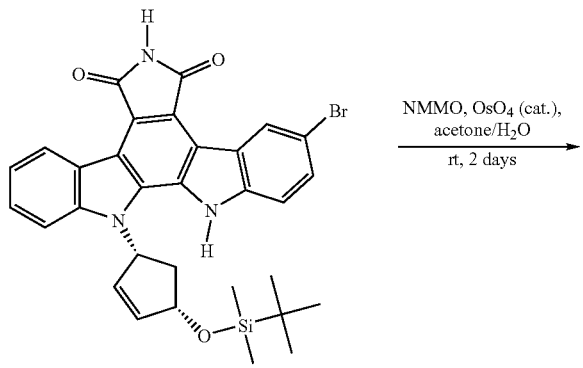

DMP, pTsOH
THF, rt, 16 hours
→

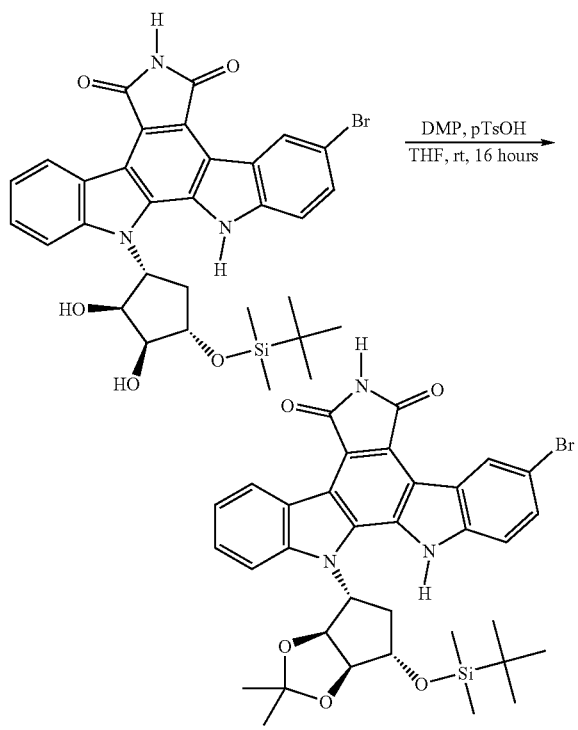

2,2-Dimethoxypropane (20 mL, large excess) and p-toluenesulfonic acid (5 mg, catalytic) were added to a solution of 75c (1.6 g, 2.5 mmol) in THF (100 mL). The reaction mixture was stirred overnight at rt and the solvent was eliminated in vacuo. The residue was taken up in EtOAc (100 mL), washed with 10% NaHCO₃ (50 mL), water (50 mL), dried over sodium sulfate, filtered and concentrated in vacuo to give the pure target compound (1.6 g, yield 93.4%).

¹H-NMR (300 MHz, DMSO-d₆): δ 0.21 (6H, d, Si(CH₃)₂), 0.90 (9H, s, tBu), 1.20 (3H, s, C(CH₃)₂), 1.50 (3H, s, C(CH₃)), 2.75 (1H, m, CH₂), 3.05 (1H, m, CH₂), 4.50 (1H, bt, CH—OSi), 4.80 (1H, m, CH—O), 5.20 (1H, m, CH—O), 5.65 (1H, bt, CH—N), 7.40 (1H, t, Harom), 7.55 (1H, t, Harom), 7.70 (1H, d, Harom), 7.80 (2H, dd, Harom), 9.25 (2H, m, Harom), 11.05 (1H, s, imide NH), 12.10 (1H, s, indole NM. MS (APCI) 674 [M+H]⁺.

75) NAD 460

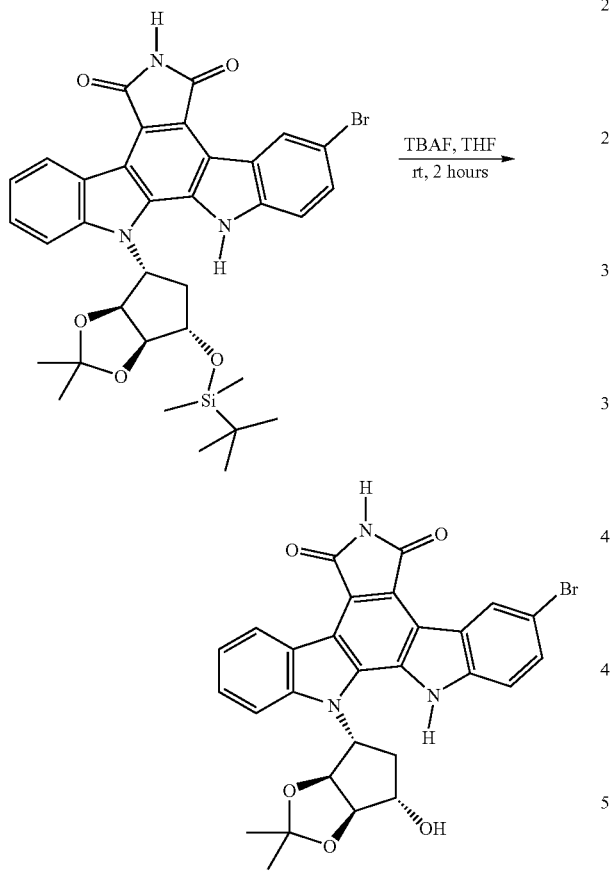

Tetrabutylammonium fluoride (1M in THF, 0.6 mL, 0.6 mmol) was added dropwise to a stirred solution of 75d (160 mg, 0.22 mmol) in dry THF (3 mL) under nitrogen atmosphere at rt. The reaction was stirred for 3 hours, then AcOH (15 drops) and EtOAc (50 mL) were added. The solution was washed with sat. NaHCO₃ (20 mL). The organic layer was dried over sodium sulfate, filtered and concentrated in vacuo. The residue (120 mg) was triturated in hot MeOH (2×1 mL), filtered and dried in vacuo to yield the pure target compound as a yellow solid (100 mg, yield 69.3%).

¹H-NMR (300 MHz, DMSO-d₆): δ 1.20 (3H, s, C(CH₃)), 1.50 (3H, s, C(CH₃), 2.70 (1H, m, CH₂), 3.25 (1H, m, CH₂) 4.50 (1H, bt, CH—OH), 4.80 (1H, m, CH—O), 5.25 (1H, m, CH—O), 5.65 (2H, m, CH—N+OH), 7.55 (1H, t, Harom), 7.70 (1H, t, Harom), 7.85 (2H, m, Harom), 8.00 (1H, d, Harom), 9.25 (2H, m, Harom), 11.05 (1H, s, imide NH), 12.35 (1H, s, indole NH). MS (APCI) 560 [M+H]⁺.

Example 76

NAD 462

76)

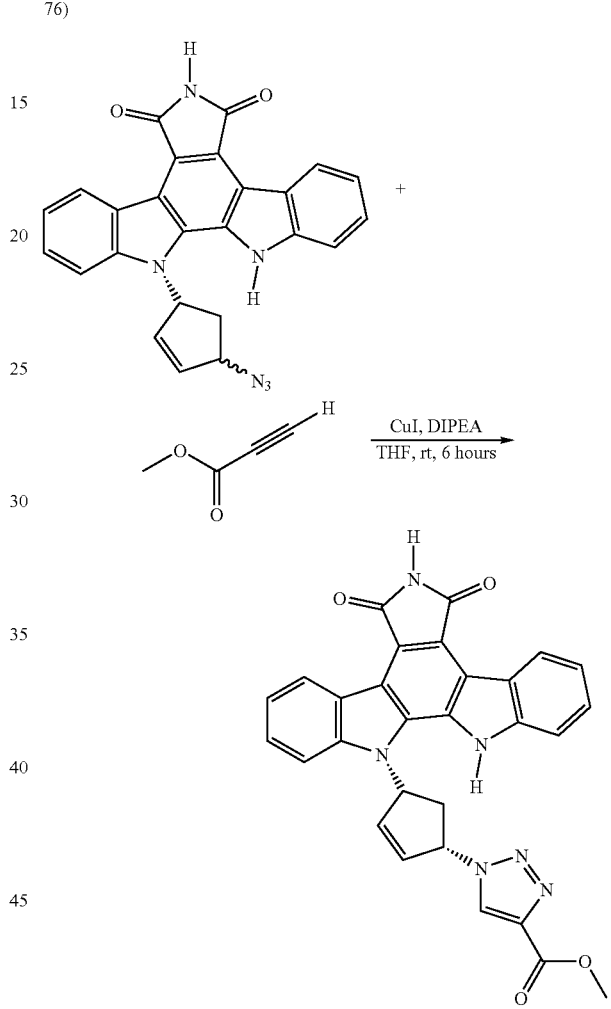

5a (8/2 trans/cis, 432 mg, 0.1 mmol) in THF (40 mL) was added to a mixture of methylacetylene carboxylate (250 μL, 3 mmol), copper (I) iodide (570 mg, 3 mmol) and diisopropylethylamine (8.5 mL, 50 mmol) in THF (10 mL). The reaction mixture was stirred for 6 hours at rt and 1N HCl (20 mL) was added. The aqueous phase was extracted with THF. The combined organic layers were dried over sodium sulfate, filtered and concentrated in vacuo. The residue was purified by flash chromatography (silica gel, PE/EtOAc 4/6 as eluant mixture) and gave the pure target compound (40 mg, yield 7.8%) as a minor component together with the trans isomer.

¹H-NMR (300 MHz, DMSO-d₆): δ 2.70 (1H, m, CH₂), 3.60 (1H, m, CH₂), 3.95 (3H, s, COOMe), 6.10 (1H, bd, CH-Nind), 6.60 (1H, bd, CH-Ntriaz), 6.80 (2H, d, CH=CH), 7.40 (2H, m, Harom), 7.65 (2H, m, Harom), 7.85 (1H, d, Harom), 8.05 (1H, d, Harom), 9.10 (1H, s, triazole CH), 9.15 (1H, d, indole H-4), 9.25 (1H, d, indole H-4) 11.05 (1H, s, imide NH), 12.25 (1H, bs, indole NH). MS (APCI) 517 [M+14]⁺.

Example 77

NAD 463

77)

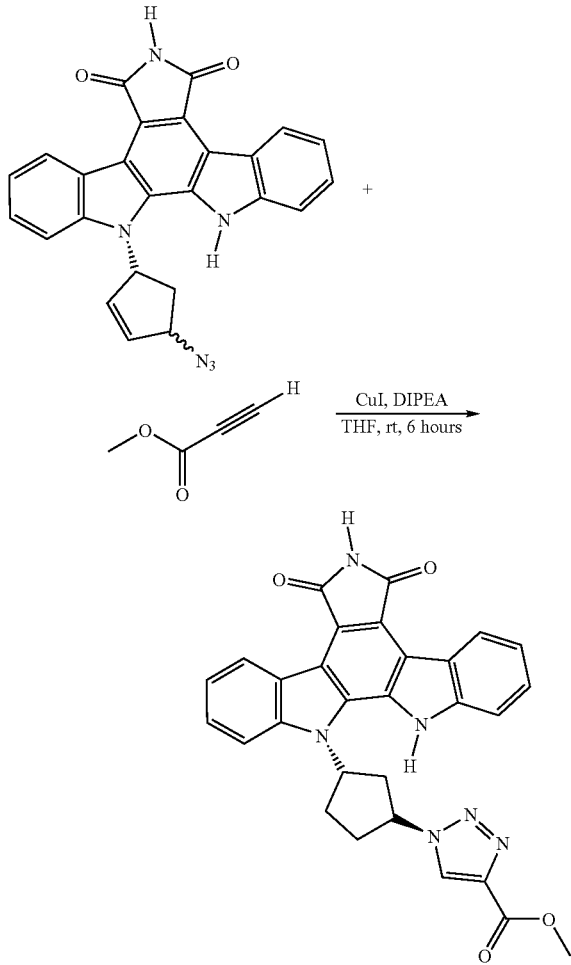

5a (8/2 trans/cis, 432 mg, 0.1 mmol) in THF (40 mL) was added to a mixture of methylacetylene carboxylate (250 mL, 3 mmol), copper (I) iodide (570 mg, 3 mmol) and diisopropylethylamine (8.5 mL, 50 mmol) in TH: (10 mL). The reaction mixture was stirred for 6 hours at rt and 1N HCl (20 mL) was added. The aqueous phase was extracted with THF. The combined organic layers were dried over sodium sulfate, filtered and concentrated in vacuo. The residue was purified by flash chromatography (silica gel, PE/EtOAc 4/6 as eluant mixture) and gave the pure target compound (55 mg, yield 10.6%) together with the cis isomer.

¹H-NMR (300 MHz, DMSO-d₆): δ 3.05 (2H, m, CH₂), 3.95 (3H, s, COOMe), 6.45 (1H, bd, CH-Nind), 6.55 (1H, d, CH=), 6.80 (1H, d, CH=), 7.00 (1H, bd, CH-Ntriaz), 7.40 (2H, m, Harom), 7.60 (2H, m, Harom), 7.75 (1H, d, Harom), 7.85 (1H, d, Harom), 9.00 (1H, s, triazole CH), 9.15 (1H, d, indole H-4), 9.25 (1H, d, indole H-4), 11.05 (1H, s, imide I), 12.30 (1H, bs, indole NH). MS (APCI) 517 [M+H]⁺.

Example 78

NAD 473

78)

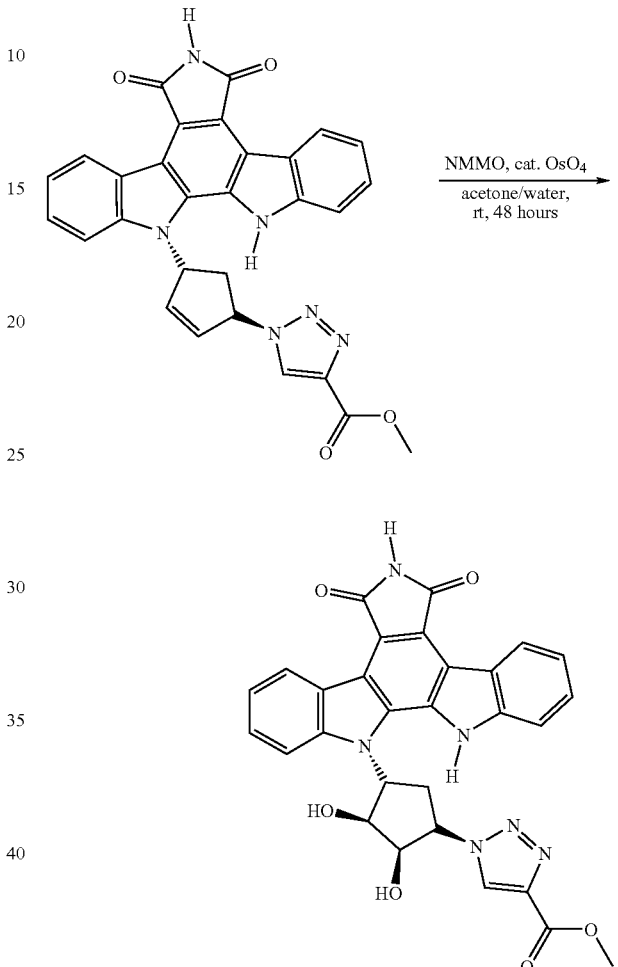

A solution of 77 (110 mg, 0.11 mmol) in acetone (10 mL) was treated with N-methylmorpholine N-oxide (110 mg, 0.9 mmol), osmium tetroxide (2.5% in tBuOH, 0.5 mL, catalytic) and water (5 drops). The suspension was vigorously stirred for 2 days at rt. The solvent was removed in vacuo and the residue was diluted with THF (50 mL) and AcOEt (100 mL), washed with 10% NaHSO₃ (100 mL), then 1N HCl (100 mL). The organic layer was dried over sodium sulfate, filtered and concentrated to give a solid residue (100 mg). Purification by preparative TLC (silica gel, PE/EtOAc 4/6 as eluant mixture) gave the pure target compound (35 mg, yield 30.4%).

¹H-NMR (300 MHz, DMSO-d₆): δ 3.20 (2H, m, CH₂), 3.85 (3H, s, COOMe), 4.30 (1H, d, OH), 5.00 (1H, m, CH—OH), 5.55 (1H, m, CH—OH), 5.65 (1H, d, OH), 5.90 (1H, m, CH-Nind), 6.10 (1H, CH-Ntriaz), 7.40 (2H, m, Harom), 7.60 (2H, m, Harom), 7.85 (1H, d, Harom), 7.95 (1H, d, Harom), 9.10 (1H, s, triazole CH), 9.15 (1H, d, indole H-4), 9.25 (1H, d, indole H-4), 11.05 (1H, s, imide NH), 12.30 (1H, bs, indole NH). MS (APCI) 549 [M+H]⁺.

The inhibition of enzymatic activity by the N-monosubstituted carbacyclic indolocarbazoles of the present invention can be determined using, for example, the following assays:
1. Extracellular signal Regulated Kinase 2 inhibition assay (ERK2)
2. Protein Kinase A inhibition assay (PKA)
3. Protein Kinase C inhibition assay (PKC)
4. Glycogen Synthase Kinase 3β inhibition assay (GSK30).

Description of these assays are set below. The results obtained therein are reported in Table 1. The results are intended to be illustrative and not to be construed as limiting the scope of the disclosure.

For convenience, certain abbreviations are defined as follows: "µg" for microgram, "ring" for milligram, "g" for gram, "µL" for microliter, "mL" for milliliter, "L" for liter, "nM" for nanomolar, "µM" for micromolar, "mM" for millimolar, and "M" for molar. The compounds of the present invention preferably demonstrate measurable inhibition in the assays described herein at a concentration of about 100 µM to about 10 µM. More preferably, compounds of the present invention demonstrate measurable inhibition at a concentration of about 10 µM to about 1 µM. Even more preferably, compounds of the present invention demonstrate measurable inhibition at concentrations lower than 1 µM.

Inhibition of Extracellular Signal Regulated Kinase 2 (ERK 2) Activity

The ERK2 kinase activity assay utilizes a radioactivity-based format in a 96-well PCR plate with radioactive readout. The ERK2 activity was assayed in a 25 µL assay mixture containing 25 mM HEPES (pH 7.0), 250 µM ATP, 1 µM MgCl$_2$, 1 mM DTT, 2% DMSO, 150 ng/mL Myelin Basic Protein (MBP, Sigma M-1891), and 13.6 ng/mL His tagged ERK2 (specific activity=38.1 nmol/min*mg). Compounds were screened for inhibition of the ERK2 kinase activity at a concentration of 10 µM. The kinase reaction was allowed to proceed at 37° C. for 30 minutes, then reaction was stopped by the addition of 5 µL of 0.5M EDTA (pH 8). 15 µL of each solution were then spotted onto the corresponding square of a filtermat (8×12 glassfibre mat 90×120 mm. PE-Wallac 1450–421). The filtermat was allowed to dry and washed once with 10% TCA, 2% PPA, 500 mM NaCl each for 30 minutes at rt. Two further washings in 10% TCA and 2% PPA for 30 minutes were performed, then a final 30 minute wash in 99% EtOH at rt was done and the filtermat was air dried. The dry filtermat was then placed in a sample bag with a Meltilex sheet (Melt-on scintillator sheets 73×10$^9$ mm, PE-Wallac 1450–441 for filtermat A) over the filtermat. The bag was trimmed to fit into the microplate heatsealer (PE-Wallac 1495–021). The heatsealer is used to melt the Meltilex on the filtermat. The bag containing the filtermat and the melted Meltilex was then placed into a filter cassette and counted using the Microbeta Jet Scintillation and Luminescence Counter PE-Wallac 1450. The results for compounds showing a >50% inhibition at the tested concentration are summarized in Table 1.

Inhibition of Protein Kinase A Activity

The PKA kinase activity assay utilizes a radioactivity-based format in a 96-well PCR plate with radioactive readout. The PKA activity was assayed in a 25 µL assay mixture containing 25 mM HEPES (pH 7.0), 250 µM ATP, 10 mM MgCl$_2$, 1 mM DTT, 1 mM EBTA (pH 8), 2% DMSO, 250 ng/mL Histone H2B (Roche 223 514), and 2 ng/mL PKA (catalytic subunit, bovine heart, Calbiochem 539486, specific activity=1170 µmol/min*µg). Compounds were screened for inhibition of the PKA kinase activity at a concentration of 10 µM. The kinase reaction was allowed to proceed at 37° C. for 30 minutes, then the reaction was stopped by addition of 5 µL of 0.5M EDTA (pH 8). The remainder of the protocol is identical to the one reported for ERK2. The results for compounds showing a >50% inhibition at the tested concentration are summarized in Table 1.

Inhibition of Protein Kinase C Activity

The PKA kinase activity assay utilizes a radioactivity-based format in a 96-well PCR plate with radioactive readout. The PKA activity was assayed in a 25 µL assay mixture containing 25 mM HEPES (pH 7.0), 250 µM ATP, 10 mM MgCl$_2$, 1 mM DTT, 1 mM EDTA (pH 8), 2 mM CaCl$_2$, 2% DMSO, 250 ng/mL Histone H1 (Roche 1 004 875), and 165 ng/mL PKC (rat brain, Calbiochem 539494, specific activity=1600 nmol/min*mg), Compounds were screened for inhibition of the PKC kinase activity at a concentration of 10 µM. The kinase reaction was allowed to proceed at 37° C. for 30 minutes, then the reaction was stopped by addition of 5 µL of 0.5M EDTA (pH 8). The remainder of the protocol is identical to the one reported for ERK2. The results for compounds showing a >50% inhibition at the tested concentration are summarized in Table 1.

Inhibition of Glycogen Synthase Kinase 3, Activity

The GSK3, kinase activity assay utilizes a radioactivity-based format in a 96-well PCR plate with radioactive readout. The GSK3β activity was assayed in a 25 µL assay mixture containing 8 mM HEPES (pH 7.0), 250 µM ATP, 0.2 mM EDTA (pH 8), 2% DMSO, 250 ng/mL Myelin Basic Protein (MBP, Sigma M-1891), and 12 ng/mL GSK3 (Upstate Discovery, specific activity=607 nmol/min*GS2 peptide, concentration of 6.05 mg/mL). Compounds were screened for inhibition of the GSK3 P kinase activity at a concentration of 10 µM. The kinase reaction was allowed to proceed at 37° C. for 30 minutes, then the reaction was stopped by addition of 5 µL of 0.5M EDTA (pH 8).

The compounds given in FIG. 16 have been prepared and characterized. The results of the activity tests are summarized in Table 1. The concentration of each compound necessary to show a >50% inhibition of a protein kinase at the tested concentration, is shown.

TABLE 1

| NAD Compound | % Inhibition[a] | | | |
| --- | --- | --- | --- | --- |
| | ERK2 | PKA | PKC | GSK3β |
| NAD003 | NA[b] | NA | 52.22 | NA |
| NAD006 | 84.22 | 18.84 | 45.48 | 83.44 |
| NAD018 | NA | NA | 52.77 | NA |
| NAD040 | 97.85 | 98.02 | 81.34 | 69.76 |
| NAD048 | 45.46 | 78.43 | 65.89 | NA |
| NAD080 | 71.28 | 36.29 | 60.42 | 79.11 |
| NAD085 | 57.19 | 43.43 | 41.98 | 52.17 |
| NAD101 | 77.80 | 98.03 | 62.16 | 27.61 |
| NAD102 | 44.11 | 74.99 | 87.55 | NA |
| NAD106 | 53.38 | 17.15 | 52.00 | 25.41 |
| NAD116 | 24.31 | NA | 67.47 | 18.37 |
| NAD117 | 59.95 | NA | 68.74 | 24.97 |
| NAD119 | 18.89 | NA | 73.20 | NA |
| NAD130 | NA | NA | 85.20 | NA |
| NAD131 | NA | 19.80 | 71.37 | 22.93 |
| NAD132 | NA | 17.16 | 105.57 | 24.98 |
| NAD133 | NA | NA | 102.77 | NA |
| NAD135 | 43.17 | 17.27 | 84.32 | 60.75 |
| NAD136 | NA | NA | 93.58 | NA |
| NAD137 | NA | NA | 88.57 | 15.76 |
| NAD148 | 41.61 | 26.47 | 111.91 | 54.09 |
| NAD149 | 93.33 | 35.19 | 55.37 | 94.14 |

TABLE 1-continued

| NAD Compound | % Inhibition[a] | | | |
|---|---|---|---|---|
| | ERK2 | PKA | PKC | GSK3β |
| NAD154 | NA | NA | 58.82 | 15.90 |
| NAD157 | NA | NA | 55.37 | 20.23 |
| NAD160 | 23.27 | NA | 72.37 | 30.18 |
| NAD161 | NA | NA | 85.69 | 20.33 |
| NAD162 | 37.37 | 19.86 | 58.82 | 61.20 |

[a] 10 μM compound;
[b] NA = not active.

What is claimed is:

1. A protein kinase inhibitor of general formula (I)

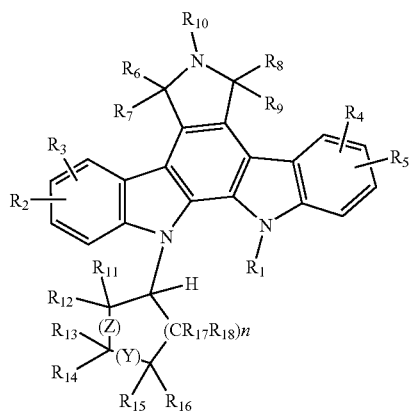

(I)

including diastereomeric and enantiomeric forms, mixtures of diastereomeric and enantiomeric forms, or pharmaceutically acceptable salt forms,
wherein
$R_1$ is selected from the group consisting of H, lower alkyl, aryl or heteroaryl, $COR_{19}$, $COOR_{19}$, $CONR_{20}R_{21}$ wherein $R_{19}$, $R_{20}$ and $R_{21}$ can be the same or different and are independently selected from the group consisting of H, a lower alkyl, aryl and heteroaryl;

$R_2,R_3,R_4,R_5$ taken alone can be the same or different and are each independently selected from the group consisting of H, halogen, lower alkyl, lower alkenyl, lower alkynyl, aryl, heteroaryl, CN, $COR_{22}$, $COOR_{22}$, $CONHR_{22}$, $CONR_{22}R_{23}$, $CSR_{22}$, $CSSR_{22}$, $NR_{22}R_{23}$, $NHCOR_{22}$, $NHCOOR_{22}$, $NHSO_2R_{22}$, $N_3$, $NO_2$, $OR_{22}$, $OCOR_{22}$, $SR_{22}$, $SO_2R_{22}$, and $SiR_{24}R_{25}R_{26}$; or when $R_2$ and $R_3$ or $R_4$ and $R_5$ are taken together they are an optionally substituted alkylene group, containing 2 to 4 carbon atoms or heteroatoms without substituents;

$R_6,R_7$ when taken alone they are both H, or one of them is H and the other is OH, or when taken together they are the oxygen atom of a carbonyl group or the sulfur atom of a thiocarbonyl group; and with the proviso that when $R_8,R_9$ are different from carbonyl $R_6,R_7$ taken together are the oxygen atom of a carbonyl group or the sulfur atom of a thiocarbonyl group;

$R_8,R_9$ when taken alone they are both H, or one of them is H and the other is OH, or when taken together they are the oxygen atom of a carbonyl group or the sulfur atom of a thiocarbonyl group; and with the proviso that when $R_6,R_7$ are different from carbonyl $R_8,R_9$ taken together are the oxygen atom of a carbonyl group or the sulfur atom of a thiocarbonyl group;

$R_{10}$ is selected from the group consisting of H, lower alkyl, aryl, heteroaryl, $COR_{22}$, $COOR_{22}$, $NR_{22}R_{23}$, and $OR_{22}$;

$R_{11},R_{12}$ when taken alone they can be the same or different and are selected from the group consisting of H, halogen, lower alkyl, lower alkenyl, lower alkynyl, aryl, heteroaryl, CN, $COR_{22}$, $COOR_{22}$, $CONHR_2$, $CONR_{22}R_{23}$, $CSR_{22}$, $CSSR_{22}$, $NR_{22}R_{23}$, $NHCOR_{22}$, $NHCOOR_{22}$, $NHSO_2R_{22}$, $N_3$, $OR_2$, $OCOR_{22}$, $OCONHR_{22}$, $SR_{22}$, $SO_2R_2$, and $SiR_{24}R_{25}R_{26}$; when taken together they are an oxygen atom of a carbonyl group, the nitrogen atom of a substituted imine or the carbon atom of a substituted alkenyl;

$R_{13},R_{14}$ when taken alone they can be the same or different and are selected from the group consisting of H, halogen, lower alkyl, lower alkenyl, lower alkynyl, aryl, heteroaryl, CN, $COR_{22}$, $COOR_2$, $CONHR_2$, $CONR_{22}R_{23}$, $CSR_2$, $CSSR_{22}$, $NR_{22}R_{23}$, $NHCOR_{22}$, $NHCOOR_{22}$, $NHSO_2R_2$, $N_3$, $OR_{22}$, $OCOR_{22}$, $SR_{22}$, $SO_2R_{22}$, and $SiR_{24}R_{25}R_{26}$; when taken together they are an oxygen atom of a carbonyl group, the nitrogen atom of a substituted imine or the carbon atom of a substituted alkenyl;

$R_{15},R_{16}$ when taken alone they can be the same or different and are selected from the group consisting of H, halogen, lower alkyl, lower alkenyl, lower alkynyl, aryl, heteroaryl, CN, $COR_{22}$, $COOR_{22}$, $CONHR_{22}$, $CONR_{22}R_{23}$, $CSR_{22}$, $CSSR_{22}$, $NR_{22}R_{23}$, wherein $R_{22}$ and $R_{23}$ may be taken together to form a —$CH_2$—$CH_2$—O—$CH_2$—$CH_2$— group, $NHCOR_{22}$, $NHCOOR_{22}$, $NHSO_2R_{22}$, $N_3$, $OR_{22}$, $OCOR_{22}$, $SR_{22}$, $SO_2R_{22}$, $SiR_{24}R_{25}R_{26}$ and $OSiR_{24}R_{25}R_{26}$; when taken together they are an oxygen atom of a carbonyl group, the nitrogen atom of a substituted imine or the carbon atom of a substituted alkenyl;

$R_{17},R_{18}$ when taken alone they can be the same or different and are selected from the group consisting of H, halogen, lower alkyl, lower alkenyl, lower alkynyl, aryl, heteroaryl, CN, $COR_{22}$, $COOR_{22}$, $CONHR_{22}$, $CONR_{22}R_{23}$, $CSR_{22}$, $CSSR_{22}$, $NR_{22}R_{23}$, $NHCOR_{22}$, $NHCOOR_{22}$, $NHSO_2R_{22}$, $N_3$, $OR_{22}$, $OCOR_{22}$, $SR_{22}$, $SO_2R_{22}$, and $SiR_{24}R_{25}R_{26}$; when taken together they are an oxygen atom of a carbonyl group, the nitrogen atom of a substituted imine or the carbon atom of a substituted alkenyl;

$R_{22}$, $R_{23}$, $R_{24}$, $R_{25}$ and $R_{26}$
can be the same or different and are independently selected from the group consisting of H, a lower alkyl, aryl, benzyl and heteroaryl;

Z,Y are both single bonds or one single and one double bond;

n is 1 or 2;

$R_{11}$ and $R_{13}$, $R_{12}$ and $R_{14}$, $R_{15}$ and $R_{17}$ or $R_{16}$ and $R_{18}$
may be taken together to form a —O—$C(R_{22})_2$—O— group wherein $R_{22}$ is H or methyl;
wherein when n is 2 it is to be understood that the two substituents $R_{17}$ may be the same or different and that the two substituents $R_{18}$ may be the same or different.

2. The protein kinase inhibitor according to claim 1 having the general formula (II)

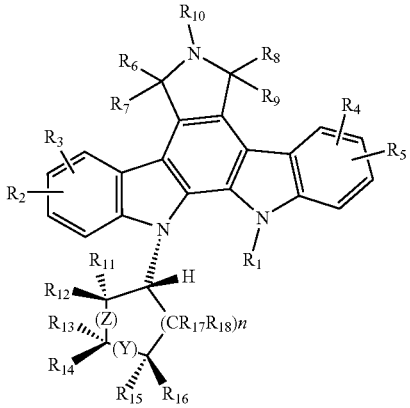

including diastereomeric and enantiomeric forms, mixtures of diastereomeric and enantiomeric forms, or pharmaceutically acceptable salt forms, wherein $R_1$ to $R_{18}$, Z, Y and n are as defined in claim 1.

3. The protein kinase inhibitor according to claim 1 having the general formula (IIa) or (IIb)

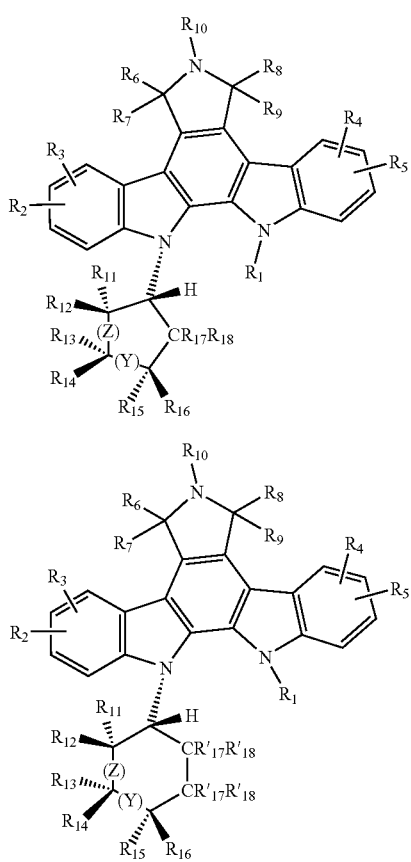

including diastereomeric and enantiomeric forms, mixtures of diastereomeric and enantiomeric forms, or pharmaceutically acceptable salt forms, wherein $R_1$ to $R_{18}$, Z, and Y are as defined in claim 1 and $R'_{17}$ and $R'_{18}$ when taken alone they can be the same or different and are selected from the group consisting of H, halogen, lower alkyl, lower alkenyl, lower alkynyl, aryl, heteroaryl, CN, $COR_{22}$, $COOR_{22}$, $CONHR_{22}$, $CONR_{22}R_{23}$, $CSR_{22}$, $CSSR_{22}$, $NR_{22}R_{23}$, $NHCOR_{22}$, $NHCOOR_{22}$, $NHSO_2R_{22}$, $N_3$, $OR_{22}$, $OCOR_{22}$, $SR_{22}$, $SO_2R_{22}$, and $SiR_{24}R_{25}R_{26}$; when taken together they are an oxygen atom of a carbonyl group, the nitrogen atom of a substituted imine or the carbon atom of a substituted alkenyl, wherein $R_{22}$ to $R_{26}$ are as defined in claim 1.

4. The protein kinase inhibitor according to claim 1, wherein $R_1$ is H or lower alkyl;

$R_2, R_3, R_4, R_5$ can be the same or different and are each independently selected from the group consisting of H, halogen, lower alkyl, aryl, heteroaryl, $COR_{22}$, $COOR_{22}$, $CONHR_{22}$, $NR_{22}R_{23}$, $NHCOR_{22}$, $NHSO_2R_2$, $OR_2$, and $OCOR_{22}$, wherein $R_{22}$ and $R_{23}$ can be the same or different and are independently selected from the group consisting of H, lower alkyl, aryl and heteroaryl;

$R_6, R_7$ when taken alone they are both H, or one of them is H and the other is OH, or when taken together they are the oxygen atom of a carbonyl group; when $R_8, R_9$ are different from carbonyl $R_6, R_7$ taken together are the oxygen atom of a carbonyl group;

$R_8, R_9$ when taken alone they are both H, or one of them is H and the other is OH, or when taken together they are the oxygen atom of a carbonyl group; when $R_6, R_7$ are different from carbonyl $R_8, R_9$ taken together are the oxygen atom of a carbonyl group;

$R_{10}$ is H or lower alkyl;

$R_{11}, R_{12}$ when taken alone they can be the same or different and are selected from the group consisting of H, halogen, lower alkyl, $COOR_{22}$, $CONHR_{22}$, $CONR_{22}R_{23}$, $NR_{22}R_{23}$, $NHCOR_{22}$, $NHSO_2R_{22}$, and $OR_{22}$, wherein $R_{22}$ and $R_{23}$ can be the same or different and are independently selected from the group consisting of H, a lower alkyl, aryl and heteroaryl; when taken together they are the oxygen atom of a carbonyl group;

$R_{13}, R_{14}$ when taken alone they can be the same or different and are selected from the group consisting of H, halogen, lower alkyl, $COOR_{22}$, $CONHR_{22}$, $CONR_{22}R_{23}$, $NR_{22}R_{23}$, $NHCOR_{22}$, $NHSO_2R_{22}$, and $OR_{22}$, wherein $R_{22}$ and $R_{23}$ can be the same or different and are independently selected from the group consisting of H, a lower alkyl, aryl and heteroaryl; when taken together they are the oxygen atom of a carbonyl group;

$R_{15}, R_{16}$ when taken alone they can be the same or different and are selected from the group consisting of H, halogen, lower alkyl, $COOR_{22}$, $CONHR_{22}$, $CONR_{22}R_{23}$, $NR_{22}R_{23}$, $NHCOR_{22}$, $NHSO_2R_{22}$, and $OR_{22}$, wherein $R_{22}$ and $R_{23}$ can be the same or different and are independently selected from the group consisting of H, a lower alkyl, aryl and heteroaryl; when taken together they are the oxygen atom of a carbonyl group;

$R_{17}, R_{18}$ when taken alone they can be the same or different and are selected from the group consisting of H, halogen, lower alkyl, $COOR_{22}$, $CONHR_{22}$, $CONR_{22}R_{23}$, $NR_{22}R_{23}$, $NHCOR_{22}$, $NHSO_2R_{22}$, and $OR_{22}$, wherein $R_{22}$ and $R_{23}$ can be the same or different and are independently selected from the group consisting of H, a lower alkyl, aryl and heteroaryl; when taken together they are the oxygen atom of a carbonyl group;

Z,Y are both single bonds or one single and one double bond;

n is 1 or 2.

5. The protein kinase inhibitor according to claim 1, wherein $R_2, R_3, R_4, R_5$ are all H.

6. The protein kinase inhibitor according to claim 1, wherein $R_{11}, R_{12}$ are selected from the group consisting of H, and $OR_{22}$, wherein $R_{22}$ is selected from the group consisting of H and lower alkyl.

7. The protein kinase inhibitor according to claim 1, wherein $R_{13}, R_{14}$ are selected from the group consisting of H, and $OR_{22}$, wherein $R_{22}$ is selected from the group consisting of H and lower alkyl.

8. A protein kinase inhibitor having the general formula (I), (II), (IIa), or (IIb),

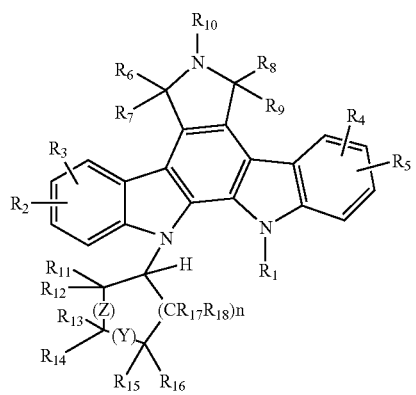

(I)

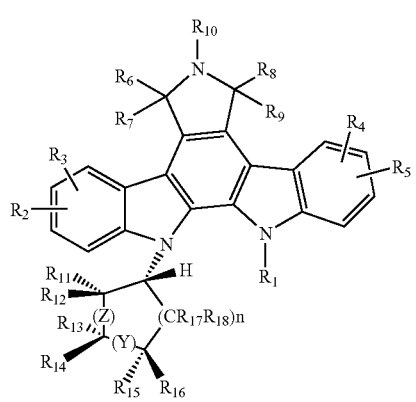

(II)

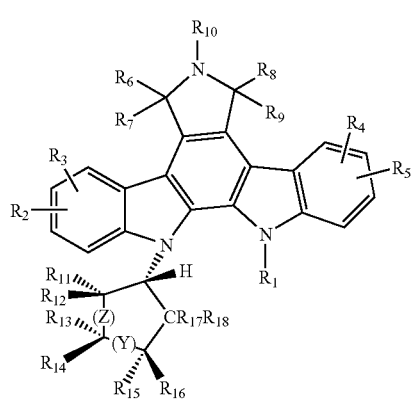

(IIa)

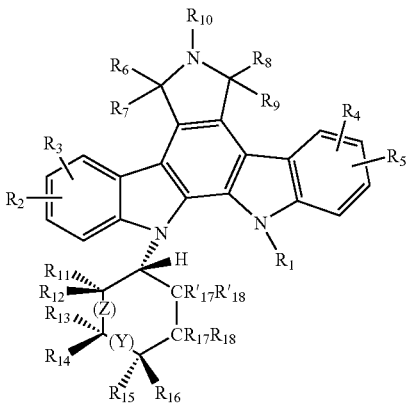

(IIb)

wherein $R_1$ is selected from the group consisting of H, lower alkyl, aryl and heteroaryl;

$R_2, R_3, R_4, R_5$ taken alone can be the same or different and are each independently selected from the group consisting of H, halogen, lower alkyl, lower alkenyl, lower alkynyl, aryl, heteroaryl, CN, $COR_{22}$, $COOR_{22}$, $CONHR_{22}$, $CONR_{22}R_{23}$, $CSR_{22}$, $CSSR_{22}$, $NR_{22}R_{23}$, $NHCOR_{22}$, $NHCOOR_{22}$, $NHSO_2R_{22}$, $N_3$, $OR_{22}$, $OCOR_{22}$, $SR_{22}$, $SO_2R_{22}$, and $SiR_{24}R_{25}R_{26}$ wherein $R_{22}, R_{23}, R_{24}, R_{25}$ and $R_{26}$ can be the same or different and are independently selected from the group consisting of H, lower alkyl, aryl and heteroaryl; or when $R_2$ and $R_3$ or $R_4$ and $R_5$ are taken together they are an optionally substituted alkylene group, containing 2 to 4 carbon atoms or heteroatoms without substituents;

$R_6, R_7$ when taken alone they are both H, or one of them is H and the other is OH, or when taken together they are the oxygen atom of a carbonyl group; and when $R_8, R_9$ are different from carbonyl $R_6, R_7$ taken together are the oxygen atom of a carbonyl group;

$R_8, R_9$ when taken alone they are both H, or one of them is H and the other is OH, or when taken together they are the oxygen atom of a carbonyl group; and when $R_6, R_7$ are different from carbonyl $R_8, R_9$ taken together are the oxygen atom of a carbonyl group;

$R_{10}$ is selected from the group consisting of H, lower alkyl, aryl, heteroaryl, $NR_{22}R_{23}$, and $OR_{22}$, wherein $R_{24}$ and $R_{25}$ are a lower alkyl, substituted aryl or heteroaryl;

$R_{11}, R_{12}$ when taken alone they can be the same or different and are selected from the group consisting of H, halogen, lower alkyl, aryl, heteroaryl, $COR_{22}$, $COOR_{22}$, $CONHR_{22}$, $CONR_{22}R_{23}$, $NR_{22}R_{23}$, $NHCOR_{22}$, $NHSO_2R_{22}$, and $OR_{22}$, wherein $R_{22}$ and $R_{23}$ can be the same or different and are independently selected from the group consisting of H, a lower alkyl, aryl and heteroaryl; when taken together they are the oxygen atom of a carbonyl group, the nitrogen atom of a substituted imine or the carbon atom of a substituted alkenyl;

$R_{13}, R_{14}$ when taken alone they can be the same or different and are selected from the group consisting of H, halogen, loweralkyl, aryl, heteroaryl, $COR_{22}$, $COOR_{22}$, $CONHR_{22}$, $CONR_{22}R_{23}$, $NR_{22}R_{23}$, $NHCOR_{22}$, $NHSO_2R_{22}$, and $OR_{22}$, wherein $R_{22}$ and $R_{23}$ can be the same or different and are independently selected from the group consisting of H, a lower alkyl, aryl and heteroaryl; when taken together they are the oxygen atom of a carbonyl group, the nitrogen atom of a substituted imine or the carbon atom of a substituted alkenyl;

$R_{15}, R_{16}$ when taken alone they can be the same or different and are selected from the group consisting of H, halogen, lower alkyl, aryl, heteroaryl, $COR_{22}$, $COOR_{22}$, $CONHR_{22}$, $CONR_{22}R_{23}$, $NR_{22}R_{23}$, $NHCOR_{22}$, $NHSO_2R_{22}$, and $OR_{22}$, wherein $R_{22}$ and $R_{23}$ can be the same or different and are independently selected from the group consisting of H, a lower alkyl, aryl and heteroaryl; when taken together they are the oxygen atom of a carbonyl group, the nitrogen atom of a substituted imine or the carbon atom of a substituted alkenyl;

$R_{17}, R_{18}$ when taken alone they can be the same or different and are selected from the group consisting of H, halogen, lower alkyl, aryl, heteroaryl, $COR_{22}$, $COOR_{22}$, $CONHR_{22}$, $CONR_{22}R_{23}$, $NR_{22}R_3$, $NHCOR_{22}$, $NHSO_2R_{22}$, and $OR_{22}$, wherein $R_{22}$ and $R_{23}$ can be the same or different and are independently selected from the group consisting of H, a lower alkyl, aryl and heteroaryl; when taken together they are the oxygen atom of a carbonyl group, the nitrogen atom of a substituted imine or the carbon atom of a substituted alkenyl;

Z,Y are both single bonds or one single and one double bond;

n is 1 or 2.

9. The protein kinase inhibitor according to claim 8, wherein $R_1$ is H or lower alkyl;

$R_2, R_3, R_4, R_5$ can be the same or different and are each independently selected from the group consisting of H, halogen, lower alkyl, aryl, heteroaryl, $COR_{22}$, $COOR_{22}$, $CONHR_{22}$, $NR_{22}R_{23}$, $NHCOR_{22}$, $NHSO_2R_2$, $OR_2$, and $OCOR_{22}$, wherein $R_{22}$ and $R_{23}$ can be the same or different and are independently selected from the group consisting of H, lower alkyl, aryl and heteroaryl;

$R_6, R_7$ when taken alone they are both H, or one of them is H and the other is OH, or when taken together they are the oxygen atom of a carbonyl group; when $R_8, R_9$ are different from carbonyl $R_6, R_7$ taken together are the oxygen atom of a carbonyl group;

$R_8, R_9$ when taken alone they are both H, or one of them is H and the other is OH, or when taken together they are the oxygen atom of a carbonyl group; when $R_6, R_7$ are different from carbonyl $R_8, R_9$ taken together are the oxygen atom of a carbonyl group;

$R_{10}$ is H or lower alkyl;

$R_{11}, R_{12}$ when taken alone they can be the same or different and are selected from the group consisting of H, halogen, lower alkyl, $COOR_{22}$, $CONHR_{22}$, $CONR_{22}R_{23}$, $NR_{22}R_{23}$, $NHCOR_{22}$, $NHSO_2R_{22}$, and $OR_{22}$, wherein $R_{22}$ and $R_{23}$ can be the same or different and are independently selected from the group consisting of H, a lower alkyl, aryl and heteroaryl; when taken together they are the oxygen atom of a carbonyl group;

$R_{13}, R_{14}$ when taken alone they can be the same or different and are selected from the group consisting of H, halogen, lower alkyl, $COOR_{22}$, $CONHR_{22}$, $CONR_{22}R_{23}$, $NR_{22}R_{23}$, $NHCOR_{22}$, $NHSO_2R_{22}$, and $OR_{22}$, wherein $R_{22}$ and $R_{23}$ can be the same or different and are independently selected from the group consisting of H, a lower alkyl, aryl and heteroaryl; when taken together they are the oxygen atom of a carbonyl group;

$R_{15}, R_{16}$ when taken alone they can be the same or different and are selected from the group consisting of H, halogen, lower alkyl, $COOR_{22}$, $CONHR_{22}$, $CONR_{22}R_{23}$, $NR_{22}R_{23}$, $NHCOR_{22}$, $NHSO_2R_{22}$, and $OR_{22}$, wherein $R_{22}$ and $R_{23}$ can be the same or different and are independently selected from the group consisting of H, a lower alkyl, aryl and heteroaryl; when taken together they are the oxygen atom of a carbonyl group;

$R_{17}, R_{18}$ when taken alone they can be the same or different and are selected from the group consisting of H, halogen, lower alkyl, $COOR_{22}$, $CONHR_{22}$, $CONR_{22}R_{23}$, $NR_{22}R_{23}$, $NHCOR_{22}$, $NHSO_2R_{22}$, and $OR_{22}$, wherein $R_{22}$ and $R_{23}$ can be the same or different and are independently selected from the group consisting of H, a lower alkyl, aryl and heteroaryl; when taken together they are the oxygen atom of a carbonyl group;

Z,Y are both single bonds or one single and one double bond;

n is 1 or 2.

10. The protein kinase inhibitor according to claim 8, wherein $R_2, R_3, R_4, R_5$ are all H.

11. The protein kinase inhibitor according to claim 8, wherein $R_{11}, R_{12}$ are selected from the group consisting of H, and $OR_{22}$, wherein $R_{22}$ is selected from the group consisting of H and lower alkyl.

12. The protein kinase inhibitor according to claim 8, wherein $R_{13}, R_{14}$ are selected from the group consisting of H, and $OR_{22}$, wherein $R_{22}$ is selected from the group consisting of H and lower alkyl.

13. The protein kinase inhibitor having the general formula (IIc) or (III)

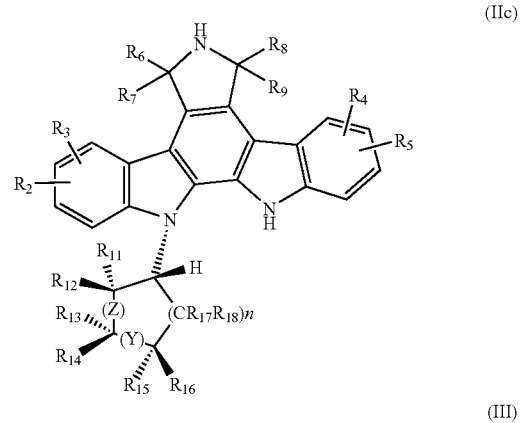

(IIc)

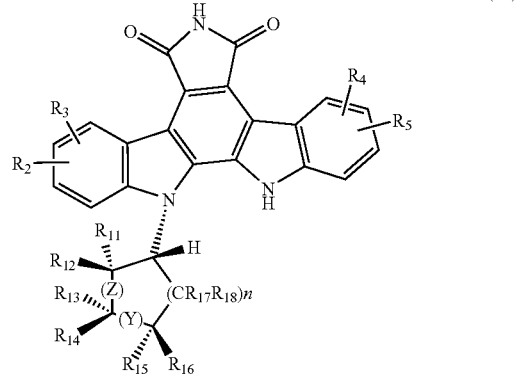

(III)

wherein in formula (IIc)

- $R_6,R_7$ when taken alone they are both H, or when taken together they are the oxygen atom of a carbonyl group; with the proviso that when $R_8,R_9$ are different from carbonyl $R_6,R_7$ taken together are the oxygen atom of a carbonyl group;
- $R_8,R_9$ when taken alone they are both H, or when taken together they are the oxygen atom of a carbonyl group; with the proviso that when $R_6,R_7$ are different from carbonyl $R_8,R_9$ taken together are the oxygen atom of a carbonyl group;

and wherein in formulae (IIc) and (III)

- $R_2,R_3,R_4,R_5$ can be the same or different and are each independently selected from the group consisting of H, halogen, lower alkyl, $COOR_{22}$, $CONHR_{22}$, $NR_{22}R_{23}$, $NHCOR_{22}$, and $OR_{22}$, wherein $R_2$ and $R_{23}$ can be the same or different and are independently selected from the group consisting of H and lower alkyl;
- $R_{11},R_{12}$ when taken alone they can be the same or different and are selected from the group consisting of H, halogen, $COOR_{22}$, $CONHR_{22}$, $NR_{22}R_{23}$, $NHCOR_2$, and $OR_{22}$, wherein $R_{22}$ and $R_{23}$ can be the same or different and are independently selected from the group consisting of H and a lower alkyl; when taken together they are the oxygen atom of a carbonyl group;
- $R_{13},R_{14}$ when taken alone they can be the same or different and are selected from the group consisting of H, halogen, $COOR_{22}$, $CONHR_{22}$, $NR_{22}R_{23}$, $NHCOR_{22}$, and $OR_{22}$, wherein $R_{22}$ and $R_{23}$ can be the same or different and are independently selected from the group consisting of H and a lower alkyl; when taken together they are the oxygen atom of a carbonyl group;
- $R_{15},R_{16}$ when taken alone they can be the same or different and are selected from the group consisting of H, halogen, $COOR_{22}$, $CONHR_{22}$, $NR_{22}R_{23}$, $NHCOR_{22}$, and $OR_{22}$, wherein $R_{22}$ and $R_{23}$ can be the same or different and are independently selected from the group consisting of H and a lower alkyl; when taken together they are the oxygen atom of a carbonyl group;
- $R_{17},R_{18}$ when taken alone they can be the same or different and are selected from the group consisting of H, halogen, $COOR_{22}$, $CONHR_{22}$, $NR_{22}R_{23}$, $NHCOR_{22}$, and $OR_{22}$, wherein $R_{22}$ and $R_{23}$ can be the same or different and are independently selected from the group consisting of H and a lower alkyl; when taken together they are an oxygen atom of a carbonyl group;
- Z,Y are both single bonds or one single and one double bond;
- n is 1 or 2.

14. The protein kinase inhibitor according to claim 13, wherein $R_2,R_3,R_4,R_5$ are all H.

15. The protein kinase inhibitor according to claim 13, wherein $R_{11},R_{12}$ are selected from the group consisting of H, and $OR_{22}$, wherein $R_{22}$ is selected from the group consisting of H and lower alkyl.

16. The protein kinase inhibitor according to claim 13, wherein $R_{13},R_{14}$ are selected from the group consisting of H, and $OR_{22}$, wherein $R_{22}$ is selected from the group consisting of H and lower alkyl.

* * * * *